US011560554B2

(12) United States Patent
Quinn et al.

(10) Patent No.: US 11,560,554 B2
(45) **Date of Patent: *Jan. 24, 2023**

(54) LYSOSOMAL STORAGE DISEASE ENZYMES

(71) Applicant: Alexion Pharmaceuticals, Inc., Boston, MA (US)

(72) Inventors: Anthony Quinn, Chestnut Hill, MA (US); Alex J. Harvey, Athens, GA (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 5 days.

This patent is subject to a terminal disclaimer.

(21) Appl. No.: 17/093,074

(22) Filed: Nov. 9, 2020

(65) Prior Publication Data

US 2021/0171922 A1 Jun. 10, 2021

Related U.S. Application Data

(63) Continuation of application No. 16/506,558, filed on Jul. 9, 2019, now Pat. No. 10,858,638, which is a continuation of application No. 15/429,247, filed on Feb. 10, 2017, now Pat. No. 10,407,671, which is a continuation of application No. 15/285,025, filed on Oct. 4, 2016, now abandoned, which is a continuation of application No. 15/177,867, filed on Jun. 9, 2016, now abandoned, which is a continuation of application No. 13/642,790, filed as application No. PCT/US2011/033699 on Apr. 23, 2011, now abandoned.

(60) Provisional application No. 61/343,177, filed on Apr. 23, 2010, provisional application No. 61/396,376, filed on May 26, 2010, provisional application No. 61/403,011, filed on Sep. 9, 2010, provisional application No. 61/456,014, filed on Oct. 29, 2010, provisional application No. 61/432,372, filed on Jan. 13, 2011.

(51) Int. Cl.

| | |
|---|---|
| ***C12N 9/20*** | (2006.01) |
| ***A61K 38/46*** | (2006.01) |
| ***A01K 67/027*** | (2006.01) |
| ***A61K 31/194*** | (2006.01) |
| ***A61K 38/38*** | (2006.01) |

(52) U.S. Cl.

CPC ............ *C12N 9/20* (2013.01); *A01K 67/0278* (2013.01); *A61K 31/194* (2013.01); *A61K 38/385* (2013.01); *A61K 38/465* (2013.01); *C12Y 301/01013* (2013.01); *A01K 2217/052* (2013.01); *A01K 2227/30* (2013.01); *A01K 2267/01* (2013.01); *C12N 2740/10041* (2013.01)

(58) Field of Classification Search

CPC ............ C12N 9/20; C12N 2740/10041; C12Y 301/01013; A61P 1/16; A61P 9/00; A61P 43/00; A61P 35/04; A61P 1/00; A61P 3/06; A61P 3/00; A61K 38/465; A61K 31/194; A61K 38/385; A01K 2267/01; A01K 2217/052; A01K 2227/30; A01K 67/0278

See application file for complete search history.

(56) References Cited

U.S. PATENT DOCUMENTS

| | | | |
|---|---|---|---|
| 5,767,115 A | 6/1998 | Rosenblum et al. | |
| 5,929,304 A | 7/1999 | Radin | |
| 6,534,300 B1 | 3/2003 | Canfield | |
| 6,670,165 B2 | 12/2003 | Canfield | |
| 6,800,472 B2 | 10/2004 | Canfield et al. | |
| 6,849,257 B2 | 2/2005 | Grabowski et al. | |
| 7,033,780 B1 | 4/2006 | McCarthy et al. | |
| 8,124,732 B2 | 2/2012 | Harvey | |
| 8,178,609 B2 | 5/2012 | Grynkiewicz et al. | |
| 8,183,003 B2 | 5/2012 | Crawford et al. | |
| 8,232,073 B2 | 7/2012 | Crawford et al. | |
| 8,663,631 B2 | 3/2014 | Quinn | |
| 8,945,542 B2 | 2/2015 | Heartlein | |
| 10,166,274 B2 | 1/2019 | Quinn | |
| 10,407,671 B2 * | 9/2019 | Quinn | A61K 38/465 |
| 2002/0193303 A1 | 12/2002 | Kapeller-Libermann | |
| 2003/0059420 A1 | 3/2003 | Grabowski et al. | |
| 2003/0064467 A1 | 4/2003 | Baker et al. | |
| 2004/0038365 A1 | 2/2004 | Xiao | |
| 2004/0175798 A1 | 9/2004 | Wan et al. | |
| 2004/0223960 A1 | 11/2004 | Grabowski et al. | |

(Continued)

FOREIGN PATENT DOCUMENTS

| | | |
|---|---|---|
| EP | 1267914 | 4/2009 |
| RU | 2140983 C1 | 11/1999 |

(Continued)

OTHER PUBLICATIONS

Broun et al., Catalytic plasticity of fatty acid modification enzymes underlying chemical diversity of plant lipids. Science, 1998, vol. 282: 1315-1317. (Year: 1998).*

(Continued)

*Primary Examiner* — Ganapathirama Raghu
(74) *Attorney, Agent, or Firm* — Clark & Elbing LLP

(57) ABSTRACT

The present invention provides compositions of recombinant human lysosomal acid lipase having particular glycosylation patterns for internalization into target cells, a vector containing the nucleic acid encoding human lysosomal acid lipase, a host cell transformed with the vector, pharmaceutical compositions comprising the recombinant human lysosomal acid lipase and method of treating conditions associated with lysosomal acid lipase deficiency.

13 Claims, 38 Drawing Sheets

Specification includes a Sequence Listing.

(56) References Cited

U.S. PATENT DOCUMENTS

2005/0112691 A1 5/2005 Callewaert et al.
2005/0181474 A1 8/2005 Giordano et al.
2007/0009500 A1 1/2007 Blazer et al.
2007/0264249 A1 11/2007 Grabowski et al.
2007/0270364 A1 11/2007 Janknecht
2007/0270367 A1 11/2007 Testa et al.
2008/0025958 A1 1/2008 Daneman et al.
2008/0025959 A1 1/2008 Daneman
2008/0206223 A1 8/2008 Van Bree et al.
2008/0249287 A1 10/2008 Rossomando et al.
2008/0255050 A1 10/2008 ZhongMao
2008/0292618 A1 11/2008 Weisbart
2009/0178147 A1 7/2009 Harvey
2009/0297496 A1 12/2009 Grabowski
2010/0160253 A1 6/2010 Coombe et al.
2010/0184947 A1 7/2010 Kuik-Romeijn et al.
2010/0196393 A1 8/2010 Banks et al.
2010/0233084 A1 9/2010 Narasimhaswamy et al.
2010/0062982 A1 11/2010 Harvey
2010/0291060 A1 11/2010 Sturk et al.
2011/0091442 A1 4/2011 Boyd et al.
2011/0213328 A1 9/2011 Keimel et al.
2011/0230416 A1 9/2011 Khrestchatisky et al.
2012/0064055 A1 3/2012 Quinn
2012/0093795 A1 4/2012 Garcia et al.
2012/0190642 A1 7/2012 Grynkiewicz et al.
2012/0232133 A1 9/2012 Balazes et al.
2012/0288447 A1 11/2012 Lee et al.
2013/0209436 A1 8/2013 Quinn et al.
2015/0030582 A1 1/2015 Harvey

FOREIGN PATENT DOCUMENTS

RU 2008134120 2/2010
WO 1991/18923 A1 12/1991
WO 1992/16212 10/1992
WO 1995/008532 3/1995
WO 1996/04001 2/1996
WO 1997/05771 2/1997
WO 1998/11206 3/1998
WO 2000/09153 2/2000
WO 2000/77239 12/2000
WO 2001/56596 8/2001
WO 2001/97829 12/2001
WO 2007/030375 3/2007
WO 2007/084737 7/2007
WO 2007/137303 11/2007
WO 2010/033854 A2 3/2010
WO 2011/133960 10/2011
WO 2012/050695 4/2012
WO 2012/112677 8/2012
WO 2012/112681 8/2012
WO 2012/159052 11/2012
WO 2012/162807 12/2012
WO 2012/177639 12/2012
WO 2012/177778 12/2012
WO 2013/020064 2/2013

OTHER PUBLICATIONS

Devos et al., Practical limits of function prediction. Proteins: Structure, Function, and Genetics. 2000, vol. 41: 98-107. (Year: 2000).*

Seffernick et al., Melamine deaminase and Atrazine chlorohydrolase: 98 percent identical but functionally different. J. Bacteriol., 2001, vol. 183 (8): 2405-2410. (Year: 2001).*

Whisstock et al., Prediction of protein function from protein sequence. Q. Rev. Biophysics., 2003, vol. 36 (3): 307-340. (Year: 2003).*

Witkowski et al., Conversion of b-ketoacyl synthase to a Malonyl Decarboxylase by replacement of the active cysteine with glutamine. Biochemistry, 1999, vol. 38: 11643-11650. (Year: 1999).*

Chowdhury et al., "A Fourteen Years Old Boy with Cholesterol Ester Storage Disease," J Medicine, 10:146-148 (2009).

Christomanou et al., "Prenatal Monitoring for Wolman's Disease in a Pregnancy at Risk," Clinical Case Reports, 57:440-441 (1981).

Coates et al., "Prenatal Diagnosis of Wolman Disease," American Journal of Medical Genetics, 2:397-407(1978).

Colin et al., "Modification of Pancreatic Lipase Properties by Directed Molecular Evolution," Protein Engineering, Design and Selection, pp. 1-9, (2010) downloaded from peds.oxfordjournals.org.

File History dated Sep. 23, 2010 from European Patent Application No. 01906927.7.

Cortner et al., "Genetic Variation of Lysosomal Acid Lipase," Pediatric Research, 10:927-932 (1976).

Crocker et al., "Wolmans Disease: Three New Patients with a Recently Described Lipidosis," Pediatrics, 35:627-640 (1965).

Cummings et al., Increased Hepatic Secretion of Very-Low-Density Lipoprotein Apolipoprotein B-100 in Cholesteryl Ester Storage Disease, 41(1):111-114 (1995).

D'Agostino et al., "Cholesterol Ester Storage Disease: Clinical, Biochemical, and pathological Studies of Four New Cases," Journal of Pediatric Gastroenterology and Nutrition, 7:446-450 (1988).

Dahl et al., "Hepatosplenomegalic Lipidosis: What Unless Gaucher? Adult Cholesteryl Ester Storage Disease (CESD) with Anemia, Mesenteric Lipodystrophy, Increased Plasma Chitotriosidase Activity and a Homozygous Lysosomal Acid Lipase—1 Exon 8 /Splice Junction Mutation," Journal of Hepatology 31:741-746 (1999).

Daly et al., "Neonatal Gene Transfer Leads to Widespread Correction of Pathology in a Murine Model of Lysosomal Storage Disease," Proc. Natl. Acad, 96:2296-2300 (1999).

Davis, et al., Role of Acid Lipase in Cholesteryl Ester Accumulation During Atherogenesis; Correlation of Enzyme Activity with Acid Lipase-Containing Macrophages in Rabbit and Human Lesions, Atherosclerosis, 55:205-215 (1985).

De Duve "The Participation of Lysosomes in the Transformation of Smooth Muscle Cells to Foamy Cells in the Aorta of Cholesterol-Fed Rabbits," Acta Cardiologica Suppl., pp. 9-25 (1975).

De Grey et al., "Medical Bioremediation: Prospects for the Application of Microbial Catabolic Diversity to aging and Several Major Age-Related Diseases," Ageing Research Reviews, 4:315-338 (2005).

Decarlis et al., "Combined Hyperlipidaemia as a Presenting Sign of Cholesteryl Ester Storage Disease," JIMD Short Report, Online, 3 pages (2009).

Desai et al., "Cholesteryl Ester Storage Disease: Pathologic Changes in an Affected Fetus," American Journal of Medical Genetics, 26:689-698 (1987).

Desnick et al., "Toward Enzyme Therapy for Lysosomal Storage Diseases," Physiological Reviews, 56(1):56-98 (1976).

Di Bisceglie, Cholesteryl Ester Storage Disease: Hepatopathology and Effects of Therapy with Lovastatin, Hepatology, 11(5):764-772 (1990).

Doebber et al., "Enhanced Macrophage Uptake of Synthetically Glycosylated Human Placental β-Glucocerebrosidase," The Journal of Biological Chemistry, 257(5):2193-2199 (1982).

Drebber et al., "Severe Chronic Diarrhea and Weight Loss in Cholesteryl Ester Storage Disease: A Case Report," World Journal Gastroenterol, 11(15):2364-2366 (2005).

Du et al., "Human Transcription Factor USF Stimulates Transcription through the Initiator Elements of the HIV-1 and the Ad-ML Promoters," The EMBO Journal, 12(2):501-511 (1993).

Du et al., "Lysosomal Acid Lipase-Deficient Mice: Depletion of White and Brown Fat, Severe Hepatosplenomegaly, anti Shortened Life Span," Journal of Lipid Research, 42(4):489-500 (2001).

Du et al., "Reduction of Atherosclerotic Plaques by Lysosomal Acid Lipase Supplementation," Arterioscler Thromb. Vasc. Biol., 24:147-154 (2004).

Du et al., "Lysosomal Acid Lipase and Atherosclerosis," Curr. Opin. Lipidol., 15:539-544 (2004).

Du et al., "Mouse Lysosomal Acid Lipase: Characterization of the Gene and Analysis of Promoter Activity," Gene, 208:285-295(1998).

Dustin et al., "A Mannose 6-Phosphate-Containing N-Linked Glycopeptide Derived from Lysosomal Acid Lipase is Bound to MHC ClassII in B Lymphoblastoid Cell Lines," J. Immunol., 156:1841-1847 (1996).

(56) References Cited

OTHER PUBLICATIONS

Elleder et al., "Testis—A Novel Storage Site in Human Cholesteryl Ester Storage Disease Autopsy Report of an Adult Case with a Long-Standing Subclinical Course Complicated by Accelerated Atherosclerosis and Liver Carcinoma," Virchows Arch, 436:82-87 (2000).
Elleder et al., Subclinical Course of Cholesteryl Ester Storage Disease in an Adult with Hypercholesterolemia, Accelerated Atherosclerosis, and Liver Cancer, Journal of Hepatology, 32:528-534 (2000).
Written Opinion dated Nov. 5, 2001 from PCT Application No. PCT/US01/03481.
Essa et al., "Wolman Disease: A Review," Curr. Paed. Res., 3:(1):1-12 (1999).
Ezekowitz et al., "Molecular Characterization of the Human Macrophage Mannose Receptor: Demonstration of Multiple Carbohydrate Recognition-Like Domains and Phagocytosis of Yeasts in Cos-1 Cells," J. Exp. Med., 172:1785-1794 (1990).
Ezekowitz et al., "The Structure and Function of Vertebrate Mannose Lectin-Like Proteins," J. Cell. Sci. Suppl., 9:121-133 (1988).
Fadden et al., "Molecular Characterization of the Rat Kupffer Cell Glycoprotein Receptor," Glycobiology, 13(7):529-537 (2003).
Fiete et al., "The macrophage/endothelial cell mannose receptor cDNA encodes a protein that binds oligosaccharides terminating with S04-4-GalNAc,31,4GlcNAcf3 or Man at independent sites," Proc. Natl. Acad. Sci., 94:11256-11261 (1997).
Fitoussi et al., "New Pathogenetic Hypothesis for Wolman Disease: Possible Role of Oxidized Low-Density Lipoproteins in Adrenal Necrosis and Calcification," Biochem, J., 301:267-273 (1994).
Fitzky et al., "7-Dehydrocholesterol-Dependent Proteolysis of HMG-CoA Reductase Suppresses Sterol Biosynthesis in a Mouse Model of Smith-Lemli-Opitz/RSH Syndrome," The Journal of Clinical Investigation, 108(6):905-915 (2001).
Foger et al., "Unusual Presentation of Cholesterol Ester Storage Disease (CESD): Report on New Family," Atherosclerosis, 109:132 Abstract 155 (1994).
Folch et al., "A Simple Method for the Isolation and Purification of Total Lipide from Animal Tissues," J. Bio. Chem, 226:497-509 (1957).
Friedman et al., "A Comparison of the Pharmacological Properties of Carbohydrate Remodeled Recombinant and Placental-Derived b-Glucocerebrosidase: Implications for Clinical Efficacy in Treatement of Gaucher Disease," Blood, 93(9):2807-2816 (1999).
Fujiyama et al., "A New Mutation (LIPA Tyr22X) of Lysosomal Acid Lipase Gene in a Japanese Patient with Wolman Disease," Human Mutation, 8:377-380 (1996).
Gasche et al., "A Novel Variant of Lysosomal Acid Lipase in Cholesteryl Ester Storage Disease Associated with Mild Phenotype and Improvement on Lovastatin," Journal of Hepatology, 27:744-750 (1997).
Gerlai et al., "Gene-Targeting Studies of Mammalian Behavior: Is it the Mutation or the Background Genotype," Trends Neurosci, 19:177-181 (1996).
Gidiri et al., Letter to the Editor, European Journal of Obstetrics and Gynecology and Reproductive Biology, 142:81-87 (2009).
Ginsberg et al., Suppression of Apolipoprotein B Production during Treatment of Cholesteryl Ester Storage Disease with Lovastatin, J. Clin. Invest., 80:1692-1697 (1987).
Glueck et al., "Safety and Efficacy of Treatment of Pediatric Cholesteryl Ester Storage Disease with Lovastatin," Pediatric Research, 32:559-565 (1992).
Goldstein et al., "Role of Lysosomal Acid Lipase in the Metabolism of Plasma Low Density Lipoprotein," The Journal of Biological Chemistry, 250(21):8487-8795, (1975).
Grabowski et al., "Enzyme Therapy for Lysosomal Storage Disease: Principles, Practice and Prospects," Annu. Rev. Genomics Hum. Genet., 4:403-436 (2003).
Groener et al., "Difference in Substrate Specificity Between Human and Mouse Lysosomal Acid Lipase: Low Affinity for cholesteryl Ester in Mouse Lysosomal Acid Lipase," Biochimica et Biophysica Acta, 1487:155-162 (2000).
Opposition against European Patent 1267914, dated Jan. 28, 2010.
Guazzi et al., "Wolman's Disease. Distribution and Significance of the Central Nervous System lesions," Path. Europ., 3:266-277 (1968).
Sanyal et al., "Endpoints and Clinical Trial Design for Nonalcoholic Steatohepatitis," Hepatology, 54(1):344-345 (2011).
Thavarungkul et al., "Cholesterol Ester Storage Disease: A Reported Case," J. Med. Assoc. Thai; 78(3):164-168 (1995).
Tylki-Szymańska et al, "Clinical, biochemical and histological analysis of seven patients with cholesteryl ester storage disease," Acta Paediatrica Japonica, 39:643-646 (1997).
Pagani et. al, "Cysteine residues in human lysosomal acid lipase are involved in selective cholesteryl esterase activity," Biochem J. 326:265-269 (1997).
Pagani et al., "A histidine to tyrosine replacement in lysosomal acid lipase causes cholesteryl ester storage disease," Human Molecular Genetics, 3(9): 1605-1609 (1994).
Pagani et al., "Expression of lysosomal acid lipase mutants detected in three patients with cholesteryl ester storage disease," Human Molecular Genetics, 5(10):1611-1617 (1996).
Patrick et al., "Deficiency of an Acid Lipase in Wolman's Disease," Nature, 222:1067-1068 (1969).
Pentchev et al., "Incorporation of Exogenous Enzymes into Lysosomes: A Theoretical and Practical Means for Correcting Lysosomal Blockage," American Chemical Society, 150-151 (1978).
Poorthuis et al., "The frequency of lysosomal storage disease in the Netherlands," Hum genet, 105:151-156 (1999).
Poupětová et al., "LSDS with Neurologic Involvement: The birth prevalence of lysosomal storage disorders in the Czech Republic: comparison with data in different populations," J. Inherit Metab Dis, 33:387-396 (2010).
Raivio et al., "Genetic Diseases of Metabolism," Annu. Rev. Biochem 41:543-576 (1972).
Redonnet-Vernhet et al., "Cholesteryl Ester Storage Disease: Relationship between Molecular Defects and in Situ Activity of Lysosomal Acid Lipase," Biochemical and Molecular Medicine, 62:42-49 (1997).
Ries et al., "Different Missense Mutations in Histidine-108 of Lysosomal Acid Lipase Cause Cholesteryl Ester Storage Diseases in Unrelated Compound Heterozygous and Hemizygous Individuals," Human Mutation, 12:44-51 (1998).
Ries et al., "Transcriptional regulation of lysosomal acid lipase in differentiating monocytes is mediated by transcription factors Sp1 and AP-2," Journal of Lipid Research, 39:2125-2126 (1998).
Ries et al., "A new mutation in the gene for lysosomal acid lipase leads to Wolman disease in an African kindred," Journal of Lipid Research, 37:1761-1762 (1996).
Riva et al., "Hepatocarcinoma in a child with cholesterol ester storage disease," Digestive and Liver Disease, 40:784 (2008).
Rosenbaum et al., "Thiadiazole Carbamates: Potent Inhibitors of Lysosomal Acid Lipase and Potential Neimann-Pick Type C Disease Therapeutics," J Med Chem., 53(14):5281-5289 (2010).
Rosenthal, "Nonalcoholic Fatty Liver Disease in Pediatric Patients—A Problem that is 'Enormous' and 'Growing,'" JPEN J Parenter Enteral Nutr 36:7S (2012).
Rothe, et al., "Altered mononuclear phagocyte differentiation associated with genetic defects of the lysosomal acid lipase," Atherosclerosis, 130:215-221 (1997).
Roussel et al., "Crystal Structure of Human Gastric Lipase and Model of Lysosomal Acid Lipase, Two Lipolytic Enzymes of Medical Interest," The Journal of Biological Chemistry, 274( 24):16995-17002 (1999).
Röyttä et al., "Wolman disease: morphological, clinical and genetic studies on the first Scandinavian cases," Clin Genet, 42:1-7 (1992).
Russell et al., "Recombinant proteins for genetic disease," Clin Gent 55:389-394 (1999).
Salvetti et al., "Gene therapy of lysosomal storage disorders," British Medical Bulletin, 51(1):106-122 (1995).

(56) References Cited

OTHER PUBLICATIONS

Sando et al., "Intercellular Transport of lysosomal acid lipase mediates lipoprotein cholesteryl ester metabolism in a human vascular endothelial cell-fibroblast coculture system," Cell Regulation, 1:661-674 (1990).
Schaub et al., "Wolman's Disease: Clinical, Biochemical and Ultrastructural in an Unusual Case Without Striking Adrenal Calcification" Eur. J. Ped., 135:45-53 (1980).
Schiff et al., "Hepatic Cholesterol Ester Storage Disease, A Familial Disorder," American Journal of Medicine, 44:538-546 (1968).
Yu et al., "Boosting Brain Uptake of a Therapeutic Antibody by Reducing Its Affinity for a Transcytosis Target," Sci Transl Med, 3:84ra44 (2011).
Phillipps et al., "Secretion of insulin-like growth factor-II into bile of rats of different ages," Biol Neonate, 78(2):106-12 (2000).
Seedorf et al., "A Novel Variant of Lysosomal Acid Lipase (Lue336→Pro) Associated With Acid Lipase Deficiency and Cholesterol Ester Storage Disease," Arteriosclerosis, Thrombosis, and Vascular Biology, 15:773-778 (1995).
Shimada et al., "Suppression of diet-induced atherosclerosis in low density lipoprotein receptor knockout mice overexpressing lipoprotein lipase," Proc. Natl. Acad. Sci. USA, 93:7242-7246 (1996).
Skinner et al., "Cholesterol Curves to Identify Norms by Age and Sex in Healthy Weight Children," Clin Pediatr, 51:233 (2012).
Sloan et al., "Enzyme Deficiency in Cholesteryl Ester Storage Disease," the Journal of Clinical Investigation, 51:1923-1924 (1972).
Sly et al., "Enzyme therapy in mannose receptor-null mucopolysaccharidosis VII mice defines roles for the mannose 6-phosphate and mannose receptors," PNAS, 103(41):15172-15177 (2006).
Spiegel-Adolf et al., "Hematologic Studies in Niemann-Pick and Wolman's Disease," Confin. Neurol, 28:399-406 (1966).
Stahl et al., "Evidence for receptor-mediated binding of glycoproteins, glycoconjugates, and lysosomal gylcosidases by alveolar macrophages," Cell Biology, 75(3):1399-1403 (1978).
Sternby et al., "Carboxyl Ester Lipase (Bile Salt-Stimulated Lipase), Colipase, Lipase, and Phospholipase A2 Levels in Pancreatic Enzyme Supplements," Scand J Gastroenterol 32:261-267 (1997).
Surve et al., "Wolman Disease: Diagnosis by Leucocyte Acid Lipase Estimation," Indian Journal of Pediatrics, 72:353-354 (2005).
Suzuki et al., "Are animal models useful for understanding the pathophysiology of lysosomal storage disease?" Acta Paediatr Suppl, 443:54-62 (2003).
Takahashi et al., "Distribution of murine mannose receptor expression from early embryogenesis through to adulthood," Cell Tissue Res 292:311-323 (1998).
Takasaki et al., "Structure of the N-Asparagine-linked Oligosaccharide Units of Human Placental β-Glucocerebrosidase," The Journal of Biological Chemistry, 259(16):10112-10117 (1984).
Tarantino et al., "Lovastatin therapy for cholesterol ester storage disease in two sisters," The Journal of Ped., 118(1):131-135 (1991).
Thompson et al., "Role of cholesterol in regulating apolipoprotein B secretion by the liver," Journal of Lipid Research, 37:439-440 (1996).
Todoroki et al., "Accumulated lipids, aberrant fatty acid composition and defective cholesterol ester hydrolase activity in cholesterol ester storage disease," Ann Clin Biochem, 37:187-193 (2000).
Tolar et al., "Long-term metabolic, endocrine, and neuropsychological outcome of hematopoietic cell transplantation for Wolman disease," Bone Marrow Transplantation, 43:21-27 (2009).
Uniyal et al., "Wolman's Disease," Indian Pediatrics, 32:232-233 (1995).
Van Berkel, "The role of non-parenchymal cells in liver metabolism," TIBS 202-205, Sep. 1979.
Van Erum et al., "Cholesteryl Ester Storage Disease with Secondary Lecithin Cholesterol Acyl Transferase Deficiency," J. Inher. Metab. Dis 11 Suppl. 2:146-148 (1988).
Varki et al., "Studies of synthesis, structure and function of the phosphorylated oligosaccharides of lysosomal enzymes," J. Biosci, 5(1):101-104 (1983).
vom Dahl et al., "Lysosomal storage disease as differential diagnosis of hepatosplenomegaly," Best Practice & Research Clinical Gastroenterology, 24:619-628 (2010).
von Figura et al., "Lysosomal Enzymes and Their Receptors," Ann. Rev. Biochem, 55:167-193 (1986).
Gunning et al., "Isolation and Characterization of Full-Length cDNA Clones for Human a-, 13-, and γ-Actin mRNAs: Skeletal but Not Cyoplasmic Actins Have an Amino-Terminal Cysteine that is Subsequently Removed," Molecular and Cellular Biology, 3(5):787-795 (1983).
Guzzetta et al., "Elective Subtotal Splenectomy," Ann. Surg., 211 (1): 34-42 (1990).
Hafner et al., "The Human Primary Hepatocyte Transcriptome Reveals Novel Insights into Atorvastatin and Rosuvastatin Action," Pharmacogenetics and Genomics, 21(11):741-750 (2011).
Hakala et al., "Lysosomal Enzymes are Released from cultured Human macrophages, Hydrolyze LDL in Vitro, and are Present Extracellularly in Human Atherosclerotic Lesions," Arteriosclerosis, Thrombosis, and Vascular Biology, 23:1430-1436, (2003).
Hoeg et al., "Characterization of Neutral and Acid Ester Hydrolase in Wolman's Disease," Biochimica et Biophysica Acta, 711:59-65 (1982).
Hoeg et al., "Cholesteryl Ester Storage Disease and Wolman Disease: Phenotypic Variants of Lysosomal Acid Cholesteryl Ester Hydrolase Deficiency," Am. J. Hum. Genet, 36:1190-1203 (1984).
Holbrook et al., "Tolerization as a Tool for Generating Novel Monoclonal Antibodies," Immunology and Cell Biology, 80:319-322 (2002).
Hollak et al., "Alglucerase Practical Guidance on Appropriate Dosage and Administration in Patients with Gaucher Disease," Biodrugs, 9(1):11-23 (1998).
Hooper et al., "A Novel Missense LIPA Gene Mutation, N98S, in a Patient with Cholesteryl Ester Storage Disease," Clinica Chimica Acta, 398:152-154 (2008).
Hopkins et al., "Human Genetics and Coronary Heart Perspective," Annu. Rev. Nutr., 9:303-45 (1989).
Hua et al., "SREBP-2, A Second Basic-Helix-Leucine Zipper Protein that Stimulates Transcription by Binding to a Sterol Regulatory Element," Proc. Natl. Acad. Sci., 90:11603-11607 (1993).
Heinz et al., "Identification and in Situ Localization of the Insulin-Like Growth Factor-1 l/Mannose-6-Phosphate (IGF-II/M6P) Receptor in the Rat Gastrointestinal Tract: Comparison with the IGF-1 Receptor," U.S. National Institutes of Health, 129(4):1769-1778 (1991).
Imanaka et al., "Characterization of Lysosomal Acid Lipase Purified from Rabbit Liver," J. Biochem. 96:1089-1101 (1984).
Ishibashi et al., "Hypercholesterolemia in Low Density Lipoprotein Receptor Knockout Mice and its Reversal by Adenovirus-Mediated Gene Delivery," J. Clin. Invest., 92:883-893 (1993).
Hatanaka et al., "Human IgA-Binding Peptides Selected from Random Peptide Libraries: Affinity Maturation and Application in IgA Purification," J. Bio. Chem. in Press, M112 389742, pp. 1-12 (2012).
Jirtle et al., "Modulation of Insulin-Like Growth Factor-II/Mannose 6-Phosphate Receptors and Transforming Growth Factor-β1 during Liver Regeneration," The Journal of Biological Chemistry, 266(33):22444-22450 (1991).
Jolly et al., "Lysosomal Storage Diseases of Animals: an Essay in Comparative Pathology," Vet Pathol., 34:527-548 (1997).
Kahana et al., "Primary Familial Xanthomatosis with Adrenal Involvement (Wolman's Disease); Report of a further Case with Nervous System Involvement and pathogenetic Considerations," Pediatrics, 42(1):71-76 (1968).
Kale et al., "End Stage Renal Disease in a Patient with Cholesteryl Ester Storage disease Following Successful Liver Transplantation and Cyclosporine Immunosuppression," Journal of Pediatric Gastroenterology and Nutrition, 20:95-97 (1995).
Kawashiri et al., "Gene Therapy for Lipid Disorders," Curr. Control Trials Cardiovascular Med., 1:120-127 (2000).
Kelly et al., "Characterization of Plasma Lipids and Lipoproteins in Cholesteryl Ester Storage Disease," Biochemical Medicine, 33:29-37 (1985).

(56) References Cited

OTHER PUBLICATIONS

Kikuchi et al., "Evaluation of Jejunal Function in Wolman's Disease," Journal of Pediatric Gastroenterology and Nutrition, 12(1): 6569 (1991).
Klima et al., "A Splice Junction Mutation Causes Deletion of a 72-Base Exon from the mRNA for Lysosomal Acid Lipase in a Patient with Cholesteryl Ester Storage Disease," J. Clin. Invest., 92:2713-2718 (1993).
Koch et al., "Assignment of LIPA, Associated with Human Acid Lipase Deficiency, to Human Chromosome 10 and Comparative Assignment to Mouse Chromosome 19," Somatic Cell Genetics, 7(3):345-358 (1981).
Kodlitsch et al., "Splice-Site Mutations in Atherosclerosis Candidate Genes Relating Individual Information to Phenotype," Circulation, 100:693-699 (1999).
Kolodny et al., "Current Concepts in Genetics; Lysosomal Storage Disease," The New England Journal of Medicine, 294(22):1217-1220 (1976).
Kostner et al., "Plasma Lipids and Lipoproteins of a Patient with Cholesteryl Ester Storage Disease," J. Inher. Metab. Dis. 8:9-12 (1985).
Kowel et al., "Low Density Lipoprotein Receptor-Related Protein Mediated Uptake of Cholesteryl Esters Derived from apoprotein E-Enriched Lipoproteins," Proc. Natl. Acad. Sci., 86:5810-5814 (1989).
Krivit et al., "Wolman Disease Successfully Treated by Bone Marrow Transplantation," Bone Marrow Transplantation, 26:567-570 (2000).
Kuriwaki et al., Morphological Characteristics of Lipid Accumulation in Liver-Constituting Cells of Acid Lipase Deficiency Rats (Wolman's Disease Model Rats), Pathology International, 49:291-297 (1999).
Laird et al., "Simplified Mammalian DNA Isolation Procedure," Nucleic Acids Research, 19(15):4293 (1991).
Lake et al., "Wolman's Disease Deficiency of E600-Resistant Acid Esterase Activity with Storage of Lipids in Lysosomes," The Journal of Pediatrics, 76(2):262-266 (1970).
Lake et al., "Histochemical Detection of the Enzyme Deficiency in Blood Films in Wolman's Disease," J. Clin. Path., 24:617-620 (1971).
Lashford et al., "Lysosomal Storage Disorders," Gene Therapy Technologies, Applications and Regulations, John Wiley & Sons, 1999.
Lee et al., "Mannose Receptor-Mediated Regulation of Serum Glycoprotein Homeostasis," Science, 295:1898-1901 (2002).
Lee et al., "Intragenic Deletion as a Novel Type of Mutation in Wolman Disease," Molecular Genetics and Metabolism, 104:703-705 (2011).
Leonova et al., "Proteolytic Processing Patterns of prosaposin in Insect and Mammalian Cells," The Journal of Biological Chemistry, 271(29):17312-17320 (1996).
Leslie et al., "A Mouse Model of Galactose-1-Phosphate Uridyl Transferase Deficiency," Biochemical and Molecular Medicine, 59:7-12 (1996).
Levy et al., "Cholesteryl Ester Storage Disease: Complex Molecular Effects of Chronic Lovastatin Therapy," Journal of Lipid Research, 33:1005-1015 (1992).
Lew et al., "A Mannose Receptor Mediates Mannosyl-Rich glycoprotein-Induced Mitogenesis in Bovine Airway Smooth Muscle Cells," J. Clin. Invest., 94:1855-1863 (1994).
Li et al., "Gsh-1, An Orphan Hox Gene, is Required for Normal pituitary Development," The EMBO Journal, 15(4):714-724 (1996).
Lohse et al., "Human Lysosomal Acid Lipase/Cholesteryl Ester Hydrolase and Human Gastric Lipase: Identification of the Catalytically Active Serine, Aspartic Acid, and Histidine Residues," Journal of Lipid Research, 38:892-903 (1997).
Lohse et al., "Human Lysosomal Acid Lipase/Cholesteryl Ester Hydrolase and Human Gastric Lipase:Site-Directed Mutagenesis of Cys227 and Cys236 Results in Substrate-Dependent Reduction of Enzymatic Activity," Journal of Lipid Research,38:1896-1905 (1997).
Lohse et al., "The Acid Lipase Gene Family: Three Enzymes, One Highly Conserved Gene Structure," Journal of Lipid Research, 38:881-891 (1997).
Lohse et al., "Molecular Defects Underlying Wolman Disease Appear to be More Heterogeneous than those Resulting in Cholesteryl Ester Storage Disease," Journal of Lipid Research, 40:221-228 (1999).
Lohse et al., "Compound Heterozygosity for a Wolman Mutation is Frequent Among Patients with Cholesteryl Ester Storage Disease," Journal of Lipid Research, 41:23-31 (2000).
Longhi et al., "Cholesteryl Ester Storage Disease: Risk Factors for Atherosclerosis in a 15-Year-Old Boy," J. Inher. Metab. Dis., 11(2):143-145 (1988).
Lough et al., "Wolman's Disease: An Electron Microscope, Histochemical, and Biochemical Study," Arch. Path, 89:103-110 (1970).
Lowden et al., "Wolman's Disease: A Microscopic and Biochemical Study Showing Accumulation of Ceroid and Esterified Cholesterol," C.M.A. Journal, 102:402-405 (1970).
Lübke et al., "Proteomics of the Lysosome," Biochim Biophys Acta, 1793(4):625-635 (2009).
Suzuki, N. et al., "Site-specific N-glycosylation of chicken serum IgG", Glycobiology, vol. 14, No. 3, pp. 275-292, 2004.
NCBI Reference Sequence: NP_000226, Nov. 3, 2010: Lysosomal acid lipase/cholesteryl ester hydrolase precursor [*Homo sapiens*].
Beltroy, E. P. et al., "Lysosomal unesterified cholesterol content correlates with liver cell death in murine Niemann-Pick type C disease," Journal of Lipid Research, 2007, 48(4), 869-881.
Ameis, Detlev, et al., "Purification, characterization and molecular cloning of human hepatic lysosomal acid lipase," Eur. J. Biochem., vol. 219, 905-914, 1994.
Anderson, Richard A., et al., "Cloning and Expression of cDNA encoding Human Lysosmal Acid Lipase/Cholesteryl Ester Hydrolase," The Journal of Biological Chemistry, vol. 266 No. 33, 22479-22484, 1991.
Anderson, Richard A., et al., "In Situ Localization of the Genetic Locus Encoding the Lysosomal Acid Lipase/Cholesteryl Esterase (LIPA) Deficient in Wolman Disease to Chromosome 10q23.2-q23.3," Genomics 15, 245-247, 1993.
Du Hong, et al., "Wolman disease/cholesteryl ester storage disease: efficacy of plant-produced human lysosomal acid lipase in mice," Journal of Lipid Research, vol. 49, 1646-1657, 2008.
Du, Hong, et al., "Enzyme therapy for lysosomal acid lipase deficiency in the mouse," Human Molecular Genetics, vol. 10, No. 16, 1639-1648, 2001.
Du, Hong, et al., "Molecular and Enzymatic Analyses of Lysosomal Acid Lipase in Cholesteryl Ester Storage Disease," Molecular Genetics and Metabolism, vol. 64, 126-134, 1998.
Du, Hong, et al., "The role of Mannosylated Enzyme and the Mannose Receptor in Enzyme Replacement Therapy," Am. J. Hum. Genet., vol. 77, 1061-1074, 2005.
Office Action issued in U.S. Appl. No. 13/229,558 dated Jan. 18, 2013.
Zschenker et al., "Systematic Mutagenesis of Potential Glycosylation Sites of Lysosmal Acid Lipase," J. Biochem., 137:387-394 (2005).
GenBank Accession No. AAA59519: Lysosomal Acid Lipase/Cholesteryl Esterase [*Homo sapiens*] 7. (1995).
Skropeta, "The Effect of Individual N-Glycans on Enzyme Activity," Bioorg. Med. Chem., 17:2645-2653 (2009).
Anderson et al., "Cloning and Expression of cDNA Encoding Human Lysosomal Acid Lipase/Cholesteryl Ester Hydrolase," J. Biol. Chem., 266:22479-22484 (1991).
Smith et al., "Peptide Sequences Mediating Tropism to Intact Blood-Brain Barrier: An In Vivo Biodistribution Study Using Phage Display," Peptides, 38:172-180 (2012).
Jeyakumar et al., "Storage Solutions: Treating Lysosomal Disorders of the Brain," Nature Reviews Neuroscience, 6:713-725 (2005).
Begley et al., "Lysosomal Storage Diseases and the Blood-Brain Barrier," Current Pharmaceutical Design, 14:1566-1580 (2008).
Bertrand et al., "Transport Characteristics of a Novel Peptide Platform for CNS Therapeutics," J Cell. Molecular Medicine, 14(12):2827-2839 (2010).

(56) References Cited

OTHER PUBLICATIONS

Ameis et al., "A 5' Splice-Region Mutation and a Dinucleotide Deletion in the Lysosomal Acid Lipase Gene in Two Patients with Cholesteryl Ester Storage Disease,"Journal of Lipid Research, 36:241-250 (1995).
Abramov et al., "Generalized Xanthomatosis with Calcified Adrenals," Journal of Diseases of Children, pp. 282-286 (1956).
K-T Von Trotha et al., "Influence of Lysosomal Acid Lipase Polymorphisms on Chromosome 10 on the Risk of Alzheimer's Disease and Cholesterol Metabolism," 402:(3):262-266 (2006).
Du et al., "Enzyme Therapy for Lysosomal Acid Lipase Deficiency in the Mouse Model," FASEB J. vol. 10(2):427, Abstract 2409 (1996).
Achord, et al., "Human β-Glucuronidase: In Vivo Clearance and in Vitro Uptake by a Glycoprotein Recognition System on Reticuloendothelial Cells," Cell, 15:269-278 (1978).
Al Essa et al., "Wolman Disease: A Review," Curr Paed Res, 3(1):1-12 (1999).
Aslanidis et al., "Genomic Organization of the Human Lysosomal Acid Lipase Gene (LIPA)," Genomics, 20:329-331 (1994).
Assmann et al., "Acid Lipase Deficiency: Wolman Disease and Cholesteryl Ester Storage Disease," Part 16: Lysosomal Disorders, pp. 1-49 (2001).
Asumendi et al., "Hepatic Sinusoidal Endothelium Heterogeneity with Respect to Mannose Receptor Activity is Interleukin-1 Dependent," 23(6):1521-1529 (1996).
Avert et al., "Cholesteryl Ester Hydrolysis in J774 Macrophages Occurs in the Cytoplasm and Lysosomes," Journal of Lipid Research, 40:405-414 (1999).
Baenziger et al., "Structural Determinants of Concanavalin a Specificity for Oligosaccharides," 254(7):2400-2407(1979).
Barton et al., "Therapeutic Response to Intravenous Infusions of Glucocerebrosidase in a Patient with Gaucher Disease," 87:1913-1916 (1990).
Barton et al., "Replacement Therapy for Inherited Enzyme Deficiency—Macrophage Targeted Glucocerebrosidase for Gaucher's Disease," The New England Journal of Medicine, pp. 1464-1470(1991).
Beaudet et al., "Cholesterol Ester Storage Disease: Clinical, Biochemical, and Pathological Studies," The Journal of Pediatrics, 90(6):910-914 (1977).
Cox, "Effect of Lysosomal Cholesterol Accumulation on Lysosomal and Vacuolar-Atpase Activity," Submitted to the Faculty of the Graduate School of Vanderbilt University, pp. 1-108 (2007).
Beutler et al., "Enzyme Replacement Therapy for Gaucher Disease," Blood, 78(5):1183-1189 (1991).
Biggs et al., "A Manual Colorimetric Assay of Triglycerides in Serum," Clinical Chemistry, 21(3):437-441 (1975).
Bijsterbosch et al., "Quantitative Analysis of the Targeting of Mannose-Terminal Glucocerebrosidase Predominant Uptake by Liver Endothelial Cells," Eur. J. Biochem, 237:344-349 (1996).
Bindu et al., "Cholesterol Ester Storage Disease with Unusual Neurological Manifestations in Two Siblings: A Report from South India," Journal of Child Neurology, 22(12):1401-1404 (2007).
Brady et al., "Modifying Exogenous Glucocerebrosidase for Effective Replacement Therapy in Gaucher Disease," J. Inher. Metab. Dis., 17:510-519 (1994).
Brecher et al., "Effect of Atherosclerosis on Lysosomal Cholesterol Esterase Activity in Rabbit Aorta," Journal of Lipid Research, 18:154-160 (1977).
Briggs et al., "Nuclear Protein that Binds Sterol Regulatory Element of Low Density Lipoprotein Receptor Promoter," 268(19):14490-14496 (1993).
Brown et al., "Multivalent Feedback Regulation of HMG CoA Reductase, a Control Mechanism Coordinating Isoprenoid Synthesis and Cell Growth," Journal of Lipid Research, 21:505-517 (1980).
Brown et al., "A Receptor-Mediated Pathway for Cholesterol Homeostasis," Science, 232(4746):34-47 (1986).
Brumshtein et al., "Characterization of Gene-Activated Human Acid-β-Glucosidase: Crystal Structure, Glycan Composition, and Internalization into Macrophages," 20(1):24-32 (2010).
Brumshtein et al., "Structural Comparison of Differently Glycosylated Forms of acid-β-Glucosidase, the defective Enzyme in Gaucher Disease," Acta Crystallographica Section D, 62:1458-1465 (2006).
Burke et al., Deficient Activity of Hepatic Acid Lipase in Cholesterol Ester Storage Disease, Science, 176(4032):309-310 (1972).
Burton et al., "Purification and Properties of Human Placental Acid Lipase," Biochimica et Biophysica Acta, 618:449-460(1980).
Burton et al., "Lysosomal Acid Lipase in Cultivated Fibroblasts:Characterization of Enzyme Activity in Normal and Enzymatically Deficient Cell Lines," Clinica Chimica Acta, 101:25-32 (1980).
Burton et al., "Acid Lipase Cross-Reacting Material in Wolman Disease and Cholesterol Ester Storage Disease," Am J Hum Genet, 33:203-208 (1981).
Byrd et al., "Wolman's Disease: Ultrastructural Evidence of Lipid Accumulation in Central and Peripheral Nervous Systems," Acta Neuropathol, 45:37-42 (1979).
Cagle et al., "Clinicopathologic Conference: Pulmonary Hypertension in an 18-Year-Old girl with Cholesteryl Ester Storage Disease (CESD)," American Journal of Medical Genetrics, 24:711-722(1986).
Chatterjee et al., "Evaluation of Urinary Cells in Acid Cholesteryl Ester Hydrolase Deficiency," Clinical Genetics, 29:360-368 (1986).
Chobanian et al., "Effects of Hypertension and of Antihypertensive Therapy on Atherosclerosis," Suppl. I. Hypertension, 8(4):15-21 (1986).
"LIPA Gene", Genecards, available at www.genecards.org/cgi-bin/carddisp.pl?gene=LIPA, accessed on Mar. 13, 2021; Year: 2021.
Pastores, G.M., "Therapeutic approaches for lysosomal storage diseases". Ther Adv Endocrinol Metab (2010), 1(4), 177-188.
Wang, C.S. et al., "Impact of increasing alanine aminotransferase levels within normal range on incident diabetes". Journal of Formosan Medical Association (2012) 111, 201-208.
Quinn, A. et al., "SBC-102, a recombinant enzyme replacement therapy, corrects key abnormalities due to lysosomal acidlipase deficiency", Abstract Submission, American Society of Human Genetics Meeting, Nov. 6, 2010.
Quinn, A. et al., "SBC-102, a recombinant enzyme replacement therapy, corrects key abnormalities due to lysosomal acidlipase deficiency", Poster Presentation, American Society of Human Genetics Meeting, Nov. 6, 2010.
Presentation by Synageva Biopharma Corp., Jefferies Healthcare Conference, "Dedicated to Rare Diseases", Jun. 4, 2012.
Furo Ventures B.V., Opposition Papers submitted in European Patent Application No. EP 11758644.6, pp. 1-162, Nov. 25, 2015.
Summary of Product Characteristics of Kanuma.
Summary of NCT01371825 Clinical Trial, Jul. 19, 2011.
Summary of NCT01307098 Clinical Trial, Mar. 1, 2011.
"Synageva BioPharma Presents Data at the American Society of Human Genetics on SBC-102 for Lysosomal Acid Lipase Deficiency", BusinessWire News, Nov. 4, 2010.
Leavitt, M. et al., "Recombinant Lysosomal Acid Lipase Normalizes Liver Weight, Transaminases and Histopathologcial Abnormalities in an In Vivo Model of Cholesteryl Ester Storage Disease", Journal of Hepatology, 2011, vol. 54, p. S358.
Leavitt, M. et al., "Recombinant Lysosomal Acid Lipase Normalizes Liver Weight, Transaminases and Histopathologcial Abnormalities in an In Vivo Model of Cholesteryl Ester Storage Disease", Poster Presentation, The International Liver Congress, Berlin, Germany, Mar. 30, 2011.
Cagle et al., "Clinicopathologic Conference: Pulmonary Hypertension in an 18 Year Old Giri With Cholesteryl Ester Storage Disease (CESD)," Am. J. of Med. Genetics, 24:711-722 (1986).
Chatrath et al., "Cholesterol Ester Storage Disease (CESD) Diagnosed in an Asymptomatic Adult," Dig. Dis. Sci., 54:168-173 (2008).
Coates et al., "Genetic Variation of Human Mononuclear Leukocyte Lysosomal Acid Lipase Activity," Atherosclerosis, 62:11-20 (1986).
Desnick et al., "Advances in the Treatment of Inherited Metabolic Diseases," Chapter 5, pp. 281-369 (1981).

(56) References Cited

OTHER PUBLICATIONS

Du et al., "Lysosomal Acid Lipase Deficiency: Correction of Lipid Storage by Adenovirus-Mediated Gene Transfer in Mice," Hum. Gen Ther., 13:1361-1372 (2002).
Du et al., "MRI of Fat Distribution in a Mouse Model of Lysosomal Acid Lipase Deficiency," AJR 184:658-662 (2005).
Du et al., "Targeted Disruption of the Mouse Lysosomal Acid Lipase Gene: Long-Term Survival with Massive Cholesteryl Ester and Triglyceride Storage," Hum. Mol. Genet., 7:1347-1354 (1998).
Du et al., "Tissue and Cellular Specific Expression of Murine Lysosomal Acid Lipase mRNA and Protein," Journal of Lipid Research, 37:937-949 (1996).
Du et al., "Enzyme Therapy for Lysosomal Acid Lipase Deficiency in the Mouse Model," Am. J. Hum. Genetics. 67: (4 Supp 2): 427 (2000).
Grabowski et al., "Enzyme Supplementation for Treatment of Artherosclerosis Using Lysosomal Acid Lipase," Therapy for Genetic Disorders, The American Journal of Human Genetics, 67(4) (Suppl. 2)(Abstract No. 136) (2000).
Ikeda et al., "Production of Recombinant Human Lysosomal Acid Lipase in Schizosaccharomyces Pombe: Development of a Fed-Batch Fermentation and Purification Process," J. of Bioscience and Bioengineering, 98:366-373 (2004).
Krivit et al., "Woman's Disease: A Review of Treatment with Bone Marrow Transplantation and Consideration for the Future," Bone Marrow Transplantation, 10(Suppl 1):97-101 (1992).
Kuriyama et al., "Lysosomal Acid Lipase Deficiency in Rats: Lipid Analyses and Lipase Activites in Liver and Spleen," J. of Lipid Research, 31:1605-1612 (1992).
Kyriakides et al., "Lipid Accumulations and Acid Lipase Deficiency in Fibroblasts from a Family with Woman's Disease and Their Apparent Correction in Vitro," J. of Lab. Clin. Med., 80:810-816 (1972).
Lian et al., "Lysosomal Acid Lipase Deficiency Causes Respiratory Inflammation and Destruction in the Lung," Am. J. Physio. Lung Cell Mol. Physiol., 286:L801-L807 (2004).
Meyers et al., "The Use of Parenteral Hyperalimentation and Elemental Formula Feeding in the Treatment of Wolman Disease," Nutrition Research, 5:423-429 (1985).
Pagani et al., "New Lysosomal Acid Lipase Gene Mutants Explain the Phynotype of Wolman Disease and Cholestery Ester Storage Disease," J. of Lipid Research, 39:1382-1388 (1998).
Pariyarath et al., "L273S Missense Substitution I Human Lysosomal Acid Lipase Creates a New N-Glycosylation Site," FEBS Letter, 379:79-82 (1996).
Pastores et al., "Enzyme Therapy for the Lysosomal Storage Disorders: Principles, Patents, Practice and Prospects," Expert Opin. Therapeutic Patients 13(8):1157-1172 (2003).
Pozanansky et al., "Enzyme Replacement Therapy in Fibroblast from a Patient with Cholesteryl Ester Storage Disease," FASEB J., 3:152-156 (1989).
Radar et al., "Expression of Adenoviral Vector Containing the cDNA for Human Lysosomal Acid Lipase in HELA and Wolman Cells," FASEB J. 10(3):Abstract No. 1341 (Annual Meeting of Professional Research Scientists) (1996).
Radar et al., "Gene Therapy for Dyslipidemia: Clinical Prospects," Curr. Atherosc. Rep. 1:58-69 (1999).
Rothe et al., "Altered Manonuclear Phagocyte Differentiation Associated with Genetic Defects of the Lysosomal Acid Lipase," Atherosclerosis, 130:215-221 (1997).
Sando et al., "Human Lysosomal Acid Lipase/Cholesteryl Ester Hydrolase, Purification and Properties of the Form Secreted by Fibroblasts in Microcarrier Culture," J. of Biological Chem., 260:15186-15193 (1985).
Sando et al., "Recognition and Receptor-Mediated Endocytosis of the Lysosomal Acid Lipase Secreted by Cultured Human Fibroblasts," J. of Lipid Research 23:114-123 (1982).
Stein et al., "Successful Treatment of Wolman Disease by Unrelated Umbilical Cord Blood Transplantation," Europ. J. Pediatrics, 166(7):663-666 (2007).
Wolman et al., "Wolman Disease and It's Treatment," Clin. Pediatr. , 34(4):207-212 (1995).
Yoshida et al., "Genetic Lipid Storage Disease with Lysososomal Acid Lipase Deficiency in Rats," Lab. Animal Sci., 40:486-489 (1990).
Zschenker et al., "Characterization of Lysosomal Acid Lipase Mutations in the Signal Peptide and Mature Polypeptide Regions Causing Wolman Disease," Journal of Lipid Research, 42:1033-1040 (2001).
Zschenker et al., "Lysosomal Acid Lipase as a Preproprotein," J. Biochem., 136:65-72 (2004).
International Search Report for PCT/US2011/051096, dated Feb. 2, 2012.
Office Action dated Jan. 18, 2013 from Corresponding U.S. Appl. No. 13/229,558.
Pariyarathuparambil, R.: 'Human Lysosomal Acid Lipase: Functional Characterization by Molecular Genetic Analysis and Site-Directed Mutagenesis Studies.' SISSA Digital Library PHD Thesis, [Online] 1995, Retrieved from the Internet: [retrieved on Aug. 5, 2012].
Tietge et al., "Phenotypic Correction of Lipid Storage and Growth Arrest in Wolman disease Fibroblasts by Gene Transfer of Lysosomal Acid Lipase," Human Gene Therapy, 12(3):279-289 (2001).
Supplementary European Search Report dated Aug. 6, 2014 from Corresponding European Application No. 12746845.
International Preliminary Report of Patentability dated Apr. 30, 2013 from Corresponding International Application No. PCT/US2011/033699.
Carpenter et al., "Peripheral administration of low pH solutions causes activation and sensitisation of convergent dorsal horn neurones in the anaesthetised rat," Neurosci. Lett., 298:179-182 (2001).
Zhu et al., "Production of human monoclonal antibody in eggs of chimeric chickens," Nature Biotechnology, vol. 23, No. 9, 1159-1169 (2005).
Lysosomes; http://www.ncbi.nlm.nih.gov/books/NBK9953/, 3 pages downloaded on May 13, 2015.
McCoy et al., "Treatment of Cholesteryl Ester Storage Disease with Combined Cholestyramine and Lovastatin," Ann NY Acad. Sci., pp. 453-454 (1991).
Marsh et al., "Apolipoprotein B Metabolism in Humans: Studies with Stable Isotope-Labeled Amino Acid Precursors," Atherosclerosis, 162:227-244 (2002).
Marshall et al., "Wolman's Disease: A Rare Lipidosis with Adrenal Calcification," Arch. Dis. Childhood, 44:331-341 (1969).
Shome et al., "The Middle-East Connection of Wolman Disease," Saudi. Med. J., 23(5): 597-601 (2002).
Maslen et al., "Occurrence of a mutation associated with Wolman disease in a family with cholesteryl ester storage disease," J. Inher. Metab. Dis., 18:620-623 (1995).
Mayatepek et al., "Fatal genetic defect causing Wolman Disease," J. Inher. Metab. Dis., 22:93-94 (1999).
Meikle et al., "Prevalence of Lysosomal Storage Disorders," JAMA, 281(3):249-254 (1999).
Melling et al., "Localised massive tumourous xanthomatosis of the small intestine," Int. J. Colorectal Dis., 22:1401-1404 (2007).
Michels et al., "Pulmonary vascular obstruction associated with cholesteryl ester storage disease," The Journal of Pediatrics, 94:621-622 (1979).
Michels et al., "Cholesteryl Lignocerate Hydrolysis in Adrenoleukodystrophy," Pediat. Res. 14:21-23 (1980).
Mistry et al., "Therapeutic delivery of proteins to macrophages: implications for treatment of Gaucher's disease," The Lancet, 348:1555-1556 (1996).
McPhee et al., "Effects of AAV-2 mediated aspartoacylase gene transfer in the tremor rat model of Canavan disease," Molecular Brain Research, 135:112-121 (2005).
Mori et al., "Identification of the Mannan-Binding Protein from Rat Livers as a Hepatocyte Protein Distinct from the Mannan Receptor on Sinusoidal Cells," Archives of Biochemistry and Biophysics, 222(2):542-552 (1983).
Muntoni et al., "Prevalence of Cholesteryl Ester Storage Disease," Arterioscler. Thomb. Vasc. Biol., 27:1866-1868 (2007).

(56) References Cited

OTHER PUBLICATIONS

Muntoni et al., "Homozygosity for a splice junction mutation in exon 8 of the gene encoding lysosomal acid lipase in a Spanish kindred with cholesterol ester disease (CESD)," Hum Genet, 95:491-494 (1995).
Muntoni et al., "A missense mutation (Thr-6Pro) in the lysosomal acid lipase (LAL) gene is present with a high frequency in three different ethnic populations: impact on serum lipoprotein concentrations," Hum Genet, 97:265-267 (1996).
Nakagawa et al., "Cloning of rat lysosomal acid lipase cDNA and identification of the mutation in the rat model of Wolman's disease," J. Lipra Res 36:2212-2213 (1995).
Nègre-Salvayre et al., "UV-treated lipoproteins J. Lipid Res. as a model system for the study of the biological effects of lipid peroxides on cultured cells. 4. Calcium is involved in the cytotoxicity of UV-treated LDL on lymphoid cell lines," Biochimica et Biophysica Acta, 1123:1207-215 (1992).
Nobili et al., "Treatment of nonalcoholic fatty liver disease in adults and children: a closer look at the arsenal," J Gastroenterol, (2011). DOI 10.1007/s00535-011-0467.
Noorman et al., "The mannose receptor, localization and role in the clearance of tissue-type plasminogen activator," Fibrinolysis & Proteolysis, 12(4):241-250 (1998).
Odievre, "Clinical presentation of Metabolic Liver Disease," J. Inher. Metab. Dis., 14:526-530 (1991).
Özmen et al., "Wolman's disease: ultrasonographic and computed tomographic findings," Pediatr Radiol, 22:541-542 (1992).
Ameis et al., "Lysosomal acid lipase: A pivotal enzyme in the pathogenesis of cholesteryl ester storage disease and Wolman disease," Z Gastroenterol (Suppl. 3) 34:66-67 (1996).
Beaudet et al., "Acid lipase in cultured fibroblasts: cholesterol ester storage disease," J. Lab. Clin. Med., 84:54-55 (1974).
Brown et al., "Use of Nile Red Stain in the Detection of Cholesteryl Ester Accumulation in Acid Lipase-Deficient Fibroblasts," Arch Pathol Lab Med, 112:295-296 (1988).
Carter et al., "Cholesterol Ester Storage Disease," Pediat. Radiol, 2:135-136 (1974).
Coelho et al., "Cholesterylester Storage Disease Report of a case," Arq Gastroenterol, 24(3/4):184-187, (1987).
Dincsoy et al., "Cholesterol Ester Storage Disease and Mesenteric Lipodystrophy," Am. J. Pathol., 81:263-264 (1984).
Drevon et al., "The Effects of Cholesterol/Fat Feeding on Lipid Levels and Morphological Structures in Liver, Kidney and Spleen in Guinea Pigs," Acta path. microbial. scand. Sect. A, 85:1-18 (1977).
Edelstein, et al., "Cholesteryl Ester Storage Disease: A Patient with Massive Splenomegaly and Splenic Abscess," The American Journal of Gastroenterology, 83:687-688. (1988).
Elleder et al., "Subclinical course of cholesterol ester storage disease (CESD) diagnosed in adulthood," Virchows Archiv A Pathological Anatomy and Histopathology, 416:3457-365 (1990).
Ferry et al., "Liver Transplantation for Cholesteryl Ester Storage Disease," Journal of Pediatric Gastroenterology and Nutrition, 12:376-378 (1991).
Fulcher, et al., "Pediatric Case of the Day", RadioGraphics, 18( 2):533-534 (1988).
Haller et al., "Gallbladder Dysfunction in Cholesterol Ester Storage Disease," JPGN, 50(5):556-557 (2010).
Hill et al., "CT Findings in Acid Lipase Deficiency: Wolman Disease and Cholesteryl Ester Storage Disease," Journal of Computer Assisted Tomography, 7(5):815-818 (1983).
Iverson et al., "Asymptomatic cholesteryl ester storage disease in an adult controlled with simvastatin," Ann Clin Biochem, 34:433-436 (1997).
Jeschke et al., "Cholesteryl Ester Storage Disease, Clinical and Morphological Aspects," Cholesterylester-Speicherkrankheit, 120(8):601-604 (1982).
Justus et al., "Lebermorphologie und Klinik eins Falls von Cholesterinester-Speicherkrankheit," Dtsch. Z. Verdau-Stoffwechs. krankh. 48:198-207 (1988).
Künnert et al., "Zur Diagnostik und Morphologie der Leber bei Cholesterolester-Speicher-krankheit," Zbl. Allg. Pathol. a. pathol. Anat. 123:71-84 (1979).
Künnert et al., "Cholesteryl ester storage disease and sea-blue histiocytes," Zentralbl. Allg. Pathol. Pathol. Anat. 133:517-525 (1987).
Kuntz et al., "Cholesterinester-Speicherkrankheit der Leber," Leber Magen Darm 11, Nr. 6:258-263 (1981).
Leone et al., "Use of simvastatin plus cholestyramine in the treatment of lysosomal acid lipase deficiency," The Journal of Pediatrics, 119(6):1008-1009 (1991).
Leone et al., "Treatment and liver transplantation for cholesterol ester storage disease," The Journal of Pediatrics, 127(3):509-510 (1995).
Liu et al., "Phenotypic Correction of Feline Lipoprotein Lipase Deficiency by Adenoviral Gene Transfer," Human Gene Therapy, 11:21-32 (2000).
Pfeifer et al., "Cholesteryl Ester Storage Disease: Report on Four Cases," Virchows Arch. B. Cel Path. 33:17-34 (1980).
Pisciotta et al., "Cholesteryl Ester Storage Disease (CESD) due to novel mutations in the LIPA gene," Molecular Genetics and Metabolism, 79:143-148 (2009).
Rassoul et al., "Long-term administration of the HMG-CoA reductase inhibitor lovastatin in two patients with cholesteryl ester storage disease," International Journal of Clinic Pharmacology and Therapeutics, vol. 39, No. 5:199-204 (2001).
Salvayre et al., "Maladie de Wolman et polycorie cholestérolique de l'adulte (cholesteryl ester storage disease): Nuoveaux moyens d'étude et de diagnostic," Ann. Biol. Clin. 44:611-617 (1986).
Vuillemenot et al., "Intrathecal tripeptidyl-peptidase 1 reduces lysosomal storage in a canine model of late infantile neuronal ceroid lipofuscinosis," Molecular Genetics and Metabolism, 104:325-337 (2011).
Walters et al., "Cholesterol esterase activities in commercial pancreatic enzyme preparations and implications for use in pancreatic insufficient cystic fibrosis," Journal of Clinical Pharmacy and Therapeutics, 26:425-431 (2001).
Wang et al., "SREBP-1, a Membrane-bound Transcription Factor Released by Sterol-Regulated Proteolysis," Cell, 77:53-62 (1994).
Warner et al., "Separation and Characterization of the Acid Lipase and Neutral Esterases from Human Liver," Am. J. Hum Genet, 32:869-879 (1980).
Warner et al., "Purification of the Lysosomal Acid Lipase from Human Liver and Its Role in Lysosomal Lipid Hydorlysis," The Journal of Biological Chemistry, 246(6):2952-2957 (1981).
Wolman, "Proposed Treatment for Infants With Wolman Disease," Pediatrics, 83:1074-1075 (1989).
Wolman, "Primary Familial Xanthomatosis with Involvement and Calcification of the Adrenals: Report of Two or More Cases in Siblings of a Previously Described Infant," Pediatrics, 28:742-757 (1961).
Xu et al., "Turnover and Distribution of Intravenously Administered Mannose-Terminated Human Acid [beta]-Glucosidase in Murine and Human Tissues," Pediatric Research, 39(2):313-322 (1996).
Yagyu et al., "Overexpressed lipoprotein lipase protects against atherosclerosis in apolipoprotein E knockout mice," Journal of Lipid research, 40:1677:1678 (1999).
Yan et al., "Macrophage-Specific Expression of Human Lysosomal Acid Lipase Corrects Inflammation and Pathogenic Phenotypes in lal-/-Mice," The American Journal of Pathology, 169(3):916-917 (2006).
Yokoyama et al., "Long-term treatment of a homozygous cholesteryl ester storage disease with combined cholestryamine and lovastatin," J. Inher. Metab. Dis. 15:219-292 (1992).
Zhang et al., "Biotherapeutic target or sink: analysis of the macrophage mannose receptor tissue distribution in murine models of lysosomal storage diseases," J. Inherit Metab Disl 34:795-809 (2011).
Young et al., "Deficiency of Acid Esterase Activity in Wolman's Disease," Archives of Disease in Childhood, 45:664-665 (1970).
Zuliani et al., "Characterization of a New Form of Inherited Hypercholesterolemia: Familial Recessive Hypercholesterolemia," Arterioscler Throm Vasc Biol, 19:802-809 (1999).

(56) References Cited

OTHER PUBLICATIONS

Wolman, "Involvement of Nervous Tissue in Primary Familial Xanthosmatosis with Adrenal Calcification," Path Europe, 3:259-265 (1968).
Hollak et al., "Alglucerase: Practical Guidance on Appropriate Dosage and Administration in Patients with Gaucher Disease," Biodrugs, 9(1):11-13.
Clarke, "Recombinant Proteins for Genetic Disease," Clin. Genet., 55(6):389-94, 1999.
Sheriff et al., Characterization of Lysosomal Acid Lipase by Site-Directed Mutagenesis and Heterologous Expression., J. Biol. Chem., 270:27766-27772 (1995).
*Synageva Biopharma Limited*, plaintiff v. *Children's Hospital Research Foundation, Children's Hospital Foundation, Cincinnati, Ohio and Children's Hospital Medical Center*, defendants, Tribunal de Grande Instance of Paris, "Conclusions of Withdrawal of Proceedings".
*Synageva Biopharma Corp., and Synageva Biopharma Limited*, plaintiffs v. *Children's Hospital Research Foundation, Children's Hospital Foundation, Cincinnati, Ohio and Children's Hospital Medical Center*, defendants, Tribunal de Grande Instance of Paris, Mar. 26, 2013, "Pleadings No. 1".
*Synageva Biopharma Corp., and Synageva Biopharma Limited*, plaintiffs v. *Children's Hospital Research Foundation, Children's Hospital Foundation, Cincinnati, Ohio and Children's Hospital Medical Center*, defendants, Summons Before the High Court of Paris, 2012.
*Synageva Biopharma Limited*, claimant v. *Children's Hospital Research Foundation*, defendant, In the High Court of Justice, Chancery division, Patents Court, Claim No. HC 12 C00211, "Statement of Opposition" (2013).
*Synageva Biopharma Limited*, claimant v. *Children's Hospital Research Foundation*, defendant, In the High Court of Justice, Chancery division, Patents Court, Claim No. HC 12 C00211, "Grounds of Invalidity" (2012).
*Synageva Biopharma Limited*, claimant v. *Children's Hospital Research Foundation*, defendant, In the High Court of Justice, Chancery division, Patents Court, Claim No. HC 12 C00211, "Amended Grounds of Invalidity" (2013).
Schiffmann, "Infusion of α-Galactosidase A Reduces Tissue Globotriaosylceramide Storage in Patients with Fabry Disease," PNAS, 97(1):365-370 (2000).
Ahn et al., "Identification of the Genes Differently Expressed in Human Dendritic Cell Subsets by cDNA Subtraction and Microarray Analysis," Blood, 100:1742-1754 (2002).
Nègre et al., "Acid Lipases and Acid Cholesterol Esterases: Wolman's Disease and Cholesteryl Ester Storage Disease," Path Biol., 36(2): 167-181 (1988).
Elleder et al., "Lysosomal Acid Lipase Deficiency. Overview of Czech Patients," Cas Lek Cesk, 13/(23),719-724 (1999).
Martinez et al., "7 Years Experience with Hepatic Transplantation in Children," 6(1):7-10 (1993).
Tanaka et al., Acid Lipase Deficiency: Wolman Disease and Cholesteryl Ester Storage Disease, Nippon Rinsho, 53(12):3004-3008 (1995).
Scriver et al., "The Metabolic and Molecular Bases of Inherited Disease," 7th Ed. V II, McGraw-Hill, New York, pp. 2563-2587, 1995.
Mao et al., "Sortase-Mediated Protein Ligation: A New Method of Protein Engineering," J. Am. Chem. Soc. 126, 2670-2671, 2004.
Salvayre et al., "Lipases et Cholesterol Esterases Acides: Maladie De Wolman et Cholesteryl Ester Storage Disease (Polycorie Cholesterolique de L'Adulte)" Path Biol, 36, 167-181, 1988.
Furbish et al., "Uptake and Distribution of Placental Glucocerebrosidase in Rat Hepatic Cells and Effects of Sequential Deglycosylation," Biochimica et Biophysica Acta, 673 425-434, 1981.
Dalgic "Cholestryl Ester Storage Disease in a Young Child Presenting as isolated Hepatomegaly Treated with Simvastatin," The Turkish Journal of Pediatrics, 48:148-151 (2006).
Tadiboylina "Treatment of Dyslipidemia with Lovastatin and Ezetimibe in an Adolescent with Cholesterol Ester Storage Disease," Lipids in Health and Disease, 4(26): 1-6 (2005).
Bailey "An Overview of Enzyme Replacement Therapy for Lysosomal Storage Diseases" The Online Journal of Issues in Nursing, 13(1):1-4 (2008).
Kim "Successful Management of Difficult Infusion-Associated Reactions in a Young Patient with Mucopolysaccharidosis Type VI Receiving Recombinant Human Arylsulfatase B (Galsulfase [Naglazyme])" Pediatrics, 121(3):714-717 (2008).
Albrecht Dehmel, Opposition Submission 1, pp. 1-56, Jan. 28, 2010 European Patent Register.
Albrecht Dehmel, Opposition Submission 2, pp. 1-17, Apr. 4, 2011, European Patent Register.
Albrecht Dehmel, Opposition Submission 3, pp. 1-8, Aug. 22, 2011, European Patent Register.
*Synageva Biopharma Corp*., v. *Children's Hospital Research Foundation*, "Grounds of Invalidity of European Patent 1267914," pp. 1-11, Jan. 16, 2012, UK High Court of Justice, Chancery Division, Patents Court.
Akcoren et al., Cholesteryl Ester Storage Disease: Case Report During Childhood, Pediatric and Developmental Pathology, 2:574-576 (1999).
Anderson et al., "Lysosomal Acid Lipase Mutations that Determine Phenotype in Wolman and Cholesterol Ester Storage Disease," Mol. Genet. Metab., 68:333-345 (1999).
Anderson et al., "Mutations at the Lysosomal Acid Cholesteryl Ester Hydrolase Gene Locus in Wolman Disease," PNAS, 91:2718-2722 (1994).
Arterburn et al., "Orthotopic Liver Transplantation for Cholesteryl Ester Storage Disease," J. Clin. Gastroenterology, 13:482-485 (1991).
Aslanidis et al., "Genetic and Biochemical Evidence that CESD and Wolman Disease are Distinguished by Residual Lysosomal Acid Lipase Activity," Genomics, 33:85-93 (1996).
Besley et al., "Cholesterol Ester Storage Disease in an Adult Presenting with Sea-Blue Histiocytosis,"Clin., Genet., 26:195-203 (1984).
Boldrini et al., "Wolman Disease and Cholesteryl Ester Storage Disease Diagnosed by Histological and Ultrastructural Examination of Intestinal and Liver Biopsy," Path. Res. Practice, 200:231-240 (2004).
Brown et al., "Restoration of a Regulatory Response to Low Density Lipoprotein in Acid Lipase Deficient Human Fibroblast," J. of Biol. Chem, 251:3277-3286 (1976).

* cited by examiner

```
        1                                                          60
rhLAL   MKMRFLGLVVCLVLWTLHSEGSGGKLTAVDPETNMNVSEIISYWGFPSEEYLVETEDGYI
Natural MKMRFLGLVVCLVLWTLHSEGSGGKLTAVDPETNMNVSEIISYWGFPSEEYLVETEDGYI

        61                                                         120
rhLAL   LCLNRIPHGRKNHSDKGPKPVVFLQHGLLADSSNWVTNLANSSLGFILADAGFDVWMGNS
Natural LCLNRIPHGRKNHSDKGPKPVVFLQHGLLADSSNWVTNLANSSLGFILADAGFDVWMGNS

        121                                                        180
rhLAL   RGNTWSRKHKTLSVSQDEFWAFSYDEMAKYDLPASINFILNKTGQEQVYYVGHSQGTTIG
Natural RGNTWSRKHKTLSVSQDEFWAFSYDEMAKYDLPASINFILNKTGQEQVYYVGHSQGTTIG

        181                                                        240
rhLAL   FIAFSQIPELAKRIKMFFALGPVASVAFCTSPMAKLGRLPDHLIKDLFGDKEFLPQSAFL
Natural FIAFSQIPELAKRIKMFFALGPVASVAFCTSPMAKLGRLPDHLIKDLFGDKEFLPQSAFL

        241                                                        300
rhLAL   KWLGTHVCTHVILKELCGNLCFLLCGFNERNLNMSRVDVYTTHSPAGTSVQNMLHWSQAV
Natural KWLGTHVCTHVILKELCGNLCFLLCGFNERNLNMSRVDVYTTHSPAGTSVQNMLHWSQAV

        301                                                        360
rhLAL   KFQKFQAFDWGSSAKNYFHYNQSYPPTYNVKDMLVPTAVWSGGHDWLADVYDVNILLTQI
Natural KFQKFQAFDWGSSAKNYFHYNQSYPPTYNVKDMLVPTAVWSGGHDWLADVYDVNILLTQI

        361                                   399
rhLAL   TNLVFHESIPEWEHLDFIWGLDAPWRLYNKIINLMRKYQ  (SEQ ID NO:1)
Natural TNLVFHESIPEWEHLDFIWGLDAPWRLYNKIINLMRKYQ  (SEQ ID NO:20)
```

FIG. 1

```
   1  ATGAAAATGC GGTTCTTGGG GTTGGTGGTC TGTTTGGTTC TCTGGACCCT
  51  GCATTCCGAG GGGTCCGGAG GGAAACTGAC AGCTGTGGAT CCTGAAACAA
 101  ACATGAATGT CAGTGAAATT ATCTCTTACT GGGGATTCCC TAGTGAGGAA
 151  TACCTAGTTG AGACAGAAGA TGGATATATT CTGTGCCTTA ACCGAATTCC
 201  TCATGGGAGG AAGAACCATT CTGACAAAGG TCCCAAACCA GTTGTCTTCC
 251  TGCAACATGG CTTGCTGGCA GATTCTAGTA ACTGGGTCAC AAACCTTGCC
 301  AACAGCAGCC TGGGCTTCAT TCTTGCTGAT GCTGGTTTTG ACGTGTGGAT
 351  GGGCAACAGC AGAGGAAATA CCTGGTCTCG GAAACATAAG ACACTCTCAG
 401  TTTCTCAGGA TGAATTCTGG GCTTTCAGTT ATGATGAGAT GGCAAAATAT
 451  GACCTACCAG CTTCCATTAA CTTCATTCTG AATAAGACTG GCCAAGAACA
 501  AGTGTATTAT GTGGGTCATT CTCAAGGCAC CACTATAGGT TTTATAGCAT
 551  TTTCACAGAT CCCTGAGCTG GCTAAAAGGA TTAAAATGTT TTTTGCCCTG
 601  GGTCCTGTGG CTTCCGTCGC CTTCTGTACT AGCCCTATGG CCAAACTGGG
 651  ACGACTGCCA GATCATCTCA TTAAGGACCT CTTTGGAGAC AAAGAATTTC
 701  TTCCCCAGAG TGCGTTTTTG AAGTGGCTGG GTACCCACGT TTGCACTCAT
 751  GTCATACTGA AGGAGCTCTG TGGAAATCTC TGTTTTCTTC TGTGTGGATT
 801  TAATGAGAGA AATTTAAATA TGTCTAGAGT GGATGTGTAT ACAACACATT
 851  CTCCTGCTGG AACTTCTGTG CAAAACATGT TACACTGGAG CCAGGCTGTT
 901  AAATTCCAAA AGTTTCAAGC CTTTGACTGG GGAAGCAGTG CCAAGAATTA
 951  TTTTCATTAC AACCAGAGTT ATCCTCCCAC ATACAATGTG AAGGACATGC
1001  TTGTGCCGAC TGCAGTCTGG AGCGGGGGTC ACGACTGGCT TGCAGATGTC
1051  TACGACGTCA ATATCTTACT GACTCAGATC ACCAACTTGG TGTTCCATGA
1101  GAGCATTCCG GAATGGGAGC ATCTTGACTT CATTTGGGGC CTGGATGCCC
```

(SEQ ID NO:5)

FIG. 2

Sequence of pALVIN-OVR1-I-SBC102-dSA (10882 bp)

| Feature | Location (bp) |
|---|---|
| SIN LTR | 521-693 (complement strand) |
| DHSIII enhancer | 1069-2720 |
| OV promoter | 2720-3851 |
| intron | 3899-5487 |
| hLAL CDS | 5505-6704 |
| OV 3'UTR | 6719-7392 |
| partial gag CDS | 7404-7657 (complement strand) |
| LTR | 7955-8300 (complement strand) |
| Ampicillin resistance gene | 9764-10621 (complement strand) |

```
   1 CTTTCCCCGT CAAGCTCTAA ATCGGGGGCT CCCTTTAGGG TTCCGATTTA GTGCTTTACG
  61 GCACCTCGAC CCCAAAAAAC TTGATTAGGG TGATGGTTCA CGTAGTGGGC CATCGCCCTG
 121 ATACACGGTT TTTCGCCCTT TGACGTTGGA GTCCACGTTC TTTAATAGTG GACTCTTGTT
 181 CCAAACTGGA ACAACACTCA ACCCTATCTC GGTCTATTCT TTTGATTTAT AAGGGATTTT
 241 GCCGATTTCG GCCTATTGGT TAAAAAATGA GCTGATTTAA CAAAAATTTA ACGCGAATTT
 301 TAACAAAATA TTAACGCTTA CAATTTCCAT TCGCCATTCA GGCTGCGCAA CTGTTGGGAA
 361 GGGCGATCGG TGCGGGCCTC TTCGCTATTA CGCCAGCTGG CGAAAGGGGG ATGTGCTGCA
 421 AGGCGATTAA GTTGGGTAAC GCCAGGGTTT TCCCAGTCAC GACGTTGTAA AACGACGGCC
 481 AGTGAGCGCG TATTCCCTAA CGATCACGTC GGGGTCACCA AATGAAGCCT TCTGCTTCAT
 541 GCATCTGCTC GTAGTCGTCA GGGAATCAAC GGTCCGGCCA TCAACCCAGG TGCACACCAA
 601 TGTGGTGAAT GGTCAAATGG CGTTTATTGT ATCGAGCTAG GCACTTAAAT ACAATATCTC
 661 TGCAATGCGG AATTCAGTGG TTCGTCCAAT CCGTCCCCCT CCCTATGCAA AAGCGAAACT
 721 ACTATATCCT GAGGGGACTC CTAACCGCGT ACAACCGAAG CCCCGCTTTT CGCCTAAACA
 781 TGCTATTGTC CCCTCAGTCA AGCCTTGCCC GTTACAACCC GATTCGCAAG CCTTGCCCTC
 841 CCCACATTAT CCGTAGCATT ATTTCCTAGC AGTCATCAGA GCTACAGAAG ATACTCTATG
 901 CTGTAGCCAA GTCTACAAGT TTACTATTCA GCGACCTCCT ATATTCCGCG TGCCAGCCGA
 961 TCAATTACCA ATCCAACCAG CTATCACACG GAATACAAGA ACTCGCCTAC GCTCTTCTTT
1021 CGGGCTGCTT ATAAGCCTCC TGTAATTTTT TTATATTCCT CGCTCGAGTC TCTTCAGAAT
1081 GGCACAGCAC CGCTGCAGAA AAATGCCAGG TGGACTATGA ACTCACATCC AAAGGAGCTT
1141 GACCTGATAC CTGATTTTCT TCAAACAGGG GAAACAACAC AATCCCACAA AACAGCTCAG
1201 AGAGAAACCA TCACTGATGG CTACAGCACC AAGGTATGCA ATGGCAATCC ATTCGACATT
1261 CATCTGTGAC CTGAGCAAAA TGATTTATCT CTCCATGAAT GGTTGCTTCT TTCCCTCATG
1321 AAAAGGCAAT TTCCACACTC ACAATATGCA ACAAAGACAA ACAGAGAACA ATTAATGTGC
1381 TCCTTCCTAA TGTTAAAATT GTAGTGGCAA AGAGGAGAAC AAAATCTCAA GTTCTGAGTA
1441 GGTTTTAGTG ATTGGATAAG AGGCTTTGAC CTGTGAGCTC ACCTGGACTT CATATCCTTT
1501 TGGATAAAAA GTGCTTTTAT AACTTTCAGG TCTCCGAGTC TTTATTCATG AGACTGTTGG
1561 TTTAGGGACA GACCCACAAT GAAATGCCTG GCATAGGAAA GGGCAGCAGA GCCTTAGCTG
1621 ACCTTTTCTT GGGACAAGCA TTGTCAAACA ATGTGTGACA AAACTATTTG TACTGCTTTG
1681 CACAGCTGTG CTGGGCAGGG CAATCCATTG CCACCTATCC CAGGTAACCT TCCAACTGCA
1741 AGAAGATTGT TGCTTACTCT CTCTAGACCC CCAAGTCAAA CCAACTATGC AGGTATGCTG
1801 ACAACACTAT GATGACAGCC TGTTCTGATC AAGATCTCAT TTGTTCATGG ACAATTTTTG
1861 TTGCTTGCAG CTGGTCTTCC ATTGGGAAAG AGTGTAGTAT ATCCTTCTCA TCTGACAGAA
1921 AAGCAGAAAT TCTCATGCTC CACACTTAAT CTACATTGTT TTAAACCACC GGCTACTTCT
1981 TGGAGAGGAA AAATGGCTTT TATAAGACTC ACAAAACAAA GCTCTGCAAC TCAAATGCAT
2041 ACAAAACTGT TCTGTAGGTC TGGAATCAGG ACACTATGTG GAAGTCAAAT AGAGCAGCTT
2101 TAAAAAGCCT TTGGGATCAT TCTCATCTTA TATTTGCAGC ACGATACTAT GACAGTGATA
2161 ACTGACATAA CTGCATCAAT TTCCTTGATA TTTTATTTGT CTTAAAGTAC AAGACATAGA
2221 GATGGACGTA AAGATGGACA TATGACTCAG GTCTGGACAG GTCCGTGGTC CATGTATGAT
2281 AAAAGAGATG AAGGGAAGGA GAATTGAGAC TGTCTAAGAA GGGCTTCAGG GACGTTCTGA
2341 AGGCAGATTT GACTGAATCA GATGTACTGT CCAAGTCTCA TATGTAGCAA TGGAAGGCTG
2401 ATATTGGAGA AATATAAAGA AATGGCTGTG AACTCAAAGT GACCCTGAAC AGAAAAGGGA
2461 TATGGAGTTA AAATAATGTC ACAGAACTGA GGTTTATATG ATATACCATG GGCTGCAGAG
2521 GGTCAGAGTG CTCCACCATG GGCCTCTCTT GGGCTGCAGG GAACTTCTGT TCTACACCTG
2581 GAACACCTCC TGCCCTCCTC CGCACTGACC TCAGTGTCAT CAGGGCTGTT TCTCTCACAT
2641 TTTCTCACTC ACCTCTCCCA ACTACCATTG TACAGCAGTT GTTCTTACAT ATTGCTCCTC
2701 CTGAGGTACA TCTAGCATCG TTAACTCCTC AGACTTGGCA AGGAGAATGT AGATTTCCAC
2761 AGTATATATG TTTTCACAAA AGGAAGGAGA GAAACAAAAG AAAATGGCAC TGACTAAACT
```

FIG. 4A

```
2821  TCAGCTAGTG GTATAGGAAA GTAATTCTGC TTAACAGAGA TTGCAGTGAT CTCTATGTAT
2881  GTCCTGAAGA ATTATGTTGT ACTTTTTTCC CCCATTTTTA AATCAAACAG TGCTTTACAG
2941  AGGTCAGAAT GGTTTCTTTA CTGTTTGTCA ATTCTATTAT TTCAATACAG AACAATAGCT
3001  TCTATAACTG AAATATATTT GCTATTGTAT ATTATGATTG TCCCTCGAAC CATGAACACT
3061  CCTCCAGCTG AATTTCACAA TTCCTCTGTC ATCTGCCAGG CCATTAAGTT ATTCATGGAA
3121  GATCTTTGAG GAACACTGCA AGTTCATATC ATAAACACAT TTGAAATTGA GTATTGTTTT
3181  GCATTGTATG GAGCTATGTT TTGCTGTATC CTCAGAATAA AAGTTTGTTA TAAAGCATTC
3241  ACACCCATAA AAAGATAGAT TTAAATATTC CAACTATAGG AAAGAAAGTG TGTCTGCTCT
3301  TCACTCTAGT CTCAGTTGGC TCCTTCACAT GCACGCTTCT TTATTTCTCC TATTTTGTCA
3361  AGAAAATAAT AGGTCAAGTC TTGTTCTCAT TTATGTCCTG TCTAGCGTGG CTCAGATGCA
3421  CATTGTACAT ACAAGAAGGA TCAAATGAAA CAGACTTCTG GTCTGTTACT ACAACCATAG
3481  TAATAAGCAC ACTAACTAAT AATTGCTAAT TATGTTTTCC ATCTCCAAGG TTCCCACATT
3541  TTTCTGTTTT CTTAAAGATC CCATTATCTG GTTGTAACTG AAGCTCAATG GAACATGAGC
3601  AATATTTCCC AGTCTTCTCT CCCATCCAAC AGTCCTGATG GATTAGCAGA ACAGGCAGAA
3661  AACACATTGT TACCCAGAAT TAAAAACTAA TATTTGCTCT CCATTCAATC CAAAATGGAC
3721  CTATTGAAAC TAAAATCTAA CCCAATCCCA TTAAATGATT TCTATGGTGT CAAAGGTCAA
3781  ACTTCTGAAG GGAACCTGTG GGTGGGTCAC AATTCAGACT ATATATTCCC CAGGGCTCAG
3841  CCAGTGTCTG TACATACAGC TAGAAAGCTG TATTGCCTTT ACCAGTCAAG CTCGAAAGGT
3901  AAGCAACTCT CTGGAATTAC CTTCTCTCTA TATTAGCTCT TACTTGCACC TAAACTTTAA
3961  AAAATTAACA ATTATTGTGC TATGTGTTGT ATCTTTAAGG GTGAAGTACC TGCGTGATAC
4021  CCCCTATAAA AACTTCTCAC CTGTGTATGC ATTCTGCACT ATTTTATTAT GTGTAAAAGC
4081  TTTGTGTTTG TTTTCAGGAG GCTTATTCTT TGTGCTTAAA ATATGTTTTT AATTTCAGAA
4141  CATCTTATCC TGTCGTTCAC TATCTGATAT GCTTTGCAGT TTGCTTGATT AACTTCTAGC
4201  CCTACAGAGT GCACAGAGAC CAAAATCATG GTGTTCAGTG AATTCTGGCG AGTTATTTTA
4261  ATGTGAAAAT TCTCTAGAAG TTTAATTCCT GCAAAGTGCA GCTGCTGATC ACTACACAAG
4321  ATAAAAATGT GGGGGGTGCA TAAACGTATA TTCTTACAAT AATAGATACA TGTGAACTTA
4381  TATACAGAAA AGAAAATGAG AAAAATGTGT GTGTGTATAC TCACACACGT GGTCAGTAAA
4441  AACTTTTGAG GGGTTTAATA CAGAAAATCC AATCCTGAGG CCCCAGCACT CAGTACGCAT
4501  ATAAAGGGCT GGGCTCTGAA GGACTTCTGA CTTTCACAGA TTATATAAAT CTCAGGAAAG
4561  CAACTAGATT CATGCTGGCT CCAAAAGCTG TGCTTTATAT AAGCACACTG GCTATACAAT
4621  AGTTGTACAG TTCAGCTCTT TATAATAGAA ACAGACAGAA CAAGTATAAA TCTTCTATTG
4681  GTCTATGTCA TGAACAAGAA TTCATTCAGT GGCTCTGTTT TATAGTAAAC ATTGCTATTT
4741  TATCATGTCT GCATTTCTCT TCTGTCTGAA TGTCACCACT AAAATTTAAC TCCACAGAAA
4801  GTTTATACTA CAGTACACAT GCATATCTTT GAGCAAAGCA AACCATACCT GAAAGTGCAA
4861  TAGAGCAGAA TATGAATTAC ATGCGTGTCT TTCTCCTAGA CTACATGACC CCATATAAAT
4921  TACATTCCTT ATCTATTCTG CCATCACCAA AACAAAGGTA AAAATACTTT TGAAGATCTA
4981  CTCATAGCAA GTAGTGTGCA ACAAACAGAT ATTTCTCTAC ATTTATTTTT AGGGAATAAA
5041  AATAAGAAAT AAAATAGTCA GCAAGCCTCT GCTTTCTCAT ATATCTGTCC AAACCTAAAG
5101  TTTACTGAAA TTTGCTCTTT GAACTTCCAG TTTTGCAAGC CTATCAGATT GTGTTTTAAT
5161  CAGAGGTACT GAAAAGTATC AATGAATTCT AGCTTTCACT GAACAAAAAT ATGTAGAGGC
5221  AACTGGCTTC TGGGACAGTT TGCTACCCAA AAGACAACTG AATGCAAATA CATAAATAGA
5281  TTTATGAATA TGGTTTTGAA CATGCACATG AGAGGTGGAT ATAGCAACAG ACACATTACC
5341  ACAGAATTAC TTTAAAACTA CTTGTTAACA TTTAATTGCC TAAAAACTGC TCGTAATTTA
5401  CTGTTGTAGC CTACCATAGA GTACCCTGCA TGGTACTATG TACAGCATTC CATCCTTACA
5461  TTTTCACTGT TCTGCTGTTT GCTCTAGACA ACTCAGAGTT CACCATGAAA ATCCGGTTCT
5521  TGGGGTTGGT GGTCTGTTTG GTTCTCTGGA CCCTGCATTC CGAGGGGTCC GGAGGGAAAC
5581  TGACAGCTGT GGATCCAGAA ACAAACATGA ATGTCAGTGA AATTATCTCT TACTGGGGAT
5641  TCCCTAGTGA GGAATACCTA GTTGAGACAG AAGATGGATA TATTCTGTGC CTTAACCGAA
5701  TTCCTCATGG GAGGAAGAAC CATTCTGACA AAGGTCCCAA ACCAGTTGTC TTCCTGCAAC
5761  ATGGCTTGCT GGCAGATTCT AGTAACTGGG TCACAAACCT TGCCAACAGC AGCCTGGGCT
5821  TCATTCTTGC TGATGCTGGT TTTGACGTGT GGATGGGCAA CAGCAGAGGA AATACCTGGT
5881  CTCGGAAACA TAAGACACTC TCAGTTTCTC AGGATGAATT CTGGGCTTTC AGTTATGATG
5941  AGATGGCAAA ATATGACCTA CCAGCTTCCA TTAACTTCAT TCTGAATAAG ACTGGCCAAG
6001  AACAAGTGTA TTATGTGGGT CATTCTCAAG GCACCACTAT AGGTTTTATA GCATTTTCAC
6061  AGATCCCTGA GCTGGCTAAA AGGATTAAAA TGTTTTTTGC CCTGGGTCCT GTGGCTTCCG
6121  TCGCCTTCTG TACTAGCCCT ATGGCCAAAC TGGGACGACT GCCAGATCAT CTCATTAAGG
6181  ACCTCTTTGG AGACAAAGAA TTTCTTCCCC AGAGTGCGTT TTTGAAGTGG CTGGGTACCC
6241  ACGTTTGCAC TCATGTCATA CTGAAGGAGC TCTGTGGAAA TCTCTGTTTT CTTCTGTGTG
6301  GATTTAATGA GAGAAATTTA AATATGTCTA GAGTGGATGT GTATACAACA CATTCTCCTG
6361  CTGGAACTTC TGTGCAAAAC ATGTTACACT GGAGCCAGGC TGTTAAATTC CAAAAGTTTC
6421  AAGCCTTTGA CTGGGGAAGC AGTGCCAAGA ATTATTTTCA TTACAACCAG AGTTATCCTC
```

FIG. 4B

| | | | | | | |
|---|---|---|---|---|---|---|
| 6481 | CCACATACAA | TGTGAAGGAC | ATGCTTGTGC | CGACTGCAGT | CTGGAGCGGG | GGTCACGACT |
| 6541 | GGCTTGCAGA | TGTCTACGAC | GTCAATATCT | TACTGACTCA | GATCACCAAC | TTGGTGTTCC |
| 6601 | ATGAGAGCAT | TCCGGAATGG | GAGCATCTTG | ACTTCATTTG | GGGCCTGGAT | GCCCCTTGGA |
| 6661 | GGCTTTATAA | CAAGATTATT | AATCTAATGA | GGAAATATCA | GTGATTCGAA | GCGGCCGCAA |
| 6721 | GAAGAAAGCT | GAAAAACTCT | GTCCCTTCCA | ACAAGACCCA | GAGCACTGTA | GTATCAGGGG |
| 6781 | TAAAATGAAA | AGTATGTTAT | CTGCTGCATC | CAGACTTCAT | AAAAGCTGGA | GCTTAATCTA |
| 6841 | GAAAAAAAAT | CAGAAAGAAA | TTACACTGTG | AGAACAGGTG | CAATTCACTT | TTCCTTTACA |
| 6901 | CAGAGTAATA | CTGGTAACTC | ATGGATGAAG | GCTTAAGGGA | ATGAAATTGG | ACTCACAGTA |
| 6961 | CTGAGTCATC | ACACTGAAAA | ATGCAACCTG | ATACATCAGC | AGAAGGTTTA | TGGGGGAAAA |
| 7021 | ATGCAGCCTT | CCAATTAAGC | CAGATATCTG | TATGACCAAG | CTGCTCCAGA | ATTAGTCACT |
| 7081 | CAAAATCTCT | CAGATTAAAT | TATCAACTGT | CACCAACCAT | TCCTATGCTG | ACAAGGCAAT |
| 7141 | TGCTTGTTCT | CTGTGTTCCT | GATACTACAA | GGCTCTTCCT | GACTTCCTAA | AGATGCATTA |
| 7201 | TAAAAATCTT | ATAATTCACA | TTTCTCCCTA | AACTTTGACT | CAATCATGGT | ATGTTGGCAA |
| 7261 | ATATGGTATA | TTACTATTCA | AATTGTTTTC | CTTGTACCCA | TATGTAATGG | GTCTTGTGAA |
| 7321 | TGTGCTCTTT | TGTTCCTTTA | ATCATAATAA | AAACATGTTT | AAGCAAACAC | TTTTCACTTG |
| 7381 | TAGTATTTGA | AGGTACCGGA | TCTCGAGCCG | CCTTCAATGC | CCCCAAAACC | AATCCCCAGG |
| 7441 | TTTTTAACTC | TCCCGATTTT | CCAAGTACCA | TAGCCCGCTG | AGAGAGCGCC | GCGGTAATGG |
| 7501 | GATCCCAGGA | CCCCGGGGAA | TATAAGTCTG | AGGGGGACGT | AAGCAACCCT | TCCTTTTGTA |
| 7561 | ACAGGGACAA | CATAGCCCCT | ATTTCCTTCT | TAGAAGGAGA | GGTTTTCCCG | CAATAGGTCT |
| 7621 | TACACGCGGA | CGAAATCACC | TTTATGACGG | CTTCCATGCT | TGATCCACCG | GGCGACCGGA |
| 7681 | ATCACGCAGA | GCAACCGGAA | TCACGCCTGG | GGTGGACCGC | TCAGTCGTCG | GGCTTCCTTC |
| 7741 | CCGTCTTCCA | ACGACTCTCT | GAGTTCTCGG | TAGGGTATGT | TGGCCCCCTG | CAGTAGGCCT |
| 7801 | CCCTCCGACG | CCACTCAGCT | TCTGCCCTCC | TAAGCCGCAG | CCCCCTCTAC | TAGGGTCATC |
| 7861 | GTCCGCTCCC | CGAATAAGCC | AGACGGATGA | GGACAGGATC | GCCACGCCGC | CTGTGGCCGA |
| 7921 | CCACTATTCC | CTAACGATCA | CGTCGGGGTC | ACCAAATGAA | GCCTTCTGCT | TCATGCATGT |
| 7981 | GCTCGTAGTC | GTCAGGGAAT | CAACGGTCCG | GCCATCAACC | CAGGTGCACA | CCAATGTGGT |
| 8041 | GAATGGTCAA | ATGGCGTTTA | TTGTATCCAG | CTAGGCACTT | AAATACAATA | TCTCTGCAAT |
| 8101 | GCGGAATTCA | GTGGTTCGTC | CAATCCGTGT | TAGACCCGTC | TGTTGCCTTC | CTAACAAGGC |
| 8161 | ACGATCATAC | CACGATCATA | CCACCTTACT | CCCACCAATC | GGCATGCACG | GTGCTTTTTC |
| 8221 | TCTCCTTATA | AGGCATGTTG | CTAACTCATC | GTTACATAAG | CATGTTGCAA | GACTACAAGA |
| 8281 | GTATTGCATA | AGACTACATT | TCCCCCTCCC | TATGCAAAAG | CGAAACTACT | ATATCCTGAG |
| 8341 | GGGACTCCTA | ACCGCGTACA | ACCGAAGCCC | CGCTTTTCGC | CTAAACATGC | TATTGTCCCC |
| 8401 | TCAGTCAAGC | CTTGCCCGTT | ACAACCCGAT | TCGCAAGCCT | TGCCCTCCCC | ACATTATCCG |
| 8461 | TAGCATTATT | TCCTACCAGT | CATCAGAGCT | ACAGAAGATA | CTCTATGCTG | TAGCCAAGTC |
| 8521 | TACAAGTTTA | CTATTCAGCG | ACCTCCTATA | TTCCGCGTGC | CAGCCGATCA | ATTACCAATG |
| 8581 | CGCGCTTGGC | GTAATCATGG | TCATAGCTGT | TTCCTGTGTG | AAATTGTTAT | CCGCTCACAA |
| 8641 | TTCCACACAA | CATACGAGCC | GGAAGCATAA | AGTGTAAAGC | CTGGGGTGCC | TAATGAGTGA |
| 8701 | GCTAACTCAC | ATTAATTGCG | TTGCGCTCAC | TGCCCGCTTT | CCAGTCGGGA | AACCTGTCGT |
| 8761 | GCCAGCTGCA | TTAATGAATC | GGCCAACGCG | CGGGGAGAGG | CGGTTTGCGT | ATTGGGCGCT |
| 8821 | CTTCCGCTTC | CTCGCTCACT | GACTCGCTGC | GCTCGGTCGT | TCGGCTGCGG | CGAGCGGTAT |
| 8881 | CAGCTCACTC | AAAGGCGGTA | ATACGGTTAT | CCACAGAATC | AGGGGATAAC | GCAGGAAAGA |
| 8941 | ACATGTGAGC | AAAAGGCCAG | CAAAAGGCCA | GGAACCGTAA | AAAGGCCGCG | TTGCTGGCGT |
| 9001 | TTTTCCATAG | GCTCCGCCCC | CCTGACGAGC | ATCACAAAAA | TCGACGCTCA | AGTCAGAGGT |
| 9061 | GGCGAAACCC | GACAGGACTA | TAAAGATACC | AGGCGTTTCC | CCCTGGAAGC | TCCCTCGTGC |
| 9121 | GCTCTCCTGT | TCCGACCCTG | CCGCTTACCG | GATACCTGTC | CGCCTTTCTC | CCTTCGGGAA |
| 9181 | GCGTGGCGCT | TTCTCATAGC | TCACGCTGTA | GGTATCTCAG | TTCGGTGTAG | GTCGTTCGCT |
| 9241 | CCAAGCTGGG | CTGTGTGCAC | GAACCCCCCG | TTCAGCCCGA | CCGCTGCGCC | TTATCCGGTA |
| 9301 | ACTATCGTCT | TGAGTCCAAC | CCGGTAAGAC | ACGACTTATC | GCCACTGGCA | GCAGCCACTG |
| 9361 | GTAACAGGAT | TAGCAGAGCG | AGGTATGTAG | GCGGTGCTAC | AGAGTTCTTG | AAGTGGTGGC |
| 9421 | CTAACTACGG | CTACACTAGA | AGGACAGTAT | TTGGTATCTG | CGCTCTGCTG | AAGCCAGTTA |
| 9481 | CCTTCGGAAA | AAGAGTTGGT | AGCTCTTGAT | CCGGCAAACA | AACCACCGCT | GGTAGCGGTG |
| 9541 | GTTTTTTTGT | TTGCAAGCAG | CAGATTACGC | GCAGAAAAAA | AGGATCTCAA | GAAGATCCTT |
| 9601 | TGATCTTTTC | TACGGGGTCT | GACGCTCAGT | GGAACGAAAA | CTCACGTTAA | GGGATTTTGG |
| 9661 | TCATGAGATT | ATCAAAAAGG | ATCTTCACCT | AGATCCTTTT | AAATTAAAAA | TGAAGTTTTA |
| 9721 | AATCAATCTA | AAGTATATAT | GAGTAAACTT | GGTCTGACAG | TTACCAATGC | TTAATCAGTG |
| 9781 | AGGCACCTAT | CTCAGCGATC | TGTCTATTTC | GTTCATCCAT | AGTTGCCTGA | CTCCCCGTCG |
| 9841 | TGTAGATAAC | TACGATACGG | GAGGGCTTAC | CATCTGGCCC | CAGTGCTGCA | ATGATACCGC |
| 9901 | GAGACCCACG | CTCACCGGCT | CCAGATTTAT | CAGCAATAAA | CCAGCCAGCC | GGAAGGGCCG |
| 9961 | AGCGCAGAAG | TGGTCCTGCA | ACTTTATCCG | CCTCCATCCA | GTCTATTAAT | TGTTGCCGGG |
| 10021 | AAGCTAGAGT | AAGTAGTTCG | CCAGTTAATA | GTTTGCGCAA | CGTTGTTGCC | ATTGCTACAG |
| 10081 | GCATCGTGGT | GTCACGCTCG | TCGTTTGGTA | TGGCTTCATT | CAGCTCCGGT | TCCCAACGAT |

FIG. 4C

```
10141   CAAGGCGAGT TACATGATCC CCCATGTTGT GCAAAAAAGC GGTTAGCTCC TTCGGTCCTC
10201   CGATCGTTGT CAGAAGTAAG TTGGCCGCAG TGTTATCACT CATGGTTATG GCAGCACTGC
10261   ATAATTCTCT TACTGTCATG CCATCCGTAA GATGCTTTTC TGTGACTGGT GAGTACTCAA
10321   CCAAGTCATT CTGAGAATAG TGTATGCGGC GACCGAGTTG CTCTTGCCCG GCGTCAATAC
10381   GGGATAATAC CGCGCCACAT AGCAGAACTT TAAAAGTGCT CATCATTGGA AAACGTTCTT
10441   CGGGGCGAAA ACTCTCAAGG ATCTTACCGC TGTTGAGATC CAGTTCGATG TAACCCACTC
10501   GTGCACCCAA CTGATCTTCA GCATCTTTTA CTTTCACCAG CGTTTCTGGG TGAGCAAAAA
10561   CAGGAAGGCA AAATGCCGCA AAAAAGGGAA TAAGGGCGAC ACGGAAATGT TGAATACTCA
10621   TACTCTTCCT TTTTCAATAT TATTGAAGCA TTTATCAGGG TTATTGTCTC ATGAGCGGAT
10681   ACATATTTGA ATGTATTTAG AAAAATAAAC AAATAGGGGT TCCGCGCACA TTTCCCCGAA
10741   AAGTGCCACC TGACGCGCCC TGTAGCGGCG CATTAAGCGC GGCGGGTGTG GTGGTTACGC
10801   GCAGCGTGAC CGCTACACTT GCCAGCGCCC TAGCGCCCGC TCCTTTCGCT TTCTTCCCTT
10861   CCTTTCTCGC CACGTTCGCC GG
```

(SEQ ID NO: 6)

FIG. 4D

DNA sequence of the proviral region (7780 bp)

| Feature | Location (bp) |
|---|---|
| SIN LTR | 1-173 (complement strand) |
| DHSIII enhancer | 549-2200 |
| OV promoter | 2200-3331 |
| Intron | 3379-4967 |
| hLAL CDS | 4985-6184 |
| OV 3'UTR | 6199-6872 |
| partial gag CDS | 6884-7137 (complement strand) |
| LTR | 7435-7780 (complement strand) |

```
   1 AATGAAGCCT TCTGCTTCAT GCATGTGCTC GTAGTCGTCA GGGAATCAAC GGTCCGGCCA
  61 TCAACCCAGG TGCACACCAA TGTGGTGAAT GGTCAAATGG CGTTTATTGT ATCGAGCTAG
 121 GCACTTAAAT ACAATATCTC TGCAATGCGG AATTCAGTGG TTCGTCCAAT CCGTCCCCCT
 181 CCCTATGCAA AAGCGAAACT ACTATATCCT GAGGGGACTC CTAACCGCGT ACAACCGAAG
 241 CCCCGCTTTT CGCCTAAACA TGCTATTGTC CCCTCAGTCA AGCCTTGCCC GTTACAACCC
 301 GATTCGCAAG CCTTGCCCTC CCCACATTAT CCGTAGCATT ATTTCCTAGC AGTCATCAGA
 361 GCTACAGAAG ATACTCTATG CTGTAGCCAA GTCTACAAGT TTACTATTCA GCGACCTCCT
 421 ATATTCCCCG TGCCAGCCGA TCAATTACCA ATCCAACCAG CTATCACACG GAATACAAGA
 481 ACTCGCCTAC GCTCTTCTTT CGGGCTGCTT ATAAGCCTCC TGTAATTTTT TTATATTCCT
 541 CGCTCGAGTC TCTTCAGAAT GGCACAGCAC CGCTGCAGAA AAATGCCAGG TGGACTATGA
 601 ACTCACATCC AAAGGAGCTT GACCTGATAC CTGATTTTCT TCAAACAGGG GAAACAACAC
 661 AATCCCACAA AACAGCTCAG AGAGAAACCA TCACTGATGG CTACAGCACC AAGGTATGCA
 721 ATGGCAATCC ATTCGACATT CATCTGTGAC CTGAGCAAAA TGATTTATCT CTCCATGAAT
 781 GGTTGCTTCT TTCCCTCATG AAAAGGCAAT TTCCACACTC ACAATATGCA ACAAAGACAA
 841 ACAGAGAACA ATTAATGTGC TCCTTCCTAA TGTTAAAATT GTAGTGGCAA AGAGCAGAAC
 901 AAAATCTCAA GTTCTGAGTA GGTTTTAGTG ATTGGATAAG AGGCTTTGAC CTGTGAGCTC
 961 ACCTGGACTT CATATCCTTT TGGATAAAAA GTGCTTTTAT AACTTTCAGG TCTCCGAGTC
1021 TTTATTCATG AGACTGTTGG TTTAGGGACA GACCCACAAT GAAATGCCTG GCATAGGAAA
1081 GGGCAGCAGA GCCTTAGCTG ACCTTTTCTT GGGACAAGCA TTGTCAAACA ATGTGTGACA
1141 AAACTATTTG TACTGCTTTG CACAGCTGTG CTGGGCAGGG CAATCCATTG CCACCTATCC
1201 CAGGTAACCT TCCAACTGCA AGAAGATTGT TGCTTACTCT CTCTAGACCC CCAAGTCAAA
1261 CCAACTATGC AGGTATGCTG ACAACACTAT GATGACAGCC TGTTCTCATC AAGATCTCAT
1321 TTGTTCATGG ACAATTTTTG TTGCTTGCAG CTGGTCTTCC ATTGGGAAAG AGTGTAGTAT
1381 ATCCTTCTCA TCTGACAGAA AAGCAGAAAT TCTCATGCTC CACACTTAAT CTACATTGTT
1441 TTAAACCACC GGCTACTTCT TGGAGAGGAA AAATGGCTTT TATAAGACTC ACAAAACAAA
1501 GCTCTGCAAG TCAAATGCAT ACAAAACTGT TCTGTAGGTC TGGAATCAGG ACACTATGTG
1561 GAAGTCAAAT AGAGCAGCTT TAAAAAGCCT TTGGGATCAT TCTCATCTTA TATTTGCAGC
1621 ACGATACTAT GACAGTGATA ACTGACATAA CTGCATCAAT TTCCTTGATA TTTTATTTGT
1681 CTTAAAGTAC AAGACATAGA GATGGACGTA AAGATGGACA TATGACTCAG GTCTGGACAG
1741 GTCCGTGGTC CATGTATGAT AAAAGAGATG AAGGGAAGGA GAATTGAGAC TGTCTAAGAA
1801 GGGCTTCAGG GACGTTCTGA AGGCAGATTT GACTGAATCA GATGTACTGT CCAAGTCTCA
1861 TATGTAGCAA TGGAAGGCTG ATATTGGAGA AATATAAAGA AATGGCTGTG AACTCAAAGT
1921 GACCCTGAAC AGAAAAGGGA TATGGAGTTA AAATAATGTC ACAGAACTGA GGTTTATATG
1981 ATATACCATG GGCTGCAGAG GGTCAGAGTG CTCCACCATG GGCCTCTCTT GGGCTGCAGG
2041 GAACTTCTGT TCTACACCTG GAACACCTCC TGCCCTCCTC CGCACTGACC TCAGTG[illegible]CAT
2101 CAGGGCTGTT TCTCTCACAT TTTCTCACTC ACCTCTCCCA ACTACCATTG TACAGCAGTT
2161 GTTCTTACAT ATTGCTCCTC CTGACGTACA TCTAGCATCG TTAAGTCCTC AGACTTGGCA
2221 AGCAGAATGT AGATTTCCAC AGTATATATG TTTTCACAAA AGGAAGGAGA GAAACAAAAG
2281 AAAATGGCAC TGACTAAACT TCAGCTAGTG GTATAGGAAA GTAATTCTGC TTAACAGAGA
2341 TTGCAGTGAT CTCTATGTAT GTCCTGAAGA ATTATGTTGT ACTTTTTTCC CCCATTTTTA
2401 AATCAAACAG TGCTTTACAG AGGTCAGAAT GGTTTCTTTA CTGTTTGTCA ATTCTATTAT
2461 TTCAATACAG AACAATAGCT TCTATAACTG AAATATATTT GCTATTGTAT ATTATGATTG
2521 TCCCTCGAAC CATGAACACT CCTCCAGCTG AATTTCACAA TTCCTCTGTC ATCTGCCAGG
2581 CCATTAAGTT ATTCATGGAA GATCTTTGAG GAACACTGCA AGTTCATATC ATAAACACAT
2641 TTGAAATTGA GTATTGTTTT GCATTGTATG GAGCTATGTT TTGCTGTATC CTCAGAATAA
2701 AAGTTTGTTA TAAAGCATTC ACACCCATAA AAAGATAGAT TTAAATATTC CAACTATAGG
2761 AAACAAAGTG TGTCTGCTCT TCACTCTAGT CTCAGTTGGC TCCTTCACAT GCACCCTTCT
2821 TTATTTCTCC TATTTTGTCA AGAAAATAAT AGGTCAAGTC TTGTTCTCAT TTATGTCCTG
```

FIG. 5A

| | | | | | | |
|---|---|---|---|---|---|---|
| 2881 | TCTAGCGTGG | CTCAGATGCA | CATTGTACAT | ACAAGAAGGA | TCAAATGAAA | CAGACTTCTG |
| 2941 | GTCTGTTACT | ACAACCATAG | TAATAAGCAC | ACTAACTAAT | AATTGCTAAT | TATGTTTTCC |
| 3001 | ATCTCCAAGG | TTCCCACATT | TTTCTGTTTT | CTTAAAGATC | CCATTATCTG | GTTGTAACTG |
| 3061 | AAGCTCAATG | GAACATGAGC | AATATTTCCC | AGTCTTCTCT | CCCATCCAAC | AGTCCTGATG |
| 3121 | GATTAGCAGA | ACAGGCAGAA | AACACATTGT | TACCCAGAAT | TAAAAACTAA | TATTTGCTCT |
| 3181 | CCATTCAATC | CAAAATGGAC | CTATTGAAAC | TAAAATCTAA | CCCAATCCCA | TTAAATGATT |
| 3241 | TCTATGGTGT | CAAAGGTCAA | ACTTCTGAAG | GGAACCTGTG | GGTGGGTCAC | AATTCAGACT |
| 3301 | ATATATTCCC | CAGGGCTCAG | CCAGTGTCTG | TACATACAGC | TAGAAAGCTG | TATTGCCTTT |
| 3361 | AGCAGTCAAG | CTCGAAAGGT | AAGCAACTCT | CTGGAATTAC | CTTCTCTCTA | TATTAGCTCT |
| 3421 | TACTTGCACC | TAAACTTTAA | AAAATTAACA | ATTATTGTCC | TATGTGTTGT | ATCTTTAAGG |
| 3481 | GTGAAGTACC | TGCGTGATAC | CCCCTATAAA | AACTTCTCAC | CTGTGTATGC | ATTCTGCACT |
| 3541 | ATTTTATTAT | GTGTAAAAGC | TTTGTGTTTG | TTTTCAGGAG | GCTTATTCTT | TGTGCTTAAA |
| 3601 | ATATGTTTTT | AATTTCAGAA | CATCTTATCC | TGTCGTTCAC | TATCTGATAT | GCTTTGCAGT |
| 3661 | TTGCTTGATT | AACTTCTAGC | CCTACAGAGT | GCACAGAGAG | CAAAATCATG | GTGTTCAGTG |
| 3721 | AATTCTGGGG | AGTTATTTTA | ATGTGAAAAT | TCTCTAGAAG | TTTAATTCCT | GCAAAGTGCA |
| 3781 | GCTGCTGATC | ACTACACAAG | ATAAAAATGT | GGGGGGTGCA | TAAACGTATA | TTCTTACAAT |
| 3841 | AATAGATACA | TGTGAACTTA | TATACAGAAA | AGAAAATGAG | AAAAATGTGT | GTGTGTATAC |
| 3901 | TCACACACGT | GGTCAGTAAA | AACTTTTGAG | GGGTTTAATA | CAGAAAATCC | AATCCTGAGG |
| 3961 | CCCCAGCACT | CAGTACGCAT | ATAAAGGGCT | GGGCTCTGAA | GGACTTCTGA | CTTTCACAGA |
| 4021 | TTATATAAAT | CTCAGGAAAG | CAACTAGATT | CATGCTGGCT | CCAAAAGCTG | TGCTTTATAT |
| 4081 | AAGCACACTG | GCTATACAAT | AGTTGTACAG | TTCAGCTCTT | TATAATAGAA | ACAGACACAA |
| 4141 | CAAGTATAAA | TCTTCTATTG | GTCTATGTCA | TGAACAAGAA | TTCATTCAGT | GGCTCTGTTT |
| 4201 | TATAGTAAAC | ATTGCTATTT | TATCATGTCT | GCATTTCTCT | TCTGTCTGAA | TGTCACCACT |
| 4261 | AAAATTTAAC | TCCACAGAAA | GTTTATACTA | CAGTACACAT | GCATATCTTT | GAGCAAAGCA |
| 4321 | AACCATACCT | GAAAGTGCAA | TAGAGCAGAA | TATGAATTAC | ATGCGTGTCT | TTCTCCTAGA |
| 4381 | CTACATGACC | CCATATAAAT | TACATTCCTT | ATCTATTCTG | CCATCACCAA | AACAAAGGTA |
| 4441 | AAAATACTTT | TGAAGATCTA | CTCATAGCAA | GTAGTGTGCA | ACAAACAGAT | ATTTCTCTAC |
| 4501 | ATTTATTTTT | AGGGAATAAA | AATAAGAAAT | AAAATAGTCA | GCAAGCCTCT | GCTTTCTCAT |
| 4561 | ATATCTGTCC | AAACCTAAAG | TTTACTGAAA | TTTGCTCTTT | GAATTTCCAG | TTTTGCAAGC |
| 4621 | CTATCAGATT | GTGTTTTAAT | CAGAGGTACT | GAAAAGTATC | AATGAATTCT | AGCTTTCACT |
| 4681 | GAACAAAAAT | ATGTAGAGGC | AACTGGCTTC | TGGGACAGTT | TCCTACCCAA | AAGACAACTG |
| 4741 | AATGCAAATA | CATAAATAGA | TTTATGAATA | TGGTTTTGAA | CATGCACATG | AGAGGTGGAT |
| 4801 | ATAGCAACAG | ACACATTACC | ACAGAATTAC | TTTAAAACTA | CTTGTTAACA | TTTAATTGCC |
| 4861 | TAAAAACTGC | TCGTAATTTA | CTGTTGTAGC | CTACCATAGA | GTACCCTGCA | TGGTACTATG |
| 4921 | TACAGCATTC | CATCCTTACA | TTTTCACTGT | TCTGCTGTTT | GCTCTAGACA | ACTCAGAGTT |
| 4981 | CACCATGAAA | ATGCGGTTCT | TGGGGTTGGT | GGTCTGTTTG | GTTCTCTGGA | CCCTGCATTC |
| 5041 | CGAGGGGTCC | GGAGGGAAAC | TGACAGCTGT | GGATCCAGAA | ACAAACATGA | ATGTCAGTGA |
| 5101 | AATTATCTCT | TACTGGGGAT | TCCCTAGTGA | GGAATACCTA | GTTGAGACAG | AAGATGGATA |
| 5161 | TATTCTGTGC | CTTAACCGAA | TTCCTCATGG | GAGGAAGAAC | CATTCTGACA | AAGGTCCCAA |
| 5221 | ACCAGTTGTC | TTCCTGCAAC | ATGGCTTGCT | GGCAGATTCT | AGTAACTGGG | TCACAAACCT |
| 5281 | TGCCAACAGC | AGCCTGGGCT | TCATTCTTGC | TGATGCTGGT | TTTGACGTGT | GGATGGGCAA |
| 5341 | CAGCAGAGGA | AATACCTGGT | CTCGGAAACA | TAAGACACTC | TCAGTTTCTC | AGGATGAATT |
| 5401 | CTGGGCTTTC | AGTTATGATG | AGATGGCAAA | ATATGACCTA | CCAGCTTCCA | TTAACTTCAT |
| 5461 | TCTGAATAAG | ACTGGCCAAG | AACAAGTGTA | TTATGTGGGT | CATTCTCAAG | GCACCACTAT |
| 5521 | AGGTTTTATA | GCATTTTCAC | AGATCCCTGA | GCTGGCTAAA | AGGATTAAAA | TGTTTTTTGC |
| 5581 | CCTGGGTCCT | GTGGCTTCCG | TCGCCTTCTG | TACTAGCCCT | ATGGCCAAAC | TGGGACGACT |
| 5641 | GCCAGATCAT | CTCATTAAGG | ACCTCTTTGG | AGACAAAGAA | TTTCTTCCCC | ACAGTGCGTT |
| 5701 | TTTGAAGTGG | CTGGGTACCC | ACGTTTGCAC | TCATGTCATA | CTGAAGGAGC | TCTGTGGAAA |
| 5761 | TCTCTGTTTT | CTTCTGTGTG | GATTTAATGA | GAGAAATTTA | AATATGTCTA | GAGTGGATGT |
| 5821 | GTATACAACA | CATTCTCCTG | CTGGAACTTC | TGTGCAAAAC | ATGTTACACT | GGAGCCAGGC |
| 5881 | TGTTAAATTC | CAAAAGTTTC | AAGCCTTTGA | CTGGGGAAGC | AGTGCCAAGA | ATTATTTTCA |
| 5941 | TTACAACCAG | AGTTATCCTC | CCACATACAA | TGTGAAGGAC | ATGCTTGTGC | CGACTGCAGT |
| 6001 | CTGGAGCGGG | GGTCACGACT | GGCTTGCAGA | TGTCTACGAC | GTCAATATCT | TACTGACTCA |
| 6061 | GATCACCAAC | TTGGTGTTCC | ATGAGAGCAT | TCCGGAATGG | GAGCATCTTG | ACTTCATTTG |
| 6121 | GGGCCTGGAT | GCCCCTTGGA | GGCTTTATAA | TAAGATTATT | AATCTAATGA | GGAAATATCA |
| 6181 | GTGATTCGAA | GCCGCCGCAA | GAAGAAAGCT | GAAAAACTCT | GTCCCTTCCA | ACAAGACCCA |
| 6241 | GAGCACTGTA | GTATCAGGGG | TAAAATGAAA | AGTATGTTAT | CTGCTGCATC | CAGACTTCAT |
| 6301 | AAAAGCTGGA | GCTTAATCTA | GAAAAAAAAT | CAGAAAGAAA | TTACACTGTG | AGAACAGGTG |
| 6361 | CAATTCACTT | TTCCTTTACA | CAGAGTAATA | CTGGTAACTC | ATGGATGAAG | GCTTAAGGGA |
| 6421 | ATGAAATTGG | ACTCACAGTA | CTGAGTCATC | ACACTGAAAA | ATGCAACCTG | ATACATCAGC |
| 6481 | AGAAGGTTTA | TGGGGGAAAA | ATGCAGCCTT | CCAATTAAGC | CAGATATCTG | TATGACCAAG |

FIG. 5B

```
6541 CTGCTCCAGA ATTAGTCACT CAAAATCTCT CAGATTAAAT TATCAACTGT CACCAACCAT
6601 TCCTATGCTG ACAAGGCAAT TCCTTGTTCT CTGTGTTCCT GATACTACAA GGCTCTTCCT
6661 GACTTCCTAA AGATGCATTA TAAAAATCTT ATAATTCACA TTTCTCCCTA AACTTTGACT
6721 CAATCATGGT ATGTTGGCAA ATATGGTATA TTACTATTCA AATTGTTTTC CTTGTACCCA
6781 TATGTAATGG GTCTTGTGAA TGTGCTCTTT TGTTCCTTTA ATCATAATAA AAACATGTTT
6841 AAGCAAACAC TTTTCACTTG TAGTATTTGA AGGTACCGGA TCTCGAGCCG CCTTCAATGC
6901 CCCCAAAACC AATCCCCAGG TTTTTAACTC TCCCGATTTT CCAAGTACCA TAGCCCGCTG
6961 AGAGAGCGCC GCGGTAATGG GATCCCAGGA CCCCGGGGAA TATAAGTCTG AGGGGGACGT
7021 AAGCAACCCT TCCTTTTGTA ACAGGGACAA CATAGCCCCT ATTTCCTTCT TAGAAGGAGA
7081 GGTTTTCCCG CAATAGGTCT TACACGCGGA CGAAATCACC TTTATGACGG CTTCCATGCT
7141 TGATCCACCG GGCGACCGGA ATCACGCAGA GCAACCGGAA TCACGCCTGG GGTGGACCGC
7201 TCAGTCGTCG GGCTTCCTTC CCGTCTTCCA ACGACTCTCT GAGTTCTCGG TAGGGTATGT
7261 TGGCCCCCTG CAGTACCGCT CCCTCCGACG CCACTCAGCT TCTGCCCTCC TAAGCCCCAG
7321 CCCCCTCTAC TAGGGTCATC GTCCGCTCCC CGAATAAGCG AGACGGATGA GGACAGGATC
7381 GCCACGCCGC CTGTGGCCGA CCACTATTCC CTAACGATCA CGTCGGGGTC ACCAAATGAA
7441 GCCTTCTGCT TCATGCATGT GCTCGTAGTC GTCAGGGAAT CAACGGTCCG GCCATCAACC
7501 CAGGTGCACA CCAATGTGGT GAATGGTCAA ATGGCGTTTA TTGTATCGAG CTAGGCACTT
7561 AAATACAATA TCTCTGCAAT GCGGAATTCA GTGGTTCGTC CAATCCGTGT TAGACCCGTC
7621 TGTTGCCTTC CTAACAAGGC ACGATCATAC CACGATCATA CCACCTTACT CCCACCAATC
7681 GGCATGCACG GTGCTTTTTC TCTCCTTATA AGGCATGTTG CTAACTCATC GTTACATAAG
7741 CATGTTGCAA GACTACAAGA GTATTGCATA AGACTACATT
```

(SEQ ID NO:7)

FIG. 5C

DNA Sequence of pALVIN-OV-1.1-I (10762 bp)

| Feature | Location (bp) |
|---|---|
| Stuffer | 1-2734 |
| OV 3'UTR | 2750-3423 |
| partial gag CDS | 3435-3688 (complement strand) |
| LTR | 3986-4331 (complement strand) |
| Ampicillin resistance gene | 5795-6652 (complement strand) |
| SIN LTR | 7434-7606 (complement strand) |
| OV promoter | 7975-9106 |
| Intron | 9154-10742 |
| ATG of ovalbumin or POI | 10760-10762 |

```
   1 nnnnnnnnnn nnnnnnnnnn nnnnnnnnnn nnnnnnnnnn nnnnnnnnnn nnnnnnnnnn
  61 nnnnnnnnnn nnnnnnnnnn nnnnnnnnnn nnnnnnnnnn nnnnnnnnnn nnnnnnnnnn
 121 nnnnnnnnnn nnnnnnnnnn nnnnnnnnnn nnnnnnnnnn nnnnnnnnnn nnnnnnnnnn
 181 nnnnnnnnnn nnnnnnnnnn nnnnnnnnnn nnnnnnnnnn nnnnnnnnnn nnnnnnnnnn
 241 nnnnnnnnnn nnnnnnnnnn nnnnnnnnnn nnnnnnnnnn nnnnnnnnnn nnnnnnnnnn
 301 nnnnnnnnnn nnnnnnnnnn nnnnnnnnnn nnnnnnnnnn nnnnnnnnnn nnnnnnnnnn
 361 nnnnnnnnnn nnnnnnnnnn nnnnnnnnnn nnnnnnnnnn nnnnnnnnnn nnnnnnnnnn
 421 nnnnnnnnnn nnnnnnnnnn nnnnnnnnnn nnnnnnnnnn nnnnnnnnnn nnnnnnnnnn
 481 nnnnnnnnnn nnnnnnnnnn nnnnnnnnnn nnnnnnnnnn nnnnnnnnnn nnnnnnnnnn
 541 nnnnnnnnnn nnnnnnnnnn nnnnnnnnnn nnnnnnnnnn nnnnnnnnnn nnnnnnnnnn
 601 nnnnnnnnnn nnnnnnnnnn nnnnnnnnnn nnnnnnnnnn nnnnnnnnnn nnnnnnnnnn
 661 nnnnnnnnnn nnnnnnnnnn nnnnnnnnnn nnnnnnnnnn nnnnnnnnnn nnnnnnnnnn
 721 nnnnnnnnnn nnnnnnnnnn nnnnnnnnnn nnnnnnnnnn nnnnnnnnnn nnnnnnnnnn
 781 nnnnnnnnnn nnnnnnnnnn nnnnnnnnnn nnnnnnnnnn nnnnnnnnnn nnnnnnnnnn
 841 nnnnnnnnnn nnnnnnnnnn nnnnnnnnnn nnnnnnnnnn nnnnnnnnnn nnnnnnnnnn
 901 nnnnnnnnnn nnnnnnnnnn nnnnnnnnnn nnnnnnnnnn nnnnnnnnnn nnnnnnnnnn
 961 nnnnnnnnnn nnnnnnnnnn nnnnnnnnnn nnnnnnnnnn nnnnnnnnnn nnnnnnnnnn
1021 nnnnnnnnnn nnnnnnnnnn nnnnnnnnnn nnnnnnnnnn nnnnnnnnnn nnnnnnnnnn
1081 nnnnnnnnnn nnnnnnnnnn nnnnnnnnnn nnnnnnnnnn nnnnnnnnnn nnnnnnnnnn
1141 nnnnnnnnnn nnnnnnnnnn nnnnnnnnnn nnnnnnnnnn nnnnnnnnnn nnnnnnnnnn
1201 nnnnnnnnnn nnnnnnnnnn nnnnnnnnnn nnnnnnnnnn nnnnnnnnnn nnnnnnnnnn
1261 nnnnnnnnnn nnnnnnnnnn nnnnnnnnnn nnnnnnnnnn nnnnnnnnnn nnnnnnnnnn
1321 nnnnnnnnnn nnnnnnnnnn nnnnnnnnnn nnnnnnnnnn nnnnnnnnnn nnnnnnnnnn
1381 nnnnnnnnnn nnnnnnnnnn nnnnnnnnnn nnnnnnnnnn nnnnnnnnnn nnnnnnnnnn
1441 nnnnnnnnnn nnnnnnnnnn nnnnnnnnnn nnnnnnnnnn nnnnnnnnnn nnnnnnnnnn
1501 nnnnnnnnnn nnnnnnnnnn nnnnnnnnnn nnnnnnnnnn nnnnnnnnnn nnnnnnnnnn
1561 nnnnnnnnnn nnnnnnnnnn nnnnnnnnnn nnnnnnnnnn nnnnnnnnnn nnnnnnnnnn
1621 nnnnnnnnnn nnnnnnnnnn nnnnnnnnnn nnnnnnnnnn nnnnnnnnnn nnnnnnnnnn
1681 nnnnnnnnnn nnnnnnnnnn nnnnnnnnnn nnnnnnnnnn nnnnnnnnnn nnnnnnnnnn
1741 nnnnnnnnnn nnnnnnnnnn nnnnnnnnnn nnnnnnnnnn nnnnnnnnnn nnnnnnnnnn
1801 nnnnnnnnnn nnnnnnnnnn nnnnnnnnnn nnnnnnnnnn nnnnnnnnnn nnnnnnnnnn
1861 nnnnnnnnnn nnnnnnnnnn nnnnnnnnnn nnnnnnnnnn nnnnnnnnnn nnnnnnnnnn
1921 nnnnnnnnnn nnnnnnnnnn nnnnnnnnnn nnnnnnnnnn nnnnnnnnnn nnnnnnnnnn
1981 nnnnnnnnnn nnnnnnnnnn nnnnnnnnnn nnnnnnnnnn nnnnnnnnnn nnnnnnnnnn
2041 nnnnnnnnnn nnnnnnnnnn nnnnnnnnnn nnnnnnnnnn nnnnnnnnnn nnnnnnnnnn
2101 nnnnnnnnnn nnnnnnnnnn nnnnnnnnnn nnnnnnnnnn nnnnnnnnnn nnnnnnnnnn
2161 nnnnnnnnnn nnnnnnnnnn nnnnnnnnnn nnnnnnnnnn nnnnnnnnnn nnnnnnnnnn
2221 nnnnnnnnnn nnnnnnnnnn nnnnnnnnnn nnnnnnnnnn nnnnnnnnnn nnnnnnnnnn
2281 nnnnnnnnnn nnnnnnnnnn nnnnnnnnnn nnnnnnnnnn nnnnnnnnnn nnnnnnnnnn
2341 nnnnnnnnnn nnnnnnnnnn nnnnnnnnnn nnnnnnnnnn nnnnnnnnnn nnnnnnnnnn
2401 nnnnnnnnnn nnnnnnnnnn nnnnnnnnnn nnnnnnnnnn nnnnnnnnnn nnnnnnnnnn
2461 nnnnnnnnnn nnnnnnnnnn nnnnnnnnnn nnnnnnnnnn nnnnnnnnnn nnnnnnnnnn
2521 nnnnnnnnnn nnnnnnnnnn nnnnnnnnnn nnnnnnnnnn nnnnnnnnnn nnnnnnnnnn
2581 nnnnnnnnnn nnnnnnnnnn nnnnnnnnnn nnnnnnnnnn nnnnnnnnnn nnnnnnnnnn
2641 nnnnnnnnnn nnnnnnnnnn nnnnnnnnnn nnnnnnnnnn nnnnnnnnnn nnnnnnnnnn
2701 nnnnnnnnnn nnnnnnnnnn nnnnnnnnnn nnnnnTTCGA AGCGGCCGCA AGAAGAAAGC
2761 TGAAAAACTC TGTCCCTTCC AACAAGACCC AGAGCACTGT AGTATCAGGG GTAAAATGAA
```

FIG. 6A

```
2821 AAGTATGTTA TCTGCTGCAT CCAGACTTCA TAAAAGCTGG AGCTTAATCT AGAAAAAAAA
2881 TCAGAAAGAA ATTACACTGT GAGAACAGGT GCAATTCACT TTTCCTTTAC ACAGAGTAAT
2941 ACTGGTAACT CATGGATGAA GGCTTAAGGG AATGAAATTG GACTCACAGT ACTGAGTCAT
3001 CACACTGAAA AATGCAACCT GATACATCAG CAGAAGGTTT ATGGGGGAAA AATGCAGCCT
3061 TCCAATTAAG CCAGATATCT GTATGACCAA GCTGCTCCAG AATTAGTCAC TCAAAATCTC
3121 TCAGATTAAA TTATCAACTG TCACCAACCA TTCCTATGCT GACAAGGCAA TTGCTTGTTC
3181 TCTGTGTTCC TGATACTACA AGGCTCTTCC TGACTTCCTA AAGATGCATT ATAAAAATCT
3241 TATAATTCAC ATTTCTCCCT AAACTTTGAC TCAATCATGG TATGTTGGCA AATATGGTAT
3301 ATTACTATTC AAATTGTTTT CCTTGTACCC ATATGTAATG GGTCTTGTGA ATGTGCTCTT
3361 TTGTTCCTTT AATCATAATA AAAACATGTT TAAGCAAACA CTTTTCACTT GTAGTATTTG
3421 AAGGTACCGG ATCTCGAGCC GCCTTCAATG CCCCCAAAAC CAATCCCCAG GTTTTTAACT
3481 CTCCCGATTT TCCAAGTACC ATAGCCCGCT GAGAGAGCGC CGCGGTAATG GGATCCCAGG
3541 ACCCCGGGGA ATATAAGTCT GAGGGGGACG TAAGCAACCC TTCCTTTTGT AACACGGACA
3601 ACATAGCCCC TATTTCCTTC TTAGAAGGAG AGGTTTTCCC GCAATAGGTC TTACACGCCG
3661 ACGAAATCAC CTTTATGACG GCTTCCATGC TTGATCCACC GGCCGACCGC AATCACGCAG
3721 AGCAACCGGA ATCACGCCTG GGGTGGACCG CTCAGTCGTC GGGCTTCCTT CCCGTCTTCC
3781 AACGACTCTC TGAGTTCTCG GTAGGGTATG TTGGCCCCCT GCAGTAGGGC TCCCTCCGAC
3841 GCCACTCAGC TTCTGCCCTC CTAACCCGCA GCCCCCTCTA CTAGGGTCAT CGTCCGCTCC
3901 CCGAATAAGC CAGACGGATG AGGACAGGAT CGCCACGCCG CCTGTGGCCG ACCACTATTC
3961 CCTAACGATC ACGTCGGGGT CACCAAATGA AGCCTTCTGC TTCATGCATG TGCTCGTAGT
4021 CGTCAGGGAA TCAACGGTCC GGCCATCAAC CCAGGTGCAC ACCAATGTGG TGAATGGTCA
4081 AATGGCGTTT ATTGTATCGA GCTAGGCACT TAAATACAAT ATCTCTGCAA TGCGGAATTC
4141 AGTGGTTCGT CCAATCCGTG TTAGACCCGT CTGTTGCCTT CCTAACAAGG CACGATCATA
4201 CCACGATCAT ACCACCTTAC TCCCACCAAT CGGCATGCAC GGTGCTTTTT CTCTCCTTAT
4261 AAGGCATGTT GCTAACTCAT CGTTACATAA GCATGTTGCA AGACTACAAG AGTATTGCAT
4321 AAGACTACAT TTCCCCCTCC CTATGCAAAA GCGAAACTAC TATATCCTGA GGGGACTCCT
4381 AACCGCGTAC AACCGAAGCC CCGCTTTTCG CCTAAACATG CTATTGTCCC CTCAGTCAAG
4441 CCTTGCCCCT TACAACCCGA TTCGCAAGCC TTGCCCTCCC CACATTATCC GTAGCATTAT
4501 TTCCTAGCAG TCATCAGAGC TACAGAAGAT ACTCTATGCT GTAGCCAAGT CTACAAGTTT
4561 ACTATTCAGC GACCTCCTAT ATTCCGCGTG CCAGCCGATC AATTACCAAT CCGCGCTTGG
4621 CGTAATCATG GTCATAGCTG TTTCCTGTGT GAAATTGTTA TCCGCTCACA ATTCCACACA
4681 ACATACGAGC CGGAAGCATA AAGTGTAAAG CCTGGGGTGC CTAATGAGTG AGCTAACTCA
4741 CATTAATTGC GTTGCGCTCA CTGCCCGCTT TCCAGTCGGG AAACCTGTCG TGCCAGCTGC
4801 ATTAATGAAT CGGCCAACGC GCGGGGAGAG GCGGTTTGCG TATTGGGCGC TCTTCCGCTT
4861 CCTCGCTCAC TGACTCGCTG CGCTCGGTCG TTCGGCTGCG GCGAGCGGTA TCAGCTCACT
4921 CAAAGGCGGT AATACGGTTA TCCACAGAAT CAGGGGATAA CGCAGGAAAG AACATGTGAG
4981 CAAAAGGCCA GCAAAAGGCC AGGAACCGTA AAAAGGCCGC GTTGCTGGCG TTTTTCCATA
5041 GGCTCCGCCC CCCTGACGAG CATCACAAAA ATCGACGCTC AAGTCAGAGG TGGCGAAACC
5101 CGACAGGACT ATAAAGATAC CAGGCGTTTC CCCCTGGAAG CTCCCTCGTG CGCTCTCCTG
5161 TTCCGACCCT GCCGCTTACC GGATACCTGT CCGCCTTTCT CCCTTCGGGA AGCGTGGCGC
5221 TTTCTCATAG CTCACGCTGT AGGTATCTCA GTTCGGTGTA GGTCGTTCGC TCCAAGCTGG
5281 GCTGTGTGCA CGAACCCCCC GTTCAGCCCG ACCGCTGCGC CTTATCCGGT AACTATCGTC
5341 TTGAGTCCAA CCCGGTAAGA CACGACTTAT CGCCACTGGC AGCAGCCACT GGTAACAGGA
5401 TTAGCAGAGC GAGGTATGTA GGCGGTGCTA CAGAGTTCTT GAAGTGGTGG CCTAACTACG
5461 GCTACACTAG AAGGACAGTA TTTGGTATCT GCGCTCTGCT GAAGCCAGTT ACCTTCGGAA
5521 AAAGAGTTGG TAGCTCTTGA TCCGGCAAAC AAACCACCGC TGGTAGCGGT GGTTTTTTTG
5581 TTTGCAAGCA GCAGATTACG CGCAGAAAAA AAGGATCTCA AGAAGATCCT TTGATCTTTT
5641 CTACGGGGTC TGACGCTCAG TGGAACGAAA ACTCACGTTA AGGGATTTTG GTCATGAGAT
5701 TATCAAAAAG GATCTTCACC TAGATCCTTT TAAATTAAAA ATGAAGTTTT AAATCAATCT
5761 AAAGTATATA TGAGTAAACT TGGTCTGACA GTTACCAATG CTTAATCAGT GAGGCACCTA
5821 TCTCAGCGAT CTGTCTATTT CGTTCATCCA TAGTTGCCTG ACTCCCCGTC GTGTAGATAA
5881 CTACGATACG GGAGGGCTTA CCATCTGGCC CCAGTGCTGC AATGATACCG CGAGACCCAC
5941 GCTCACCGGC TCCAGATTTA TCAGCAATAA ACCAGCCAGC CGGAAGGGCC GAGCGCAGAA
6001 GTGGTCCTGC AACTTTATCC GCCTCCATCC AGTCTATTAA TTGTTGCCGG GAAGCTAGAG
6061 TAAGTAGTTC GCCAGTTAAT AGTTTGCGCA ACGTTGTTGC CATTGCTACA GGCATCGTGG
6121 TGTCACGCTC GTCGTTTGGT ATGGCTTCAT TCAGCTCCGG TTCCCAACGA TCAAGGCGAG
6181 TTACATGATC CCCCATGTTG TGCAAAAAAG CGGTTAGCTC CTTCGGTCCT CCGATCGTTG
6241 TCAGAAGTAA GTTGGCCGCA GTGTTATCAC TCATGGTTAT GGCAGCACTG CATAATTCTC
6301 TTACTGTCAT GCCATCCGTA AGATGCTTTT CTGTGACTGG TGAGTACTCA ACCAAGTCAT
6361 TCTGAGAATA GTGTATGCGG CGACCGAGTT GCTCTTGCCC GGCGTCAATA CGGGATAATA
6421 CCGCGCCACA TAGCAGAACT TTAAAAGTGC TCATCATTGG AAAACGTTCT TCGGGGCGAA
```

FIG. 6B

```
6481   AACTCTCAAG GATCTTACCG CTGTTGAGAT CCAGTTCGAT GTAACCCACT CGTGCACCCA
6541   ACTGATCTTC AGCATCTTTT ACTTTCACCA GCGTTTCTGG GTGAGCAAAA ACAGGAAGGC
6601   AAAATGCCGC AAAAAAGGGA ATAAGGGCGA CACGGAAATG TTGAATACTC ATACTCTTCC
6661   TTTTTCAATA TTATTGAAGC ATTTATCAGG GTTATTGTCT CATGAGCGGA TACATATTTG
6721   AATGTATTTA GAAAAATAAA CAAATAGGGG TTCCGCGCAC ATTTCCCCGA AAAGTGCCAC
6781   CTGACGCGCC CTGTAGCGGC GCATTAAGCG CGGCGGGTGT GGTGGTTACG CGCAGCGTGA
6841   CCGCTACACT TGCCAGCGCC CTAGCGCCCG CTCCTTTCGC TTTCTTCCCT TCCTTTCTCG
6901   CCACGTTCGC CGGCTTTCCC CGTCAAGCTC TAAATCGGGG GCTCCCTTTA GGGTTCCGAT
6961   TTAGTGCTTT ACGGCACCTC GACCCCAAAA AACTTGATTA GGGTGATGGT TCACGTAGTG
7021   GGCCATCGCC CTGATAGACG GTTTTTCGCC CTTTGACGTT GGAGTCCACG TTCTTTAATA
7081   GTGGACTCTT GTTCCAAACT GGAACAACAC TCAACCCTAT CTCGGTCTAT TCTTTTGATT
7141   TATAAGGGAT TTTGCCGATT TCGGCCTATT GGTTAAAAAA TGAGCTGATT TAACAAAAAT
7201   TTAACGCGAA TTTTAACAAA ATATTAACGC TTACAATTTC CATTCGCCAT TCAGGCTGCG
7261   CAACTGTTGG GAAGGGCGAT CGGTGCGGGC CTCTTCGCTA TTACGCCAGC TGGCGAAAGG
7321   GGGATGTGCT GCAAGGCGAT TAAGTTGGGT AACGCCAGGG TTTTCCCAGT CACGACGTTG
7381   TAAAACGACG GCCAGTGAGC GCGTATTCCC TAACGATCAC GTCGGGGTCA CCAAATGAAG
7441   CCTTCTGCTT CATGCATGTG CTCGTAGTCG TCAGGGAATC AACGGTCCGG CCATCAACCC
7501   AGGTGCACAC CAATGTGGTG AATGGTCAAA TGGCGTTTAT TGTATCGAGC TAGGCACTTA
7561   AATACAATAT CTCTGCAATG CGGAATTCAG TGGTTCGTCC AATCCGTCCC CCTCCCTATG
7621   CAAAAGCGAA ACTACTATAT CCTGAGGGGA CTCCTAACCG CGTACAACCG AAGCCCCGCT
7681   TTTCGCCTAA ACATGCTATT GTCCCCTCAG TCAAGCCTTG CCCGTTACAA CCCGATTCGC
7741   AAGCCTTGCC CTCCCCACAT TATCCGTAGC ATTATTTCCT AGCAGTCATC AGAGCTACAG
7801   AAGATACTCT ATGCTGTAGC CAAGTCTACA AGTTTACTAT TCAGCGACCT CCTATATTCC
7861   GCGTGCCAGC CGATCAATTA CCAATCCAAC CAGCTATCAC ACGGAATACA AGAACTCGCC
7921   TACGCTCTTC TTTCGGGCTG CTTATAAGCC TCCTGTAATT TTTTTATATT CCTCGTTAAG
7981   TCCTCAGACT TGGCAAGGAG AATGTAGATT TCCACAGTAT ATATGTTTTC ACAAAAGGAA
8041   GGAGAGAAAC AAAAGAAAAT GGCACTGACT AAACTTCAGC TAGTGGTATA GGAAAGTAAT
8101   TCTGCTTAAC AGAGATTGCA GTGATCTCTA TGTATGTCCT GAAGAATTAT GTTGTACTTT
8161   TTTCCCCCAT TTTTAAATCA AACAGTGCTT TACAGAGGTC AGAATGGTTT CTTTACTGTT
8221   TGTCAATTCT ATTATTTCAA TACAGAACAA TACCTTCTAT AACTGAAATA TATTTGCTAT
8281   TGTATATTAT GATTGTCCCT CGAACCATGA ACACTCCTCC AGCTGAATTT CACAATTCCT
8341   CTGTCATCTG CCAGGCCATT AAGTTATTCA TGGAAGATCT TTGAGGAACA CTGCAAGTTC
8401   ATATCATAAA CACATTTGAA ATTGAGTATT GTTTTGCATT GTATGGAGCT ATGTTTTGCT
8461   GTATCCTCAG AATAAAACTT TGTTATAAAG CATTCACACC CATAAAAAGA TAGATTTAAA
8521   TATTCCAACT ATAGGAAAGA AAGTGTGTCT GCTCTTCACT CTAGTCTCAG TTGGCTCCTT
8581   CACATGCACG CTTCTTTATT TCTCCTATTT TGTCAAGAAA ATAATAGGTC AAGTCTTGTT
8641   CTCATTTATG TCCTGTCTAG CGTGGCTCAG ATGCACATTG TACATACAAG AAGGATCAAA
8701   TGAAACAGAC TTCTGGTCTG TTACTACAAC CATAGTAATA AGCACACTAA CTAATAATTG
8761   CTAATTATGT TTTCCATCTC CAAGGTTCCC ACATTTTTCT GTTTTCTTAA AGATCCCATT
8821   ATCTGGTTGT AACTGAAGCT CAATGGAACA TGAGCAATAT TTCCCAGTCT TCTCTCCCAT
8881   CCAACAGTCC TGATGGATTA GCAGAACAGG CAGAAAACAC ATTGTTACCC AGAATTAAAA
8941   ACTAATATTT GCTCTCCATT CAATCCAAAA TGGACCTATT GAAACTAAAA TCTAACCCAA
9001   TCCCATTAAA TGATTTCTAT GGTGTCAAAG GTCAAACTTC TGAAGGGAAC CTGTGGGTGG
9061   GTCACAATTC AGACTATATA TTCCCCAGGG CTCAGCCAGT GTCTGTACAT ACAGCTAGAA
9121   AGCTGTATTG CCTTTAGCAG TCAAGCTCGA AAGGTAAGCA ACTCTCTGGA ATTACCTTCT
9181   CTCTATATTA GCTCTTACTT GCACCTAAAC TTTAAAAAAT TAACAATTAT TGTGCTATGT
9241   GTTGTATCTT TAAGGGTGAA GTACCTGCGT GATACCCCCT ATAAAAACTT CTCACCTGTG
9301   TATGCATTCT GCACTATTTT ATTATGTGTA AAAGCTTTGT GTTTGTTTTC AGGAGGCTTA
9361   TTCTTTGTGC TTAAAATATG TTTTTAATTT CAGAACATCT TATCCTGTCG TTCACTATCT
9421   GATATGCTTT GCAGTTTGCT TGATTAACTT CTAGCCCTAC AGAGTGCACA CAGAGCAAAA
9481   TCATGGTGTT CAGTGAATTC TGGGGAGTTA TTTTAATGTG AAAATTCTCT AGAAGTTTAA
9541   TTCCTGCAAA GTGCAGCTGC TGATCACTAC ACAAGATAAA AATGTGGGGG GTGCATAAAC
9601   GTATATTCTT ACAATAATAG ATACATGTGA ACTTATATAC AGAAAAGAAA ATGAGAAAAA
9661   TGTGTGTGTG TATACTCACA CACGTGGTCA GTAAAAACTT TTGAGGGGTT TAATACAGAA
9721   AATCCAATCC TGAGGCCCCA GCACTCAGTA CGCATATAAA GCCCTGGGCT CTGAAGGACT
9781   TCTGACTTTC ACAGATTATA TAAATCTCAG GAAAGCAACT AGATTCATGC TGGCTCCAAA
9841   AGCTGTGCTT TATATAAGCA CACTGGCTAT ACAATAGTTC TACAGTTCAG CTCTTTATAA
9901   TAGAAACAGA CAGAACAAGT ATAAATCTTC TATTGGTCTA TGTCATGAAC AAGAATTCAT
9961   TCAGTGGCTC TGTTTTATAG TAAACATTGC TATTTTATCA TGTCTGCATT TCTCTTCTGT
10021  CTGAATGTCA CCACTAAAAT TTAACTCCAC AGAAAGTTTA TACTACAGTA CACATGCATA
10081  TCTTTGAGCA AAGCAAACCA TACCTGAAAG TGCAATAGAG CAGAATATGA ATTACATGCC
```

FIG. 6C

```
10141   TGTCTTTCTC CTAGACTACA TGACCCCATA TAAATTACAT TCCTTATCTA TTCTGCCATC
10201   ACCAAAACAA AGGTAAAAAT ACTTTTGAAG ATCTACTCAT ACCAAGTAGT GTGCAACAAA
10261   CAGATATTTC TCTACATTTA TTTTTAGGGA ATAAAAATAA GAAATAAAAT AGTCAGCAAG
10321   CCTCTGCTTT CTCATATATC TGTCCAAACC TAAAGTTTAC TGAAATTTGC TCTTTGAATT
10381   TCCAGTTTTG CAAGCCTATC AGATTGTGTT TTAATCAGAG GTACTGAAAA GTATCAATGA
10441   ATTCTAGCTT TCACTGAACA AAAATATGTA GAGGCAACTG GCTTCTGGGA CAGTTTGCTA
10501   CCCAAAAGAC AACTGAATGC AAATACATAA ATAGATTTAT GAATATGGTT TTGAACATGC
10561   ACATGAGAGG TGGATATAGC AACAGACACA TTACCACAGA ATTACTTTAA AACTACTTGT
10621   TAACATTTAA TTGCCTAAAA ACTGCTCGTA ATTTACTGTT GTAGCCTACC ATAGAGTACC
10681   CTGCATGGTA CTATGTACAG CATTCCATCC TTACATTTTC ACTGTTCTGC TGTTTGCTCT
10741   AGACAACTCA GAGTTCACCA TG
```

(SEQ ID NO:8)

FIG. 6D

DNA sequence of SBC102 adaptor (242 bp)

| Feature | Location (bp) |
|---|---|
| From OV gene | 1-149 |
| Partial hLAL CDS | 150-242 |

```
  1  CCCGGGTTGT TAACATTTAA TTGCCTAAAA ACTGCTCGTA ATTTACTGTT GTAGCCTACC
 61  ATAGAGTACC CTGCATGGTA CTATGTACAG CATTCCATCC TTACATTTTC ACTGTTCTGC
121  TGTTTGCTCT AGACAACTCA GAGTTCACCA TGAAAATGCG GTTCTTGGGG TTGGTGGTCT
181  GTTTGGTTCT CTGGACCCTG CATTCCGAGG GGTCCGGAGG GAAACTGACA GCTGTGGATC
241  CT
```

(SEQ ID NO:9)

FIG. 7

DNA sequence of Syn SBC102 (1575 bp)

| Feature | Location (bp) |
|---|---|
| Partial OV promoter | 1-355 |
| hLAL CDS | 356-1575 |

```
   1  CCATTATCTG GTTGTAACTG AAGCTCAATG GAACATGAGC AATATTTCCC AGTCTTCTCT
  61  CCCATCCAAC AGTCCTGATG GATTAGCAGA ACAGGCAGAA AACACATTGT TACCCAGAAT
 121  TAAAAACTAA TATTTGCTCT CCATTCAATC CAAAATGGAC CTATTGAAAC TAAAATCTAA
 181  CCCAATCCCA TTAAATGATT TCTATGGTGT CAAAGGTCAA ACTTCTGAAG GGAACCTGTG
 241  GGTGGGTCAC AATTCAGACT ATATATTCCC CAGGGCTCAG CCAGTGTCTG TACATACAGC
 301  TAGAAAGCTG TATTGCCTTT AGCAGTCAAG CTCGAAAGAC AACTCAGAGT TCACCATGAA
 361  AATGCGGTTC TTGGGGTTGG TGGTCTGTTT GGTTCTCTGG ACCCTGCATT CCGAGGGGTC
 421  CGGAGGGAAA CTGACAGCTG TGGATCCTGA AACAAACATG AATGTCAGTG AAATTATCTC
 481  TTACTGGGGA TTCCCTAGTG AGGAATACCT AGTTGAGACA GAAGATGGAT ATATTCTGTG
 541  CCTTAACCGA ATTCCTCATG GGAGGAAGAA CCATTCTGAC AAAGGTCCCA AACCAGTTGT
 601  CTTCCTGCAA CATGGCTTGC TGGCAGATTC TAGTAACTGG GTCACAAACC TTGCCAACAG
 661  CAGCCTGGGC TTCATTCTTG CTGATGCTGG TTTTGACGTG TGGATGGGCA ACAGCAGAGG
 721  AAATACCTGG TCTCGGAAAC ATAAGACACT CTCAGTTTCT CAGGATGAAT TCTGGGCTTT
 781  CAGTTATGAT GAGATGGCAA AATATGACCT ACCAGCTTCC ATTAACTTCA TTCTGAATAA
 841  GACTGGCCAA GAACAAGTGT ATTATGTGGG TCATTCTCAA GGCACCACTA TAGGTTTTAT
 901  AGCATTTTCA CAGATCCCTG AGCTGGCTAA AAGGATTAAA ATGTTTTTTG CCCTGGGTCC
 961  TGTGGCTTCC GTCGCCTTCT GTACTAGCCC TATGGCCAAA CTGGGACGAC TGCCAGATCA
1021  TCTCATTAAG GACCTCTTTG GAGACAAAGA ATTTCTTCCC CAGAGTGCGT TTTTGAAGTG
1081  GCTGGGTACC CACGTTTGCA CTCATGTCAT ACTGAAGGAG CTCTGTGGAA ATCTCTGTTT
1141  TCTTCTGTGT GGATTTAATG AGAGAAATTT AAATATGTCT AGAGTGGATG TGTATACAAC
1201  ACATTCTCCT GCTGGAACTT CTGTGCAAAA CATGTTACAC TGGAGCCAGG CTGTTAAATT
1261  CCAAAAGTTT CAAGCCTTTG ACTGGGGAAG CAGTGCCAAG AATTATTTTC ATTACAACCA
1321  GAGTTATCCT CCCACATACA ATGTGAAGGA CATGCTTGTG CCGACTGCAG TCTGGAGCGG
1381  GGGTCACGAC TGGCTTGCAG ATGTCTACGA CGTCAATATC TTACTGACTC AGATCACCAA
1441  CTTGGTGTTC CATGAGAGCA TTCCGGAATG GGAGCATCTT GACTTCATTT GGGGCCTGGA
1501  TGCCCCTTGG AGGCTTTATA ATAAGATTAT TAATCTAATG AGGAAATATC AGTGATTCGA
1561  AGCGGCCGCC CCGGG
```

(SEQ ID NO:10)

FIG. 8

DNA sequence of OVR1 promoter (2789 bp)

| Feature | Location (bp) |
|---|---|
| From DHSIII region of OV gene | 7-1658 |
| OV promoter | 1658-2789 |

```
   1 CTCGAGTCTC TTCAGAATGG CACAGCACCG CTGCAGAAAA ATGCCAGGTG GACTATGAAC
  61 TCACATCCAA AGGAGCTTGA CCTGATACCT GATTTTCTTC AAACAGGGGA AACAACACAA
 121 TCCCACAAAA CAGCTCAGAG AGAAACCATC ACTGATGGCT ACAGCACCAA GGTATGCAAT
 181 GGCAATCCAT TCGACATTCA TCTGTGACCT GAGCAAAATG ATTTATCTCT CCATGAATGG
 241 TTGCTTCTTT CCCTCATGAA AAGGCAATTT CCACACTCAC AATATGCAAC AAAGACAAAC
 301 AGAGAACAAT TAATGTGCTC CTTCCTAATG TTAAAATTGT AGTGGCAAAG AGGAGAACAA
 361 AATCTCAAGT TCTGAGTAGG TTTTAGTGAT TGGATAAGAG GCTTTGACCT GTGAGCTCAC
 421 CTGGACTTCA TATCCTTTTG GATAAAAAGT GCTTTTATAA CTTTCAGGTC TCCGAGTCTT
 481 TATTCATGAG ACTGTTGGTT TAGGGACAGA CCCACAATGA AATGCCTGGC ATAGGAAAGG
 541 GCAGCAGAGC CTTAGCTGAC CTTTTCTTGG GACAAGCATT GTCAAACAAT GTGTGACAAA
 601 ACTATTTGTA CTGCTTTGCA CAGCTGTGCT GGGCAGGGCA ATCCATTGCC ACCTATCCCA
 661 GGTAACCTTC CAACTGCAAG AAGATTGTTG CTTACTCTCT CTAGACCCCC AAGTCAAACC
 721 AACTATGCAG GTATGCTGAC AACACTATGA TGACAGCCTG TTCTGATCAA GATCTCATTT
 781 GTTCATGGAC AATTTTTGTT GCTTGCAGCT GGTCTTCCAT TGGGAAAGAG TGTAGTATAT
 841 CCTTCTCATC TGACAGAAAA GCAGAAATTC TCATGCTCCA CACTTAATCT ACATTGTTTT
 901 AAACCACCGG CTACTTCTTG GAGAGGAAAA ATGGCTTTTA TAAGACTCAC AAAACAAAGC
 961 TCTGCAAGTC AAATGCATAC AAAACTGTTC TGTAGGTCTG GAATCAGGAC ACTATGTGGA
1021 AGTCAAATAG AGCAGCTTTA AAAAGCCTTT GGGATCATTC TCATCTTATA TTTGCAGCAC
1081 GATACTATGA CAGTGATAAC TGACATAACT GCATCAATTT CCTTGATATT TTATTTGTCT
1141 TAAAGTACAA GACATAGAGA TGGACGTAAA GATGGACATA TGACTCAGGT CTGGACAGGT
1201 CCGTGGTCCA TGTATGATAA AAGAGATGAA GGGAAGGAGA ATTGAGACTG TCTAAGAAGG
1261 GCTTCAGGGA CGTTCTGAAG GCAGATTTGA CTGAATCAGA TGTACTGTCC AAGTCTCATA
1321 TGTAGCAATG GAAGGCTGAT ATTGGAGAAA TATAAAGAAA TGGCTGTGAA CTCAAAGTGA
1381 CCCTGAACAG AAAAGGGATA TGGAGTTAAA ATAATGTCAC AGAACTGAGG TTTATATGAT
1441 ATACCATGGG CTGCAGAGGG TCAGAGTGCT CCACCATGGG CCTCTCTTGG GCTGCAGGGA
1501 ACTTCTGTTC TACACCTGGA ACACCTCCTG CCCTCCTCCG CACTGACCTC AGTGTCATCA
1561 GGGCTGTTTC TCTCACATTT TCTCACTCAC CTCTCCCAAC TACCATTGTA CAGCAGTTGT
1621 TCTTACATAT TGCTCCTCCT GAGGTACATC TAGCATCGTT AAGTCCTCAG ACTTGGCAAG
1681 GAGAATGTAG ATTTCCACAG TATATATGTT TTCACAAAAG GAAGGAGAGA AACAAAAGAA
1741 AATGGCACTG ACTAAACTTC AGCTAGTGGT ATAGGAAAGT AATTCTGCTT AACAGAGATT
1801 GCAGTGATCT CTATGTATGT CCTGAAGAAT TATGTTGTAC TTTTTTCCCC CATTTTTAAA
1861 TCAAACAGTG CTTTACAGAG GTCAGAATGG TTTCTTTACT GTTTGTCAAT TCTATTATTT
1921 CAATACAGAA CAATAGCTTC TATAACTGAA ATATATTTGC TATTGTATAT TATGATTGTC
1981 CCTCGAACCA TGAACACTCC TCCAGCTGAA TTTCACAATT CCTCTGTCAT CTGCCAGGCC
2041 ATTAAGTTAT TCATGGAAGA TCTTTGAGGA ACACTGCAAG TTCATATCAT AAACACATTT
2101 GAAATTGAGT ATTGTTTTGC ATTGTATGGA GCTATGTTTT GCTGTATCCT CAGAATAAAA
2161 GTTTGTTATA AAGCATTCAC ACCCATAAAA AGATAGATTT AAATATTCCA ACTATAGGAA
2221 AGAAAGTGTG TCTGCTCTTC ACTCTAGTCT CAGTTGGCTC CTTCACATGC ACGCTTCTTT
2281 ATTTCTCCTA TTTTGTCAAG AAAATAATAG GTCAAGTCTT GTTCTCATTT ATGTCCTGTC
2341 TAGCGTGGCT CAGATGCACA TTGTACATAC AAGAAGGATC AAATGAAACA GACTTCTGGT
2401 CTGTTACTAC AACCATAGTA ATAAGCACAC TAACTAATAA TTGCTAATTA TGTTTTCCAT
2461 CTCCAAGGTT CCCACATTTT TCTGTTTTCT TAAAGATCCC ATTATCTGGT TGTAACTGAA
2521 GCTCAATGGA ACATGAGCAA TATTTCCCAG TCTTCTCTCC CATCCAACAG TCCTGATGGA
2581 TTAGCAGAAC AGGCAGAAAA CACATTGTTA CCCAGAATTA AAAACTAATA TTTGCTCTCC
2641 ATTCAATCCA AAATGGACCT ATTGAAACTA AAATCTAACC CAATCCCATT AAATGATTTC
2701 TATGGTGTCA AAGGTCAAAC TTCTGAAGGG AACCTGTGGG TGGGTCACAA TTCAGACTAT
2761 ATATTCCCCA GGGCTCAGCC AGTGTCTGT
```

(SEQ ID NO: 11)

FIG. 9

Square = N-Acetyl Glucosamine

Filled Square =Mannose-6-Phosphate

Circle = Mannose

Filled Circle = Galactose

Filled Triangle = Fucose

| | liver | spleen | mesenteric LN | duodenum | jejunum | ileum |
|---|---|---|---|---|---|---|
| LAL -/- dosed with vehicle (N=3) | 11.85% | 0.84% | 0.59% | 1.11% | 3.80% | 3.01% |
| LAL -/- dosed with SBC-102 (N=3) | 5.57% | 0.32% | 0.35% | 0.48% | 2.00% | 1.46% |
| LAL +/+ controls (N=3) | 4.75% | 0.25% | 0.07% | 0.30% | 1.61% | 1.38% |

SEQUENCE LISTING

```
<160> NUMBER OF SEQ ID NOS: 20

<210> SEQ ID NO 1
<211> LENGTH: 399
<212> TYPE: PRT
<213> ORGANISM: HOMO SAPIENS

<400> SEQUENCE: 1

Met Lys Met Arg Phe Leu Gly Leu Val Val Cys Leu Val Leu Trp Thr
```

-continued

```
1               5                   10                  15

Leu His Ser Glu Gly Ser Gly Gly Lys Leu Thr Ala Val Asp Pro Glu
            20                  25                  30

Thr Asn Met Asn Val Ser Glu Ile Ile Ser Tyr Trp Gly Phe Pro Ser
        35                  40                  45

Glu Glu Tyr Leu Val Glu Thr Glu Asp Gly Tyr Ile Leu Cys Leu Asn
    50                  55                  60

Arg Ile Pro His Gly Arg Lys Asn His Ser Asp Lys Gly Pro Lys Pro
65                  70                  75                  80

Val Val Phe Leu Gln His Gly Leu Leu Ala Asp Ser Ser Asn Trp Val
                85                  90                  95

Thr Asn Leu Ala Asn Ser Ser Leu Gly Phe Ile Leu Ala Asp Ala Gly
            100                 105                 110

Phe Asp Val Trp Met Gly Asn Ser Arg Gly Asn Thr Trp Ser Arg Lys
        115                 120                 125

His Lys Thr Leu Ser Val Ser Gln Asp Glu Phe Trp Ala Phe Ser Tyr
    130                 135                 140

Asp Glu Met Ala Lys Tyr Asp Leu Pro Ala Ser Ile Asn Phe Ile Leu
145                 150                 155                 160

Asn Lys Thr Gly Gln Glu Gln Val Tyr Tyr Val Gly His Ser Gln Gly
                165                 170                 175

Thr Thr Ile Gly Phe Ile Ala Phe Ser Gln Ile Pro Glu Leu Ala Lys
            180                 185                 190

Arg Ile Lys Met Phe Phe Ala Leu Gly Pro Val Ala Ser Val Ala Phe
        195                 200                 205

Cys Thr Ser Pro Met Ala Lys Leu Gly Arg Leu Pro Asp His Leu Ile
    210                 215                 220

Lys Asp Leu Phe Gly Asp Lys Glu Phe Leu Pro Gln Ser Ala Phe Leu
225                 230                 235                 240

Lys Trp Leu Gly Thr His Val Cys Thr His Val Ile Leu Lys Glu Leu
                245                 250                 255

Cys Gly Asn Leu Cys Phe Leu Leu Cys Gly Phe Asn Glu Arg Asn Leu
            260                 265                 270

Asn Met Ser Arg Val Asp Val Tyr Thr Thr His Ser Pro Ala Gly Thr
        275                 280                 285

Ser Val Gln Asn Met Leu His Trp Ser Gln Ala Val Lys Phe Gln Lys
    290                 295                 300

Phe Gln Ala Phe Asp Trp Gly Ser Ser Ala Lys Asn Tyr Phe His Tyr
305                 310                 315                 320

Asn Gln Ser Tyr Pro Pro Thr Tyr Asn Val Lys Asp Met Leu Val Pro
                325                 330                 335

Thr Ala Val Trp Ser Gly Gly His Asp Trp Leu Ala Asp Val Tyr Asp
            340                 345                 350

Val Asn Ile Leu Leu Thr Gln Ile Thr Asn Leu Val Phe His Glu Ser
        355                 360                 365

Ile Pro Glu Trp Glu His Leu Asp Phe Ile Trp Gly Leu Asp Ala Pro
    370                 375                 380

Trp Arg Leu Tyr Asn Lys Ile Ile Asn Leu Met Arg Lys Tyr Gln
385                 390                 395
```

<210> SEQ ID NO 2
<211> LENGTH: 378
<212> TYPE: PRT
<213> ORGANISM: HOMO SAPIENS

<400> SEQUENCE: 2

```
Ser Gly Gly Lys Leu Thr Ala Val Asp Pro Glu Thr Asn Met Asn Val
1               5                   10                  15

Ser Glu Ile Ile Ser Tyr Trp Gly Phe Pro Ser Glu Glu Tyr Leu Val
            20                  25                  30

Glu Thr Glu Asp Gly Tyr Ile Leu Cys Leu Asn Arg Ile Pro His Gly
        35                  40                  45

Arg Lys Asn His Ser Asp Lys Gly Pro Lys Pro Val Val Phe Leu Gln
    50                  55                  60

His Gly Leu Leu Ala Asp Ser Ser Asn Trp Val Thr Asn Leu Ala Asn
65                  70                  75                  80

Ser Ser Leu Gly Phe Ile Leu Ala Asp Ala Gly Phe Asp Val Trp Met
                85                  90                  95

Gly Asn Ser Arg Gly Asn Thr Trp Ser Arg Lys His Lys Thr Leu Ser
            100                 105                 110

Val Ser Gln Asp Glu Phe Trp Ala Phe Ser Tyr Asp Glu Met Ala Lys
        115                 120                 125

Tyr Asp Leu Pro Ala Ser Ile Asn Phe Ile Leu Asn Lys Thr Gly Gln
    130                 135                 140

Glu Gln Val Tyr Tyr Val Gly His Ser Gln Gly Thr Thr Ile Gly Phe
145                 150                 155                 160

Ile Ala Phe Ser Gln Ile Pro Glu Leu Ala Lys Arg Ile Lys Met Phe
                165                 170                 175

Phe Ala Leu Gly Pro Val Ala Ser Val Ala Phe Cys Thr Ser Pro Met
            180                 185                 190

Ala Lys Leu Gly Arg Leu Pro Asp His Leu Ile Lys Asp Leu Phe Gly
        195                 200                 205

Asp Lys Glu Phe Leu Pro Gln Ser Ala Phe Leu Lys Trp Leu Gly Thr
    210                 215                 220

His Val Cys Thr His Val Ile Leu Lys Glu Leu Cys Gly Asn Leu Cys
225                 230                 235                 240

Phe Leu Leu Cys Gly Phe Asn Glu Arg Asn Leu Asn Met Ser Arg Val
                245                 250                 255

Asp Val Tyr Thr Thr His Ser Pro Ala Gly Thr Ser Val Gln Asn Met
            260                 265                 270

Leu His Trp Ser Gln Ala Val Lys Phe Gln Lys Phe Gln Ala Phe Asp
        275                 280                 285

Trp Gly Ser Ser Ala Lys Asn Tyr Phe His Tyr Asn Gln Ser Tyr Pro
    290                 295                 300

Pro Thr Tyr Asn Val Lys Asp Met Leu Val Pro Thr Ala Val Trp Ser
305                 310                 315                 320

Gly Gly His Asp Trp Leu Ala Asp Val Tyr Asp Val Asn Ile Leu Leu
                325                 330                 335

Thr Gln Ile Thr Asn Leu Val Phe His Glu Ser Ile Pro Glu Trp Glu
            340                 345                 350

His Leu Asp Phe Ile Trp Gly Leu Asp Ala Pro Trp Arg Leu Tyr Asn
        355                 360                 365

Lys Ile Ile Asn Leu Met Arg Lys Tyr Gln
    370                 375
```

<210> SEQ ID NO 3
<211> LENGTH: 376
<212> TYPE: PRT

```
<213> ORGANISM: HOMO SAPIENS

<400> SEQUENCE: 3

Gly Lys Leu Thr Ala Val Asp Pro Glu Thr Asn Met Asn Val Ser Glu
1               5                   10                  15

Ile Ile Ser Tyr Trp Gly Phe Pro Ser Glu Glu Tyr Leu Val Glu Thr
            20                  25                  30

Glu Asp Gly Tyr Ile Leu Cys Leu Asn Arg Ile Pro His Gly Arg Lys
        35                  40                  45

Asn His Ser Asp Lys Gly Pro Lys Pro Val Val Phe Leu Gln His Gly
    50                  55                  60

Leu Leu Ala Asp Ser Ser Asn Trp Val Thr Asn Leu Ala Asn Ser Ser
65                  70                  75                  80

Leu Gly Phe Ile Leu Ala Asp Ala Gly Phe Asp Val Trp Met Gly Asn
                85                  90                  95

Ser Arg Gly Asn Thr Trp Ser Arg Lys His Lys Thr Leu Ser Val Ser
            100                 105                 110

Gln Asp Glu Phe Trp Ala Phe Ser Tyr Asp Glu Met Ala Lys Tyr Asp
        115                 120                 125

Leu Pro Ala Ser Ile Asn Phe Ile Leu Asn Lys Thr Gly Gln Glu Gln
    130                 135                 140

Val Tyr Tyr Val Gly His Ser Gln Gly Thr Thr Ile Gly Phe Ile Ala
145                 150                 155                 160

Phe Ser Gln Ile Pro Glu Leu Ala Lys Arg Ile Lys Met Phe Phe Ala
                165                 170                 175

Leu Gly Pro Val Ala Ser Val Ala Phe Cys Thr Ser Pro Met Ala Lys
            180                 185                 190

Leu Gly Arg Leu Pro Asp His Leu Ile Lys Asp Leu Phe Gly Asp Lys
        195                 200                 205

Glu Phe Leu Pro Gln Ser Ala Phe Leu Lys Trp Leu Gly Thr His Val
    210                 215                 220

Cys Thr His Val Ile Leu Lys Glu Leu Cys Gly Asn Leu Cys Phe Leu
225                 230                 235                 240

Leu Cys Gly Phe Asn Glu Arg Asn Leu Asn Met Ser Arg Val Asp Val
                245                 250                 255

Tyr Thr Thr His Ser Pro Ala Gly Thr Ser Val Gln Asn Met Leu His
            260                 265                 270

Trp Ser Gln Ala Val Lys Phe Gln Lys Phe Gln Ala Phe Asp Trp Gly
        275                 280                 285

Ser Ser Ala Lys Asn Tyr Phe His Tyr Asn Gln Ser Tyr Pro Pro Thr
    290                 295                 300

Tyr Asn Val Lys Asp Met Leu Val Pro Thr Ala Val Trp Ser Gly Gly
305                 310                 315                 320

His Asp Trp Leu Ala Asp Val Tyr Asp Val Asn Ile Leu Leu Thr Gln
                325                 330                 335

Ile Thr Asn Leu Val Phe His Glu Ser Ile Pro Glu Trp Glu His Leu
            340                 345                 350

Asp Phe Ile Trp Gly Leu Asp Ala Pro Trp Arg Leu Tyr Asn Lys Ile
        355                 360                 365

Ile Asn Leu Met Arg Lys Tyr Gln
    370                 375

<210> SEQ ID NO 4
<211> LENGTH: 373
```

```
<212> TYPE: PRT
<213> ORGANISM: HOMO SAPIENS

<400> SEQUENCE: 4

Thr Ala Val Asp Pro Glu Thr Asn Met Asn Val Ser Glu Ile Ile Ser
1               5                   10                  15

Tyr Trp Gly Phe Pro Ser Glu Glu Tyr Leu Val Glu Thr Glu Asp Gly
            20                  25                  30

Tyr Ile Leu Cys Leu Asn Arg Ile Pro His Gly Arg Lys Asn His Ser
        35                  40                  45

Asp Lys Gly Pro Lys Pro Val Val Phe Leu Gln His Gly Leu Leu Ala
    50                  55                  60

Asp Ser Ser Asn Trp Val Thr Asn Leu Ala Asn Ser Ser Leu Gly Phe
65                  70                  75                  80

Ile Leu Ala Asp Ala Gly Phe Asp Val Trp Met Gly Asn Ser Arg Gly
                85                  90                  95

Asn Thr Trp Ser Arg Lys His Lys Thr Leu Ser Val Ser Gln Asp Glu
            100                 105                 110

Phe Trp Ala Phe Ser Tyr Asp Glu Met Ala Lys Tyr Asp Leu Pro Ala
        115                 120                 125

Ser Ile Asn Phe Ile Leu Asn Lys Thr Gly Gln Glu Gln Val Tyr Tyr
    130                 135                 140

Val Gly His Ser Gln Gly Thr Thr Ile Gly Phe Ile Ala Phe Ser Gln
145                 150                 155                 160

Ile Pro Glu Leu Ala Lys Arg Ile Lys Met Phe Phe Ala Leu Gly Pro
                165                 170                 175

Val Ala Ser Val Ala Phe Cys Thr Ser Pro Met Ala Lys Leu Gly Arg
            180                 185                 190

Leu Pro Asp His Leu Ile Lys Asp Leu Phe Gly Asp Lys Glu Phe Leu
        195                 200                 205

Pro Gln Ser Ala Phe Leu Lys Trp Leu Gly Thr His Val Cys Thr His
    210                 215                 220

Val Ile Leu Lys Glu Leu Cys Gly Asn Leu Cys Phe Leu Leu Cys Gly
225                 230                 235                 240

Phe Asn Glu Arg Asn Leu Asn Met Ser Arg Val Asp Val Tyr Thr Thr
                245                 250                 255

His Ser Pro Ala Gly Thr Ser Val Gln Asn Met Leu His Trp Ser Gln
            260                 265                 270

Ala Val Lys Phe Gln Lys Phe Gln Ala Phe Asp Trp Gly Ser Ser Ala
        275                 280                 285

Lys Asn Tyr Phe His Tyr Asn Gln Ser Tyr Pro Pro Thr Tyr Asn Val
    290                 295                 300

Lys Asp Met Leu Val Pro Thr Ala Val Trp Ser Gly Gly His Asp Trp
305                 310                 315                 320

Leu Ala Asp Val Tyr Asp Val Asn Ile Leu Leu Thr Gln Ile Thr Asn
                325                 330                 335

Leu Val Phe His Glu Ser Ile Pro Glu Trp Glu His Leu Asp Phe Ile
            340                 345                 350

Trp Gly Leu Asp Ala Pro Trp Arg Leu Tyr Asn Lys Ile Ile Asn Leu
        355                 360                 365

Met Arg Lys Tyr Gln
    370

<210> SEQ ID NO 5
```

<211> LENGTH: 1150
<212> TYPE: DNA
<213> ORGANISM: HOMO SAPIENS

<400> SEQUENCE: 5

```
atgaaaatgc ggttcttggg gttggtggtc tgtttggttc tctggaccct gcattccgag     60

gggtccggag ggaaactgac agctgtggat cctgaaacaa acatgaatgt cagtgaaatt    120

atctcttact ggggattccc tagtgaggaa tacctagttg agacagaaga tggatatatt    180

ctgtgcctta accgaattcc tcatgggagg aagaaccatt ctgacaaagg tcccaaacca    240

gttgtcttcc tgcaacatgg cttgctggca gattctagta actgggtcac aaaccttgcc    300

aacagcagcc tgggcttcat tcttgctgat gctggttttg acgtgtggat gggcaacagc    360

agaggaaata cctggtctcg gaaacataag acactctcag tttctcagga tgaattctgg    420

gctttcagtt atgatgagat ggcaaaatat gacctaccag cttccattaa cttcattctg    480

aataagactg gccaagaaca agtgtattat gtgggtcatt ctcaaggcac cactataggt    540

tttatagcat tttcacagat ccctgagctg gctaaaagga ttaaaatgtt ttttgccctg    600

ggtcctgtgg cttccgtcgc cttctgtact agccctatgg ccaaactggg acgactgcca    660

gatcatctca ttaaggacct ctttggagac aaagaatttc ttccccagag tgcgtttttg    720

aagtggctgg gtacccacgt ttgcactcat gtcatactga aggagctctg tggaaatctc    780

tgttttcttc tgtgtggatt taatgagaga aatttaaata tgtctagagt ggatgtgtat    840

acaacacatt ctcctgctgg aacttctgtg caaaacatgt tacactggag ccaggctgtt    900

aaattccaaa agtttcaagc ctttgactgg ggaagcagtg ccaagaatta ttttcattac    960

aaccagagtt atcctcccac atacaatgtg aaggacatgc ttgtgccgac tgcagtctgg   1020

agcgggggtc acgactggct tgcagatgtc tacgacgtca atatcttact gactcagatc   1080

accaacttgg tgttccatga gagcattccg gaatgggagc atcttgactt catttggggc   1140

ctggatgccc                                                          1150
```

<210> SEQ ID NO 6
<211> LENGTH: 10882
<212> TYPE: DNA
<213> ORGANISM: Artificial Sequence
<220> FEATURE:
<223> OTHER INFORMATION: pALVIN-OVR1-I-SBC102-dSA

<400> SEQUENCE: 6

```
ctttccccgt caagctctaa atcgggggct ccctttaggg ttccgattta gtgctttacg     60

gcacctcgac cccaaaaaac ttgattaggg tgatggttca cgtagtgggc catcgccctg    120

atagacggtt tttcgccctt tgacgttgga gtccacgttc tttaatagtg gactcttgtt    180

ccaaactgga acaacactca accctatctc ggtctattct tttgatttat aagggatttt    240

gccgatttcg gcctattggt taaaaaatga gctgatttaa caaaaattta acgcgaattt    300

taacaaaata ttaacgctta caatttccat tcgccattca ggctgcgcaa ctgttgggaa    360

gggcgatcgg tgcgggcctc ttcgctatta cgccagctgg cgaaaggggg atgtgctgca    420

aggcgattaa gttgggtaac gccagggttt tcccagtcac gacgttgtaa aacgacggcc    480

agtgagcgcg tattccctaa cgatcacgtc ggggtcacca aatgaagcct tctgcttcat    540

gcatgtgctc gtagtcgtca gggaatcaac ggtccggcca tcaacccagg tgcacaccaa    600

tgtggtgaat ggtcaaatgg cgtttattgt atcgagctag gcacttaaat acaatatctc    660

tgcaatgcgg aattcagtgg ttcgtccaat ccgtcccct ccctatgcaa aagcgaaact    720
```

```
actatatcct gaggggactc ctaaccgcgt acaaccgaag ccccgctttt cgcctaaaca    780
tgctattgtc ccctcagtca agccttgccc gttacaaccc gattcgcaag ccttgccctc    840
cccacattat ccgtagcatt atttcctagc agtcatcaga gctacagaag atactctatg    900
ctgtagccaa gtctacaagt ttactattca gcgacctcct atattccgcg tgccagccga    960
tcaattacca atccaaccag ctatcacacg gaatacaaga actcgcctac gctcttcttt   1020
cgggctgctt ataagcctcc tgtaattttt ttatattcct cgctcgagtc tcttcagaat   1080
ggcacagcac cgctgcagaa aaatgccagg tggactatga actcacatcc aaaggagctt   1140
gacctgatac ctgattttct tcaaacaggg gaaacaacac aatcccacaa aacagctcag   1200
agagaaacca tcactgatgg ctacagcacc aaggtatgca atggcaatcc attcgacatt   1260
catctgtgac ctgagcaaaa tgatttatct ctccatgaat ggttgcttct ttccctcatg   1320
aaaaggcaat ttccacactc acaatatgca acaaagacaa acagagaaca attaatgtgc   1380
tccttcctaa tgttaaaatt gtagtggcaa agaggagaac aaaatctcaa gttctgagta   1440
ggttttagtg attggataag aggctttgac ctgtgagctc acctggactt catatccttt   1500
tggataaaaa gtgcttttat aactttcagg tctccgagtc tttattcatg agactgttgg   1560
tttagggaca gacccacaat gaaatgcctg gcataggaaa gggcagcaga gccttagctg   1620
accttttctt gggacaagca ttgtcaaaca atgtgtgaca aaactatttg tactgctttg   1680
cacagctgtg ctgggcaggg caatccattg ccacctatcc caggtaacct tccaactgca   1740
agaagattgt tgcttactct ctctagaccc ccaagtcaaa ccaactatgc aggtatgctg   1800
acaacactat gatgacagcc tgttctgatc aagatctcat ttgttcatgg acaatttttg   1860
ttgcttgcag ctggtcttcc attgggaaag agtgtagtat atccttctca tctgacagaa   1920
aagcagaaat tctcatgctc cacacttaat ctacattgtt ttaaaccacc ggctacttct   1980
tggagaggaa aaatggcttt tataagactc acaaaacaaa gctctgcaag tcaaatgcat   2040
acaaaactgt tctgtaggtc tggaatcagg acactatgtg gaagtcaaat agagcagctt   2100
taaaaagcct ttgggatcat tctcatctta tatttgcagc acgatactat gacagtgata   2160
actgacataa ctgcatcaat ttccttgata ttttatttgt cttaaagtac aagacataga   2220
gatggacgta aagatggaca tatgactcag gtctggacag gtccgtggtc catgtatgat   2280
aaaagagatg aagggaagga gaattgagac tgtctaagaa gggcttcagg gacgttctga   2340
aggcagattt gactgaatca gatgtactgt ccaagtctca tatgtagcaa tggaaggctg   2400
atattggaga aatataaaga aatggctgtg aactcaaagt gaccctgaac agaaaaggga   2460
tatggagtta aaataatgtc acagaactga ggtttatatg atataccatg ggctgcagag   2520
ggtcagagtg ctccaccatg ggcctctctt gggctgcagg gaacttctgt tctacacctg   2580
gaacacctcc tgccctcctc cgcactgacc tcagtgtcat cagggctgtt tctctcacat   2640
tttctcactc acctctccca actaccattg tacagcagtt gttcttacat attgctcctc   2700
ctgaggtaca tctagcatcg ttaagtcctc agacttggca aggagaatgt agatttccac   2760
agtatatatg ttttcacaaa aggaaggaga gaaacaaaag aaaatggcac tgactaaact   2820
tcagctagtg gtataggaaa gtaattctgc ttaacagaga ttgcagtgat ctctatgtat   2880
gtcctgaaga attatgttgt actttttcc cccattttta aatcaaacag tgctttacag   2940
aggtcagaat ggtttcttta ctgtttgtca attctattat ttcaatacag aacaatagct   3000
tctataactg aaatatattt gctattgtat attatgattg tccctcgaac catgaacact   3060
```

```
cctccagctg aatttcacaa ttcctctgtc atctgccagg ccattaagtt attcatggaa   3120
gatctttgag gaacactgca agttcatatc ataaacacat ttgaaattga gtattgtttt   3180
gcattgtatg gagctatgtt ttgctgtatc ctcagaataa aagtttgtta taaagcattc   3240
acacccataa aaagatagat ttaaatattc caactatagg aaagaaagtg tgtctgctct   3300
tcactctagt ctcagttggc tccttcacat gcacgcttct ttatttctcc tattttgtca   3360
agaaaataat aggtcaagtc ttgttctcat ttatgtcctg tctagcgtgg ctcagatgca   3420
cattgtacat acaagaagga tcaaatgaaa cagacttctg gtctgttact acaaccatag   3480
taataagcac actaactaat aattgctaat tatgttttcc atctccaagg ttcccacatt   3540
tttctgtttt cttaaagatc ccattatctg gttgtaactg aagctcaatg gaacatgagc   3600
aatatttccc agtcttctct cccatccaac agtcctgatg gattagcaga acaggcagaa   3660
aacacattgt tacccagaat taaaaactaa tatttgctct ccattcaatc caaaatggac   3720
ctattgaaac taaaatctaa cccaatccca ttaaatgatt tctatggtgt caaaggtcaa   3780
acttctgaag ggaacctgtg ggtgggtcac aattcagact atatattccc cagggctcag   3840
ccagtgtctg tacatacagc tagaaagctg tattgccttt agcagtcaag ctcgaaaggt   3900
aagcaactct ctggaattac cttctctcta tattagctct tacttgcacc taaactttaa   3960
aaaattaaca attattgtgc tatgtgttgt atctttaagg gtgaagtacc tgcgtgatac   4020
cccctataaa aacttctcac ctgtgtatgc attctgcact attttattat gtgtaaaagc   4080
tttgtgtttg ttttcaggag gcttattctt tgtgcttaaa atatgttttt aatttcagaa   4140
catcttatcc tgtcgttcac tatctgatat gctttgcagt ttgcttgatt aacttctagc   4200
cctacagagt gcacagagag caaaatcatg gtgttcagtg aattctgggg agttatttta   4260
atgtgaaaat tctctagaag tttaattcct gcaaagtgca gctgctgatc actacacaag   4320
ataaaaatgt ggggggtgca taaacgtata ttcttacaat aatagataca tgtgaactta   4380
tatacagaaa agaaaatgag aaaaatgtgt gtgtgtatac tcacacacgt ggtcagtaaa   4440
aacttttgag ggtttaata cagaaaatcc aatcctgagg ccccagcact cagtacgcat   4500
ataaagggct gggctctgaa ggacttctga ctttcacaga ttatataaat ctcaggaaag   4560
caactagatt catgctggct ccaaaagctg tgctttatat aagcacactg gctatacaat   4620
agttgtacag ttcagctctt tataatagaa acagacagaa caagtataaa tcttctattg   4680
gtctatgtca tgaacaagaa ttcattcagt ggctctgttt tatagtaaac attgctattt   4740
tatcatgtct gcatttctct tctgtctgaa tgtcaccact aaaatttaac tccacagaaa   4800
gtttatacta cagtacacat gcatatcttt gagcaaagca aaccatacct gaaagtgcaa   4860
tagagcagaa tatgaattac atgcgtgtct ttctcctaga ctacatgacc ccatataaat   4920
tacattcctt atctattctg ccatcaccaa aacaaaggta aaaatacttt tgaagatcta   4980
ctcatagcaa gtagtgtgca acaaacagat atttctctac atttattttt agggaataaa   5040
aataagaaat aaaatagtca gcaagcctct gctttctcat atatctgtcc aaacctaaag   5100
tttactgaaa tttgctcttt gaatttccag ttttgcaagc ctatcagatt gtgttttaat   5160
cagaggtact gaaaagtatc aatgaattct agctttcact gaacaaaaat atgtagaggc   5220
aactggcttc tgggacagtt tgctacccaa aagacaactg aatgcaaata cataaataga   5280
tttatgaata tggttttgaa catgcacatg agaggtggat atagcaacag acacattacc   5340
acagaattac tttaaaacta cttgttaaca tttaattgcc taaaaactgc tcgtaattta   5400
ctgttgtagc ctaccataga gtaccctgca tggtactatg tacagcattc catccttaca   5460
```

```
ttttcactgt tctgctgttt gctctagaca actcagagtt caccatgaaa atgcggttct   5520
tggggttggt ggtctgtttg gttctctgga ccctgcattc cgaggggtcc ggagggaaac   5580
tgacagctgt ggatccagaa acaaacatga atgtcagtga aattatctct tactggggat   5640
tccctagtga ggaataccta gttgagacag aagatggata tattctgtgc cttaaccgaa   5700
ttcctcatgg gaggaagaac cattctgaca aaggtcccaa accagttgtc ttcctgcaac   5760
atggcttgct ggcagattct agtaactggg tcacaaacct tgccaacagc agcctgggct   5820
tcattcttgc tgatgctggt tttgacgtgt ggatgggcaa cagcagagga aatacctggt   5880
ctcggaaaca taagacactc tcagtttctc aggatgaatt ctgggctttc agttatgatg   5940
agatggcaaa atatgaccta ccagcttcca ttaacttcat tctgaataag actggccaag   6000
aacaagtgta ttatgtgggt cattctcaag gcaccactat aggttttata gcattttcac   6060
agatccctga gctggctaaa aggattaaaa tgtttttgc cctgggtcct gtggcttccg    6120
tcgccttctg tactagccct atggccaaac tgggacgact gccagatcat ctcattaagg   6180
acctctttgg agacaaagaa tttcttcccc agagtgcgtt tttgaagtgg ctgggtaccc   6240
acgtttgcac tcatgtcata ctgaaggagc tctgtggaaa tctctgtttt cttctgtgtg   6300
gatttaatga gagaaattta aatatgtcta gagtggatgt gtatacaaca cattctcctg   6360
ctggaacttc tgtgcaaaac atgttacact ggagccaggc tgttaaattc caaaagtttc   6420
aagcctttga ctggggaagc agtgccaaga attattttca ttacaaccag agttatcctc   6480
ccacatacaa tgtgaaggac atgcttgtgc cgactgcagt ctggagcggg ggtcacgact   6540
ggcttgcaga tgtctacgac gtcaatatct tactgactca gatcaccaac ttggtgttcc   6600
atgagagcat tccggaatgg gagcatcttg acttcatttg gggcctggat gccccttgga   6660
ggctttataa taagattatt aatctaatga ggaaatatca gtgattcgaa gcggccgcaa   6720
gaagaaagct gaaaaactct gtcccttcca acaagaccca gagcactgta gtatcagggg   6780
taaaatgaaa agtatgttat ctgctgcatc cagacttcat aaaagctgga gcttaatcta   6840
gaaaaaaaat cagaaagaaa ttacactgtg agaacaggtg caattcactt ttcctttaca   6900
cagagtaata ctggtaactc atggatgaag gcttaaggga atgaaattgg actcacagta   6960
ctgagtcatc acactgaaaa atgcaacctg atacatcagc agaaggttta tgggggaaaa   7020
atgcagcctt ccaattaagc cagatatctg tatgaccaag ctgctccaga attagtcact   7080
caaaatctct cagattaaat tatcaactgt caccaaccat tcctatgctg acaaggcaat   7140
tgcttgttct ctgtgttcct gatactacaa ggctcttcct gacttcctaa agatgcatta   7200
taaaaatctt ataattcaca tttctcccta aactttgact caatcatggt atgttggcaa   7260
atatggtata ttactattca aattgttttc cttgtaccca tatgtaatgg gtcttgtgaa   7320
tgtgctcttt tgttccttta atcataataa aaacatgttt aagcaaacac ttttcacttg   7380
tagtatttga aggtaccgga tctcgagccg ccttcaatgc ccccaaaacc aatccccagg   7440
tttttaactc tcccgatttt ccaagtacca tagcccgctg agagagcgcc gcggtaatgg   7500
gatcccagga ccccggggaa tataagtctg agggggacgt aagcaaccct tccttttgta   7560
acagggacaa catagcccct atttccttct tagaaggaga ggttttcccg caataggtct   7620
tacacgcgga cgaaatcacc tttatgacgg cttccatgct tgatccaccg ggcgaccgga   7680
atcacgcaga gcaaccggaa tcacgcctgg ggtggaccgc tcagtcgtcg ggcttccttc   7740
ccgtcttcca acgactctct gagttctcgg tagggtatgt tggcccccctg cagtagggct  7800
```

```
ccctccgacg ccactcagct tctgccctcc taagccgcag ccccctctac tagggtcatc   7860
gtccgctccc cgaataagcg agacggatga ggacaggatc gccacgccgc ctgtggccga   7920
ccactattcc ctaacgatca cgtcggggtc accaaatgaa gccttctgct tcatgcatgt   7980
gctcgtagtc gtcagggaat caacggtccg gccatcaacc caggtgcaca ccaatgtggt   8040
gaatggtcaa atggcgttta ttgtatcgag ctaggcactt aaatacaata tctctgcaat   8100
gcggaattca gtggttcgtc caatccgtgt tagacccgtc tgttgccttc ctaacaaggc   8160
acgatcatac cacgatcata ccaccttact cccaccaatc ggcatgcacg gtgctttttc   8220
tctccttata aggcatgttg ctaactcatc gttacataag catgttgcaa gactacaaga   8280
gtattgcata agactacatt tccccctccc tatgcaaaag cgaaactact atatcctgag   8340
gggactccta accgcgtaca accgaagccc cgcttttcgc ctaaacatgc tattgtcccc   8400
tcagtcaagc cttgcccgtt acaacccgat tcgcaagcct tgccctcccc acattatccg   8460
tagcattatt tcctagcagt catcagagct acagaagata ctctatgctg tagccaagtc   8520
tacaagttta ctattcagcg acctcctata ttccgcgtgc cagccgatca attaccaatg   8580
cgcgcttggc gtaatcatgg tcatagctgt ttcctgtgtg aaattgttat ccgctcacaa   8640
ttccacacaa catacgagcc ggaagcataa agtgtaaagc ctggggtgcc taatgagtga   8700
gctaactcac attaattgcg ttgcgctcac tgcccgcttt ccagtcggga aacctgtcgt   8760
gccagctgca ttaatgaatc ggccaacgcg cggggagagg cggtttgcgt attgggcgct   8820
cttccgcttc ctcgctcact gactcgctgc gctcggtcgt tcggctgcgg cgagcggtat   8880
cagctcactc aaaggcggta atacggttat ccacagaatc aggggataac gcaggaaaga   8940
acatgtgagc aaaaggccag caaaaggcca ggaaccgtaa aaaggccgcg ttgctggcgt   9000
ttttccatag gctccgcccc cctgacgagc atcacaaaaa tcgacgctca agtcagaggt   9060
ggcgaaaccc gacaggacta taaagatacc aggcgtttcc ccctggaagc tccctcgtgc   9120
gctctcctgt tccgaccctg ccgcttaccg gatacctgtc cgcctttctc ccttcgggaa   9180
gcgtggcgct ttctcatagc tcacgctgta ggtatctcag ttcggtgtag gtcgttcgct   9240
ccaagctggg ctgtgtgcac gaaccccccg ttcagcccga ccgctgcgcc ttatccggta   9300
actatcgtct tgagtccaac ccggtaagac acgacttatc gccactggca gcagccactg   9360
gtaacaggat tagcagagcg aggtatgtag gcggtgctac agagttcttg aagtggtggc   9420
ctaactacgg ctacactaga aggacagtat ttggtatctg cgctctgctg aagccagtta   9480
ccttcggaaa aagagttggt agctcttgat ccggcaaaca aaccaccgct ggtagcggtg   9540
gtttttttgt ttgcaagcag cagattacgc gcagaaaaaa aggatctcaa gaagatcctt   9600
tgatcttttc tacggggtct gacgctcagt ggaacgaaaa ctcacgttaa gggattttgg   9660
tcatgagatt atcaaaaagg atcttcacct agatcctttt aaattaaaaa tgaagtttta   9720
aatcaatcta aagtatatat gagtaaactt ggtctgacag ttaccaatgc ttaatcagtg   9780
aggcacctat ctcagcgatc tgtctatttc gttcatccat agttgcctga ctccccgtcg   9840
tgtagataac tacgatacgg gagggcttac catctggccc cagtgctgca atgataccgc   9900
gagacccacg ctcaccggct ccagatttat cagcaataaa ccagccagcc ggaagggccg   9960
agcgcagaag tggtcctgca actttatccg cctccatcca gtctattaat tgttgccggg  10020
aagctagagt aagtagttcg ccagttaata gtttgcgcaa cgttgttgcc attgctacag  10080
gcatcgtggt gtcacgctcg tcgtttggta tggcttcatt cagctccggt tcccaacgat  10140
caaggcgagt tacatgatcc cccatgttgt gcaaaaaagc ggttagctcc ttcggtcctc  10200
```

```
cgatcgttgt cagaagtaag ttggccgcag tgttatcact catggttatg gcagcactgc  10260

ataattctct tactgtcatg ccatccgtaa gatgcttttc tgtgactggt gagtactcaa  10320

ccaagtcatt ctgagaatag tgtatgcggc gaccgagttg ctcttgcccg gcgtcaatac  10380

gggataatac cgcgccacat agcagaactt taaaagtgct catcattgga aaacgttctt  10440

cggggcgaaa actctcaagg atcttaccgc tgttgagatc cagttcgatg taacccactc  10500

gtgcacccaa ctgatcttca gcatctttta ctttcaccag cgtttctggg tgagcaaaaa  10560

caggaaggca aaatgccgca aaaaagggaa taagggcgac acggaaatgt tgaatactca  10620

tactcttcct ttttcaatat tattgaagca tttatcaggg ttattgtctc atgagcggat  10680

acatatttga atgtatttag aaaaataaac aaataggggt tccgcgcaca tttccccgaa  10740

aagtgccacc tgacgcgccc tgtagcggcg cattaagcgc ggcgggtgtg gtggttacgc  10800

gcagcgtgac cgctacactt gccagcgccc tagcgcccgc tcctttcgct ttcttccctt  10860

cctttctcgc cacgttcgcc gg                                           10882
```

```
<210> SEQ ID NO 7
<211> LENGTH: 7780
<212> TYPE: DNA
<213> ORGANISM: Artificial Sequence
<220> FEATURE:
<223> OTHER INFORMATION: Proviral sequence of pALVIN-OVR1-I-SBC102-dSA

<400> SEQUENCE: 7
```

```
aatgaagcct tctgcttcat gcatgtgctc gtagtcgtca gggaatcaac ggtccggcca     60

tcaacccagg tgcacaccaa tgtggtgaat ggtcaaatgg cgtttattgt atcgagctag    120

gcacttaaat acaatatctc tgcaatgcgg aattcagtgg ttcgtccaat ccgtccccct    180

ccctatgcaa aagcgaaact actatatcct gaggggactc ctaaccgcgt acaaccgaag    240

ccccgctttt cgcctaaaca tgctattgtc ccctcagtca agccttgccc gttacaaccc    300

gattcgcaag ccttgccctc cccacattat ccgtagcatt atttcctagc agtcatcaga    360

gctacagaag atactctatg ctgtagccaa gtctacaagt ttactattca gcgacctcct    420

atattccgcg tgccagccga tcaattacca atccaaccag ctatcacacg gaatacaaga    480

actcgcctac gctcttcttt cgggctgctt ataagcctcc tgtaattttt ttatattcct    540

cgctcgagtc tcttcagaat ggcacagcac cgctgcagaa aaatgccagg tggactatga    600

actcacatcc aaaggagctt gacctgatac ctgattttct tcaaacaggg gaaacaacac    660

aatcccacaa aacagctcag agagaaacca tcactgatgg ctacagcacc aaggtatgca    720

atggcaatcc attcgacatt catctgtgac ctgagcaaaa tgatttatct ctccatgaat    780

ggttgcttct ttccctcatg aaaaggcaat ttccacactc acaatatgca acaaagacaa    840

acagagaaca attaatgtgc tccttcctaa tgttaaaatt gtagtggcaa agaggagaac    900

aaaatctcaa gttctgagta ggttttagtg attggataag aggctttgac ctgtgagctc    960

acctggactt catatccttt tggataaaaa gtgcttttat aactttcagg tctccgagtc   1020

tttattcatg agactgttgg tttagggaca gacccacaat gaaatgcctg gcataggaaa   1080

gggcagcaga gccttagctg accttttctt gggacaagca ttgtcaaaca atgtgtgaca   1140

aaactatttg tactgctttg cacagctgtg ctgggcaggg caatccattg ccacctatcc   1200

caggtaacct tccaactgca agaagattgt tgcttactct ctctagaccc ccaagtcaaa   1260

ccaactatgc aggtatgctg acaacactat gatgacagcc tgttctgatc aagatctcat   1320
```

```
ttgttcatgg acaattttttg ttgcttgcag ctggtcttcc attgggaaag agtgtagtat   1380
atccttctca tctgacagaa aagcagaaat tctcatgctc cacacttaat ctacattgtt   1440
ttaaaccacc ggctacttct tggagaggaa aaatggcttt tataagactc acaaaacaaa   1500
gctctgcaag tcaaatgcat acaaaactgt tctgtaggtc tggaatcagg acactatgtg   1560
gaagtcaaat agagcagctt taaaaagcct ttgggatcat tctcatctta tatttgcagc   1620
acgatactat gacagtgata actgacataa ctgcatcaat ttccttgata ttttatttgt   1680
cttaaagtac aagacataga gatggacgta aagatggaca tatgactcag gtctggacag   1740
gtccgtggtc catgtatgat aaaagagatg aagggaagga gaattgagac tgtctaagaa   1800
gggcttcagg gacgttctga aggcagattt gactgaatca gatgtactgt ccaagtctca   1860
tatgtagcaa tggaaggctg atattggaga aatataaaga aatggctgtg aactcaaagt   1920
gaccctgaac agaaaaggga tatggagtta aaataatgtc acagaactga ggtttatatg   1980
atataccatg ggctgcagag ggtcagagtg ctccaccatg ggcctctctt gggctgcagg   2040
gaacttctgt tctacacctg gaacacctcc tgccctcctc cgcactgacc tcagtgtcat   2100
cagggctgtt tctctcacat tttctcactc acctctccca actaccattg tacagcagtt   2160
gttcttacat attgctcctc ctgaggtaca tctagcatcg ttaagtcctc agacttggca   2220
aggagaatgt agatttccac agtatatatg ttttcacaaa aggaaggaga gaaacaaaag   2280
aaaatggcac tgactaaact tcagctagtg gtataggaaa gtaattctgc ttaacagaga   2340
ttgcagtgat ctctatgtat gtcctgaaga attatgttgt acttttttcc cccattttta   2400
aatcaaacag tgctttacag aggtcagaat ggtttcttta ctgtttgtca attctattat   2460
ttcaatacag aacaatagct tctataactg aaatatattt gctattgtat attatgattg   2520
tccctcgaac catgaacact cctccagctg aatttcacaa ttcctctgtc atctgccagg   2580
ccattaagtt attcatggaa gatctttgag gaacactgca agttcatatc ataaacacat   2640
ttgaaattga gtattgtttt gcattgtatg gagctatgtt ttgctgtatc ctcagaataa   2700
aagtttgtta taaagcattc acacccataa aaagatagat ttaaatattc caactatagg   2760
aaagaaagtg tgtctgctct tcactctagt ctcagttggc tccttcacat gcacgcttct   2820
ttatttctcc tattttgtca agaaaataat aggtcaagtc ttgttctcat ttatgtcctg   2880
tctagcgtgg ctcagatgca cattgtacat acaagaagga tcaaatgaaa cagacttctg   2940
gtctgttact acaaccatag taataagcac actaactaat aattgctaat tatgttttcc   3000
atctccaagg ttcccacatt tttctgtttt cttaaagatc ccattatctg gttgtaactg   3060
aagctcaatg gaacatgagc aatatttccc agtcttctct cccatccaac agtcctgatg   3120
gattagcaga acaggcagaa aacacattgt tacccagaat taaaaactaa tatttgctct   3180
ccattcaatc caaaatggac ctattgaaac taaaatctaa cccaatccca ttaaatgatt   3240
tctatggtgt caaaggtcaa acttctgaag ggaacctgtg ggtgggtcac aattcagact   3300
atatattccc cagggctcag ccagtgtctg tacatacagc tagaaagctg tattgccttt   3360
agcagtcaag ctcgaaaggt aagcaactct ctggaattac cttctctcta tattagctct   3420
tacttgcacc taaactttaa aaaattaaca attattgtgc tatgtgttgt atctttaagg   3480
gtgaagtacc tgcgtgatac cccctataaa aacttctcac ctgtgtatgc attctgcact   3540
attttattat gtgtaaaagc tttgtgtttg ttttcaggag gcttattctt tgtgcttaaa   3600
atatgttttt aatttcagaa catcttatcc tgtcgttcac tatctgatat gctttgcagt   3660
ttgcttgatt aacttctagc cctacagagt gcacagagag caaaatcatg gtgttcagtg   3720
```

```
aattctgggg agttatttta atgtgaaaat tctctagaag tttaattcct gcaaagtgca   3780
gctgctgatc actacacaag ataaaaatgt ggggggtgca taaacgtata ttcttacaat   3840
aatagataca tgtgaactta tatacagaaa agaaaatgag aaaaatgtgt gtgtgtatac   3900
tcacacacgt ggtcagtaaa aacttttgag ggtttaata cagaaaatcc aatcctgagg   3960
ccccagcact cagtacgcat ataaagggct gggctctgaa ggacttctga ctttcacaga   4020
ttatataaat ctcaggaaag caactagatt catgctggct ccaaaagctg tgctttatat   4080
aagcacactg gctatacaat agttgtacag ttcagctctt tataatagaa acagacagaa   4140
caagtataaa tcttctattg gtctatgtca tgaacaagaa ttcattcagt ggctctgttt   4200
tatagtaaac attgctattt tatcatgtct gcatttctct tctgtctgaa tgtcaccact   4260
aaaatttaac tccacagaaa gtttatacta cagtacacat gcatatcttt gagcaaagca   4320
aaccatacct gaaagtgcaa tagagcagaa tatgaattac atgcgtgtct ttctcctaga   4380
ctacatgacc ccatataaat tacattcctt atctattctg ccatcaccaa aacaaaggta   4440
aaaatacttt tgaagatcta ctcatagcaa gtagtgtgca acaaacagat atttctctac   4500
atttattttt agggaataaa aataagaaat aaaatagtca gcaagcctct gctttctcat   4560
atatctgtcc aaacctaaag tttactgaaa tttgctcttt gaatttccag ttttgcaagc   4620
ctatcagatt gtgttttaat cagaggtact gaaaagtatc aatgaattct agctttcact   4680
gaacaaaaat atgtagaggc aactggcttc tgggacagtt tgctacccaa aagacaactg   4740
aatgcaaata cataaataga tttatgaata tggttttgaa catgcacatg agaggtggat   4800
atagcaacag acacattacc acagaattac tttaaaacta cttgttaaca tttaattgcc   4860
taaaaactgc tcgtaattta ctgttgtagc ctaccataga gtaccctgca tggtactatg   4920
tacagcattc catccttaca ttttcactgt tctgctgttt gctctagaca actcagagtt   4980
caccatgaaa atgcggttct tggggttggt ggtctgtttg gttctctgga ccctgcattc   5040
cgaggggtcc ggagggaaac tgacagctgt ggatccagaa acaaacatga atgtcagtga   5100
aattatctct tactggggat tccctagtga ggaataccta gttgagacag aagatggata   5160
tattctgtgc cttaaccgaa ttcctcatgg gaggaagaac cattctgaca aaggtcccaa   5220
accagttgtc ttcctgcaac atggcttgct ggcagattct agtaactggg tcacaaacct   5280
tgccaacagc agcctgggct tcattcttgc tgatgctggt tttgacgtgt ggatgggcaa   5340
cagcagagga aatacctggt ctcggaaaca taagacactc tcagtttctc aggatgaatt   5400
ctgggctttc agttatgatg agatggcaaa atatgaccta ccagcttcca ttaacttcat   5460
tctgaataag actggccaag aacaagtgta ttatgtgggt cattctcaag gcaccactat   5520
aggttttata gcattttcac agatccctga gctggctaaa aggattaaaa tgttttttgc   5580
cctgggtcct gtggcttccg tcgccttctg tactagccct atggccaaac tgggacgact   5640
gccagatcat ctcattaagg acctctttgg agacaaagaa tttcttcccc agagtgcgtt   5700
tttgaagtgg ctgggtaccc acgtttgcac tcatgtcata ctgaaggagc tctgtggaaa   5760
tctctgtttt cttctgtgtg gatttaatga gagaaattta aatatgtcta gagtggatgt   5820
gtatacaaca cattctcctg ctggaacttc tgtgcaaaac atgttacact ggagccaggc   5880
tgttaaattc caaaagtttc aagcctttga ctggggaagc agtgccaaga attattttca   5940
ttacaaccag agttatcctc ccacatacaa tgtgaaggac atgcttgtgc cgactgcagt   6000
ctggagcggg ggtcacgact ggcttgcaga tgtctacgac gtcaatatct tactgactca   6060
```

```
gatcaccaac ttggtgttcc atgagagcat tccggaatgg gagcatcttg acttcatttg   6120

gggcctggat gccccttgga ggctttataa taagattatt aatctaatga ggaaatatca   6180

gtgattcgaa gcggccgcaa gaagaaagct gaaaaactct gtcccttcca acaagaccca   6240

gagcactgta gtatcagggg taaaatgaaa agtatgttat ctgctgcatc cagacttcat   6300

aaaagctgga gcttaatcta gaaaaaaaat cagaaagaaa ttacactgtg agaacaggtg   6360

caattcactt ttcctttaca cagagtaata ctggtaactc atggatgaag gcttaaggga   6420

atgaaattgg actcacagta ctgagtcatc acactgaaaa atgcaacctg atacatcagc   6480

agaaggttta tgggggaaaa atgcagcctt ccaattaagc cagatatctg tatgaccaag   6540

ctgctccaga attagtcact caaaatctct cagattaaat tatcaactgt caccaaccat   6600

tcctatgctg acaaggcaat tgcttgttct ctgtgttcct gatactacaa ggctcttcct   6660

gacttcctaa agatgcatta taaaaatctt ataattcaca tttctcccta aactttgact   6720

caatcatggt atgttggcaa atatggtata ttactattca aattgttttc cttgtaccca   6780

tatgtaatgg gtcttgtgaa tgtgctcttt tgttccttta atcataataa aaacatgttt   6840

aagcaaacac ttttcacttg tagtatttga aggtaccgga tctcgagccg ccttcaatgc   6900

ccccaaaacc aatccccagg tttttaactc tcccgatttt ccaagtacca tagcccgctg   6960

agagagcgcc gcggtaatgg gatcccagga ccccggggaa tataagtctg agggggacgt   7020

aagcaaccct tccttttgta acagggacaa catagcccct atttccttct tagaaggaga   7080

ggttttcccg caataggtct tacacgcgga cgaaatcacc tttatgacgg cttccatgct   7140

tgatccaccg ggcgaccgga atcacgcaga gcaaccggaa tcacgcctgg ggtggaccgc   7200

tcagtcgtcg ggcttccttc ccgtcttcca acgactctct gagttctcgg tagggtatgt   7260

tggcccccctg cagtagggct ccctccgacg ccactcagct tctgccctcc taagccgcag   7320

ccccctctac tagggtcatc gtccgctccc cgaataagcg agacggatga ggacaggatc   7380

gccacgccgc ctgtggccga ccactattcc ctaacgatca cgtcggggtc accaaatgaa   7440

gccttctgct tcatgcatgt gctcgtagtc gtcagggaat caacggtccg gccatcaacc   7500

caggtgcaca ccaatgtggt gaatggtcaa atggcgttta ttgtatcgag ctaggcactt   7560

aaatacaata tctctgcaat gcggaattca gtggttcgtc caatccgtgt tagacccgtc   7620

tgttgccttc ctaacaaggc acgatcatac cacgatcata ccaccttact cccaccaatc   7680

ggcatgcacg gtgctttttc tctccttata aggcatgttg ctaactcatc gttacataag   7740

catgttgcaa gactacaaga gtattgcata agactacatt                         7780
```

```
<210> SEQ ID NO 8
<211> LENGTH: 10762
<212> TYPE: DNA
<213> ORGANISM: Artificial Sequence
<220> FEATURE:
<223> OTHER INFORMATION: pALVIN-OV-1.1-I
<220> FEATURE:
<221> NAME/KEY: misc_feature
<222> LOCATION: (1)..(2735)
<223> OTHER INFORMATION: n is a, c, g, or t

<400> SEQUENCE: 8
```

```
nnnnnnnnnn nnnnnnnnnn nnnnnnnnnn nnnnnnnnnn nnnnnnnnnn nnnnnnnnnn     60

nnnnnnnnnn nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240
```

```
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnnn nnnnnnnnnn nnnnnnnnnn   1080
nnnnnnnnnn nnnnnnnnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnnnnn   1200
nnnnnnnnnn nnnnnnnnnn nnnnnnnnnn nnnnnnnnnn nnnnnnnnnn nnnnnnnnnn   1260
nnnnnnnnnn nnnnnnnnnn nnnnnnnnnn nnnnnnnnnn nnnnnnnnnn nnnnnnnnnn   1320
nnnnnnnnnn nnnnnnnnnn nnnnnnnnnn nnnnnnnnnn nnnnnnnnnn nnnnnnnnnn   1380
nnnnnnnnnn nnnnnnnnnn nnnnnnnnnn nnnnnnnnnn nnnnnnnnnn nnnnnnnnnn   1440
nnnnnnnnnn nnnnnnnnnn nnnnnnnnnn nnnnnnnnnn nnnnnnnnnn nnnnnnnnnn   1500
nnnnnnnnnn nnnnnnnnnn nnnnnnnnnn nnnnnnnnnn nnnnnnnnnn nnnnnnnnnn   1560
nnnnnnnnnn nnnnnnnnnn nnnnnnnnnn nnnnnnnnnn nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
nnnnnnnnnn nnnnnnnnnn nnnnnnnnnn nnnnnnnnnn nnnnnnnnnn nnnnnnnnnn   1800
nnnnnnnnnn nnnnnnnnnn nnnnnnnnnn nnnnnnnnnn nnnnnnnnnn nnnnnnnnnn   1860
nnnnnnnnnn nnnnnnnnnn nnnnnnnnnn nnnnnnnnnn nnnnnnnnnn nnnnnnnnnn   1920
nnnnnnnnnn nnnnnnnnnn nnnnnnnnnn nnnnnnnnnn nnnnnnnnnn nnnnnnnnnn   1980
nnnnnnnnnn nnnnnnnnnn nnnnnnnnnn nnnnnnnnnn nnnnnnnnnn nnnnnnnnnn   2040
nnnnnnnnnn nnnnnnnnnn nnnnnnnnnn nnnnnnnnnn nnnnnnnnnn nnnnnnnnnn   2100
nnnnnnnnnn nnnnnnnnnn nnnnnnnnnn nnnnnnnnnn nnnnnnnnnn nnnnnnnnnn   2160
nnnnnnnnnn nnnnnnnnnn nnnnnnnnnn nnnnnnnnnn nnnnnnnnnn nnnnnnnnnn   2220
nnnnnnnnnn nnnnnnnnnn nnnnnnnnnn nnnnnnnnnn nnnnnnnnnn nnnnnnnnnn   2280
nnnnnnnnnn nnnnnnnnnn nnnnnnnnnn nnnnnnnnnn nnnnnnnnnn nnnnnnnnnn   2340
nnnnnnnnnn nnnnnnnnnn nnnnnnnnnn nnnnnnnnnn nnnnnnnnnn nnnnnnnnnn   2400
nnnnnnnnnn nnnnnnnnnn nnnnnnnnnn nnnnnnnnnn nnnnnnnnnn nnnnnnnnnn   2460
nnnnnnnnnn nnnnnnnnnn nnnnnnnnnn nnnnnnnnnn nnnnnnnnnn nnnnnnnnnn   2520
nnnnnnnnnn nnnnnnnnnn nnnnnnnnnn nnnnnnnnnn nnnnnnnnnn nnnnnnnnnn   2580
```

```
nnnnnnnnnn nnnnnnnnnn nnnnnnnnnn nnnnnnnnnn nnnnnnnnnn nnnnnnnnnn   2640
nnnnnnnnnn nnnnnnnnnn nnnnnnnnnn nnnnnnnnnn nnnnnnnnnn nnnnnnnnnn   2700
nnnnnnnnnn nnnnnnnnnn nnnnnnnnnn nnnnnttcga agcggccgca agaagaaagc   2760
tgaaaaactc tgtcccttcc aacaagaccc agagcactgt agtatcaggg gtaaaatgaa   2820
aagtatgtta tctgctgcat ccagacttca taaaagctgg agcttaatct agaaaaaaaa   2880
tcagaaagaa attacactgt gagaacaggt gcaattcact tttcctttac acagagtaat   2940
actggtaact catggatgaa ggcttaaggg aatgaaattg gactcacagt actgagtcat   3000
cacactgaaa aatgcaacct gatacatcag cagaaggttt atgggggaaa aatgcagcct   3060
tccaattaag ccagatatct gtatgaccaa gctgctccag aattagtcac tcaaaatctc   3120
tcagattaaa ttatcaactg tcaccaacca ttcctatgct gacaaggcaa ttgcttgttc   3180
tctgtgttcc tgatactaca aggctcttcc tgacttccta aagatgcatt ataaaaatct   3240
tataattcac atttctccct aaactttgac tcaatcatgg tatgttggca aatatggtat   3300
attactattc aaattgtttt ccttgtaccc atatgtaatg ggtcttgtga atgtgctctt   3360
ttgttccttt aatcataata aaaacatgtt taagcaaaca cttttcactt gtagtatttg   3420
aaggtaccgg atctcgagcc gccttcaatg cccccaaaac caatccccag gtttttaact   3480
ctcccgattt tccaagtacc atagcccgct gagagagcgc cgcggtaatg ggatcccagg   3540
accccgggga atataagtct gagggggacg taagcaaccc ttccttttgt aacagggaca   3600
acatagcccc tatttccttc ttagaaggag aggttttccc gcaataggtc ttacacgcgg   3660
acgaaatcac ctttatgacg gcttccatgc ttgatccacc gggcgaccgg aatcacgcag   3720
agcaaccgga atcacgcctg ggtggaccg ctcagtcgtc gggcttcctt cccgtcttcc   3780
aacgactctc tgagttctcg gtagggtatg ttggcccccct gcagtagggc tccctccgac   3840
gccactcagc ttctgccctc ctaagccgca gcccccctcta ctagggtcat cgtccgctcc   3900
ccgaataagc gagacggatg aggacaggat cgccacgccg cctgtggccg accactattc   3960
cctaacgatc acgtcggggt caccaaatga agccttctgc ttcatgcatg tgctcgtagt   4020
cgtcagggaa tcaacggtcc ggccatcaac ccaggtgcac accaatgtgg tgaatggtca   4080
aatggcgttt attgtatcga gctaggcact taaatacaat atctctgcaa tgcggaattc   4140
agtggttcgt ccaatccgtg ttagacccgt ctgttgcctt cctaacaagg cacgatcata   4200
ccacgatcat accaccttac tcccaccaat cggcatgcac ggtgcttttt ctctccttat   4260
aaggcatgtt gctaactcat cgttacataa gcatgttgca agactacaag agtattgcat   4320
aagactacat ttccccctcc ctatgcaaaa gcgaaactac tatatcctga ggggactcct   4380
aaccgcgtac aaccgaagcc ccgcttttcg cctaaacatg ctattgtccc ctcagtcaag   4440
ccttgcccgt tacaacccga ttcgcaagcc ttgccctccc cacattatcc gtagcattat   4500
ttcctagcag tcatcagagc tacagaagat actctatgct gtagccaagt ctacaagttt   4560
actattcagc gacctcctat attccgcgtg ccagccgatc aattaccaat gcgcgcttgg   4620
cgtaatcatg gtcatagctg tttcctgtgt gaaattgtta tccgctcaca attccacaca   4680
acatacgagc cggaagcata aagtgtaaag cctggggtgc ctaatgagtg agctaactca   4740
cattaattgc gttgcgctca ctgcccgctt tccagtcggg aaacctgtcg tgccagctgc   4800
attaatgaat cggccaacgc gcggggagag gcggtttgcg tattgggcgc tcttccgctt   4860
cctcgctcac tgactcgctg cgctcggtcg ttcggctgcg gcgagcggta tcagctcact   4920
caaaggcggt aatacggtta tccacagaat caggggataa cgcaggaaag aacatgtgag   4980
```

```
caaaaggcca gcaaaaggcc aggaaccgta aaaaggccgc gttgctggcg tttttccata   5040
ggctccgccc ccctgacgag catcacaaaa atcgacgctc aagtcagagg tggcgaaacc   5100
cgacaggact ataaagatac caggcgtttc cccctggaag ctccctcgtg cgctctcctg   5160
ttccgaccct gccgcttacc ggatacctgt ccgcctttct cccttcggga agcgtggcgc   5220
tttctcatag ctcacgctgt aggtatctca gttcggtgta ggtcgttcgc tccaagctgg   5280
gctgtgtgca cgaacccccc gttcagcccg accgctgcgc cttatccggt aactatcgtc   5340
ttgagtccaa cccggtaaga cacgacttat cgccactggc agcagccact ggtaacagga   5400
ttagcagagc gaggtatgta ggcggtgcta cagagttctt gaagtggtgg cctaactacg   5460
gctacactag aaggacagta tttggtatct gcgctctgct gaagccagtt accttcggaa   5520
aaagagttgg tagctcttga tccggcaaac aaaccaccgc tggtagcggt ggtttttttg   5580
tttgcaagca gcagattacg cgcagaaaaa aaggatctca agaagatcct ttgatctttt   5640
ctacggggtc tgacgctcag tggaacgaaa actcacgtta agggattttg gtcatgagat   5700
tatcaaaaag gatcttcacc tagatccttt taaattaaaa atgaagtttt aaatcaatct   5760
aaagtatata tgagtaaact tggtctgaca gttaccaatg cttaatcagt gaggcaccta   5820
tctcagcgat ctgtctattt cgttcatcca tagttgcctg actccccgtc gtgtagataa   5880
ctacgatacg ggagggctta ccatctggcc ccagtgctgc aatgataccg cgagacccac   5940
gctcaccggc tccagattta tcagcaataa accagccagc cggaagggcc gagcgcagaa   6000
gtggtcctgc aactttatcc gcctccatcc agtctattaa ttgttgccgg gaagctagag   6060
taagtagttc gccagttaat agtttgcgca acgttgttgc cattgctaca ggcatcgtgg   6120
tgtcacgctc gtcgtttggt atggcttcat tcagctccgg ttcccaacga tcaaggcgag   6180
ttacatgatc ccccatgttg tgcaaaaaag cggttagctc cttcggtcct ccgatcgttg   6240
tcagaagtaa gttggccgca gtgttatcac tcatggttat ggcagcactg cataattctc   6300
ttactgtcat gccatccgta agatgctttt ctgtgactgg tgagtactca accaagtcat   6360
tctgagaata gtgtatgcgg cgaccgagtt gctcttgccc ggcgtcaata cgggataata   6420
ccgcgccaca tagcagaact ttaaaagtgc tcatcattgg aaaacgttct tcggggcgaa   6480
aactctcaag gatcttaccg ctgttgagat ccagttcgat gtaacccact cgtgcaccca   6540
actgatcttc agcatctttt actttcacca gcgtttctgg gtgagcaaaa acaggaaggc   6600
aaaatgccgc aaaaaaggga ataagggcga cacggaaatg ttgaatactc atactcttcc   6660
tttttcaata ttattgaagc atttatcagg gttattgtct catgagcgga tacatatttg   6720
aatgtattta gaaaaataaa caaatagggg ttccgcgcac atttccccga aaagtgccac   6780
ctgacgcgcc ctgtagcggc gcattaagcg cggcgggtgt ggtggttacg cgcagcgtga   6840
ccgctacact tgccagcgcc ctagcgcccg ctcctttcgc tttcttccct tcctttctcg   6900
ccacgttcgc cggctttccc cgtcaagctc taaatcgggg gctcccttta gggttccgat   6960
ttagtgcttt acggcacctc gaccccaaaa aacttgatta gggtgatggt tcacgtagtg   7020
ggccatcgcc ctgatagacg gtttttcgcc ctttgacgtt ggagtccacg ttctttaata   7080
gtggactctt gttccaaact ggaacaacac tcaaccctat ctcggtctat tcttttgatt   7140
tataagggat tttgccgatt tcggcctatt ggttaaaaaa tgagctgatt taacaaaaat   7200
ttaacgcgaa ttttaacaaa atattaacgc ttacaatttc cattcgccat tcaggctgcg   7260
caactgttgg gaagggcgat cggtgcgggc ctcttcgcta ttacgccagc tggcgaaagg   7320
```

```
gggatgtgct gcaaggcgat taagttgggt aacgccaggg ttttcccagt cacgacgttg   7380
taaaacgacg gccagtgagc gcgtattccc taacgatcac gtcggggtca ccaaatgaag   7440
ccttctgctt catgcatgtg ctcgtagtcg tcagggaatc aacggtccgg ccatcaaccc   7500
aggtgcacac caatgtggtg aatggtcaaa tggcgtttat tgtatcgagc taggcactta   7560
aatacaatat ctctgcaatg cggaattcag tggttcgtcc aatccgtccc cctccctatg   7620
caaaagcgaa actactatat cctgagggga ctcctaaccg cgtacaaccg aagccccgct   7680
tttcgcctaa acatgctatt gtcccctcag tcaagccttg cccgttacaa cccgattcgc   7740
aagccttgcc ctccccacat tatccgtagc attatttcct agcagtcatc agagctacag   7800
aagatactct atgctgtagc caagtctaca agtttactat tcagcgacct cctatattcc   7860
gcgtgccagc cgatcaatta ccaatccaac cagctatcac acggaataca agaactcgcc   7920
tacgctcttc tttcgggctg cttataagcc tcctgtaatt tttttatatt cctcgttaag   7980
tcctcagact tggcaaggag aatgtagatt tccacagtat atatgttttc acaaaaggaa   8040
ggagagaaac aaaagaaaat ggcactgact aaacttcagc tagtggtata ggaaagtaat   8100
tctgcttaac agagattgca gtgatctcta tgtatgtcct gaagaattat gttgtacttt   8160
tttcccccat ttttaaatca aacagtgctt tacagaggtc agaatggttt ctttactgtt   8220
tgtcaattct attatttcaa tacagaacaa tagcttctat aactgaaata tatttgctat   8280
tgtatattat gattgtccct cgaaccatga acactcctcc agctgaattt cacaattcct   8340
ctgtcatctg ccaggccatt aagttattca tggaagatct ttgaggaaca ctgcaagttc   8400
atatcataaa cacatttgaa attgagtatt gttttgcatt gtatggagct atgttttgct   8460
gtatcctcag aataaaagtt tgttataaag cattcacacc cataaaaaga tagatttaaa   8520
tattccaact ataggaaaga aagtgtgtct gctcttcact ctagtctcag ttggctcctt   8580
cacatgcacg cttctttatt tctcctattt tgtcaagaaa ataataggtc aagtcttgtt   8640
ctcatttatg tcctgtctag cgtggctcag atgcacattg tacatacaag aaggatcaaa   8700
tgaaacagac ttctggtctg ttactacaac catagtaata agcacactaa ctaataattg   8760
ctaattatgt tttccatctc caaggttccc acatttttct gttttcttaa agatcccatt   8820
atctggttgt aactgaagct caatggaaca tgagcaatat ttcccagtct tctctcccat   8880
ccaacagtcc tgatggatta gcagaacagg cagaaaacac attgttaccc agaattaaaa   8940
actaatattt gctctccatt caatccaaaa tggacctatt gaaactaaaa tctaacccaa   9000
tcccattaaa tgatttctat ggtgtcaaag gtcaaacttc tgaagggaac ctgtgggtgg   9060
gtcacaattc agactatata ttccccaggg ctcagccagt gtctgtacat acagctagaa   9120
agctgtattg cctttagcag tcaagctcga aaggtaagca actctctgga attaccttct   9180
ctctatatta gctcttactt gcacctaaac tttaaaaaat taacaattat tgtgctatgt   9240
gttgtatctt taagggtgaa gtacctgcgt gataccccct ataaaaactt ctcacctgtg   9300
tatgcattct gcactatttt attatgtgta aaagctttgt gtttgttttc aggaggctta   9360
ttctttgtgc ttaaaatatg tttttaattt cagaacatct tatcctgtcg ttcactatct   9420
gatatgcttt gcagtttgct tgattaactt ctagccctac agagtgcaca gagagcaaaa   9480
tcatggtgtt cagtgaattc tggggagtta ttttaatgtg aaaattctct agaagtttaa   9540
ttcctgcaaa gtgcagctgc tgatcactac acaagataaa aatgtggggg gtgcataaac   9600
gtatattctt acaataatag atacatgtga acttatatac agaaaagaaa atgagaaaaa   9660
tgtgtgtgtg tatactcaca cacgtggtca gtaaaaactt ttgaggggtt taatacagaa   9720
```

```
aatccaatcc tgaggcccca gcactcagta cgcatataaa gggctgggct ctgaaggact   9780

tctgactttc acagattata taaatctcag gaaagcaact agattcatgc tggctccaaa   9840

agctgtgctt tatataagca cactggctat acaatagttg tacagttcag ctctttataa   9900

tagaaacaga cagaacaagt ataaatcttc tattggtcta tgtcatgaac aagaattcat   9960

tcagtggctc tgttttatag taaacattgc tattttatca tgtctgcatt tctcttctgt  10020

ctgaatgtca ccactaaaat ttaactccac agaaagttta tactacagta cacatgcata  10080

tctttgagca aagcaaacca tacctgaaag tgcaatagag cagaatatga attacatgcg  10140

tgtctttctc ctagactaca tgaccccata taaattacat tccttatcta ttctgccatc  10200

accaaaacaa aggtaaaaat acttttgaag atctactcat agcaagtagt gtgcaacaaa  10260

cagatatttc tctacattta tttttaggga ataaaaataa gaaataaaat agtcagcaag  10320

cctctgcttt ctcatatatc tgtccaaacc taaagtttac tgaaatttgc tctttgaatt  10380

tccagttttg caagcctatc agattgtgtt ttaatcagag gtactgaaaa gtatcaatga  10440

attctagctt tcactgaaca aaaatatgta gaggcaactg gcttctggga cagtttgcta  10500

cccaaaagac aactgaatgc aaatacataa atagatttat gaatatggtt ttgaacatgc  10560

acatgagagg tggatatagc aacagacaca ttaccacaga attactttaa aactacttgt  10620

taacatttaa ttgcctaaaa actgctcgta atttactgtt gtagcctacc atagagtacc  10680

ctgcatggta ctatgtacag cattccatcc ttacattttc actgttctgc tgtttgctct  10740

agacaactca gagttcacca tg                                            10762
```

<210> SEQ ID NO 9
<211> LENGTH: 242
<212> TYPE: DNA
<213> ORGANISM: Artificial Sequence
<220> FEATURE:
<223> OTHER INFORMATION: Adaptor sequence

<400> SEQUENCE: 9

```
cccgggttgt taacatttaa ttgcctaaaa actgctcgta atttactgtt gtagcctacc     60

atagagtacc ctgcatggta ctatgtacag cattccatcc ttacattttc actgttctgc    120

tgtttgctct agacaactca gagttcacca tgaaaatgcg gttcttgggg ttggtggtct    180

gtttggttct ctggaccctg cattccgagg ggtccggagg gaaactgaca gctgtggatc    240

ct                                                                   242
```

<210> SEQ ID NO 10
<211> LENGTH: 1575
<212> TYPE: DNA
<213> ORGANISM: Artificial Sequence
<220> FEATURE:
<223> OTHER INFORMATION: Syn SBC102

<400> SEQUENCE: 10

```
ccattatctg gttgtaactg aagctcaatg gaacatgagc aatatttccc agtcttctct     60

cccatccaac agtcctgatg gattagcaga acaggcagaa aacacattgt tacccagaat    120

taaaaactaa tatttgctct ccattcaatc caaaatggac ctattgaaac taaaatctaa    180

cccaatccca ttaaatgatt tctatggtgt caaaggtcaa acttctgaag ggaacctgtg    240

ggtgggtcac aattcagact atatattccc cagggctcag ccagtgtctg tacatacagc    300

tagaaagctg tattgccttt agcagtcaag ctcgaaagac aactcagagt tcaccatgaa    360
```

```
aatgcggttc ttggggttgg tggtctgttt ggttctctgg accctgcatt ccgaggggtc    420

cggagggaaa ctgacagctg tggatcctga aacaaacatg aatgtcagtg aaattatctc    480

ttactgggga ttccctagtg aggaatacct agttgagaca gaagatggat atattctgtg    540

ccttaaccga attcctcatg ggaggaagaa ccattctgac aaaggtccca aaccagttgt    600

cttcctgcaa catggcttgc tggcagattc tagtaactgg gtcacaaacc ttgccaacag    660

cagcctgggc ttcattcttg ctgatgctgg ttttgacgtg tggatgggca acagcagagg    720

aaatacctgg tctcggaaac ataagacact ctcagtttct caggatgaat tctgggcttt    780

cagttatgat gagatggcaa aatatgacct accagcttcc attaacttca ttctgaataa    840

gactggccaa gaacaagtgt attatgtggg tcattctcaa ggcaccacta taggttttat    900

agcattttca cagatccctg agctggctaa aaggattaaa atgttttttg ccctgggtcc    960

tgtggcttcc gtcgccttct gtactagccc tatggccaaa ctgggacgac tgccagatca   1020

tctcattaag gacctctttg gagacaaaga atttcttccc cagagtgcgt tttgaagtg    1080

gctgggtacc cacgtttgca ctcatgtcat actgaaggag ctctgtggaa atctctgttt   1140

tcttctgtgt ggatttaatg agagaaattt aaatatgtct agagtggatg tgtatacaac   1200

acattctcct gctggaactt ctgtgcaaaa catgttacac tggagccagg ctgttaaatt   1260

ccaaaagttt caagcctttg actggggaag cagtgccaag aattattttc attacaacca   1320

gagttatcct cccacataca atgtgaagga catgcttgtg ccgactgcag tctggagcgg   1380

gggtcacgac tggcttgcag atgtctacga cgtcaatatc ttactgactc agatcaccaa   1440

cttggtgttc catgagagca ttccggaatg ggagcatctt gacttcattt ggggcctgga   1500

tgccccttgg aggctttata ataagattat taatctaatg aggaaatatc agtgattcga   1560

agcggccgcc ccggg                                                    1575
```

<210> SEQ ID NO 11
<211> LENGTH: 2789
<212> TYPE: DNA
<213> ORGANISM: Artificial Sequence
<220> FEATURE:
<223> OTHER INFORMATION: OVR1 promoter

<400> SEQUENCE: 11

```
ctcgagtctc ttcagaatgg cacagcaccg ctgcagaaaa atgccaggtg gactatgaac     60

tcacatccaa aggagcttga cctgatacct gattttcttc aaacagggga aacaacacaa    120

tcccacaaaa cagctcagag agaaaccatc actgatggct acagcaccaa ggtatgcaat    180

ggcaatccat tcgacattca tctgtgacct gagcaaaatg atttatctct ccatgaatgg    240

ttgcttcttt ccctcatgaa aaggcaattt ccacactcac aatatgcaac aaagacaaac    300

agagaacaat taatgtgctc cttcctaatg ttaaaattgt agtggcaaag aggagaacaa    360

aatctcaagt tctgagtagg ttttagtgat tggataagag gctttgacct gtgagctcac    420

ctggacttca tatccttttg gataaaaagt gcttttataa ctttcaggtc tccgagtctt    480

tattcatgag actgttggtt tagggacaga cccacaatga aatgcctggc ataggaaagg    540

gcagcagagc cttagctgac cttttcttgg gacaagcatt gtcaaacaat gtgtgacaaa    600

actatttgta ctgctttgca cagctgtgct gggcagggca atccattgcc acctatccca    660

ggtaaccttc caactgcaag aagattgttg cttactctct ctagaccccc aagtcaaacc    720

aactatgcag gtatgctgac aacactatga tgacagcctg ttctgatcaa gatctcattt    780

gttcatggac aatttttgtt gcttgcagct ggtcttccat tgggaaagag tgtagtatat    840
```

```
ccttctcatc tgacagaaaa gcagaaattc tcatgctcca cacttaatct acattgtttt    900

aaaccaccgg ctacttcttg gagaggaaaa atggctttta taagactcac aaaacaaagc    960

tctgcaagtc aaatgcatac aaaactgttc tgtaggtctg gaatcaggac actatgtgga   1020

agtcaaatag agcagcttta aaaagccttt gggatcattc tcatcttata tttgcagcac   1080

gatactatga cagtgataac tgacataact gcatcaattt ccttgatatt ttatttgtct   1140

taaagtacaa gacatagaga tggacgtaaa gatggacata tgactcaggt ctggacaggt   1200

ccgtggtcca tgtatgataa aagagatgaa gggaaggaga attgagactg tctaagaagg   1260

gcttcaggga cgttctgaag gcagatttga ctgaatcaga tgtactgtcc aagtctcata   1320

tgtagcaatg gaaggctgat attggagaaa tataaagaaa tggctgtgaa ctcaaagtga   1380

ccctgaacag aaaagggata tggagttaaa ataatgtcac agaactgagg tttatatgat   1440

ataccatggg ctgcagaggg tcagagtgct ccaccatggg cctctcttgg gctgcaggga   1500

acttctgttc tacacctgga acacctcctg ccctcctccg cactgacctc agtgtcatca   1560

gggctgtttc tctcacattt tctcactcac ctctcccaac taccattgta cagcagttgt   1620

tcttacatat tgctcctcct gaggtacatc tagcatcgtt aagtcctcag acttggcaag   1680

gagaatgtag atttccacag tatatatgtt ttcacaaaag gaaggagaga aacaaaagaa   1740

aatggcactg actaaacttc agctagtggt ataggaaagt aattctgctt aacagagatt   1800

gcagtgatct ctatgtatgt cctgaagaat tatgttgtac ttttttcccc catttttaaa   1860

tcaaacagtg ctttacagag gtcagaatgg tttctttact gtttgtcaat tctattattt   1920

caatacagaa caatagcttc tataactgaa atatatttgc tattgtatat tatgattgtc   1980

cctcgaacca tgaacactcc tccagctgaa tttcacaatt cctctgtcat ctgccaggcc   2040

attaagttat tcatggaaga tctttgagga acactgcaag ttcatatcat aaacacattt   2100

gaaattgagt attgttttgc attgtatgga gctatgtttt gctgtatcct cagaataaaa   2160

gtttgttata aagcattcac acccataaaa agatagattt aaatattcca actataggaa   2220

agaaagtgtg tctgctcttc actctagtct cagttggctc cttcacatgc acgcttcttt   2280

atttctccta ttttgtcaag aaaataatag gtcaagtctt gttctcattt atgtcctgtc   2340

tagcgtggct cagatgcaca ttgtacatac aagaaggatc aaatgaaaca gacttctggt   2400

ctgttactac aaccatagta ataagcacac taactaataa ttgctaatta tgttttccat   2460

ctccaaggtt cccacatttt tctgttttct taaagatccc attatctggt tgtaactgaa   2520

gctcaatgga acatgagcaa tatttcccag tcttctctcc catccaacag tcctgatgga   2580

ttagcagaac aggcagaaaa cacattgtta cccagaatta aaaactaata tttgctctcc   2640

attcaatcca aaatggacct attgaaacta aaatctaacc caatcccatt aaatgatttc   2700

tatggtgtca aaggtcaaac ttctgaaggg aacctgtggg tgggtcacaa ttcagactat   2760

atattcccca gggctcagcc agtgtctgt                                     2789
```

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12

```
agaaactgag agtgtcttat                                                 20
```

<210> SEQ ID NO 13
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 13
tgacagctgt ggatccagaa acaaacatg 29

<210> SEQ ID NO 14
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 14
gccgctcgag cgaggaatat aaaaaaatt 29

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
tccgcgcaca tttccccgaa 20

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 16
acgactggct tgcagatgtc t 21

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
ccccaaatga agtcaagatg ct 22

<210> SEQ ID NO 18
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 18
ccggaatgct ctcatggaac accaa 25

<210> SEQ ID NO 19
<211> LENGTH: 372
<212> TYPE: PRT
<213> ORGANISM: HOMO SAPIENS

<400> SEQUENCE: 19

```
Ala Val Asp Pro Glu Thr Asn Met Asn Val Ser Glu Ile Ile Ser Tyr
1               5                   10                  15

Trp Gly Phe Pro Ser Glu Glu Tyr Leu Val Glu Thr Glu Asp Gly Tyr
            20                  25                  30

Ile Leu Cys Leu Asn Arg Ile Pro His Gly Arg Lys Asn His Ser Asp
        35                  40                  45

Lys Gly Pro Lys Pro Val Val Phe Leu Gln His Gly Leu Leu Ala Asp
    50                  55                  60

Ser Ser Asn Trp Val Thr Asn Leu Ala Asn Ser Ser Leu Gly Phe Ile
65                  70                  75                  80

Leu Ala Asp Ala Gly Phe Asp Val Trp Met Gly Asn Ser Arg Gly Asn
                85                  90                  95

Thr Trp Ser Arg Lys His Lys Thr Leu Ser Val Ser Gln Asp Glu Phe
            100                 105                 110

Trp Ala Phe Ser Tyr Asp Glu Met Ala Lys Tyr Asp Leu Pro Ala Ser
        115                 120                 125

Ile Asn Phe Ile Leu Asn Lys Thr Gly Gln Glu Gln Val Tyr Tyr Val
    130                 135                 140

Gly His Ser Gln Gly Thr Thr Ile Gly Phe Ile Ala Phe Ser Gln Ile
145                 150                 155                 160

Pro Glu Leu Ala Lys Arg Ile Lys Met Phe Phe Ala Leu Gly Pro Val
                165                 170                 175

Ala Ser Val Ala Phe Cys Thr Ser Pro Met Ala Lys Leu Gly Arg Leu
            180                 185                 190

Pro Asp His Leu Ile Lys Asp Leu Phe Gly Asp Lys Glu Phe Leu Pro
        195                 200                 205

Gln Ser Ala Phe Leu Lys Trp Leu Gly Thr His Val Cys Thr His Val
    210                 215                 220

Ile Leu Lys Glu Leu Cys Gly Asn Leu Cys Phe Leu Leu Cys Gly Phe
225                 230                 235                 240

Asn Glu Arg Asn Leu Asn Met Ser Arg Val Asp Val Tyr Thr Thr His
                245                 250                 255

Ser Pro Ala Gly Thr Ser Val Gln Asn Met Leu His Trp Ser Gln Ala
            260                 265                 270

Val Lys Phe Gln Lys Phe Gln Ala Phe Asp Trp Gly Ser Ser Ala Lys
        275                 280                 285

Asn Tyr Phe His Tyr Asn Gln Ser Tyr Pro Pro Thr Tyr Asn Val Lys
    290                 295                 300

Asp Met Leu Val Pro Thr Ala Val Trp Ser Gly Gly His Asp Trp Leu
305                 310                 315                 320

Ala Asp Val Tyr Asp Val Asn Ile Leu Leu Thr Gln Ile Thr Asn Leu
                325                 330                 335

Val Phe His Glu Ser Ile Pro Glu Trp Glu His Leu Asp Phe Ile Trp
            340                 345                 350

Gly Leu Asp Ala Pro Trp Arg Leu Tyr Asn Lys Ile Ile Asn Leu Met
        355                 360                 365

Arg Lys Tyr Gln
    370
```

<210> SEQ ID NO 20
<211> LENGTH: 399
<212> TYPE: PRT
<213> ORGANISM: HOMO SAPIENS

<400> SEQUENCE: 20

```
Met Lys Met Arg Phe Leu Gly Leu Val Val Cys Leu Val Leu Trp Thr
1               5                   10                  15

Leu His Ser Glu Gly Ser Gly Gly Lys Leu Thr Ala Val Asp Pro Glu
            20                  25                  30

Thr Asn Met Asn Val Ser Glu Ile Ile Ser Tyr Trp Gly Phe Pro Ser
        35                  40                  45

Glu Glu Tyr Leu Val Glu Thr Glu Asp Gly Tyr Ile Leu Cys Leu Asn
    50                  55                  60

Arg Ile Pro His Gly Arg Lys Asn His Ser Asp Lys Gly Pro Lys Pro
65                  70                  75                  80

Val Val Phe Leu Gln His Gly Leu Leu Ala Asp Ser Ser Asn Trp Val
                85                  90                  95

Thr Asn Leu Ala Asn Ser Ser Leu Gly Phe Ile Leu Ala Asp Ala Gly
            100                 105                 110

Phe Asp Val Trp Met Gly Asn Ser Arg Gly Asn Thr Trp Ser Arg Lys
        115                 120                 125

His Lys Thr Leu Ser Val Ser Gln Asp Glu Phe Trp Ala Phe Ser Tyr
    130                 135                 140

Asp Glu Met Ala Lys Tyr Asp Leu Pro Ala Ser Ile Asn Phe Ile Leu
145                 150                 155                 160

Asn Lys Thr Gly Gln Glu Gln Val Tyr Tyr Val Gly His Ser Gln Gly
                165                 170                 175

Thr Thr Ile Gly Phe Ile Ala Phe Ser Gln Ile Pro Glu Leu Ala Lys
            180                 185                 190

Arg Ile Lys Met Phe Phe Ala Leu Gly Pro Val Ala Ser Val Ala Phe
        195                 200                 205

Cys Thr Ser Pro Met Ala Lys Leu Gly Arg Leu Pro Asp His Leu Ile
    210                 215                 220

Lys Asp Leu Phe Gly Asp Lys Glu Phe Leu Pro Gln Ser Ala Phe Leu
225                 230                 235                 240

Lys Trp Leu Gly Thr His Val Cys Thr His Val Ile Leu Lys Glu Leu
                245                 250                 255

Cys Gly Asn Leu Cys Phe Leu Leu Cys Gly Phe Asn Glu Arg Asn Leu
            260                 265                 270

Asn Met Ser Arg Val Asp Val Tyr Thr Thr His Ser Pro Ala Gly Thr
        275                 280                 285

Ser Val Gln Asn Met Leu His Trp Ser Gln Ala Val Lys Phe Gln Lys
    290                 295                 300

Phe Gln Ala Phe Asp Trp Gly Ser Ser Ala Lys Asn Tyr Phe His Tyr
305                 310                 315                 320

Asn Gln Ser Tyr Pro Pro Thr Tyr Asn Val Lys Asp Met Leu Val Pro
                325                 330                 335

Thr Ala Val Trp Ser Gly Gly His Asp Trp Leu Ala Asp Val Tyr Asp
            340                 345                 350

Val Asn Ile Leu Leu Thr Gln Ile Thr Asn Leu Val Phe His Glu Ser
        355                 360                 365

Ile Pro Glu Trp Glu His Leu Asp Phe Ile Trp Gly Leu Asp Ala Pro
    370                 375                 380

Trp Arg Leu Tyr Asn Lys Ile Ile Asn Leu Met Arg Lys Tyr Gln
385                 390                 395
```

LYSOSOMAL STORAGE DISEASE ENZYMES

RELATED APPLICATIONS

This application is a continuation of U.S. patent application Ser. No. 16/506,558, filed Jul. 9, 2019, which is a continuation of U.S. patent application Ser. No. 15/429,247, filed on Feb. 10, 2017, which is a continuation of U.S. patent application Ser. No. 15/285,025, filed on Oct. 4, 2016, which is a continuation of U.S. patent application Ser. No. 15/177,867, filed on Jun. 9, 2016, which is a continuation of U.S. patent application Ser. No. 13/642,790, filed on Apr. 30, 2013, which is a U.S. national stage of PCT/US2011/033699, filed Apr. 23, 2011, which claims the benefit of U.S. Provisional Application No. 61/343,177, filed on Apr. 23, 2010, U.S. Provisional Application No. 61/396,376, filed on May 26, 2010, U.S. Provisional Application No. 61/403,011, filed on Sep. 9, 2010, U.S. Provisional Application No. 61/456,014, filed on Oct. 29, 2010, U.S. Provisional Application No. 61/432,372, filed on Jan. 13, 2011. The entire teachings of the above applications are incorporated herein by reference.

SEQUENCE LISTING

The instant application contains a Sequence Listing, which has been submitted electronically in ASCII format and is hereby incorporated by reference in its entirety. Said ASCII copy, created on Dec. 14, 2017 is named 079-WO_Sequence Listing Final_ST25.txt and is 67.1 KB bytes in size.

BACKGROUND OF THE INVENTION

Lysosomal Acid Lipase (LAL) deficiency is a very rare lysosomal storage disease (LSD) characterized by a failure to breakdown cholesteryl esters (CE) and triglycerides (TAG) in lysosomes due to a deficiency of the enzyme. LAL deficiency resembles other lysosomal storage disorders with the accumulation of substrate in a number of tissues and cell types. In LAL deficiency substrate accumulation is most marked in cells of the reticuloendothelial system including Kupffer cells in the liver, histiocytes in the spleen and in the lamina propria of the small intestine. Reticuloendothelial cells express the macrophage mannose/N-acetylglucosamine receptor (also known as macrophage mannose receptor or MMR, CD206), which mediates binding, cell uptake and lysosomal internalization of proteins with GlcNAc or mannose terminated N-glycans, and provides a pathway for the potential correction of the enzyme deficiency in these key cell types.

LAL deficiency is a multi-system disease that most commonly manifests with gastrointestinal, liver and cardiovascular complications and is associated with significant morbidity and mortality. The clinical effects of LAL deficiency are due to a massive accumulation of lipid material in the lysosomes in a number of tissues and a profound disturbance in cholesterol and lipid homeostatic mechanisms, including substantial increases in hepatic cholesterol synthesis. LAL deficiency presents of at least two phenotypes, Wolman Disease (WD) and Cholesteryl Ester Storage Disease (CESD).

Wolman Disease is the most aggressive presentation of LAL deficiency. This phenotype is characterized by gastrointestinal and hepatic manifestations including growth failure, malabsorption, steatorrhea, profound weight loss and hepatomegaly. Wolman Disease is rapidly progressive and fatal usually within the first year of life. Case report review indicates survival beyond 12 months of age is highly unusual for patients who present with growth failure due to LAL deficiency in the first year of life. In this most aggressive form, growth failure is the predominant clinical feature and is a key contributor to the early mortality. Hepatic involvement as evidenced by liver enlargement and elevation of transaminases is also common in infants. Physical findings include abdominal distention with hepatomegaly and splenomegaly, and radiographic examination often reveals calcification of the adrenal glands. Laboratory evaluations typically reveal elevated levels of serum transaminases and absent or markedly reduced LAL enzyme activity. Elevated blood levels of cholesterol and triglycerides are also seen in patients.

Current treatment options for Wolman Disease are extremely limited. Antibiotics are administered to infants with pyrexia and/or evidence of infection. Steroid replacement therapy for adrenal insufficiency and specialized nutritional support may be prescribed and while there is no evidence that these interventions prevents death, it is also unclear at present if they have an impact on short term survival. In a series of four patients with LAL deficiency treated with bone marrow transplantation, all four patients died due to complications of the procedure within months of transplantation.

Patients with LAL deficiency can also present later in life with predominant liver and cardiovascular involvement and this is often called Cholesteryl Ester Storage Disease (CESD). In CESD, the liver is severely affected with marked hepatomegaly, hepatocyte necrosis, elevation of transaminases, cirrhosis and fibrosis. Due to the increased levels of CE and TG, hyperlipidemia and accelerated atherosclerosis are also seen in LAL deficiency. Particularly, an accumulation of fatty deposits on the artery walls is described early in life. The deposits narrow the arterial lumen and can lead to vessel occlusion increasing the risk of significant cardiovascular events including myocardial infarction and strokes. The presentation of CESD is highly variable with some patients going undiagnosed until complications manifest in late adulthood, while others can have liver dysfunction presenting in early childhood. CESD is associated with shortened lifespan and significant ill health; the life expectancy of those with CESD depends on the severity of the associated complications.

Current treatment options for the CESD phenotype are focused on controlling lipid accumulation through diet that excludes foods rich in cholesterol and triglycerides and suppression of cholesterol synthesis and apolipoprotein B production through administration of cholesterol lowering drugs. Although some clinical improvement may be seen, the underlying disease manifestations persist and disease progression still occurs.

In most cases, therapy for LAL deficiencies requires life-long treatment. In addition, due to the high cost of protein therapeutics, it is desirable to administer a minimum effective amount of therapeutic to treat LAL deficiency. However, to date, there is no effective therapy for treating LAL deficiency, particularly the patients suffering from Wolman Disease and CESD. Therefore, there is a strong need for an effective therapy with a minimized frequency of administration in order to improve the quality of life for patients. There is also a need for a high expressing and robust protein production platform which can produce LAL proteins that are stable and efficiently targeted to the lysosomal compartment in the affected tissue cells in patients.

SUMMARY OF THE INVENTION

Disclosed herein are compositions of LAL which are particularly suited for use in therapy, for example, for treatment of conditions associated with LAL deficiency. The LAL molecules described herein contain particular glycan structures which afford efficient and rapid uptake into lysosomes of cells when administered into a subject, for example, a human subject.

In one aspect, the compositions disclosed herein comprise human LAL wherein a substantial percentage of the human LAL contain at least one mannose-6-phosphate glycan moiety, which can serve as a ligand for internalization by the mannose-6-phosphate receptor on the surface of cells found, for example, on hepatocytes. In one embodiment, 30% or more, for example, at least 30%, at least 40%, at least 50%, at least 60%, at least 70%, at least 80%, at least 90%, at least 95%, at least 97%, or at least 99%, of the LAL contained in the composition contains at least one mannose-6-phosphate moiety. The mannose-6-phosphate moiety can be found, for example, on an N-glycan structure located at one or more residues selected from the group consisting of $Asn^{15}$, $Asn^{51}$, $Asn^{80}$, $Asn^{140}$, $Asn^{252}$ and $Asn^{300}$ of SEQ ID NO:2.

In another aspect, the compositions disclosed herein comprise human LAL wherein a substantial percentage of the human LAL does not contain a sialic acid moiety in any of its N-glycan structures, which can sometimes interfere with internalization of the enzyme into cells. In one embodiment, 15% or less, for example, 10% or less, 5% or less, 2% or less, 1% or less, or essentially none, of the LAL contained in the composition contains a sialic acid moiety in any of its N-glycan structures.

In another aspect, the compositions disclosed herein comprise human LAL wherein a substantial percentage of the human LAL does not contain a fucose moiety in any of its N-glycan structures. In one embodiment, 50% or less, for example, 50% or less, 40% or less, 30% or less, 20% or less, 10% or less, 5% or less, 2% or less, 1% or less, or essentially none, of the LAL contained in the composition contains a fucose moiety in any of its N-glycan structures.

In yet another aspect, vectors, host cells, expression systems and associated methods suitable for producing the LAL-containing compositions are described.

Typically, the LAL of the invention discussed and disclosed herein is human LAL. In one embodiment, the composition comprising LAL includes the mature LAL having the amino acid sequence of:

```
                                            (SEQ ID NO: 2)
SGGKLTAVDPETNMNVSEIISYWGFPSEEYLVETEDGYILCLNRIPHGRK
NHSDKGPKPVVFLQHGLLADSSNWVTNLANSSLGFILADAGFDVWMGNSR
GNTWSRKHKTLSVSQDEFWAFSYDEMAKYDLPASINFILNKTGQEQVYYV
GHSQGTTIGFIAFSQIPELAKRIKMFFALGPVASVAFCTSPMAKLGRLPD
HLIKDLFGDKEFLPQSAFLKWLGTHVCTHVILKELCGNLCFLLCGFNERN
LNMSRVDVYTTHSPAGTSVQNMLHWSQAVKFQKFQAFDWGSSAKNYFHYN
QSYPPTYNVKDMLVPTAVWSGGHDWLADVYDVNILLTQITNLVFHESIPE
WEHLDFIWGLDAPWRLYNKIINLMRKYQ.
```

In another embodiment, the mature LAL has the amino acid sequence of:

```
                                            (SEQ ID NO: 3)
GKLTAVDPETNMNVSEIISYWGFPSEEYLVETEDGYILCLNRIPHGRKNH
SDKGPKPVVFLQHGLLADSSNWVTNLANSSLGFILADAGFDVWMGNSRGN
TWSRKHKTLSVSQDEFWAFSYDEMAKYDLPASINFILNKTGQEQVYYVGH
SQGTTIGFIAFSQIPELAKRIKMFFALGPVASVAFCTSPMAKLGRLPDHL
IKDLFGDKEFLPQSAFLKWLGTHVCTHVILKELCGNLCFLLCGFNERNLN
MSRVDVYTTHSPAGTSVQNMLHWSQAVKFQKFQAFDWGSSAKNYFHYNQS
YPPTYNVKDMLVPTAVWSGGHDWLADVYDVNILLTQITNLVFHESIPEWE
HLDFIWGLDAPWRLYNKIINLMRKYQ.
```

In another embodiment, the mature LAL has the amino acid sequence of:

```
                                            (SEQ ID NO: 4)
TAVDPETNMNVSEIISYWGFPSEEYLVETEDGYILCLNRIPHGRKNHSDK
GPKPVVFLQHGLLADSSNWVTNLANSSLGFILADAGFDVWMGNSRGNTWS
RKHKTLSVSQDEFWAFSYDEMAKYDLPASINFILNKTGQEQVYYVGHSQG
TTIGFIAFSQIPELAKRIKMFFALGPVASVAFCTSPMAKLGRLPDHLIKD
LFGDKEFLPQSAFLKWLGTHVCTHVILKELCGNLCFLLCGFNERNLNMSR
VDVYTTHSPAGTSVQNMLHWSQAVKFQKFQAFDWGSSAKNYFHYNQSYPP
TYNVKDMLVPTAVWSGGHDWLADVYDVNILLTQITNLVFHESIPEWEHLD
FIWGLDAPWRLYNKIINLMRKYQ.
```

In another embodiment, the mature LAL has the amino acid sequence of:

```
                                            (SEQ ID NO: 19)
AVDPETNMNVSEIISYWGFPSEEYLVETEDGYILCLNRIPHGRKNHSDKG
PKPVVFLQHGLLADSSNWVTNLANSSLGFILADAGFDVWMGNSRGNTWSR
KHKTLSVSQDEFWAFSYDEMAKYDLPASINFILNKTGQEQVYYVGHSQGT
TIGFIAFSQIPELAKRIKMFFALGPVASVAFCTSPMAKLGRLPDHLIKDL
FGDKEFLPQSAFLKWLGTHVCTHVILKELCGNLCFLLCGFNERNLNMSRV
DVYTTHSPAGTSVQNMLHWSQAVKFQKFQAFDWGSSAKNYFHYNQSYPPT
YNVKDMLVPTAVWSGGHDWLADVYDVNILLTQITNLVFHESIPEWEHLDF
IWGLDAPWRLYNKIINLMRKYQ.
```

In another embodiment, the mature LAL is a mixture of at least two polypeptides selected from the group consisting of: SEQ ID NO:2, SEQ ID NO:3, SEQ ID NO:4, and SEQ ID NO:19.

The invention also provides for compositions which contain isolated mixtures of an individual type of useful protein molecule, such as those proteins disclosed herein, where one or more of the protein molecules contained in the mixture has a specific oligosaccharide structure attached, in particular an oligosaccharide structure disclosed herein. For example, the invention provides for isolated mixtures of LAL molecules, for example, human LAL molecules which contain an LAL molecule glycosylated with one or more of the following structures A-n to O-n:

A-n
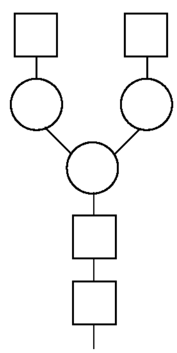
B-n
C-n
D-n
-continued
E-n
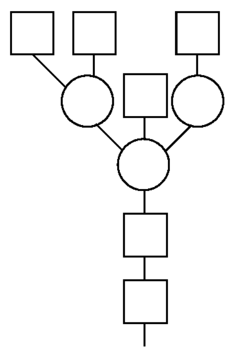
F-n
G-n
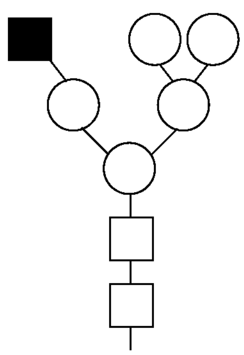
H-n

-continued

I-n

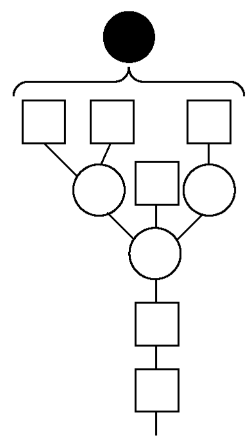

J-n

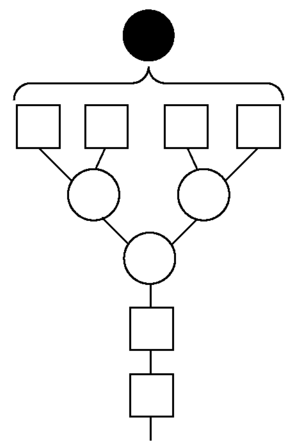

K-n

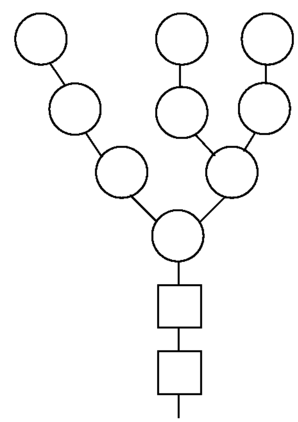

L-n

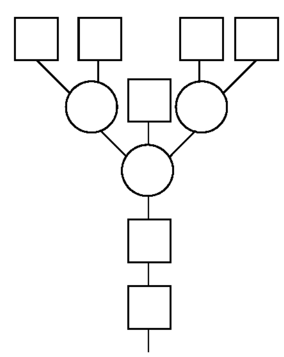

-continued

M-n

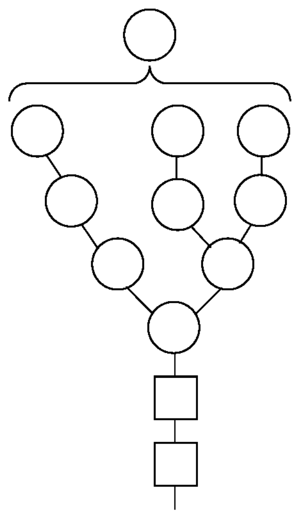

N-n

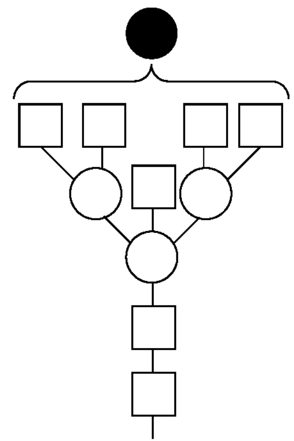

O-n

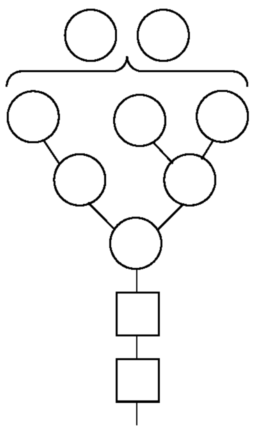

Square = N-Acetyl Glucosamine
Filled Square = Mannose-6-Phosphate
Circle = Mannose
Filled Circle = Galactose
Filled Triangle = Fucose According to one aspect of the present invention, a composition comprises any isolated individual or combination of the polypeptides described above. In one embodiment, the composition can be a pharmaceutical composition, for example, a formulation that further comprises pharmaceutically acceptable carriers, such that the composition is, for example, suitable for administration into a subject (e.g., a human, particularly a patient suffering from or diagnosed with a condition). The composition can be administered any number of ways, including by intravenous administration. In another embodiment, the composition can further comprise a second agent. Such an agent can be a medicament, or an agent which can influence or modify a biological process when administered into a subject. For example, the second agent can be an immunomodulatory agent. Such immunomodulatory agents can include any agent which, when administered together (i.e., administered at the same time as, or shortly before or after) with any of the LAL compositions described herein, may have the effect of reducing the immunogenicity of the LAL composition in the subject (e.g., Rituximab, or any other B-cell depleting antibody).

In a final aspect, methods and compositions for the treatment of symptoms associated with LAL deficiency are disclosed.

Additional objects and aspects of the present invention will become more apparent upon review of the detailed description set forth below when taken in conjunction with the accompanying figures and sequences.

BRIEF DESCRIPTION OF THE DRAWINGS

FIG. 1 depicts the amino acid sequences of human LAL. The amino acid sequence of the recombinant hLAL shows 100% homologous to that of natural human LAL. The mature form of hLAL is underlined.

FIG. 2 depicts the nucleotide sequence of recombinant hLAL, the rhLAL transgene of pALVIN-OVR1-I-hLAL-dSA.

FIG. 3A depicts a diagram of human LAL retrovirus expression vector used in the production of transducing particles is diagrammed (the DNA sequence of the plasmid is located in Appendix A). FIG. 3A depicts pALVIN-OVR1-I-hLAL-dSA proviral region that has been integrated into the genome. SIN LTR, self-inactivating long terminal repeat; OV DHSIII enhancer, DNase hypersensitive site III of the ovalbumin gene; OV Intron; ovalbumin 5' untranslated region and intron 1; hLAL, human LAL cDNA; OV 3' UTR, ovalbumin gene 3' untranslated region; partial gag, partial gag gene; LTR, long terminal repeat.

FIGS. 4A-4D depicts a nucleotide sequence of pALVIN-OVR1-I-hLAL-dSA.

FIGS. 5A-5C depicts a nucleotide sequence of pALVIN-OVR1-I-hLAL-dSA proviral region that has been integrated into the genome.

FIGS. 6A-6D depicts a nucleotide sequence of pALVIN-OV-1.1-I vector.

FIG. 7 depicts a nucleotide sequence of rhLAL adaptor.

FIG. 8 depicts a nucleotide sequence of rhLAL including the partial ovalbumin promoter.

FIG. 9 depicts a nucleotide sequence of OVR1 promoter.

FIG. 12A illustrates schematic of the integrated transgene and flanking genomic regions is shown with the known position of the transgene BlpI site and predicted position of the flanking genomic BlpI sites. The position of the OV promoter probe and the hLAL coding sequence probe (hLAL probe) are indicated by the black bars. The positions of the 4.3 kb and 10.6 kb bands detected in the Southern analysis are shown as well as the predicted sizes of the genomic and transgene portions of the 4.3 kb and 10.6 kb bands. FIG. 12B illustrates a Southern blot of genomic DNA digested with BlpI and probed with the OV probe. WT CTRL is genomic DNA isolated from a non-transgenic chicken. The ID numbers of the G1 transgenics are indicated above the lanes. The position and size (kb) of the molecular weight markers are shown to the left of the blot. The position and size of the detected transgene fragment (4.3 kb) and endogenous ovalbumin gene (4.1 kb) are shown to the right of the blot. FIG. 12C depicts a Southern blot was probed with the hLAL probe. The position and size of the detected transgene fragment (10.6 kb) is shown to the right of the blot. FIG. 12D depicts a section of the image shown in FIG. 12B at a larger scale to demonstrate the presence of the 4.1 and 4.3 kb bands.

DETAILED DESCRIPTION OF THE INVENTION

Definitions

Figure 3A:
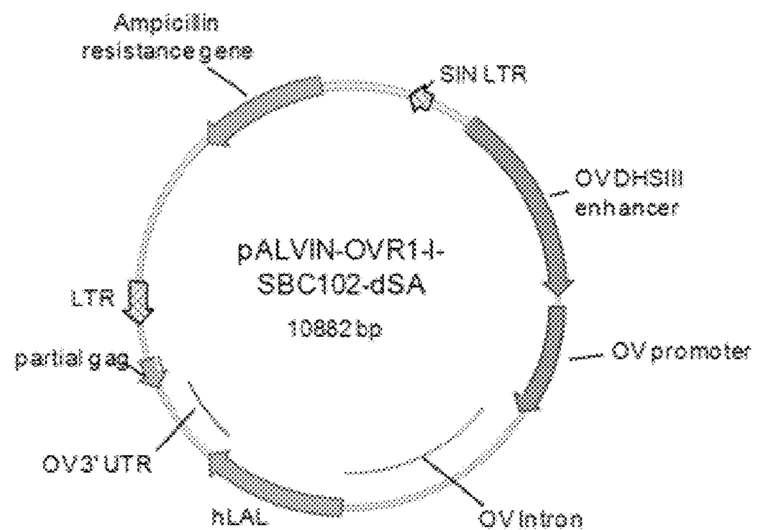
FIGS. 3A and 3B depict diagrams of pALVIN-OVR1-I-hLAL-dSA and its proviral region.

Certain definitions are set forth herein to illustrate and define the meaning and scope of the various terms used to describe the invention herein.

As used herein, the term "acceptable" with respect to a formulation, composition or ingredient, as used herein, means having no persistent detrimental effect on the general health of the subject being treated.

As used herein, the term "administration" or "administering" refers to providing a recombinant human lysosomal acid lipase of the invention to a subject in need of treatment.

A "nucleic acid or polynucleotide sequence" includes, but is not limited to, eukaryotic mRNA, cDNA, genomic DNA, and synthetic DNA and RNA sequences, comprising the natural nucleoside bases adenine, guanine, cytosine, thymidine, and uracil. The term also encompasses sequences having one or more modified bases.

The term "avian" as used herein refers to any species, subspecies or race of organism of the taxonomic class ava, such as, but not limited to chicken, turkey, duck, goose, quail, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, N.H., R.I., Australorp, Minorca, Amrox, Calif. Gray), as well as strains of turkeys, pheasants, quails, duck, ostriches and other poultry commonly bred in commercial quantities. It also includes an individual avian organism in all stages of development, including embryonic and fetal stages.

"Therapeutic proteins" or "pharmaceutical proteins" include an amino acid sequence which in whole or in part makes up a drug.

A "coding sequence" or "open reading frame" refers to a polynucleotide or nucleic acid sequence which can be transcribed and translated (in the case of DNA) or translated (in the case of mRNA) into a polypeptide in vitro or in vivo when placed under the control of appropriate regulatory sequences. The boundaries of the coding sequence are determined by a translation start codon at the 5' (amino) terminus and a translation stop codon at the 3' (carboxy) terminus. A transcription termination sequence is usually located 3' to the coding sequence. A coding sequence may be flanked on the 5' and/or 3' ends by untranslated regions.

"Exon" refers to that part of a gene which, when transcribed into a nuclear transcript, is "expressed" in the cytoplasmic mRNA after removal of the introns or intervening sequences by nuclear splicing.

Nucleic acid "control sequences" or "regulatory sequences" refer to promoter sequences, translational start and stop codons, ribosome binding sites, polyadenylation signals, transcription termination sequences, upstream regulatory domains, enhancers, and the like, as necessary and sufficient for the transcription and translation of a given coding sequence in a defined host cell. Examples of control sequences suitable for eukaryotic cells are promoters, polyadenylation signals, and enhancers. All of these control sequences need not be present in a recombinant vector so long as those necessary and sufficient for the transcription and translation of the desired gene are present.

"Operably or operatively linked" refers to the configuration of the coding and control sequences so as to perform the desired function. Thus, control sequences operably linked to a coding sequence are capable of effecting the expression of the coding sequence. A coding sequence is operably linked to or under the control of transcriptional regulatory regions in a cell when DNA polymerase binds the promoter sequence and transcribes the coding sequence into mRNA that can be translated into the encoded protein. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "heterologous" and "exogenous" as they relate to nucleic acid sequences such as coding sequences and control sequences, denote sequences that are not normally associated with a region of a recombinant construct or with a particular chromosomal locus, and/or are not normally associated with a particular cell. Thus, an "exogenous" region of a nucleic acid construct is an identifiable segment of nucleic acid within or attached to another nucleic acid molecule that is not found in association with the other molecule in nature. For example, an exogenous region of a construct could include a coding sequence flanked by sequences not found in association with the coding sequence in nature. Another example of an exogenous coding sequence is a construct where the coding sequence itself is not found in nature (e.g., synthetic sequences having codons different from the native gene). Similarly, a host cell transformed with a construct or nucleic acid which is not normally present in the host cell would be considered exogenous for purposes of this invention.

As used herein the terms "N-glycan," "oligosaccharide," "oligosaccharide structure," "glycosylation pattern," "glycosylation profile" and "glycosylation structure" have essentially the same meaning and each refer to one or more structures which are formed from sugar residues and are attached to glycosylated proteins.

"Exogenous protein" as used herein refers to a protein not naturally present in a particular tissue or cell, a protein that is the expression product of an exogenous expression construct or transgene, or a protein not naturally present in a given quantity in a particular tissue or cell. A protein that is exogenous to an egg is a protein that is not normally found in the egg. For example, a protein exogenous to an egg may be a protein that is present in the egg as a result of the expression of a coding sequence present in a transgene of the animal laying the egg.

"Endogenous gene" refers to a naturally occurring gene or fragment thereof normally associated with a particular cell.

"LAL" means "human lysosomal acid lipase," "SBC-102" or "human lysosomal acid lipase molecule" and these terms are used interchangeably throughout the specification.

The expression products described herein may consist of proteinaceous material having a defined chemical structure. However, the precise structure depends on a number of factors, particularly chemical modifications common to proteins. For example, since all proteins contain ionizable amino and carboxyl groups, the protein may be obtained in acidic or basic salt form, or in neutral form. The primary amino acid sequence may be derivatized using sugar molecules (glycosylation) or by other chemical derivatizations involving covalent or ionic attachment with, for example, lipids, phosphate, acetyl groups and the like, often occurring through association with saccharides. These modifications may occur in vitro or in vivo, the latter being performed by a host cell through post-translational processing systems. Such modifications may increase or decrease the biological activity of the molecule, and such chemically modified molecules are also intended to come within the scope of the invention.

Alternative methods of cloning, amplification, expression, and purification will be apparent to the skilled artisan. Representative methods are disclosed in Sambrook, Fritsch, and Maniatis, Molecular Cloning, a Laboratory Manual, 2nd Ed., Cold Spring Harbor Laboratory (1989).

"Vector" means a polynucleotide comprised of single strand, double strand, circular, or supercoiled DNA or RNA. A typical vector may be comprised of the following elements operatively linked at appropriate distances for allowing functional gene expression: replication origin, promoter, enhancer, 5' mRNA leader sequence, ribosomal binding site, nucleic acid cassette, termination and polyadenylation sites, and selectable marker sequences. One or more of these elements may be omitted in specific applications. The nucleic acid cassette can include a restriction site for insertion of the nucleic acid sequence to be expressed. In a functional vector the nucleic acid cassette contains the nucleic acid sequence to be expressed including translation initiation and termination sites. An intron optionally may be included in the construct, for example, 5' to the coding sequence. A vector is constructed so that the particular coding sequence is located in the vector with the appropriate regulatory sequences, the positioning and orientation of the coding sequence with respect to the control sequences being such that the coding sequence is transcribed under the "control" of the control or regulatory sequences. Modification of the sequences encoding the particular protein of interest may be desirable to achieve this end. For example, in some cases it may be necessary to modify the sequence so that it may be attached to the control sequences with the appropriate orientation; or to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site which is in reading frame with and under regulatory control of the control sequences.

A "promoter" is a site on the DNA to which RNA polymerase binds to initiate transcription of a gene. In some embodiments the promoter can be modified by the addition or deletion of sequences, or replaced with alternative sequences, including natural and synthetic sequences as well as sequences which may be a combination of synthetic and natural sequences. Many eukaryotic promoters contain two types of recognition sequences: the TATA box and the upstream promoter elements. The former, located upstream of the transcription initiation site, is involved in directing RNA polymerase to initiate transcription at the correct site, while the latter appears to determine the rate of transcription and is upstream of the TATA box. Enhancer elements can also stimulate transcription from linked promoters, but many function exclusively in a particular cell type. Many enhancer/promoter elements derived from viruses, e.g., the SV40 promoter, the cytomegalovirus (CMV) promoter, the rous-sarcoma virus (RSV) promoter, and the murine leukemia virus (MLV) promoter are all active in a wide array of cell types, and are termed "ubiquitous." Alternatively, non-constitutive promoters such as the mouse mammary tumor virus (MMTV) promoter may also be used in the present invention. The nucleic acid sequence inserted in the cloning site may have any open reading frame encoding a polypeptide of interest, with the proviso that where the coding sequence encodes a polypeptide of interest, it should lack cryptic splice sites which can block production of appropriate mRNA molecules and/or produce aberrantly spliced or abnormal mRNA molecules.

As used herein, the term "pharmaceutical composition" refers to a mixture of a compound described herein with other chemical components, such as carriers, stabilizers, diluents, dispersing agents, suspending agents, thickening agents, and/or excipients.

The term "poultry derived" or "avian derived" refers to a composition or substance produced by or obtained from poultry. "Poultry" refers to avians that can be kept as livestock, including but not limited to, chickens, duck, turkey, quail and ratites. For example, "poultry derived" may refer to chicken derived, turkey derived and/or quail derived.

A "retroviral particle," "transducing particle," or "transduction particle" refers to a replication-defective or replication-competent virus capable of transducing non-viral DNA or RNA into a cell. In one particularly useful embodiment, retroviral particles used to produce transgenic avians in accordance with the invention are made as disclosed in U.S. Pat. No. 7,524,626, issued Apr. 28, 2009, the disclosure of which is incorporated in its entirety herein by reference.

The terms "transformation," "transduction" and "transfection" all denote the introduction of a polynucleotide into an avian blastodermal cell. "Magnum" is that part of the oviduct between the infundibulum and the isthmus containing tubular gland cells that synthesize and secrete the egg white proteins of the egg.

The term "transgene" refers to heterologous nucleotide sequence inserted into an avian genome in accordance with the invention. "Transgene" can specifically refer to an exogenous coding sequence, an exogenous coding sequence linked to an exogenous promoter or other regulatory sequence, all nucleotide sequence between two retoroviral LTRs and/or retroviral LTRs and nucleotide sequence between the LTRs wherein the LTRs are of a retrovirus used to introduce the transgene.

The term "optimized" is used in the context of "optimized coding sequence", wherein the most frequently used codons for each particular amino acid found in the egg white proteins ovalbumin, lysozyme, ovomucoid, and ovotransferrin are used in the design of the optimized human interferon-α 2b (IFN-α 2b) polynucleotide sequence that is inserted into vectors of the present invention. More specifically, the DNA sequence for optimized human IFN-α 2b is based on the hen oviduct optimized codon usage and is created using the BACKTRANSLATE program of the Wisconsin Package, Version 9.1 (Genetics Computer Group Inc., Madison, Wis.) with a codon usage table compiled from the chicken (*Gallus gallus*) ovalbumin, lysozyme, ovomucoid, and ovotransferrin proteins. For example, the percent usage for the four codons of the amino acid alanine in the four egg white proteins is 34% for GCU, 31% for GCC, 26% for GCA, and 8% for GCG. Therefore, GCU is used as the codon for the majority of alanines in an optimized coding sequence. The vectors containing the gene for the optimized human protein are used to produce transgenic avians that express transgenic poultry derived protein in their tissues and eggs.

As used herein, the term "subject" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like.

As used herein, the term "therapeutically effective amount" refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The term "treat," "treating" or "treatment" refers to methods of alleviating, abating or ameliorating a disease or condition symptoms, preventing additional symptoms, ameliorating or preventing the underlying causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

LAL Compositions

The invention is generally drawn to compositions comprising enzymes useful for therapy, for example, in the treatment of lysosomal storage diseases. In one aspect, the invention is drawn to lysosomal storage disease enzymes such as LAL with a glycosylation pattern that renders the molecule amenable for internalization by certain cell types. Also included in the invention are recombinant human proteins including LAL in isolated or purified form. The isolation of the lysosomal storage disease enzymes (such as LAL) can be accomplished by methodologies readily apparent to a practitioner skilled in the art of protein purification.

In one embodiment, the invention is directed to lysosomal storage disease enzymes including, but not limited to, LAL, having an N-linked glycosylation pattern described herein.

In one aspect, the compositions disclosed herein comprise human LAL wherein a substantial percentage of the human LAL contain a mannose-6-phosphate glycan moiety, which can serve as a ligand for internalization by the mannose-6-phosphate receptor on the surface of cells found, for example, on hepatocytes. In one embodiment, 30% or more, for example, at least 30%, at least 40%, at least 50%, at least 60%, at least 70%, at least 80%, at least 90%, at least 95%, at least 97%, or at least 99%, of the LAL contained in the composition contains at least one mannose-6-phosphate moiety. The mannose-6-phosphate moiety can be found, for example, on an N-glycan structure located at one or more residues selected from the group consisting of $Asn^{15}$, $Asn^{51}$, $Asn^{80}$, $Asn^{140}$, $Asn^{252}$ and $Asn^{300}$ of SEQ ID NO:2. Glycan structures containing mannose-6-phosphate moieties include, for example, G-n and H-n shown in FIG. 16.

The recombinant human LAL according to the present invention contains multiple N-linked carbohydrate chains (e.g., about 5 or 6 carbohydrate chains). N-linked glycosylation structures at each of the five or six sites can be selected from one of A-n, B-n, C-n, D-n, E-n, F-n, G-n, H-n, I-n, J-n, K-n, L-n, M-n, N-n and O-n as shown in FIG. 16

Figure 16:
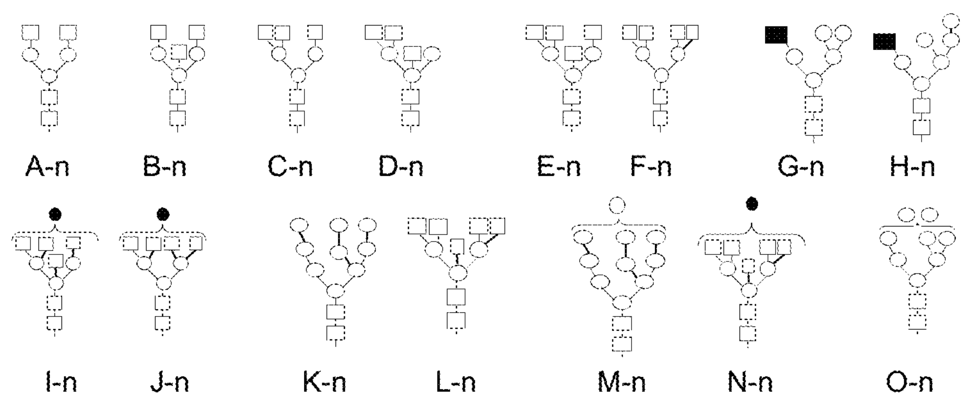
FIG. 16 depicts N-glycans found as an N-linked Glycosylation structure in LAL produced in accordance with the invention. Square, N-Acetyl glucosamine; Filled square, mannose-6-phosphate; circle, mannose; filled circle; galactose; and filled triangle, fucose.

Also described herein are a mixture of LAL molecules (e.g., more than one LAL molecule can be present in a mixture such as the LAL molecules set forth in SEQ ID NOs: 2, 3, 4 and 19) wherein some or all of the LAL molecules have one or more glycosylation structures selected from Structure A-n, Structure B-n, Structure C-n, Structure D-n, Structure E-n, Structure F-n, Structure G-n, Structure H-n, Structure I-n, Structure J-n, Structure K-n, Structure L-n, Structure M-n, Structure N-n and Structure O-n (FIG. 16). In one embodiment, the mixture of lysosomal acid lipase molecules is purified or isolated, for example, isolated from an egg or purified or isolated from egg white produced in a transgenic avian.

The invention also includes an individual LAL molecule comprising a Structure A-n. The invention also includes an individual LAL molecule comprising a Structure B-n. The invention also includes an individual LAL molecule comprising a Structure C-n. The invention also includes an individual LAL molecule comprising a Structure D-n. The invention also includes an individual LAL molecule comprising a Structure E-n. The invention also includes an individual LAL molecule comprising a Structure F-n. The invention also includes an individual LAL molecule comprising a Structure G-n. The invention also includes an individual LAL molecule comprising a Structure H-n. The invention also includes an individual LAL molecule comprising a Structure I-n. The invention also includes an individual LAL molecule comprising a Structure J-n. The invention also includes an individual LAL molecule comprising a Structure K-n. The invention also includes an individual LAL molecule comprising a Structure L-n. The invention also includes an individual lysosomal acid lipase molecule comprising a Structure M-n. The invention also includes an individual LAL molecule comprising a Structure N-n. The invention also includes an individual LAL molecule comprising a Structure O-n.

N-linked oligosaccharides attached to human LAL according to the present invention have a paucity of terminal sialic acid and galactose residues. That is, only minor amounts of the N-linked oligosaccharide structures are terminally sialylated and few galactose residues are present as well. Further, terminal N-Acetyl Glucosamine (GlcNAc) is present extensively on the N-linked oligosaccharide structures of the LAL described herein. As such, LAL produced in accordance with the invention can be targeted to cells such as monocyte macrophages and Kupffer cells.

One aspect of the invention provides compositions of LAL having essentially no sialic acid. In another aspect, the compositions disclosed herein comprise recombinant human LAL wherein a substantial percentage of the human LAL does not contain a sialic acid moiety in any of its N-glycan structures, which can interfere with internalization of the enzyme into cells. In one embodiment, 15% or less, for example, 10% or less, 5% or less, 2% or less, 1% or less, or essentially none, of the LAL contained in the composition contains a sialic acid moiety in any of its N-glycan structures.

In another embodiment, about 95% or more of the N-linked oligosaccharides present on the individual LAL molecule of the invention do not contain sialic acid. In another embodiment, about 90% or more of the N-linked oligosaccharides present on the individual LAL molecule of the invention do not contain sialic acid. In another embodiment, about 80% or more of the N-linked oligosaccharides present on the individual LAL molecule of the invention do not contain sialic acid. In another embodiment, more than about 70% or more of the N-linked oligosaccharides present on the individual LAL molecule of the invention do not contain sialic acid.

In still another embodiment, essentially none of the N-linked oligosaccharides structure types present on the LAL molecules of the invention contain sialic acid. In another embodiment, about 90% or more of the N-linked oligosaccharides structure types found to be associated with the LAL molecules of the invention do not contain sialic acid. For example, if there are 20 oligosaccharide structure types, then 18 or more of the structure types do not contain sialic acid. In another embodiment, about 80% or more of the N-linked oligosaccharides structure types found to be associated with the LAL molecules of the invention do not contain sialic acid. In another embodiment, about 70% or more of the N-linked oligosaccharides structure types found to be associated with the LAL molecules of the invention do not contain sialic acid. In another embodiment, about 60% or more of the N-linked oligosaccharides structure types found to be associated with the LAL molecules of the invention do not contain sialic acid. In another embodiment, about 50% or more of the N-linked oligosaccharides structure types found to be associated with the LAL molecules of the invention do not contain sialic acid.

According to one aspect of the invention, LAL as described herein contain high levels of terminal N-Acetyl Glucosamine. In one aspect, about 95% or more of the N-linked oligosaccharides present on the individual LAL molecule of the invention contain a terminal N-Acetyl Glucosamine. In another embodiment, about 90% or more of the N-linked oligosaccharides present on the individual LAL molecule of the invention contain a terminal N-Acetyl Glucosamine. In another embodiment, about 80% or more of the N-linked oligosaccharides present on the individual LAL molecule of the invention contain a terminal N-Acetyl Glucosamine. In another embodiment, about 70% or more of the N-linked oligosaccharides present on the individual LAL molecule of the invention contain a terminal N-Acetyl Glucosamine. In another embodiment, about 60% or more of the N-linked oligosaccharides present on the individual LAL molecule of the invention contain a terminal N-Acetyl Glucosamine. In another embodiment, about 50% or more of the N-linked oligosaccharides present on the individual LAL molecule of the invention contain a terminal N-Acetyl Glucosamine.

In one embodiment, all of the N-linked oligosaccharides structure types present on the LAL molecules of the invention contain a terminal N-Acetyl Glucosamine. In another embodiment, about 90% or more of the N-linked oligosaccharides structure types present on the LAL molecules of the invention contain a terminal N-Acetyl Glucosamine. For example, if there are 20 oligosaccharide structure types, then 18 or more of the structure types do not contain a terminal N-Acetyl Glucosamine. In another embodiment, about 80% or more of the N-linked oligosaccharides structure types present on the LAL molecules of the invention contain a terminal N-Acetyl Glucosamine. In another embodiment, about 70% or more of the N-linked oligosaccharides structure types present on the LAL molecules of the invention contain a terminal N-Acetyl Glucosamine. In another embodiment, about 60% or more of the N-linked oligosaccharides structure types present on the LAL molecules of the invention contain a terminal N-Acetyl Glucosamine. In another embodiment, about 50% or more of the N-linked oligosaccharides structure types present on the LAL molecules of the invention contain a terminal N-Acetyl Glucosamine.

In another aspect of the invention, the compositions disclosed herein comprise human LAL wherein a substantial percentage of the human LAL does not contain a fucose moiety in any of its N-glycan structure. In one embodiment, 50% or less, for example, 50% or less, 40% or less, 30% or less, 20% or less, 10% or less, 5% or less, 2% or less, 1% or less, or essentially none, of the LAL contained in the composition contains a fucose moiety in any of its N-glycan structure.

In one embodiment, fucose is essentially not present on the N-linked oligosaccharide structures of the LAL produced in accordance of the invention. In another embodiment, about 95% or more of the N-linked oligosaccharides present on the individual LAL molecule of the invention do not contain fucose. In another embodiment, about 90% or more of the N-linked oligosaccharides present on the individual LAL molecule of the invention do not contain fucose. In another embodiment, about 85% or more of the N-linked oligosaccharides present on the individual LAL molecule of the invention do not contain fucose. In another embodiment, about 80% or more of the N-linked oligosaccharides present on the individual LAL molecule of the invention do not contain fucose. In another embodiment, about 70% or more of the N-linked oligosaccharides present on the individual LAL molecule of the invention do not contain fucose. In another embodiment, about 60% or more of the N-linked oligosaccharides present on the individual LAL molecule of the invention do not contain fucose. In another embodiment, about 50% or more of the N-linked oligosaccharides present on the LAL of the invention do not contain fucose.

In one embodiment, essentially none of the N-linked oligosaccharides structure types present on the LAL molecules of the invention contain fucose. In another embodiment, about 95% or more of the N-linked oligosaccharides structure types present on the LAL molecules of the invention do not contain fucose. For example, if there are 20 oligosaccharide structure types, then 19 or more of the structure types do not contain fucose. In another embodiment, about 90% or more of the N-linked oligosaccharides structure types present on the LAL molecules of the invention do not contain fucose. In another embodiment, about 85% or more of the N-linked oligosaccharides structure types present on the LAL molecules of the invention do not contain fucose. In another embodiment, about 80% or more of the N-linked oligosaccharides structure types present on the LAL molecules of the invention do not contain fucose. In another embodiment, about 70% or more of the N-linked oligosaccharides structure types present on the LAL molecules of the invention do not contain fucose.

As discussed above, certain monosaccharides are abundantly present in LAL molecules produced in accordance with the present invention. The total monosaccharide species analyzed includes fucose, N-acetyl galactosamine, N-acetyl glucosamine, galactose, glucose, mannose, mannose-6-phosphate, N-acetyl neuraminic acid and N-glycolyl neuraminic acid. Fucose can be present between about 0% and about 1% of the total monosaccharide composition. N-acetyl galactosamine can be present between about 0% and about 1% of the total monosaccharide composition. N-acetyl glucosamine can be present between about 35% and about 50% of the total monosaccharide composition. Galactose can be present between about 1-10% of the total monosaccharide composition. Glucose is present at 0% of the total monosaccharide composition. Mannose is present between about 32% and about 50% of the total monosaccharide composition. Mannose-6-phosphate is present between about 1% and about 11% of the total monosaccharide composition.

In one embodiment, LAL produced in accordance with the present invention do not contain any xylose. In addition, because there is essentially no N-acetylgalactosamine (GalNac) in LAL produced in accordance with the invention, one aspect of the invention includes a composition of LAL having no O-linked glycosylation.

LAL has 6 potential sites in its amino acid sequence for N-linked glycosylation, for example, $Asn^{36}$, $Asn^{72}$, $Asn^{101}$, $Asn^{161}$, $Asn^{273}$, and $Asn^{321}$ as in SEQ ID NO:1. Five of these, $Asn^{36}$, $Asn^{101}$ $Asn^{161}$, $Asn^{273}$ and $Asn^{321}$ are glycosylated while $Asn^{72}$ can be unglycosylated or substantially unglycosylated (substantially unglycosylated means in a mixture of LAL molecules, fewer $Asn^{72}$ are glycosylated than any of $Asn^{36}$, $Asn^{101}$, $Asn^{161}$, $Asn^{273}$ and $Asn^{321}$) (see FIG. 17). Accordingly, one aspect of the invention is a composition of LAL which is unglycosylated and/or substantially unglycosylated at $Asn^{72}$. LAL having a glycosylated $Asn^{72}$ is within the scope of the invention. The positions of Asn described herein are based on the LAL amino acid sequence set forth in SEQ ID NO:1. It will be apparent to those skilled in the art that the numbering of Asn (i.e., the position of asparagine) can vary depending on individual LAL molecule and be readily determined in other LAL molecules such as those whose amino acid sequences are set forth in SEQ ID NOs:2, 3, 4 and 19.

Figure 17:
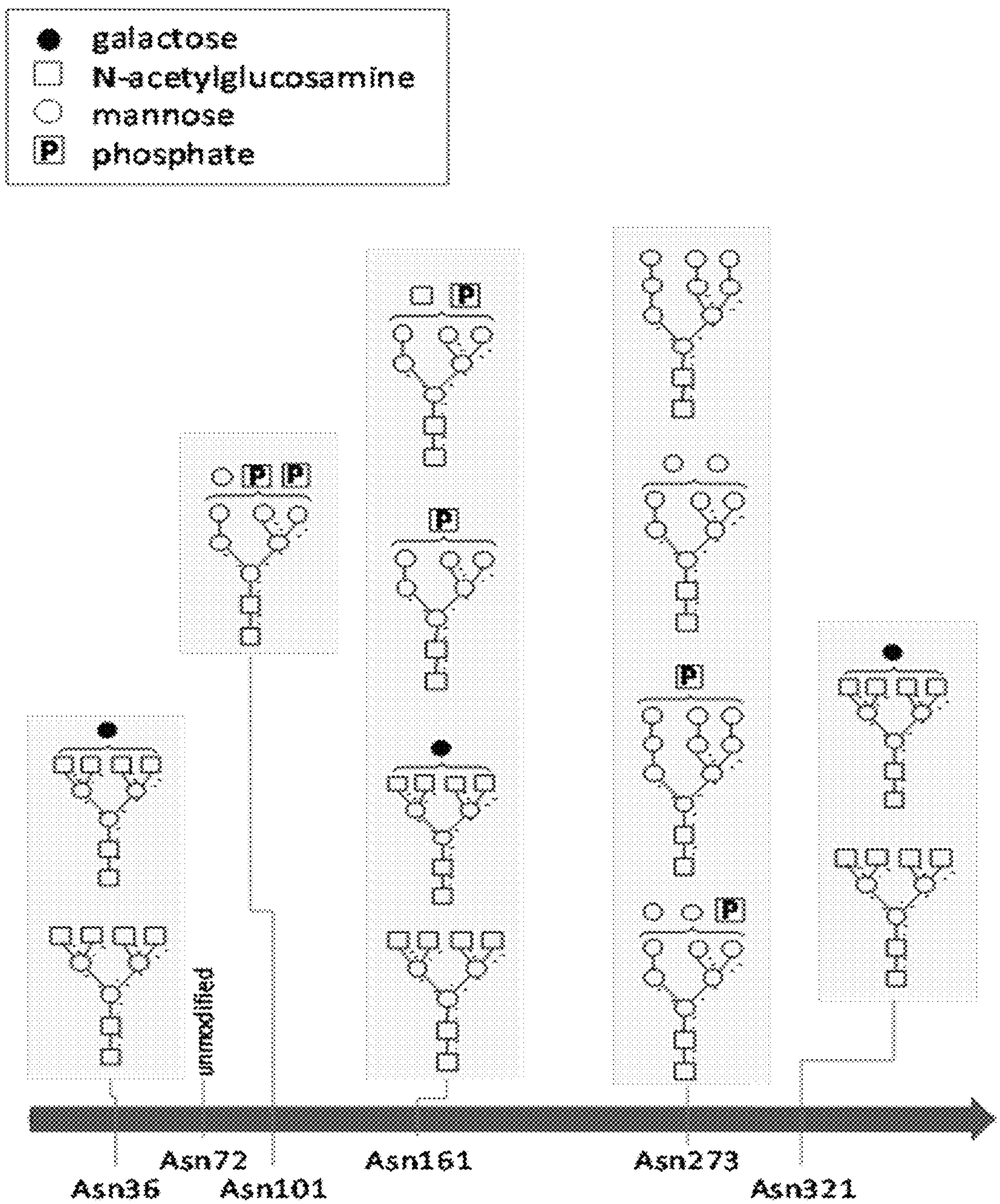
FIG. 17 depicts the relative position of predicted N-glycan sites indicated on the LAL polypeptide (arrow) set forth in SEQ ID NO:1. N-glycans that are structurally representative of those detected at each site are shown. Square, N-Acetyl glucosamine; Filled square, mannose-6-phosphate; circle, mannose; filled circle; galactose; and filled triangle, fucose.

The LAL molecules produced in accordance with the present invention contain N-glycan structures comprising a mixture of bi-, tri- and tetraantennary structures with N-acetylglucosamine, mannose and mannose-6-phosphate (M6P) as the major sugars (FIGS. 16 and 17). According to one aspect of the invention, M6P-modifed N-glycans reside at least at $Asn^{101}$, $Asn^{161}$ and $Asn^{273}$. Thus, one embodiment of the present invention includes a composition of LAL having M6P-modifed N-glycans residing at any one of $Asn^{101}$, $Asn^{161}$ or $Asn^{273}$. In yet another embodiment, the present invention includes a composition of LAL having M6P-modifed N-glycans residing at $Asn^{273}$. In another embodiment, the present invention includes a composition of LAL having monophosphorylated N-glycans (M6P) residing at any one of $Asn^{101}$, $Asn^{161}$ or $Asn^{273}$. In yet another embodiment, the present invention includes a composition of LAL having monophosphorylated N-glycans residing at $Asn^{161}$ and $Asn^{273}$. In yet another embodiment, the present invention includes a composition of LAL having monophosphorylated N-glycans residing at $Asn^{101}$ and $Asn^{273}$. In one specific embodiment, a LAL produced in accordance with the present invention can contain bisphosphorylated mannose (bis-M6P) at $Asn^{101}$.

The LAL molecules produced in accordance with the present invention contain reduced levels of galactose (e.g., "Gal"). One aspect of the present invention includes a composition of LAL having terminal galactose at any one of $Asn^{36}$, $Asn^{161}$ or $Asn^{321}$. In yet another embodiment, the present invention includes a composition of LAL having terminal galactose at $Asn^{36}$ and $Asn^{161}$. In yet another embodiment, the present invention includes a composition of LAL having terminal galactose at $Asn^{161}$ and $Asn^{321}$. In yet another embodiment, the present invention includes a composition of LAL having terminal galactose at $Asn^{36}$ and $Asn^{321}$. In yet another embodiment, the present invention includes a composition of LAL having terminal galactose at $Asn^{36}$, $Asn^{161}$ and $Asn^{321}$. In yet another embodiment, the present invention includes a composition of LAL having no terminal galactose.

Various types of N-glycans were found in LAL at different N-linked glycosylation sites. The N-glycan structures include a mixture of bi-, tri- and tetraantennary structures with N-acetylglucosamine, mannose and mannose-6-phosphate (M6P) as the major sugars. Specifically, in one embodiment of the present invention, LAL contains an N-glycan structure selected from GlcNAc4Man3GlcNAc2 or Gal1G1cNAc4Man3G1cNAc2 at the first N-linked glycosylation site (e.g., $Asn^{36}$ as in SEQ ID NO:1). In another embodiment, LAL contains no glycosylation or is substantially unglycosylated at the second N-linked glycosylation site (e.g., $Asn^{72}$ as in SEQ ID NO:1). In yet another embodiment, LAL contains Phos2Man7GlcNAc2 at its third N-linked glycosylation site (e.g., $Asn^{101}$ as in SEQ ID NO:1). In yet another embodiment, LAL contains a N-glycan structure selected from PhoslMan6G1cNAc2, GlcNAc1Phos1Man6G1cNAc2, Man3G1cNAc2, GlcNAc2Man3G1cNAc2, GlcNAc3Man3G1cNAc2, GlcNAc4Man3G1cNAc2, or Gal1G1cNAc4Man3G1cNAc2 at its fourth N-linked glycosylation site (e.g., $Asn^{161}$ as in SEQ ID NO:1). In yet another embodiment, LAL contains a N-glycan structure selected from Man7GlcNAc2, Man8GlcNAc2, Man9GlcNAc2, Phos1Man8G1cNAc2, or Phos1Man9G1cNAc2 at its fifth N-linked glycosylation site (e.g., $Asn^{273}$ as in SEQ ID NO:1). In yet another embodiment, LAL contains a N-glycan structure selected from GlcNAc2Man3G1cNAc2, GlcNAc3Man3G1cNAc2, GlcNAc4Man3GlcNAc2, Gal1GlcNAc4Man3GlcNAc2, GlcNAc5Man3GlcNAc2, Gal1G1cNAc5Man3G1cNAc2, GlcNAc6Man3G1cNAc2, or Gal1G1cNAc6Man3G1cNAc2 at its sixth N-linked glycosylation site (e.g., $Asn^{321}$ as in SEQ ID NO:1).

According to certain aspects of the invention, compositions of LAL include LAL glycosylated at $Asn^{36}$, $Asn^{72}$, $Asn^{101}$ $Asn^{161}$, $Asn^{273}$ and $Asn^{321}$ of SEQ ID NO:1 (or corresponding Asparagine residues within SEQ ID NOs: 2, 3, 4, and 19) with one N-glycan at the designated Asn position as shown below:

a) at $Asn^{36}$, GlcNAc4Man3GlcNAc2, or Gal1GlcNAc4Man3GlcNAc2;
b) at $Asn^{72}$, no glycosylation;
c) at $Asn^{101}$, Phos2Man7GlcNAc2;
d) at $Asn^{161}$, PhoslMan6GlcNAc2, GlcNAc1Phos1Man6G1cNAc2; Man3 G1cNAc2; GlcNAc2Man3 G1cNAc2; GlcNAc3Man3G1cNAc2; GlcNAc4Man3GlcNAc2, or Gal1GlcNAc4Man3GlcNAc2;
e) at $Asn^{273}$, Man7GlcNAc2, Man8GlcNAc2, Man9GlcNAc2, PhoslMan8GlcNAc2, or Phos1Man9G1cNAc2; and
f) at $Asn^{321}$, GlcNAc2Man3GlcNAc2, GlcNAc3Man3G1cNAc2, GlcNAc4Man3G1cNAc2, Gal1GlcNAc4Man3GlcNAc2, GlcNAc5Man3 G1cNAc2, Gal1GlcNAc5Man3GlcNAc2, GlcNAc6Man3G1cNAc2, or Gal1GlcNAc6Man3GlcNAc2, where Man=mannose,
GlcNAc=N-Acetyl Glucosamine,
Phos=phosphate, and
Gal=galactose.

In one embodiment, Gal1GlcNAc4Man3GlcNAc2 can be found as a glycan component at any one of $Asn^{36}$, $Asn^{161}$ or $Asn^{321}$ in LAL produced in accordance with the invention. In one specific embodiment, Gal1GlcNAc4Man3GlcNAc2 can be found as a glycan component of $Asn^{36}$, $Asn^{161}$ and $Asn^{321}$.

In the LAL of the present invention, $Asn^{101}$ and $Asn^{273}$ display the high-mannose-type having about 6 to about 10 mannose molecules (MANE-MAN10 as described herein) as a major component. Accordingly, one aspect of the present invention includes a composition of LAL having a high mannose structure at $Asn^{101}$ or $Asn^{273}$. In another embodiment, a composition of LAL of the invention can comprise a N-glycan structure having at least 6 mannose at $Asn^{101}$ or $Asn^{273}$. In another embodiment, a composition of LAL contains a N-glycan having 7, 8 or 9 mannose at $Asn^{101}$ or $Asn^{273}$. In yet another embodiment, the present invention includes a composition of LAL having 7, 8 or 9 mannose at $Asn^{101}$ and $Asn^{273}$. In yet another embodiment, the present invention includes a composition of LAL having 7, 8 or 9 mannose at $Asn^{101}$ and/or $Asn^{273}$ and at least one of the mannose is phosphorylated.

It is to be understood that the glycosylation sites and the numbers associated with Asn described above is based on the amino acid sequence of LAL set forth in SEQ ID NO:1 and that the glycosylation profiles described above in context of SEQ ID NO:1 also apply to LAL molecules set forth in SEQ ID NOs: 2, 3, 4 and 19 though the numbering of corresponding Asn may vary depending on LAL molecule. For example, $Asn^{36}$ in SEQ ID NO:1 corresponds to $Asn^{15}$ in SEQ ID NO:2, $Asn^{13}$ in SEQ ID NO:3, $Asn^{10}$ in SEQ ID NO:4 and $Asn^{9}$ in SEQ ID NO:19. $Asn^{72}$ in SEQ ID NO:1 corresponds to $Asn^{51}$ in SEQ ID NO:2, $Asn^{49}$ in SEQ ID NO:3, $Asn^{46}$ in SEQ ID NO:4 and $Asn^{45}$ in SEQ ID NO:19. $Asn^{101}$ in SEQ ID NO:1 corresponds to $Asn^{80}$ in SEQ ID NO:2, $Asn^{78}$ in SEQ ID NO:3, $Asn^{75}$ in SEQ ID NO:4 and $Asn^{74}$ in SEQ ID NO:19. $Asn^{161}$ in SEQ ID NO:1 corresponds to $Asn^{140}$ in SEQ ID NO:2, $Asn^{138}$ in SEQ ID NO:3, $Asn^{135}$ in SEQ ID NO:4 and $Asn^{134}$ in SEQ ID NO:19. $Asn^{273}$ of SEQ ID NO:1 corresponds to $Asn^{252}$ in SEQ ID NO:2, $Asn^{250}$ in SEQ ID NO:3, $Asn^{247}$ in SEQ ID NO:4 and $Asn^{246}$ in SEQ ID NO:19. $Asn^{321}$ of SEQ ID NO:1 corresponds to $Asn^{300}$ in SEQ ID NO:2, $Asn^{298}$ in SEQ ID NO:3, $Asn^{295}$ in SEQ ID NO:4 and $Asn^{294}$ in SEQ ID NO:19.

For example, in one embodiment, the LAL is N-linked glycosylated at least at one position selected from the group consisting of $Asn^{15}$, $Asn^{51}$, $Asn^{80}$, $Asn^{140}$, $Asn^{252}$ and $Asn^{300}$ of SEQ ID NO:2. In another embodiment, the LAL is N-linked glycosylated at $Asn^{15}$, $Asn^{80}$, $Asn^{140}$, $Asn^{252}$ and $Asn^{300}$ of SEQ ID NO:2. In yet another embodiment, N-glycan structures of LAL of SEQ ID NO:2 have no xylose while less than 15%, 10%, 5%, or 1% of N-glycan structures contain sialic acid; less than 50%, 40%, 30%, 20%, 10%, 5% or 1% of N-glycan structures contain fucose; and at least 30%, 50%, 60%, 70%, 80%, 90% and 95% of N-glycan structures contain phosphorylated mannose (M6P). S In one embodiment, the LAL is N-linked glycosylated at least at one position selected from the group consisting of $Asn^{13}$, $Asn^{49}$, $Asn^{78}$, $Asn^{138}$, $Asn^{250}$ and $Asn^{298}$ of SEQ ID NO:3. In another embodiment, the LAL is N-linked glycosylated at $Asn^{13}$, $Asn^{78}$, $Asn^{138}$, $Asn^{250}$ and $Asn^{298}$ of SEQ ID NO:3. In yet another embodiment, N-glycan structures of LAL of SEQ ID NO:3 have no xylose while less than 15%, 10%, 5%, or 1% of N-glycan structures contain sialic acid; less than 50%, 40%, 30%, 20%, 10%, 5% or 1% of N-glycan structures contain fucose; and at least 30%, 50%, 60%, 70%, 80%, 90% and 95% of N-glycan structures contain phosphorylated mannose (M6P).

In one embodiment, the LAL is N-linked glycosylated at least at one position selected from the group consisting of $Asn^{10}$, $Asn^{46}$, $Asn^{75}$, $Asn^{135}$, $Asn^{247}$ and $Asn^{295}$ of SEQ ID NO:4. In another embodiment, the LAL is N-linked glycosylated at $Asn^{10}$, $Asn^{75}$, $Asn^{135}$, $Asn^{247}$ and $Asn^{295}$ of SEQ ID NO:4. In yet another embodiment, N-glycan structures of LAL of SEQ ID NO:4 have no xylose while less than 15%, 10%, 5%, or 1% of N-glycan structures contain sialic acid; less than 50%, 40%, 30%, 20%, 10%, 5% or 1% of N-glycan structures contain fucose; and at least 30%, 50%, 60%, 70%, 80%, 90% and 95% of N-glycan structures contain phosphorylated mannose (M6P).

In one embodiment, the LAL is N-linked glycosylated at least at one position selected from the group consisting of $Asn^{9}$, $Asn^{45}$, $Asn^{74}$, $Asn^{134}$, $Asn^{246}$ and $Asn^{294}$ of SEQ ID NO:19. In another embodiment, the LAL is N-linked glycosylated at $Asn^{9}$, $Asn^{74}$, $Asn^{134}$, $Asn^{246}$ and $Asn^{294}$ of SEQ ID NO:19. In yet another embodiment, N-glycan structures of LAL of SEQ ID NO:4 have no xylose while less than 15%, 10%, 5%, or 1% of N-glycan structures contain sialic acid; less than 50%, 40%, 30%, 20%, 10%, 5% or 1% of N-glycan structures contain fucose; and at least 30%, 50%, 60%, 70%, 80%, 90% and 95% of N-glycan structures contain phosphorylated mannose (M6P).

The composition according to the present invention can be produced a number of ways, including by use of transgenic avians, transgenic fish, transgenic mammals, for example, transgenic goats or in transgenic plants, such as tobacco and duck weed (*Lemna minor*) and certain types of cell culture.

The present invention also contemplates compositions comprising PEGylated LAL. LAL enzyme as described herein can be PEGylated as disclosed, for example, in U.S.

Patent publication No. 20070092486, published Apr. 26, 2007, the disclosure of which is incorporated it its entirety herein by reference.

In one embodiment, the derived glycosylation pattern is obtained through expression specialized expression systems, for example, from avian oviduct cells, for example, tubular gland cells. For example, glycosylation patterns disclosed herein have been demonstrated to be present on lysosomal storage disease enzymes produced in oviduct cells of an avian such as a chicken in accordance with the present invention.

Proteins produced in accordance with the invention can be purified from egg white by any useful procedure such as those apparent to a practitioner of ordinary skill in the art of protein purification. For example, the human LAL (hLAL) produced in transgenic avians in accordance with the invention can be purified from egg white by methods apparent to practitioners of ordinary skill in the art of protein purification. An example of a purification protocol for LAL present in egg white is described in the Examples.

The invention includes the eggs and egg white and the avians (e.g., chicken turkey and quail) that lay the eggs and produce the egg white containing lysosomal acid lipase molecules of the invention comprising one or more of the glycosylation structures disclosed herein.

Expression of LAL in Avians

Disclosed herein are vectors and methods for the stable introduction of exogenous nucleic acid sequences into the genome of avians to express desired proteins such as those which benefit (e.g., attain an increased efficacy) from the addition of mannose-6-phospahate such as lysosomal enzymes including, without limitation, lysosomal acid lipase (LAL) and other proteins such as those specifically disclosed herein. In particular, transgenic avians are produced which express exogenous sequences in their oviducts and which deposit exogenous proteins, such as pharmaceutical proteins, into their eggs. Avian eggs that contain such exogenous proteins are also described herein. Also disclosed herein are novel forms of LAL which are efficiently expressed in the oviduct of transgenic avians and deposited into avian eggs.

One aspect of the invention relates to compositions containing LAL, i.e., LAL molecules produced in accordance with the invention. In a particularly useful embodiment, the LAL is purified or isolated. For example, the LAL has been removed from the contents of a hard shell egg laid by a transgenic avian. In one particularly useful embodiment, the LAL is human LAL. In one embodiment, the LAL of the invention has a glycosylation pattern resulting from the LAL being produced in an oviduct cell of an avian. For example, the compositions can contain a mixture of LAL molecules produced in avians, for example, chickens, in accordance with the invention and isolated from egg white. In one useful embodiment, the LAL containing compositions are pharmaceutical formulations.

In one aspect, the invention is drawn to compositions containing isolated LAL molecules, for example, human LAL molecules, wherein the LAL is produced in an avian which contains a transgene encoding the LAL. In one embodiment, the LAL is produced in an oviduct cell (e.g., a tubular gland cell) of a transgenic avian (e.g., transgenic chicken) and the LAL is isolated from egg white of the transgenic avian. In one embodiment, the LAL is glycosylated in the oviduct cell (e.g., tubular gland cell) of the bird, for example, a chicken.

In another aspect, methods for producing exogenous proteins such as lysosomal storage disease enzymes, for example, LAL, in specific tissues of avians, are provided. Such exogenous proteins may be expressed in the oviduct, blood and/or other cells and tissues of the avian. In one embodiment, transgenes are introduced into embryonic blastodermal cells, for example, near stage X, to produce a transgenic avian, such that the protein of interest is expressed in the tubular gland cells of the magnum of the oviduct, secreted into the lumen, and deposited into the egg white of a hard shell egg. A transgenic avian so produced can carry the transgene in its germ line providing transmission of the exogenous transgene to the avian's offspring stably in a Mendelian fashion.

The present invention encompasses methods of producing exogenous protein such as LAL in an avian oviduct. The methods may include a first step of providing a vector that contains a coding sequence and a promoter operably linked to the coding sequence, so that the promoter can effect expression of the nucleic acid in the avian oviduct. Transgenic cells and/or tissues can be produced, wherein the vector is introduced into avian embryonic blastodermal cells, either freshly isolated, in culture, or in an embryo, so that the vector sequence is inserted into the avian genome. A mature transgenic avian which expresses the exogenous protein such as LAL in its oviduct can be derived from the transgenic cells and/or tissue.

In one aspect of the invention, production of a transgenic avian is accomplished by transduction of embryonic blastodermal cells with replication-defective or replication-competent retroviral particles carrying the transgene between the 5' and 3' LTRs of the retroviral rector. For instance, an avian leukosis virus (ALV) retroviral vector or a murine leukemia virus (MLV) retroviral vector may be used which comprises a modified pNLB plasmid containing an exogenous gene that is inserted downstream of a segment of a promoter region. An RNA copy of the modified retroviral vector, packaged into viral particles, can be used to infect embryonic blastoderms which develop into transgenic avians.

Another aspect of the invention provides a vector which includes a coding sequence and a promoter in operational and positional relationship such that the coding sequence is expressed in an avian oviduct. Such vectors include, but are not limited to, an avian leukosis virus (ALV) retroviral vector, a murine leukemia virus (MLV) retroviral vector, and a lentivirus vector. In addition, the vector may be a nucleic acid sequence which includes an LTR of an avian leukosis virus (ALV) retroviral vector, a murine leukemia virus (MLV) retroviral vector, or a lentivirus vector. The promoter is sufficient for effecting expression of the coding sequence in the avian oviduct. The coding sequence codes for an exogenous protein which is deposited into the egg white of a hard shell egg. As such, the coding sequence codes for exogenous proteins such as transgenic poultry derived proteins such as transgenic poultry derived lysosomal acid lipase (TPD LAL).

In one embodiment, vectors used in the methods of the invention contain a promoter which is particularly suited for expression of exogenous proteins in avians and their eggs. As such, expression of the exogenous coding sequence may occur in the oviduct and blood of the transgenic avian and in the egg white of its avian egg. The promoters include, but are not limited to, a cytomegalovirus (CMV) promoter, a rous-sarcoma virus (RSV) promoter, a β-actin promoter (e.g., a chicken β-actin promoter), a murine leukemia virus (MLV) promoter, a mouse mammary tumor virus (MMTV) promoter, an ovalbumin promoter, a lysozyme promoter, a conalbumin promoter, an ovomucoid promoter, an ovomucin promoter, and an ovotransferrin promoter. Optionally, the promoter may be a segment of at least one promoter region, such as a segment of the ovalbumin, lysozyme, conalbumin, ovomucoid, ovomucin, and ovotransferrin promoter region. In one embodiment, the promoter is a combination or a fusion of one or more promoters or a fusion of a portion of one or more promoters such as ovalbumin, lysozyme, conalbumin, ovomucoid (MD), ovomucin, and ovotransferrin (OT) promoters.

In one embodiment, the vector includes a signal peptide coding sequence which is operably linked to the coding sequence, so that upon translation in a cell, the signal peptide directs secretion of the exogenous protein expressed by the vector, such as human LAL, into the egg white of a hard shell egg.

One aspect of the invention provides for coding sequences for exogenous proteins produced as disclosed herein wherein the coding sequence is codon optimized for expression in an avian, for example, in a chicken. Codon optimization may be determined from the codon usage of at least one, and preferably more than one, protein expressed in an avian cell (e.g., a chicken cell). For example, the codon usage may be determined from the nucleic acid sequences encoding the proteins ovalbumin, lysozyme, ovomucin and ovotransferrin of chicken. For example, the DNA coding sequence for the exogenous protein may be codon optimized using the BACKTRANSLATE® program of the Wisconsin Package, version 9.1 (Genetics Computer Group, Inc., Madison, Wis.) with a codon usage table compiled from the chicken (*Gallus gallus*) ovalbumin, lysozyme, ovomucoid, and ovotransferrin proteins.

One important aspect of the present invention relates to avian hard shell eggs (e.g., chicken hard shell eggs) which contain an exogenous peptide or protein including, but not limited to, a human LAL. The exogenous peptide or protein such as human LAL may be encoded by a transgene of a transgenic avian. Often, the exogenous peptide or protein (e.g., LAL) is glycosylated. The protein may be present in any useful amount. In one embodiment, the protein is present in an amount in a range of between about 0.01 μg per hard-shell egg and about 1 gram per hard-shell egg. In another embodiment, the protein is present in an amount in a range of between about 1 μg per hard-shell egg and about 1 gram per hard-shell egg. For example, the protein may be present in an amount in a range of between about 10 μg per hard-shell egg and about 1 gram per hard-shell egg (e.g., a range of between about 10 μg per hard-shell egg and about 400 milligrams per hard-shell egg).

In one embodiment, the exogenous protein of the invention is present in the egg white of the egg. In one embodiment, the protein is present in an amount in a range of between about 1 ng per milliliter of egg white and about 0.2 gram per milliliter of egg white. For example, the protein may be present in an amount in a range of between about 0.1 μg per milliliter of egg white and about 0.2 gram per milliliter of egg white (e.g., the protein may be present in an amount in a range of between about 1 μg per milliliter of egg white and about 100 milligrams per milliliter of egg white. In one embodiment, the protein is present in an amount in a range of between about 1 μg per milliliter of egg white and about 50 milligrams per milliliter of egg white. For example, the protein may be present in an amount in a range of about 1 μg per milliliter of egg white and about 10 milligrams per milliliter of egg white (e.g., the protein may be present in an amount in a range of between about 1 μg per milliliter of egg white and about 1 milligrams per milliliter of egg white). In one embodiment, the protein is present in an amount of more than 0.1 μg per milliliter of egg white. In one embodiment, the protein is present in an amount of more than 0.5 μg per milliliter of egg white. In one embodiment, the protein is present in an amount of more than 1 per milliliter of egg white. In one embodiment, the protein is present in an amount of more than 1.5 μg per milliliter of egg white.

The avians of the invention which produce exogenous proteins disclosed herein (e.g., LAL) which are developed from the blastodermal cells into which the vector has been introduced are the G0 generation and can be referred to as "founders." Founder birds are typically chimeric for each inserted transgene. That is, only some of the cells of the G0 transgenic bird contain the transgene(s). The G0 generation typically is also hemizygous for the transgene(s). The G0 generation may be bred to non-transgenic animals to give rise to G1 transgenic offspring which are also hemizygous for the transgene and contain the transgene(s) in essentially all of the bird's cells. The G1 hemizygous offspring may be bred to non-transgenic animals giving rise to G2 hemizygous offspring or may be bred together to give rise to G2 offspring homozygous for the transgene. Substantially all of the cells of birds which are positive for the transgene that are derived from G1 offspring contain the transgene(s). In one embodiment, hemizygotic G2 offspring from the same line can be bred to produce G3 offspring homozygous for the transgene. In one embodiment, hemizygous G0 or G1 animals, for example, are bred together to give rise to homozygous G1 offspring containing two copies of the transgene(s) in each cell of the animal. These are merely examples of certain useful breeding methods and the present invention contemplates the employment of any useful breeding method such as those known to individuals of ordinary skill in the art.

In one embodiment, the invention provides for the LAL to be isolated. That is, the LAL contained in the composition may be an isolated LAL. For example, the LAL may be isolated from egg white. The isolated LAL may be LAL molecules having a variety of glycosylation structures among the LAL molecules.

By the methods of the present invention, transgenes can be introduced into avian embryonic blastodermal cells to produce a transgenic chicken, transgenic turkey, transgenic quail and other avian species, that carry the transgene in the genetic material of its germ-line tissue in order to produce proteins of the invention. The blastodermal cells are typically stage VII-XII cells, or the equivalent thereof, and in one embodiment are near stage X.

Some vectors useful in carrying out the methods of the present invention are described herein. In one embodiment, the coding sequence and the promoter of the vector are both positioned between 5' and 3' LTRs before introduction into blastodermal cells. In one embodiment, the vector is retroviral and the coding sequence and the promoter are both positioned between the 5' and 3' LTRs of the retroviral vector. In one useful embodiment, the LTRs or retroviral vector is derived from the avian leukosis virus (ALV), murine leukemia virus (MLV), or lentivirus.

In one embodiment, vectors are used for transfecting blastodermal cells and generating stable integration into the avian genome contain a coding sequence and a promoter in operational and positional relationship to express the coding sequence in the tubular gland cell of the magnum of the avian oviduct, wherein the exogenous protein such as an lysosomal enzyme (e.g., LAL) is deposited in the egg white of a hard shell egg.

The promoter may optionally be a segment of the ovalbumin promoter region which is sufficiently large to direct expression of the coding sequence in the tubular gland cells.

Truncating the ovalbumin promoter and/or condensing the critical regulatory elements of the ovalbumin promoter so that it retains sequences required for expression in the tubular gland cells of the magnum of the oviduct, while being small enough that it can be readily incorporated into vectors is included within the scope of the invention. In one embodiment, a segment of the ovalbumin promoter region may be used. This segment comprises the 5'-flanking region of the ovalbumin gene.

The promoter may also be a promoter that is largely, but not entirely, specific to the magnum, such as the lysozyme promoter. The promoter may also be a mouse mammary tumor virus (MMTV) promoter. Alternatively, the promoter may be a constitutive promoter (e.g., a cytomegalovirus (CMV) promoter, a rous-sarcoma virus (RSV) promoter, a murine leukemia virus (MLV) promoter, etc.). In one embodiment, the promoter is a cytomegalovirus (CMV) promoter, an ovomucoid and ovotransferrin (MDOT) promoter, a rous-sarcoma virus (RSV) promoter, a murine leukemia virus (MLV) promoter, a mouse mammary tumor virus (MMTV) promoter, an ovalbumin promoter, a lysozyme promoter, a conalbumin promoter, an ovomucoid promoter, an ovomucin promoter and/or an ovotransferrin promoter. Optionally, the promoter may be at least one segment of a promoter region, such as a segment of the ovalbumin, lysozyme, conalbumin, ovomucoid (MD), ovomucin, and ovotransferrin (OT) promoter region.

In one method of transfecting blastodermal cells, a packaged retroviral-based vector is used to deliver the vector into embryonic blastodermal cells so that the vector is integrated into the avian genome.

Useful retrovirus for randomly introducing a transgene into the avian genome is the replication-deficient avian leucosis virus (ALV), the replication-deficient murine leukemia virus (MLV), or the lentivirus. In one embodiemnt, a pNLB vector is modified by inserting a region of the ovalbumin promoter and one or more exogenous genes between the 5' and 3' long terminal repeats (LTRs) of the retrovirus genome. The invention contemplates that any coding sequence placed downstream of a promoter that is active in tubular gland cells can be expressed in the tubular gland cells. For example, the ovalbumin promoter can be expressed in the tubular gland cells of the oviduct magnum because the ovalbumin promoter drives the expression of the ovalbumin protein and is active in the oviduct tubular gland cells.

Any of the vectors described herein can also optionally include a coding sequence encoding a signal peptide that directs secretion of the protein expressed by the vector's coding sequence from the tubular gland cells of the oviduct. This aspect effectively broadens the spectrum of exogenous proteins that may be deposited in avian eggs using the methods described herein. Where an exogenous protein would not otherwise be secreted, the vector containing the coding sequence is modified to comprise a DNA sequence comprising about 60 bp encoding a signal peptide from the lysozyme gene. The DNA sequence encoding the signal peptide is inserted in the vector such that it is located at the N-terminus of the protein encoded by the DNA.

Another aspect of the invention involves the use of internal ribosome entry site (IRES) elements in any of the vectors of the present invention to allow the translation of two or more proteins from a dicistronic or polycistronic mRNA. The IRES units are fused to 5' ends of one or more additional coding sequences which are then inserted into the vectors at the end of the original coding sequence, so that the coding sequences are separated from one another by an IRES.

In one embodiment when using an IRES, post-translational modification of the product is facilitated because one coding sequence can encode an enzyme capable of modifying the other coding sequence product. For example, the first coding sequence may encode collagen which would be hydroxylated and made active by the enzyme encoded by the second coding sequence wherein an IRES is employed as is understood in the art.

In another aspect, the coding sequences of vectors used in any of the methods of the present invention are provided with a 3' untranslated region (3' UTR) to confer stability to the RNA produced. When a 3' UTR is added to a retroviral vector, the orientation of the promoter, gene X and the 3' UTR must be reversed in the construct, so that the addition of the 3' UTR does not interfere with transcription of the full-length genomic RNA. In one embodiment, the 3' UTR may be that of the ovalbumin or lysozyme genes, or any 3' UTR that is functional in a magnum cell, i.e., the SV40 late region.

In one embodiment, a constitutive promoter is used to express the coding sequence of a transgene in the avian. In this case, expression is not limited to the magnum; expression also occurs in other tissues within the avian (e.g., blood). The use of such a transgene, which includes a constitutive promoter and a coding sequence, is particularly suitable for effecting or driving the expression of a protein in the oviduct and the subsequent secretion of the protein into the egg.

Transducing particles (i.e., transduction particles) are produced for the vector and titered to determine the appropriate concentration that can be used to inject embryos. Avian eggs are windowed according to the Speksnij der procedure (U.S. Pat. No. 5,897,998, the disclosure of which is incorporated in its entirety herein by reference), and eggs are injected with transducing particles. Eggs hatch about 21 days after injection and male birds are selected for breeding. In order to screen for G0 roosters which contain the transgene in their sperm, DNA is extracted from rooster sperm samples. The G0 roosters with the highest levels of the transgene in their sperm samples are bred to nontransgenic hens by artificial insemination. Blood DNA samples are screened for the presence of the transgene. The serum of transgenic roosters is tested for the presence of exogenous protein. If the exogenous protein is confirmed, the sperm of the transgenic roosters is used for artificial insemination of nontransgenic hens. A certain percent of the offspring then contains the transgene (e.g., more than 50%). When exogenous protein is present in eggs produced in accordance with the present invention the protein may be isolated. The protein may also be tested for biological activity.

The methods of the invention which provide for the production of exogenous protein in the avian oviduct and the production of eggs which contain exogenous protein involve an additional step subsequent to providing a suitable vector and introducing the vector into embryonic blastodermal cells so that the vector is integrated into the avian genome. The subsequent step involves deriving a mature transgenic avian from the transgenic blastodermal cells produced in the previous steps. Mature transgenic avians can be obtained from the cells of a blastodermal embryo which has been transfected or transduced with the vector directly within the embryo. The resulting embryo is allowed to develop and the chick allowed to mature.

The transgenic avian produced from blastodermal cells is known as a founder. Some founders will carry the transgene in tubular gland cells in the magnum of their oviducts. These avians will express the exogenous protein encoded by the transgene in their oviducts. The exogenous protein may also be expressed in other tissues (e.g., blood) in addition to the oviduct. If the exogenous protein contains the appropriate signal sequence(s), it will be secreted into the lumen of the oviduct and into the egg white of the egg.

Some founders are germ-line founders. A germ-line founder is a founder that carries the transgene in genetic material of its germ-line tissue, and may also carry the transgene in oviduct magnum tubular gland cells that express the exogenous protein. Therefore, in accordance with the invention, the transgenic avian may have tubular gland cells expressing the exogenous protein, and the offspring of the transgenic avian may also have oviduct magnum tubular gland cells that express the exogenous protein. Alternatively, the offspring express a phenotype determined by expression of the exogenous gene in specific tissue(s) of the avian. In one embodiment, the transgenic avian is a chicken or a turkey.

Pharmaceutical Compositions & Therapeutic Methods

While it is possible that, for use in therapy, therapeutic proteins produced as described herein may be administered in raw form, it is preferable to administer the therapeutic proteins as part of a pharmaceutical formulation. Therefore, further provided are pharmaceutical formulations comprising poultry derived glycosylated therapeutic proteins such as LAL or a pharmaceutically acceptable derivative thereof together with one or more pharmaceutically acceptable carriers thereof and, optionally, other therapeutic and/or prophylactic ingredients and methods of administering such pharmaceutical formulations. The carrier(s) must be "acceptable" in the sense of being compatible with the other ingredients of the formulation and not deleterious to the recipient thereof. Methods of treating a patient (e.g., quantity of pharmaceutical protein administered, frequency of administration and duration of treatment period) using pharmaceutical compositions of the invention can be determined using standard methodologies known to physicians of skill in the art.

Compositions comprising carriers, including composite molecules, are formulated by well-known conventional methods (see, for example, Remington's Pharmaceutical Sciences, 14th Ed., Mack Publishing Co., Easton, Pa.), the entire teachings of which are incorporated herein by reference. The carrier may comprise a diluent. In one embodiment, the pharmaceutical carrier can be a liquid and the recombinant human LAL can be in the form of a solution. The pharmaceutical carrier can be wax, fat, or alcohol. In one embodiment, the wax- or fat-based carrier does not contain ester. In another embodiment, the pharmaceutically acceptable carrier may be a solid in the form of a powder, a lyophilized powder, or a tablet. In one embodiment, the carrier may comprise a liposome or a microcapsule.

The pharmaceutical formulations include those suitable for administration by injection including intramuscular, subcutaneous and intravenous administration. Pharmaceutical formulations include those suitable for oral, rectal, nasal, topical (including buccal and sub-lingual), vaginal or parenteral. The pharmaceutical formulations also include those for administration by inhalation or insufflation. The formulations may, where appropriate, be conveniently presented in discrete dosage units and may be prepared by any of the methods well known in the art of pharmacy. The methods of producing the pharmaceutical formulations typically include the step of bringing the therapeutic protein into association with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution; as a suspension; or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils) or preservatives.

LAL may also be formulated for parenteral administration (e.g., by injection, for example, bolus injection or continuous infusion) and may be presented in unit dose form in ampoules, pre-filled syringes, small volume infusion or in multi-dose containers with an added preservative. The therapeutic proteins can be injected by, for example, subcutaneous injections, intramuscular injections, and intravenous infusions or injections.

The LAL may take such forms as suspensions, solutions, or emulsions in oily or aqueous vehicles, and may contain formulatory agents such as suspending, stabilizing and/or dispersing agents. It is also contemplated that the therapeutic protein may be in powder form, obtained by aseptic isolation of sterile solid or by lyophilization from solution, for constitution with a suitable vehicle, e.g., sterile, pyrogen-free water, before use.

For intravenous infusions or injection, the LAL produced in accordance of the invention can be formulated as an aqueous supension or solution. Excipients suitable for the formulation for intravenous infusion or injection can include one of the following: trisodium citrate dehydrate, citric acid and human serum albumin. The pharmaceutical formulation can also include other suitable excipients well known in the art used for other products for lysosomal storage disorders. The pH of LAL produced in accordance with the invention is maintained between about 5.6 and about 6.2. Preferably, the pH of the LAL formulation is maintained at 5.9±0.2.

For topical administration to the epidermis, the therapeutic proteins of the invention produced according to the invention may be formulated as ointments, creams or lotions, or as a transdermal patch. Ointments and creams may, for example, be formulated with an aqueous or oily base with the addition of suitable thickening and/or gelling agents. Lotions can be formulated with an aqueous or oily base and can also contain one or more emulsifying agents, stabilizing agents, dispersing agents, suspending agents, thickening agents or coloring agents.

Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably represented as unit dose suppositories. Suitable carriers include cocoa butter and other materials commonly used in the art, and the suppositories may be conveniently formed by a mixture of the active compound with the softened or melted carrier(s) followed by chilling and shaping in molds.

Formulations suitable for vaginal administration may be presented as pessaries, tampons, creams, gels, pastes, foams or sprays containing in addition to the active ingredient, such carriers as are known in the art to be appropriate.

For intra-nasal administration the therapeutic proteins of the invention may be used as a liquid spray or dispersible powder or in the form of drops. Drops may be formulated with an aqueous or non-aqueous base also comprising one or more dispersing agents, solubilizing agents or suspending agents. Liquid sprays are conveniently delivered from pressurized packs.

For administration by inhalation, therapeutic proteins according to the invention may be conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

For administration by inhalation or insufflation, the therapeutic proteins according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

When desired, the above described formulations adapted to give sustained release of the active ingredient, may be employed.

The pharmaceutical compositions described herein may also contain other active ingredients such as antimicrobial agents, or preservatives.

In addition, it is contemplated that the therapeutic proteins disclosed herein may be used in combination with other therapeutic agents. For example, the invention provides methods for pretreatment with a pharmaceutically effective dose of an antihistamine to minimize or prevent potential infusion-related anaphylactic reactions. For example, the antihistamine may be any pharmaceutically acceptable antihistamine (e.g. diphenhydramine) as disclosed herein and as known in the art. In one embodiment, the antihistamine is administered in a dose between about 1 mg and about 10 mg per kilogram of body weight. For example, the antihistamine may be administered in a dose of about 5 mg per kilogram. In one embodiment, the antihistamine is administered between about 10 minutes and about 90 minutes, for example, about 30 minutes to about 60 minutes, prior to administration of lysosomal acid lipase using an ambulatory system connected to the vascular access port. In one embodiment, the dose of diphenhydramine effectively counteracts potential anaphylactic infusion reactions.

Immunosuppresants such as antihistamines, corticosteroids, sirolimus, voclosporin, ciclosporin, methotrexate, IL-2 receptor directed antibodies, T-cell receptor directed antibodies, TNF-α directed antibodies or fusion proteins (infliximab, etanercept or adalimumab), CTLA4-Ig (e.g., abatacept), anti-OX-40 antibodies can also be administered before, during or after LAL administration if an anaphylactic reaction or adverse immune response is experienced by the patient.

The invention also contemplates therapy involving administration of LAL-containing compositions in combination with one or more cholesterol lowering agents (e.g., HMG-CoA reductase inhibitors). Non-limiting examples of such agents include: atorvastatin (Lipitor® and Torvast®), fluvastatin (Lescor®), lovastatin (Mevacor®, Altocor®, Altoprev®), pitavastatin (Livalo®, Pitava®), pravastatin (Pravachol®, Selektine®, Lipostat®), rosuvastatin (Crestor®) and simvastatin (Zocor®, Lipex®).

Compositions or proteins described herein can be used to treat a variety of conditions. For example, there are conditions for which treatment therapies are known to practitioners of skill in the art. The present invention contemplates that the therapeutic proteins (e.g., LAL) produced in an avian system containing a poultry derived glycosylation pattern can be employed to treat such conditions. That is, the treatment of conditions known to be treatable by conventionally produced therapeutic proteins by using therapeutic proteins produced as described herein is also contemplated. For example, LAL produced as described herein can be used to treat conditions resulting from or associated with LAL deficiency or insufficiency (collectively, "LAL deficiency"), such as Wolman disease and cholesteryl ester storage disease (CESD). As described herein, LAL deficiency also contemplates conditions in which expression of LAL is reduced due to a condition (e.g., a genetic mutation), physiological or environmental factors which leads to a reduction or deficiency of LAL produced in the body. LAL produced as described herein can also be used to treat other conditions such as atherosclerosis, fatty liver disease, non-alcoholic fatty liver disease, nonalcoholic steatohepatitis (NASH) and cirrhosis. LAL produced as described herein can also be used to treat other conditions such as those disclosed in U.S. Pat. No. 6,849,257, issued Feb. 1, 2005, the disclosure of which is incorporated in its entirety herein by reference, U.S. publication No. 2009/0297496, published Dec. 3, 2009; US publication No. 2004/0223960, published Nov. 11, 2004; US publication No. 2007/0264249, published Nov. 15, 2009, the disclosures of which (i.e., the disclosures of each of these four patent publications) are incorporated in their entirety herein by reference.

It is also contemplated that LAL produced as disclosed herein can be used to treat certain specific conditions including pancreatitis, for example, chronic pancreatitis and/or acute pancreatitis as well as alcohol induced pancreatic injury such as alcohol induced pancreatitis.

LAL produced by any useful method, such as the ones disclosed herein, is contemplated for use to treat diseases due to alcohol induced cell injury including, but not limited to, those alcohol induced cell injuries that result in accumulation of lipid esters in body tissue such as, but not limited to, liver, spleen, gut and cardiovascular tissue. The invention also contemplates the treating of malabsorption by administering LAL.

One aspect of the invention is drawn to methods of treating a patient comprising administering to a patient a therapeutically effective amount of a composition comprising recombinant human LAL as described herein. The patient can be suffering or diagnosed with any number of conditions, including those associated with LAL deficiency. In one embodiment, the therapeutically effective amount is an amount that increases the red blood cell count in a patient by a desired amount. It is contemplated that LAL produced in accordance with the invention can be used to treat chronic kidney disease, for example, where tissues fail to sustain production of lysosomal acid lipase.

It is also contemplated that LAL produced by any useful method may be useful for the treatment of patients with Tangier disease and familial hypoalphalipoproteinemia. Tangier disease/familial hypoalphalipoproteinemia is associated with the accumulation of cholesterol esters in macrophages accompanied by hepatosplenomegaly and/or lymphadenopathy along with low levels of high-density lipoproteins (HDL) which can be treated by the administration of LAL. For example, without wishing to limit the invention to any particular theory or mechanism of operation, it is believed that impaired LAL activity decreases ABCA1 expression and conversely an increased LAL activity obtained by the administration of LAL to a patient with Tangier disease/familial hypoalphalipoproteinemia will increase ABCA1 expression to overcome the effects of an ABCA1 gene with a reduced functional activity as a result of polymorphism.

For the treatment of a condition, generally, the dosage administered can vary depending upon known factors such as age, health and weight of the recipient, type of concurrent treatment, frequency of treatment, and the like. Usually, a dosage of active ingredient can be between about 0.0001 and about 10 milligrams per kilogram of body weight. Precise dosage, frequency of administration and time span of treatment can be determined by a physician skilled in the art of administration of the respective therapeutic protein.

In addition, it has been discovered that dosages of 1 mg/kg and less can be effective in treating LAL deficiencies. The present invention provides methods of treating conditions comprising administering to a mammal (e.g. a patient, preferably a human patient) a therapeutically effective dose of lysosomal acid lipase between one time every 5 days and one time every 25 days, for example, between one time every 7 days and one time every 14 days. In one embodiment, the dose of lysosomal acid lipase administered is between about 0.1 mg and about 50 mg per kilogram of body weight, for example, the dose may be between about 1 mg and 5 mg per kilogram.

In one particularly useful embodiment, the invention provides methods of treating a condition by administering a dose of lysosomal acid lipase of between about 0.1 mg and 1.0 mg per kilogram of body weight in accordance with any therapeutically effective dosage regime such as those described herein.

The invention provides methods for treating any complication of LAL deficiency which may benefit from administering a therapeutically effective dose of LAL. In one embodiment, malabsorption and growth failure may be treated in accordance with the methods described herein. In another embodiment, complications seen in LAL deficiency patients including but not restricted to hepatomegaly and liver dysfunction may be treated using the methods provided herein.

The invention provides for treatment with recombinant LAL (e.g. recombinant human LAL) that can be produced by any useful protein expression system, for example, transgenic mammals and avians as is understood in the art. Other protein expression systems may include, but are not limited to, cell culture, bacteria, and plant systems.

The invention encompasses the administration of recombinant LAL as a part of a pharmaceutically acceptable composition by any route which may achieve the intended therapeutic effect, as determined by a physician skilled in the art. In one embodiment, the LAL may be administered by intravenous infusion over a period of about five hours. For example, the infusion may be facilitated by an ambulatory infusion pump connected to a vascular access port (e.g. a Port-a-Cath).

The invention also includes monitoring clinical and pathological presentation of the conditions, for example, Wolman Disease and CESD, in the mammal (e.g. the human patient). In one embodiment, the assessments consist of but are not limited to: lipid analysis, chest x-ray, liver function tests, stool chart, plasma mevalonic acid, immunogenicity, plasma lysosomal acid lipase, chitotriosidase, PARC, portal hypertension, anthropometry, volume and characterization of the liver, spleen, and gastrointestinal tract using, for example, imaging technology. For example, the aforementioned imaging technology may consist of ultrasound, magnetic resonance imaging, and nuclear magnetic resonance spectroscopy.

EXAMPLES

The present invention is further exemplified by the following examples. The examples are for illustrative purpose only and are not intended, nor should they be construed as limiting the invention in any manner.

Example 1

Construction of Vector (pALVIN-OVR1-I-hLAL-dSA) Carrying Recombinant Human Lysosomal Acid Lipase (rhLAL) Coding Sequence The nucleotide sequence of the hLAL gene in the pALVIN-OVR1-I-hLAL-dSA vector encodes a protein that is identical to the amino acid sequence of the protein produced by the human lysosomal acid lipase gene (GenBank Accession, NP_000226) (FIG. 1). Transcription of this sequence and subsequent translation of the resultant mRNA produces a 399 amino acid precursor protein, which is processed to a mature 378 amino acid protein identical to human LAL (GenBank Accession, NP_000226) (FIG. 1) as set forth in SEQ ID NO:1. Expression of the hLAL gene (see FIG. 2 for the cDNA sequence) in this Example is controlled by non-coding elements derived from the ovalbumin gene including enhancer, promoter, intronic, and 5' and 3' untranslated sequences. The ovalbumin gene produces ovalbumin, the major protein constituent of egg white. Activity of the chicken ovalbumin promoter is very specific to the cells within the chicken oviduct that produce egg white; expression in other tissues is minimal.

The plasmid vector pALVIN-OVR1-I-hLAL-dSA (FIG. 3A; the nucleotide sequence of which is shown in FIG. 4) was used to produce a replication-deficient retrovirus (RDR) that stably integrated the hLAL transgene into the genome of the founder (XLL109). This plasmid vector includes retroviral nucleotide sequences required for viral RNA packaging, reverse transcription and integration, but does not contain the intact sequences for the viral gag, pol and env genes. The methods used to generate the retroviral vector and their use in subsequent transgenesis procedures are described herein.

Figure 3B:
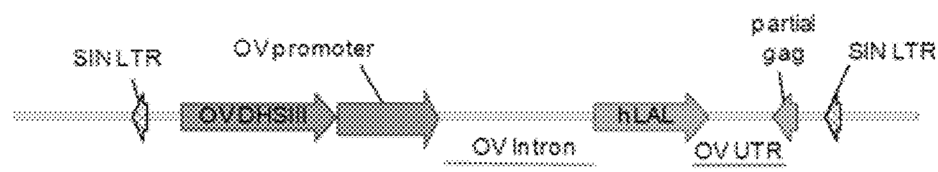

The retroviral portion of pALVIN-OVR1-I-hLAL-dSA is based on the ALV vector, pNLB. pNLB was modified such that the LTRs would be self-inactivating (SIN) (FIG. 3B). To accomplish this, 273 bp of the 3' LTR was deleted, which includes the enhancer and CAAT box of the U3 region. Because the inactivated U3 region at the 3' end of the retroviral sequence serves as a template for a new U3 region present at the 5' end of an integrated provirus, 5' LTR is normally also inactivated. The deletion of LTR sequences in the SIN construct decreases promoter interference on the internal promoter from the LTR, and minimizes the possibility for recombination of sequences to form a replication competent retrovirus. The new vector is termed pALVIN for ALV inactivation vector.

Downstream of the 5' LTR are the partial gag and env coding sequences, which were carried over from the pNLB vector. In pALVIN-OVR1-I-hLAL-dSA, a small portion (12%) of the gag protein precursor sequence remains (55% of the p19 mature peptide sequence) and a small portion (1.7%) of the env precursor sequence of RAV2 remains (GenBank Accession, AF033808). These truncated gag and env regions are unable to produce functional proteins needed to create replication competent retrovirus (Cosset, 1991).

Transcriptional and translational control elements of the chicken ovalbumin gene were inserted into pALVIN to create pALVIN-OV-1.1-I (sequence of which is shown in FIGS. 6A-6D; SEQ ID NO: 8). The first section of pALVIN-OV-1.1-I is composed of a contiguous section of the chicken ovalbumin gene which includes the 1.1 kb proximal promoter region, the first exon, first intron and part of the $2^{nd}$ exon. The next section is a stuffer insert fragment that takes the place of the ovalbumin protein coding sequences. The stuffer is followed by the 3' untranslated region (UTR) of the chicken ovalbumin gene, which includes sequences that facilitate proper processing of the mRNA, including polyadenylation. In general, the stuffer fragment is replaced by DNA fragments encoding the desired protein, in this case hLAL. The result is a vector that has specific elements that promote regulated transcriptional expression and translation of an mRNA in the oviduct of transgenic chickens, that closely mimics regulation of the endogenous ovalbumin mRNA, and that allows high expression of the protein of interest in egg white.

The pALVIN-OV-1.1-I vector includes the first intron of the ovalbumin gene. Because the intron is susceptible to splicing during the production and packaging of the retroviral RNA genome, we inserted the expression cassette in the opposite orientation relative to the LTRs. In this way the intron is not recognizable in the retroviral RNA and is packaged without splicing. For convenience all maps in this document are drawn with the LTRs in the opposite orientation and the expression cassette in the forward or clockwise orientation.

pALVIN-OV-1.1-I is the base vector into which the coding sequence (CDS) of hLAL was inserted. Two DNA fragments, hLAL adaptor and Syn hLAL, which make up the hLAL CDS and sequences required for compatibility with pALVIN-OV-1.1-I, were synthesized at Integrated DNA Technologies, Coralville, Iowa, (see FIGS. 7 and 8; SEQ ID NOs: 9 and 10). A 229 bp HpaI/BamHI fragment of hLAL adaptor and a 1113 bp BamHI/BstBI fragment of Syn hLAL were inserted into the 7882 HpaI/BstBI fragment of pALVIN-OV-1.1-I, thereby replacing the stuffer region with the hLAL CDS and creating pALVIN-OV-1.1-1-hLAL.

It was discovered that there was a cryptic splice site in the antisense strand of the hLAL CDS which prevented packaging of intact retroviral RNA. The cryptic splice site was removed by alteration of the DNA sequence without changing the amino acid sequence of hLAL. This change was performed by polymerase chain amplification of region 232 to 534 of pALVIN-OV-1.1-I-hLAL with primer 5'-AGAAACTGAGAGTGTCTTAT-3' (SEQ ID NO: 12) and primer 5'-TGACAGCTGTGGATCCAGAAACAAACATG-3' (SEQ ID NO: 13), creating a 329 bp amplicon. This amplicon was digested with BamHI and SexAI and ligated with the 8940 bp BamHI/SexAI fragment of pALVIN-OV-1.1-I-hLAL to create pALVIN-OV-1.1-I-hLAL-dSA.

Figure 10:
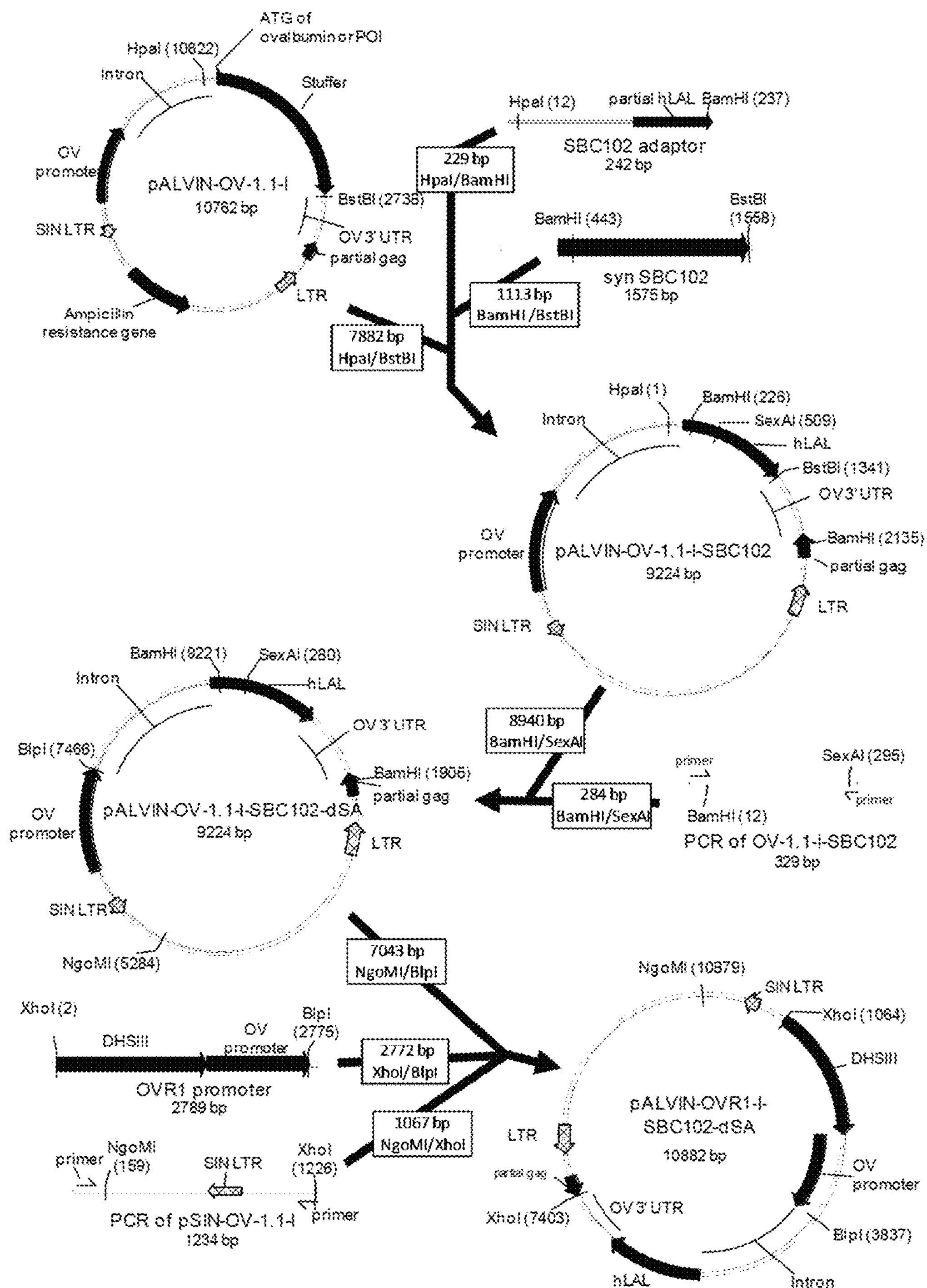
FIG. 10 depicts schematics of the steps used to construct the pALVIN-OVR1-I-hLAL-dSA vector.

A putative promoter enhancer which contains DNase hypersensitive site III (DHSIII) of the chicken ovalbumin gene (−3819 to −2169 relative to the OV promoter start site) (Kaye, Bellard et al. 1984) was inserted into pALVIN-OV-1.1-I-hLAL-dSA to create pALVIN-OVR1-I-hLAL-dSA. This was performed as follows: a DNA fragment which included the DHSIII enhancer and 1.1 kb proximal OV promoter termed OVR1 promoter (see FIG. 9; and SEQ ID NO: 11 for sequence) was isolated by digestion with XhoI and BlpI. To facilitate subcloning, an adaptor fragment, PCR of pSIN-OV-1.1-1 was generated by PCR amplification of region 6752 to 7974 of pALVIN-OV-1.1-I with primers 5'-GCCGCTCGAGCGAGGAATATAAAAAAATT-3' (SEQ ID NO: 14) and 5'-TCCGCGCACATTTCCCCGAA-3'(SEQ ID NO: 15) followed by digestion with NgoMI and XhoI. The 2772 bp XhoI/BlpI fragment of OVR1 promoter and 1067 bp NgoMI/XhoI fragment of PCR of pSIN-OV-1.1-I were inserted into the 7043 bp NgoMI/B1pI fragment of pALVIN-OV-1.1-I-hLAL-dSA, thereby creating pALVIN-OVR1-I-hLAL-dSA (see FIG. 10 for the construction schematics of pALVIN-OVR1-I-hLAL-dSA). The construction of the retroviral vector segment of the vector, denoted as pALVIN (aka pAVIJCR-A395.22.3.1-KM or pALV-SIN), is described in United States Patent Application 2008/0064862.

In addition, included is the production of LAL in accordance with the invention using a promoter and/or vector disclosed in US patent publication No. 2008/0064862, published Mar. 13, 2008, the disclosure of which is incorporated in its entirety herein by reference.

Example 2

Viral Particle Production

The G0 founder transgenic male, XLL109, carrying the hLAL transgene in its genome, was created by using a retroviral transgenesis method as follows. Replication-defective viral particles carrying the pALVIN-OVR1-I-hLAL-dSA vector were produced by transient transfection of an immortalized chicken fibroblast cell line. These chicken fibroblast cells were simultaneously transfected with three plasmids, pALVIN-OVR1-I-hLAL-dSA, pCMV-gag-pol and pCMV-VSV-G. pCMV-gag-pol expresses the gag and pol genes of RAV1 strain of the avian leukosis virus. pCMV-VSV-G expresses the envelope protein of the vesicular stomatitis virus. Four hours after transfection, the media was replaced with DMEM supplemented with 10% fetal bovine serum, 100 units/mL penicillin and 100 μg/mL streptomycin. Media was harvested at 48 hours post-transfection, filtered through a 0.45 micron filter (Millipore) and concentrated by ultracentrifugation. Concentrated retrovirus carrying the ALVIN-OVR1-I-hLAL-dSA transgene was collected and used in the transduction of early stage embryos. Note that because "p" is the notation for the plasmid form of vector, the "p" is absent from the transgene designations once the transgene is in the form of packaged vector or integrated transgene.

Example 3

Embryo Transgenesis

Integration of the ALVIN-OVR1-I-hLAL-dSA expression cassette into the genome of an embryo was achieved by transduction of early stage embryos (Speksnij der and Ivarie, 2000). Freshly laid fertilized White Leghorn eggs were obtained from a breeding colony. An aperture was made in the shell to provide access to the embryo. Seven microliters of concentrated replication deficient retrovirus particles carrying the ALVIN-OVR1-I-hLAL-dSA expression cassette described above were injected into the subgerminal cavity of the embryo. Eggs were sealed with hot glue, and then incubated and hatched under standard conditions. Progeny produced from these injections were given individual identification markers at hatch for identification and traceability. Blood samples from the progeny were transgene positive when analyzed by real-time PCR for the hLAL transgene using PCR primers specific for the hLAL coding sequence (as described below). This gave an indication that the transgenesis procedure was successful. The real-time PCR assay for the hLAL transgene utilizes Taqman® chemistry (Applied Biosystems). The forward and reverse primers were 5'-ACGACTGGCTTGCAGATGTCT-3' (SEQ ID NO: 16) and 5'-CCCCAAATGAAGTCAAGATGCT-3' (SEQ ID NO: 17), respectively. The Taqman® probe sequence was 5'-CCGGAATGCTCTCATGGAACACCAA-3'(SEQ ID NO: 18) and was labeled with FAM (as the emitter) at the 5' end and Iowa Black (as the quencher) at the 3' end. Primers, probe and 1 μl of extracted DNA was added to 30 μl Taqman® Universal Master Mix (Applied Biosystems). Control reactions included various dilutions of a plasmid bearing the hLAL sequence and DNA from wild-type chickens (data not shown). Standard cycling parameters were used on an Applied Biosystems 7500 Fast Real-Time PCR System.

Example 4

Identification of G0 Founder

Semen was collected from sexually mature males and DNA was extracted and assayed using the hLAL real-time PCR assay. The number of transgene copies in each sample was estimated using known standards (a plasmid bearing the hLAL gene) mixed with negative control semen DNA. The transgene cassette DNA content in male XLL109 was at a level that would allow transmission of the transgene to his progeny, as estimated by real-time PCR. This XLL109 male was the G0 transgenic founder and was bred with non-transgenic chickens to generate the G1 hemizygotic transgenic chickens.

Example 5

Propagation and Characterization of Hemizygotic G1 Avians

Figure 11:
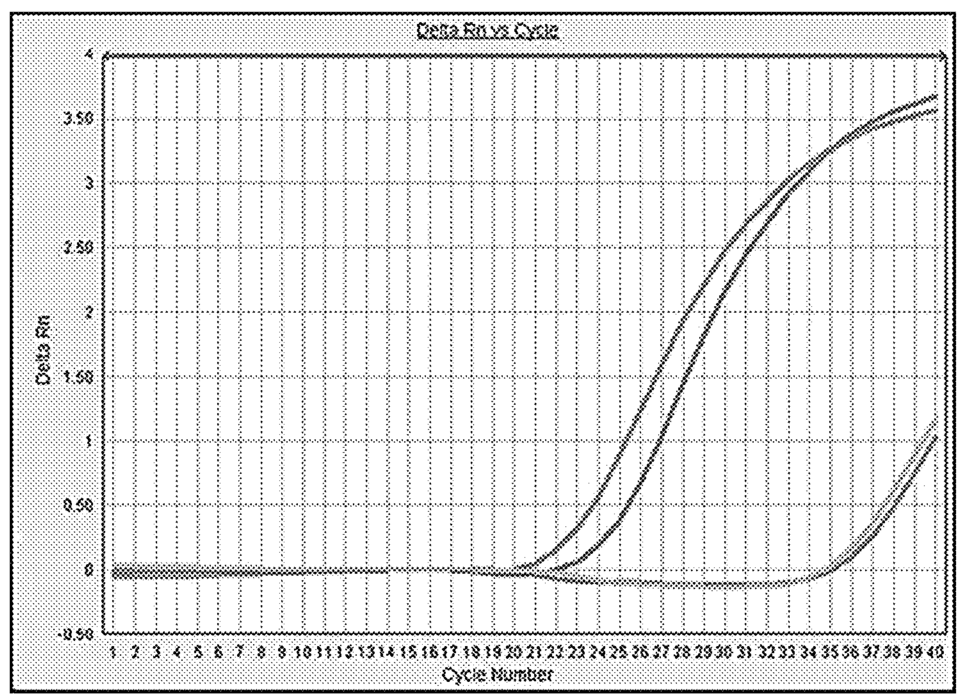
FIG. 11 depicts a real-time PCR analysis of blood DNA samples from a hemizygous transgenic G1 offspring of XLL109. The signals from duplicate DNA samples of hemizygous G1 progeny, 1LL7466, are indicated by the curves that initiate an increase in Delta Rn before cycle 22. The curves for two non-transgenic progeny are shown; these curves stay at or near baseline through at least 34 cycles.

Progeny sired by the transgenic founder XLL109 were tested for the presence of the transgene in blood cell DNA using the hLAL real-time PCR assay. Blood was collected from 1-2 week old progeny and DNA was extracted using a high-throughput technique (Harvey et al., 2002). The DNA solutions were not quantified prior to the Taqman assay to facilitate the high-throughput screen. Typically 1 μl of DNA solution contains 50 to 400 ng of DNA which is sufficient to generate a positive amplification signal. A total of 1,322 chicks sired by XLL109 were tested, and positive progeny were re-bled and tested for confirmation. According to the PCR results, 22 progeny were positive for the ALVIN-OVR1-I-hLAL-dSA transgene. An example of the Taqman results is shown in FIG. 11.

Example 6

Identification and Characterization of High-Expression Line

One of the G1 chickens, 1LL7466, laid eggs with significantly higher levels of rhLAL protein in the egg white, as compared to the other G1 chickens. Southern blot analysis was performed on 1LL7466 and sibling G1 males to identify which sibling males had the same integration site as the high expressing chicken. Digests were performed with a restriction enzyme that cut only once within the transgene (BlpI), and the Southern blots were probed with a segment of the ovalbumin promoter or the hLAL coding sequence (FIGS. 12A-D). The position of the $2^{nd}$ restriction site, which resides in the flanking genomic region, varies depending on the site of integration. Thus the size of the BlpI band detected by the OV probe or hLAL probe is unique to each line generated.

Figure 12A:
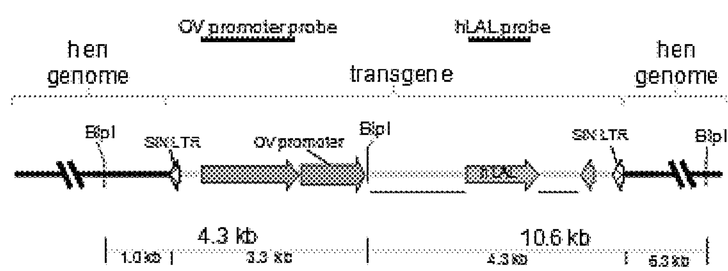
FIGS. 12A-D depict Southern analysis of G1 chickens carrying the ALVIN-OVR1-I-hLAL-dSA transgene.
Figure 12B:
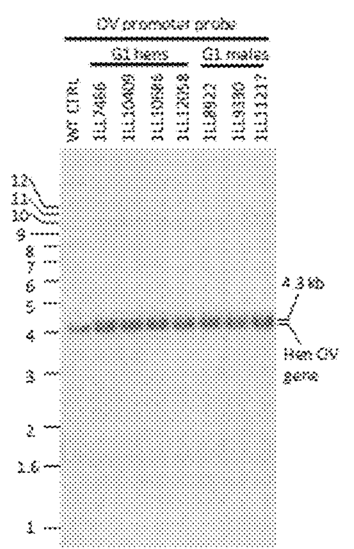
Figure 12C:
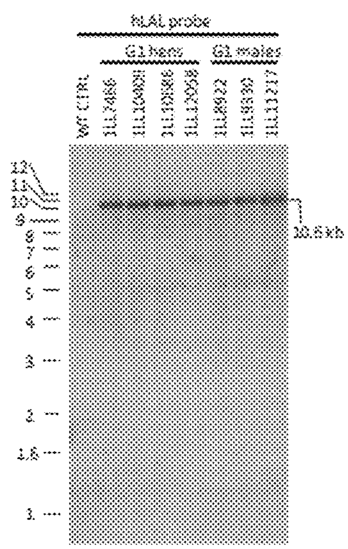
Figure 12D:
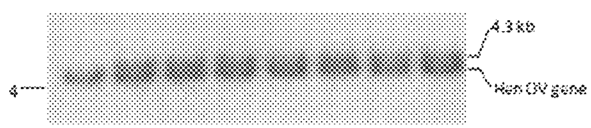

The OV probe detected a single band of 4.1 kb in BlpI-digested DNA from wild-type chickens, which corresponded to the expected size of a BlpI segment within the endogenous ovalbumin gene of the chicken genome (FIGS. 12B and 12D). A second band of 4.3 kb was detected with chicken 1LL7466, which corresponded to the transgene band. Three additional female siblings, 1LL10409, 1LL10686 and 1LL12058 and three additional male siblings, 1LL8922, 1LL9330 and 1LL11217 displayed the 4.3 kb band, indicating that these siblings might be of the same line (FIGS. 12B and 12D).

As expected the hLAL probe did not detect a band in DNA from wild-type chickens as the DNA sequence of the chicken lysosomal acid lipase gene and the coding sequence for the recombinant human lysosomal acid lipase are sufficiently differentiated to not permit hybridization under the conditions used in these Southern assays (FIG. 12C). The hLAL probe detected a single band of ~10.6 kb in BlpI-digested genomic DNA from the same chickens that were positive for the 4.3 kb band detected by the OV probe, indicating that these 7 G1 chickens have the same integration site and thus are of the same line.

No other bands were detected, indicating that 1LL7466, 1LL10409, 1LL10686, 1LL12058, 1LL8922, 1LL9330 and 1LL11217 all had a single integration site.

The Southern analysis also indicated that the transgene was integrated as the bands detected by the OV and hLAL probes were of different sizes and greater in size than from the transgene alone. A map showing the predicted structure of the integrated transgene and position of BlpI sites in the flanking genomic regions is shown in FIG. 12A.

Figure 13A:
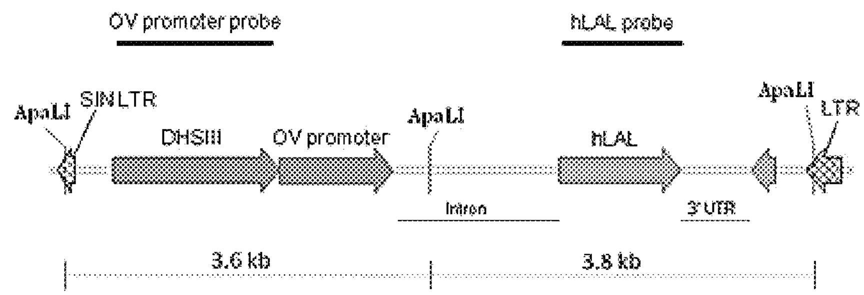
FIG. 13A depicts schematic of the ALVIN-OVR1-I-hLAL-dSA transgene. The size of ApaLI bands predicted to be detected by the OV probe and hLAL probe are also shown.
Figure 13B:
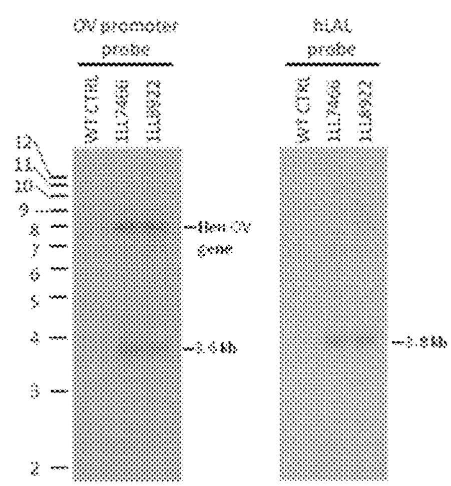
FIG. 13B depicts schematic of a Southern blot analysis of the ALVIN-OVR1-I-hLAL-dSA transgene for confirmation of transgene size. Southern blot of genomic DNA digested with ApaLI and probed with either the OV probe (left panel) or hLAL probe (right panel). WT CTRL is genomic DNA isolated from a non-transgenic chicken. The ID number of the G1s is indicated above each lane. The position and size (kb) of the molecular weight markers are shown to the left of the blots. The position and size of the detected transgene fragments (OV promoter probe, 3.6 kb; hLAL probe, 3.8 kb) and endogenous ovalbumin gene (7.7 kb) are shown to the right of the blots.

To confirm that the transgene is intact, two steps were taken. First, the hLAL coding sequence was isolated by PCR from 1LL7466. The PCR products were sequenced on both strands from the hLAL start codon to the stop codon. The DNA sequence was exactly as expected, indicating no changes in the DNA sequence of coding regions in the transgene. Second, Southern blot analysis was conducted using restriction enzyme ApaLI, which digests intact transgene into 2 segments, 3.6 and 3.8 kb (FIG. 13A). Both the 3.6 and 3.8 kb bands were detected in ApaLI-digested genomic DNA from G1 s, indicating that the transgene was integrated in a fully intact form (FIG. 13B).

Example 7

Propagation and Characterization of G2s

Figure 14:
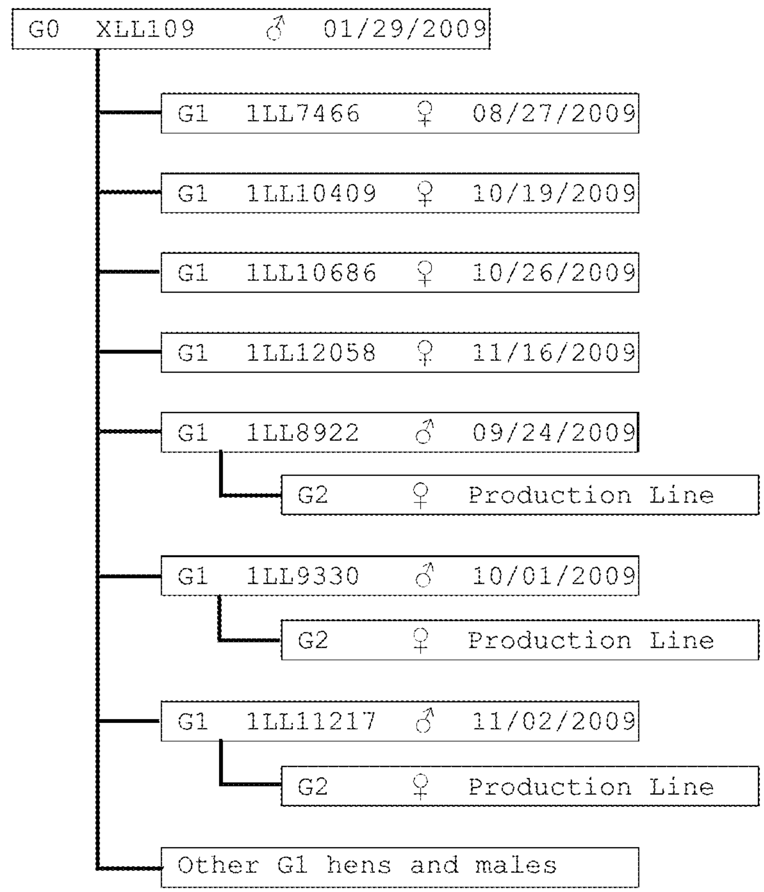
FIG. 14 depicts a lineage of transgenic chickens. Shown for each chicken are the generation number (G0, G1 or G2), identification number, gender and hatch date. Other G1 chickens are those of other lineages.

FIG. 14 shows the lineage of the hLAL G2s descended from a single G0 founder, XLL109. At the G1 stage, the transgene was characterized with regard to copy number, integrity, hLAL sequence and integration site—and seven G1 transgenics were identified and characterized (four chickens and three roosters). Propagation of the G2s was accomplished by artificial insemination of non-transgenic chickens with semen collected from the G1 sires 1LL8922, 1LL9330 and 1LL11217 (FIG. 14). Each inseminated chicken, her eggs and subsequent progeny were housed separately from the other progeny. Hatched progeny were tested for presence of the hLAL transgene using the hLAL real-time PCR assay. Because G1 founders were hemizygous with respect to the transgene, half of the progeny were expected to be transgenic G2s. Of 610 G2 progeny analyzed to date, 330 or 54% were transgenic.

Example 8

Genetic Analysis of the hLAL Avians

After identification of each G2 chicken by the hLAL real-time PCR assay of blood DNA, the production line is subjected to the following genetic assays: the hLAL gene was PCR-amplified from blood DNA and sequenced to confirm 100% homology with the human sequence; the transgene integration site was confirmed by integration site PCR, as described above. The PCR sequencing and integration site analysis was performed on: each chicken in a <10 chicken production line; 10% of chickens (minimum 10) for 11-100 chicken production line; 5% of chickens (minimum 10) for 101-1000 chicken production line; 1% of chickens (minimum 50) for 1001-10,000 chicken production line; 0.1% of chickens (minimum 100) for >10,001 chicken production line. Detailed records were maintained at every step of the growing and production phase.

Example 9

Purification of hLAL from Egg White

Egg white (EW) containing LAL was solubilized at pH 6 overnight and clarified through centrifugation (or depth filtration) with 0.2 um filtration. The EW was adjusted with 1 M NaOAc buffer (pH 4) to pH 6.

The clarified EW was loaded onto a Phenyl-HIC column (EW:column size=2:1) equilibrated with 20 mM phosphate/137 mM NaCl buffer(pH 6). After the completion of loading, the column was washed with equilibration buffer and 5 mM phosphate buffer (pH 6). The LAL was eluted with 30% propylene glycol with 5 mM Tris buffer (pH 7.2).

The eluted LAL fraction was adjusted to pH 5 with 1 M acid acid and then loaded onto a GigaCap S column (EW:column size=10:1). The column was equilibrated with 50 mM NaOAc buffer (pH 5). After completion of loading, the column was washed with the equilibration buffer. The LAL was eluted with 50 mM NaOAc/60 mM NaCl (pH 5).

Figure 15:
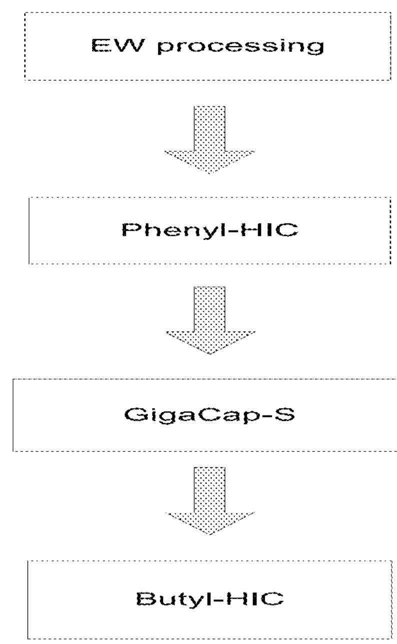
FIG. 15 depicts the purification steps of hLAL from egg white.

The LAL fraction off the GigaCap S column was adjusted to pH6 with 1 M Tris buffer and then loaded onto a Butyl-HIC column (EW:column size=10:1). The column was equilibrated with 20 mM phosphate/137 mM NaCl buffer (pH 6). After the completion of loading, the column was washed with equilibration buffer and 5 mM phosphate buffer (pH 6). The pure LAL was eluted with 50% propylene glycol with 5 mM Tris buffer (pH 7.2). FIG. 15 depicts the purification steps of hLAL from egg white.

Example 10

Carbohydrate Analysis of Transgenic Avian Derived hLAL

The oligosaccharide structures were determined for avian derived human LAL by employing the following analysis techniques as are well known to practitioners of ordinary skill in the art.

Two hundred micrograms were digested with trypsin and chymotrypsin for 18 h at 37° C. in 0.1 M Tris-HCl, pH 8.2, containing 1 mM $CaCl_2$. The digestion products were enriched and freed of contaminants by Sep-Pak C18 cartridge column. After enrichment, the glycopeptides were digested with 2 µl of PNGaseF (7.5 unit/ml) in 50 µl of 20 mM sodium phosphate buffer, pH 7.5, for 18 h at 37° C. Released oligosaccharides were separated from peptide and enzyme by passage through a Sep-Pak C18 cartridge column.

The glycan fraction was dissolved in dimethylsulfoxide and then permethylated based on the method of Anumula and Taylor (Anumula and Taylor, 1992). The reaction was quenched by addition of water and per-O-methylated carbohydrates were extracted with dichloromethane. Per-O-methylated glycans were dried under a stream of nitrogen.

MALDI/TOF-MS (Matrix assisted laser desorption ionization time-of-flight mass spectrometry) was performed in the reflector positive ion mode using a-dihydroxybenzoic acid (DHBA, 20 mg/mL solution in 50% methanol:water) as a matrix. All spectra were obtained by using a Microflex LRF (Bruker).

MALDI-TOF-MS analysis and ESI MS/MS (electrospray ionization tandem mass spectrometry) were performed on the oligosaccharides after release from the peptide backbone and purification as is understood in the art. Samples of the individual polysaccharide species were also digested with certain enzymes and the digest products were analyzed by HPLC as is understood in the art.

It is believed that there are about six N-linked glycosylation sites present on human LAL. See, Zschenker, et al (2005) J Biochem., Vol 137, p 387-394, the disclosure of which is incorporated in its entirety by reference This reference also indicates that there may be an O-linked glycosyation site on Human LAL. The N-linked oligosaccharide structures identified are shown in FIG. 16.

The data revealed that many or all of these structures were found as an N-linked Glycosylation structure in LAL produced in accordance with the invention (FIG. 16). For example, A-n is found attached to LAL produced in accordance with the invention. For example, 0-n is found attached to LAL produced in accordance with the invention. For example, at least one of B-n, C-n and D-n is found attached to LAL produced in accordance with the invention. For example, at least one of E-n and F-n is found attached to LAL produced in accordance with the invention. For example, at least one of I-n and J-n is found attached to LAL produced in accordance with the invention. For example, at least one of K-n and L-n is found attached to LAL produced in accordance with the invention. For example, at least one of M-n and N-n is found attached to LAL produced in accordance with the invention. For example, G-n is found attached to LAL produced in accordance with the invention. For example, H-n is found attached to LAL produced in accordance with the invention.

Example 11

N-glycan Species of Transgenic Avian Derived LAL

Purified samples of transgenic avian derived hLAL (600 μg/sample) were dialyzed using a Tube-O-Dialyzer (4.0 kDa cut-off membrane; G BioSciences) against nanopure water at 4° C. for about 24 hours to remove salts and other contaminants. Nanopure water was replaced four times during the entire dialysis period.

After dialysis, each of the samples was divided into three aliquots: ~¼ of sample weight for neutral and amino sugars analysis, ~¼ of sample weight for mannose-6-phosphate analysis, and ~½ of sample weight for oligosaccharide profiling. The aliquot intended for neutral and amino sugars analysis was hydrolyzed with 2 N trifluoroacetic acid (TFA) at 100° C. for 4 hours and the aliquot for mannose-6-phosphate analysis was hydrolyzed with 6.75 N TFA at 100° C. for 1.5 hours. The hydrolysates were then dried under $N_2$, redissolved with 50 μL $H_2O$, sonicated for 7 min in ice and transferred to an injection vial. However, the neutral and amino sugar samples were diluted 2 times because the peaks produced from the originally dissolved hydrolysates were too large.

A mix of standards for neutral and amino sugars, and for mannose-6-phosphate with a known number of moles was hydrolyzed in the same manner and at the same time as the sample. Four concentration of the neutral and amino sugar standard mix (Fuc & GalNAc, 0.2, 0.4, 0.8, and 1.6 nmoles per 10 μL; GlcNAc, 0.5, 1.0, 2.0, and 4.0 nmoles per 10 μL; Gal & Man, 0.3, 0.6, 1.2, and 2.4 nmoles per 10 μL; and Glc, 0.1, 0.2, 0.4, and 0.8 nmoles per 10 μL) and mannose-6-phosphate (640, 1280, 2560, 5120 picomoles per10 μL) were prepared to establish a calibration equation. The number of moles of each sugar in the sample was quantified by linear interpolation from the calibration equation.

The neutral and amino sugars and mannose-6-phosphate were analyzed by HPAEC using a Dionex ICS3000 system equipped with a gradient pump, an electrochemical detector, and an autosampler. The individual neutral and amino sugars, and mannose-6-phosphate were separated by a Dionex CarboPac PA20 (3×150 mm) analytical column with an amino trap. The gradient programs used eluents A, degassed nanopure water and B, 200 mM NaOH for neutral and amino sugars, and C, 100 mM NaOH and D, 1 M sodium acetate in 100 mM NaOH for mannose-6-phosphate. Injection (10 μL/injection) was made every 40 minutes for neutral and amino sugar determination and every 35 minutes for mannose-6-phosphate determination. All methods were based on protocols described by Hardy and Townsend (Hardy, M. R., and Townsend, R. R., "High-pH anion-exchange chromatography of glycoprotein-derived carbohydrates", 1994, Methods Enzymol. 230: 208-225). Instrument control and data acquisition were accomplished using Dionex chromeleon software. Results are shown in Table 1 below. The control sample is ovomucoid purified from EW.

TABLE 1

Monosaccharide composition of control and LAL by HPAEC.

| Sample ID | Analyte | nano-moles | nano-moles/μg | mole % |
|---|---|---|---|---|
| Control | Fucose | nd | — | — |
| | N-acetyl galactosamine | 5.066 | 0.020 | 9.6 |
| | N-acetyl glucosamine | 26.947 | 0.108 | 51.4 |
| | Galactose | 3.876 | 0.016 | 7.4 |
| | Glucose | nd | — | — |
| | Mannose | 16.565 | 0.066 | 31.6 |
| | Mannose-6-phosphate | nd | — | — |
| | N-acetyl neuraminic acid | ndm | — | — |
| | N-glycolyl neuraminic acid | ndm | — | — |
| Transgenic Avian derived hLAL | Fucose | nd | — | — |
| | N-acetyl galactosamine | nd | — | — |
| | N-acetyl glucosamine | 17.932 | 0.120 | 37.6 |
| | Galactose | 0.879 | 0.006 | 1.8 |
| | Glucose | nd | — | — |
| | Mannose | 23.290 | 0.155 | 48.8 |
| | Mannose-6-phosphate | 5.642 | 0.038 | 11.8 |
| | N-acetyl neuraminic acid | ndm | — | — |
| | N-glycolyl neuraminic acid | ndm | — | — |

nd = not detected; ndm = not determined.

Structural Features of LAL

LAL has 6 potential sites in its amino acid sequence for N-linked glycosylation, $Asn^{36}$, $Asn^{72}$, $Asn^{101}$ $Asn^{161}$, $Asn^{273}$, and $Asn^{321}$. Five of these, $Asn^{36}$, $Asn^{101}$ $Asn^{161}$, $Asn^{273}$ and $Asn^{321}$ were found to be glycosylated while $Asn^{72}$ was unglycosylated or substantially unglycosylated (substantially unglycosylated means in a mixture of LAL molecules, fewer $Asn^{72}$ are glycosylated than any of $Asn^{36}$, $Asn^{101}$ $Asn^{161}$, $Asn^{273}$ and $Asn^{321}$). Accordingly, one aspect of the invention is LAL (e.g., human LAL) which is unglycosylated and/or substantially unglycosylated at $Asn^{72}$, and production and use of such LAL. However, LAL having a glycosylated $Asn^{72}$ is within the scope of the invention. The N-glycan structures primarily consist of a mixture of bi-, tri- and tetraantennary structures with N-acetylglucosamine, mannose and mannose-6-phosphate (M6P) as the major sugars. Each site appears to have a favored set of structures (Table 2 and FIG. 17) which is one aspect of the invention. For example, M6P-modified N-glycans reside at least at $Asn^{101}$ $Asn^{161}$ and $Asn^{273}$. The non-phosphorylated structures are typical of N-glycans found on endogenous egg white proteins. No O-linked glycans were detected as determined by lack of N-acetylgalactosamine (GalNac). No sialic acid was detected which is consistent with previously determined N-glycan structures of other endogenous and exogenous proteins produced in accordance with the invention. The invention includes LAL glycosylated with one or more of the oligosaccharide structures disclosed herein.

TABLE 2

Site residence of LAL glycan structures as determined by LC/MS of glycopeptides.

| Site | Glycan structure |
|---|---|
| $Asn^{36}$ | GlcNAc4Man3GlcNAc2 |
| | Hex1GlcNAc4Man3GlcNAc2 |
| $Asn^{72}$ | None detected |
| $Asn^{101}$ | Phos2Man7GlcNAc2 |
| $Asn^{161}$ | Phos1Man6GlcNAc2 |
| | GlcNAc1Phos1Man6GlcNAc2 |
| | Man3GlcNAc2 |
| | GlcNAc2Man3GlcNAc2 |
| | GlcNAc3Man3GlcNAc2 |
| | GlcNAc4Man3GlcNAc2 |
| | Hex1GlcNAc4Man3GlcNAc2 |
| $Asn^{273}$ | Man7GlcNAc2 |
| | Man8GlcNAc2 |
| | Man9GlcNAc2 |
| | Phos1Man8GlcNAc2 |

TABLE 2-continued

| Site residence of LAL glycan structures as determined by LC/MS of glycopeptides. | |
|---|---|
| Site | Glycan structure |
| Asn$^{321}$ | Phos1Man9GlcNAc2<br>GlcNAc2Man3GlcNAc2<br>GlcNAc3Man3GlcNAc2<br>GlcNAc4Man3GlcNAc2<br>Hex1GlcNAc4Man3GlcNAc2<br>GlcNAc5Man3GlcNAc2<br>Hex1GlcNAc5Man3GlcNAc2<br>GlcNAc6Man3GlcNAc2<br>Hex1GlcNAc6Man3GlcNAc2 |

Hex, galactose;
Phos, phosphate;
Man, mannose;
GlcNAc2, N-acetylglucosamine

Methods

Monosaccharide composition, including the neutrals, amino and M6P, was determined qualitatively and quantitatively by high pH anion exchange chromatography-pulsed amperometric detection (HPAEC-PAD).

The structures of the predominant glycans were determined with data from several mass spectrometry methods (MALDI-TOF, NSI-MS/MS and glycopeptide LC-MS).

Figure 18:
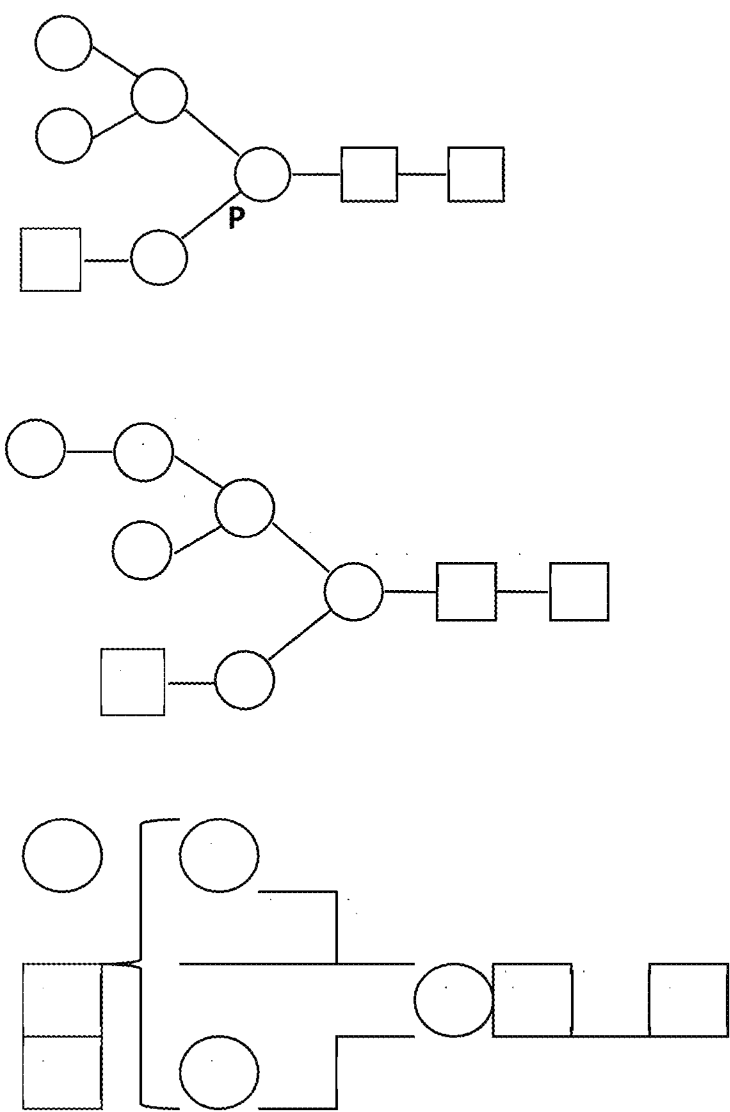
FIG. 18 depicts phosphorylated N-glycans released by PNGase and analyzed by MALDI-TOF. Structures are shown.
Figure 19:
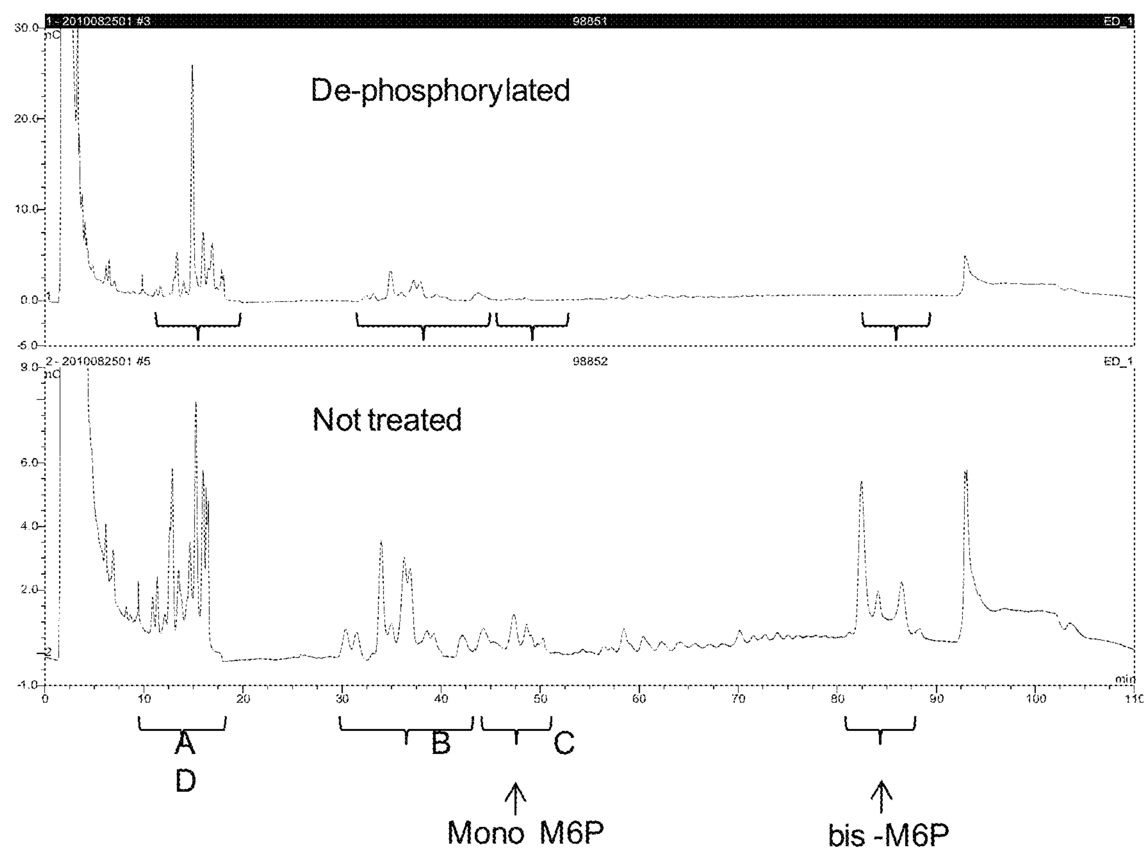
FIG. 19 depicts the effect of dephosphorylation of LAL on HPAEC-PAD retention time of N-glycans. LAL produced in accordance with the invention was dephosphorylated with bacterial alkaline phosphatase (upper panel) or left untreated (lower panel). Released N-glycans were analyzed by HPAEC-PAD.

MALDI-TOF was useful for determination of neutral N-glycans and was able to detect phosphorylated N-glycans (FIG. 18). NSI-MS/MS was employed to determine the nature of minor peaks in the MALDI-TOF spectra, some of which were attributed to phosphorylated N-glycans (FIG. 19). Efforts to improve the ability of MALDI-TOF to detect phosphorylated N-glycans were not fruitful.

LC/MS of glycopeptides was able to detect neutral and phosphorylated structures and was able to determine the position of specific structures in the amino acid sequence of LAL (data summarized in FIG. 17 and Table 2).

To determine which peaks in the HPAEC-PAD chromatogram are due to phosphorylated N-glycans, LAL was treated with phosphatase and analyzed (FIG. 3). Peaks in groups C and D decreased in area under the curve (AUC) while a peak in group A became more prominent. Peaks in group B did not change in proportion to the other peaks. Based on the knowledge that retention time is proportional to the degree of charge (either due to phosphorylation or sialylation), it is contemplated that group C is composed of N-glycans with one phosphate (mono M6P) and group D composed of N-glycans with two phosphates (bis-M6P).

The retention time was also affected by composition and relative structural position of the neutral and amino monosaccharides. Such examples include the presence of galactose, the presence of a bisecting GlcNac and the degree of GlcNac substitution. Such factors contribute to the multiplicity of peaks in the HPAEC-PAD chromatogram.

Example 12

In Vitro Enzyme Activity Analysis of Transgenic Avian Derived hLAL in Egg White

Activity of Lysosomal Acid Lipase in egg white was determined using the fluorogenic substrate 4-methylumbelliferyl-oleate assay essentially as described in Yan et al. (2006), American Journal of Pathology, Vol. 169, No. 3, p 916-926, the disclosure of which is incorporated in its entirety herein by reference.

A stock solution of 4-methylumbelliferyl oleate (4-MUO) was prepared consisting of 2.5 mM 4-MUO in 4% Triton X-100. The assay was performed in a microtiter plate each well containing 62.5 μl of 0.2 M Sodium Citrate (pH 5.5) in 0.01% Tween80, 12.5 μl of egg white sample and 25 μl of the 2.5 mM 4-MUO. Change in fluorescence was monitored for 30 minutes at 37° C. using a Bio-Tek Synergy HT fluorometric microplate reader (excitation 360 nm and emission 460 nm). Prior to assay, egg white containing the hLAL was diluted to an enzyme concentration that resulted in the reaction continuing linearly for at least 30 minutes. The reaction was stopped with 50 μl of 0.75 M Tris-HCl, pH 8.0 and the endpoint fluorescence signal was measured in the same plate reader used above (excitation 360 nm and emission 460 nm).

Units of activity were determined using 4-methylumbelliferyl as a standard. One unit (U) is defined as the amount of enzyme which results in the formation of 1 umole of 4-methylumbelliferyl/min under the assay conditions described above. Non-hLAL containing egg white was used as a negative control.

Egg white samples which were positive for hLAL contained between 1 U and 100 U of activity per ml egg white. Egg white from 21 G1 chickens was analyzed. Egg white from 10 of the chickens tested positive for hLAL activity.

Example 13

In Vitro Analysis of Transgenic Avian Derived LAL

The ability of LAL produced in the oviduct cells of transgenic avians (referred to herein as "SBC-102," "avian derived LAL," "LAL," or "hLAL") to bind to cells and be internalized to the lysosomal compartment, was examined in vitro using macrophage and fibroblast cells. When incubated with macrophage cells, fluorescently-labeled SBC-102 was found to localize to the lysosome. This effect could be attenuated by using a mannose polysaccharide competitor, implicating the N-acetylglucosamine/mannose (GlcNAc/mannose) receptor as a mechanism of recognition and uptake by these cells. SBC-102 increased the cell-associated LAL activity in both LAL-deficient human fibroblasts and normal murine fibroblasts after incubation in vitro, indicating that exposure to SBC-102 can result in substantial replacement of deficient enzymatic activity.

Mannose-6-phosphate (M6P) is present in the oligosaccharide structures of SBC-102 which have been shown to be involved in the delivery of lysosomal enzymes to a wide variety of cells types via the ubiquitous M6P receptor.

LAL was purified from the egg white of transgenic hens. Oregon Green NHS was obtained from Invitrogen™ (#0-10241). The rat alveolar macrophage line, NR8383, and the mouse fibroblast line, NIH-3T3, were obtained from ATCC. LAL-deficient Wolman's fibroblasts were obtained from Coriell Institute for Medical Research and LysoTracker® Red was obtained from Invitrogen™.

Enzyme labeling: 4 mg of transgenic avian derived LAL in PBS was labeled with Oregon Green, according to the manufacturer's recommendations and reaction was subsequently dialyzed against PBS then concentrated.

Macrophage uptake: Fluorescently-labeled transgenic avian derived LAL (5 μg/mL) and LysoTracker® Red were incubated with NR8383 cells for 2 hours. Cells were examined by co-focal fluorescence microscopy using a sequential scanning mode at 488 nm and then 514 nm.

Competitive inhibition with mannan: Fluorescently-labeled SBC-102 (5 ug/mL) and mannan were incubated with NR8383 cells for 2 hours. Cells were trypsinized and LAL uptake measured by florescence-activated cell sorting using median fluorescence intensity as the endpoint.

Figure 20:
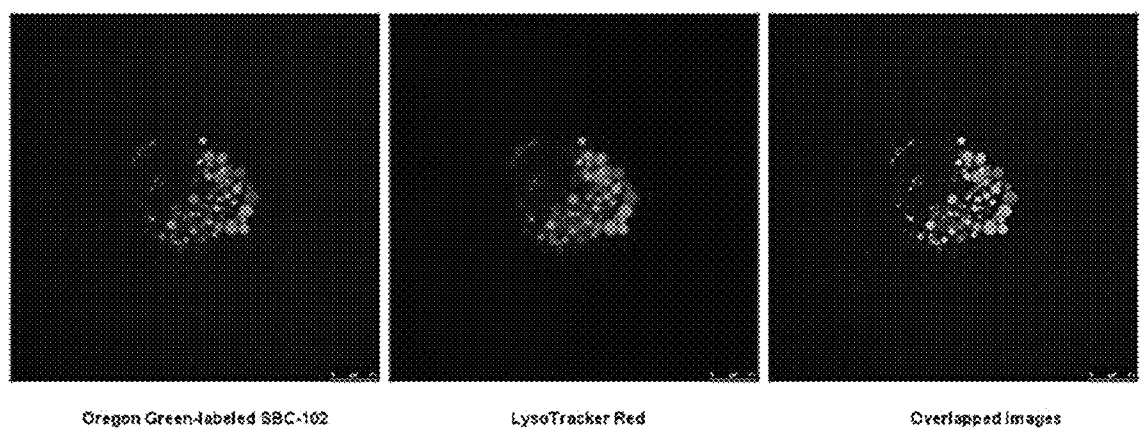
FIG. 20 depicts the co-localization of recombinant human LAL(SBC-102) and lysosomal marker in the lysosomes of these cells examined by confocal fluorescence microscopy using a sequential scanning mode.

The ability of transgenic avian derived LAL to be taken up and subsequently incorporated into the lysosomes of target cells was examined using the macrophage cell line, NR8383. Fluorescently-labeled transgenic avian derived LAL and the lysosomal marker, "LysoTracker® Red" (Invitrogen™), were incubated with cells for 2 hours. The co-localization of transgenic avian derived LAL and lysosomal marker in the lysosomes of these cells was subsequently examined by confocal fluorescence microscopy using a sequential scanning mode (FIG. 20). The LAL demonstrated localization to lysosomes, which is consistent with similar in vitro studies using rhLAL from a variety of sources.

Figure 21:
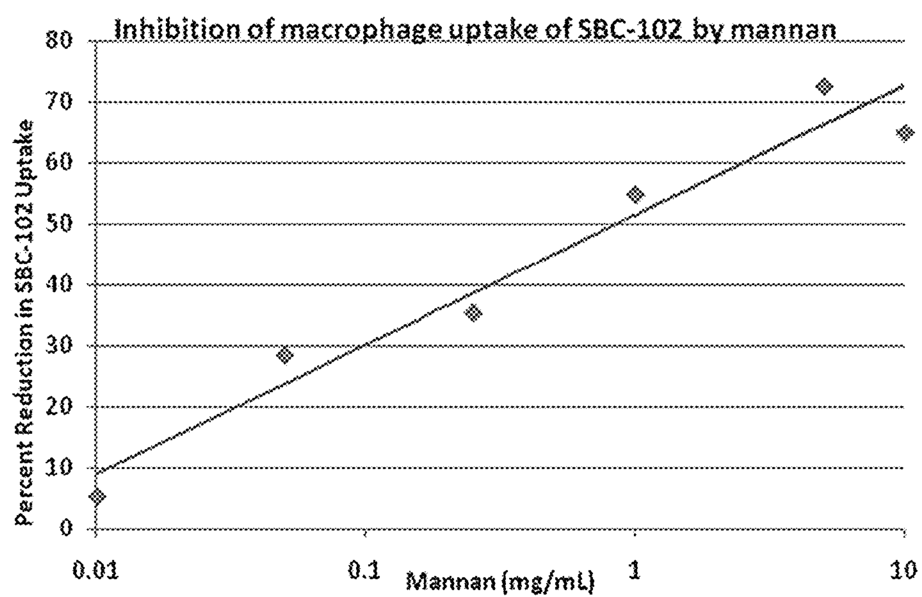
FIG. 21 depicts the binding specificity of recombinant human LAL (SBC-102) to the GlcNAc/mannose receptor assessed by competitive binding assays using the macrophage cell line, NR8383.

The binding specificity of transgenic avian derived LAL to the GlcNAc/mannose receptor has been assessed by competitive binding assays using the macrophage cell line, NR8383 (FIG. 21). Fluorescently-labeled (Oregon Green) transgenic avian derived LAL at 5 μg/mL and various concentrations of the mannose-containing oligosaccharide, mannan, were co-incubated with cells for 2 hours. The relative inhibition of transgenic avian derived LAL uptake by mannan, as compared with no mannan control, was quantified by fluorescence-activated cell sorting analysis using median fluorescence intensity as the endpoint. A mannose dose dependent inhibition in transgenic avian derived LAL binding/uptake was observed, which is consistent with transgenic avian derived LAL: GlcNAcR interaction.

In addition, mannose-6-phosphate mediated uptake in fibroblast cells was demonstrated by competition experiments with mannose-6-phosphate (results not shown).

Figure 22:
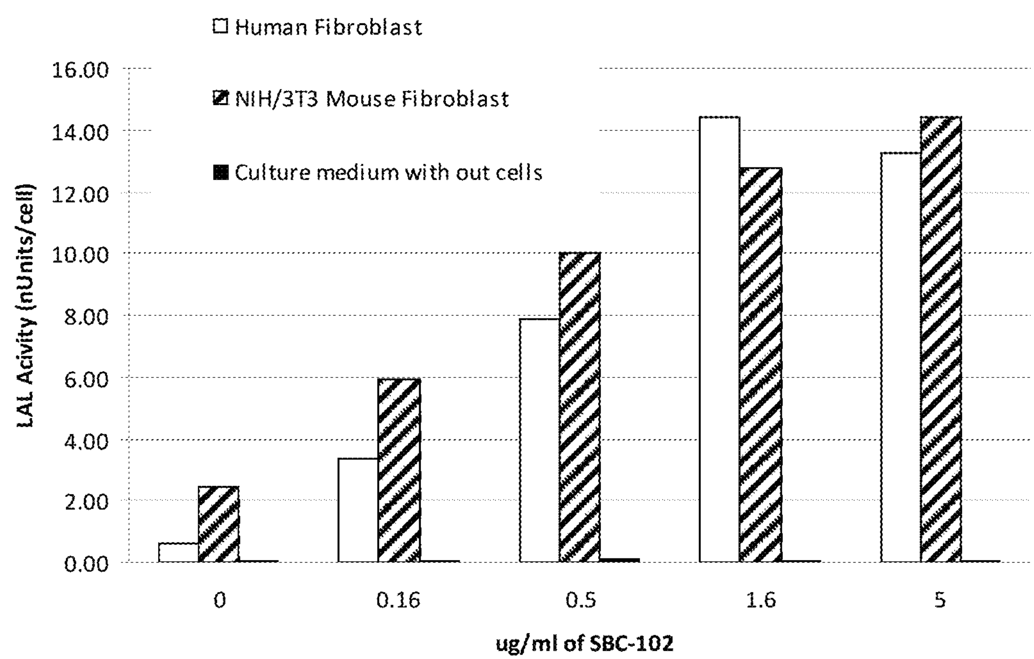
FIG. 22 depicts the activity of recombinant human LAL in cells in normal and LAL-deficient cells in vitro.

The ability of transgenic avian derived LAL exposure to increase LAL activity in cells has been examined using both normal and LAL-deficient cells in vitro. Fibroblasts isolated from a Wolman's patient and normal murine fibroblasts (NIH-3T3) were incubated in the presence of transgenic avian derived LAL at concentrations of either 0, 0.16 or 0.5 μg/mL for 5 hours. Cells were then washed to remove non-specific signal and cell lysates were assayed for LAL activity using 4-MUO substrate. Endogenous cell-associated LAL activity was lower in Wolman's fibroblasts compared to NIH-3T3 and dose-dependent increases in activity were observed in both cell types after incubation with transgenic avian derived LAL (FIG. 22).

Example 14

In Vivo Analysis of Transgenic Avian Derived LAL

LAL-deficient Yoshida Rats (i.e., Homozygous) (see Kuriyama et al. (1990), Journal of Lipid Research, vol. 31, p 1605-1611; Nakagawa et al., (1995) Journal of Lipid Research, vol. 36, p 2212-2218; and Yoshida and Kuriyama (1990) Laboratory Animal Science, vol. 40, p 486-489) were treated with either SBC-102 (5 mg/kg, IV) or placebo, once/week for four weeks beginning at four weeks of age. For each administration the SBC-102 was injected into the rat tail vein in two equal doses (2.5 mg/kg) 30 minutes apart. Rats and aged-matched wild-type controls were examined one week after the final dose. Analyses were done in triplicate.

Gross pathologic examination of the SBC-102 treated animals demonstrated normalization in liver color in addition to reduction in organ size. The SBC-102 treated rats showed essentially normal liver histology in marked contrast to the substantial accumulation of foamy macrophages in the vehicle-treated animals (data not presented). Serum alanine and aspartate transferase levels, which are elevated in $LAL^{-/-}$ rats, were also reduced in SBC-102 treated rats (not shown).

Figure 23:
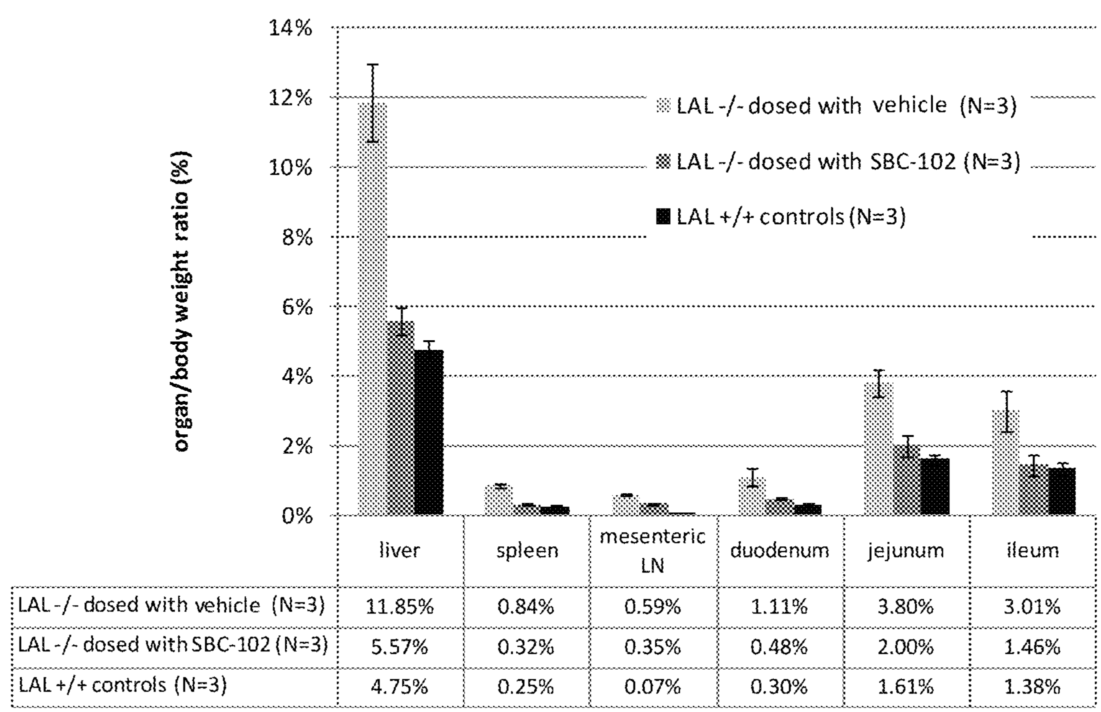
FIG. 23 depicts the effect of recombinant human LAL (SBC-102) treatment on internal organs mass of LAL deficient rats. Organ size is represented as percent of body weight determined at 8 weeks of age, in $LAL^{-/-}$ rats and $LAL^{+/+}$ rats after weekly administration of vehicle or SBC-102 at 5 mg/kg for 4 weeks.

Mass of internal organs and tissue was determined for each rat and the data is shown in FIG. 23. Organ size is represented as percent of body weight determined at 8 weeks of age, in $LAL^{-/-}$ rats and $LAL^{+/+}$ rats after weekly administration of vehicle or SBC-102 at 5 mg/kg for 4 weeks.

Figure 24:
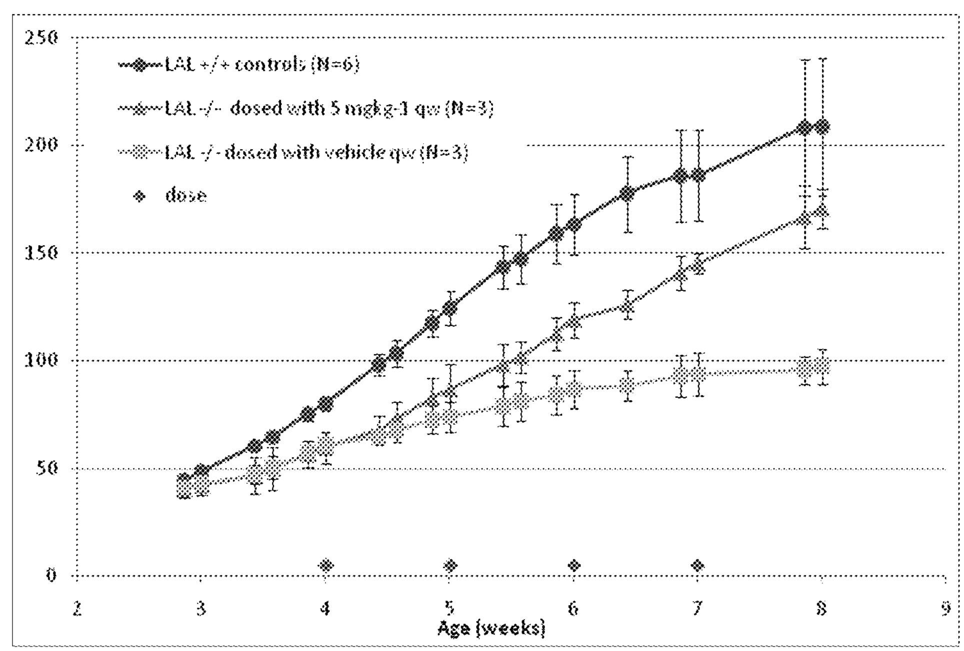
FIG. 24 depicts body weight in wild type and LAL-deficient rats after weekly administration of vehicle or SBC-102 at 5 $mg{\cdot}kg^{-1}$ for 4 weeks. Dose administration is highlighted on X-axis by diamonds starting at 4 week.

Body weight of SBC-102- or vehicle-treated Yoshida rats were compared with wild type rats, as is shown in FIG. 24. SBC-102 (5 mg/kg) or vehicle was administered by IV injection either as a single dose or as split doses (given within 4 hour period) to $LAL^{-/-}$ rats. $LAL^{+/+}$ rats are age-matched littermate controls.

Example 15

Triglyceride Analysis

Triglyceride analysis was performed on liver and spleen tissue from wild type, homozygous placebo and homozygous SBC-102 treated animals. The triglyceride analyses were performed using standard methodologies (i.e., MBL International's Triglyceride Quantification Kit Catalog #JM-K622-100) and were done in triplicate.

TABLE 3

Liver and Spleen Triglyceeride levels in wild-type and LAL deficient rats
Triglyceride (ug/mg wet tissue)

| | Wild Type (n = 3) | Placebo (n = 3) | SBC-102 (n = 3) |
|---|---|---|---|
| Liver | 48 | 84 | 57 |
| Spleen | 3 | 22 | 4 |

Liver Substrate Levels

Figure 25:
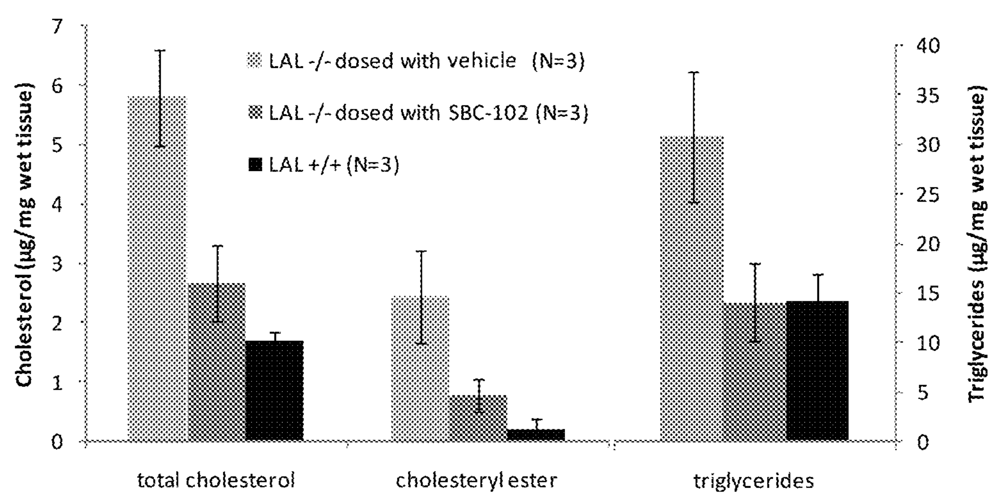
FIG. 25 shows liver cholesterol, cholesteryl ester and triglyceride levels determined at 8 weeks of age in WT and LAL deficient rats after weekly administration of vehicle or recombinant human LAL (SBC-102) at 5 $mg{\cdot}kg^{-1}$ for 4 weeks.

FIG. 25 shows liver cholesterol, cholesteryl ester and triglyceride levels determined at 8 weeks of age, in WT and LAL deficient rats after weekly administration of vehicle or SBC-102 at 5 $mg \cdot kg^{-1}$ for 4 weeks.

Example 16

Dose Response Study

Figure 26:
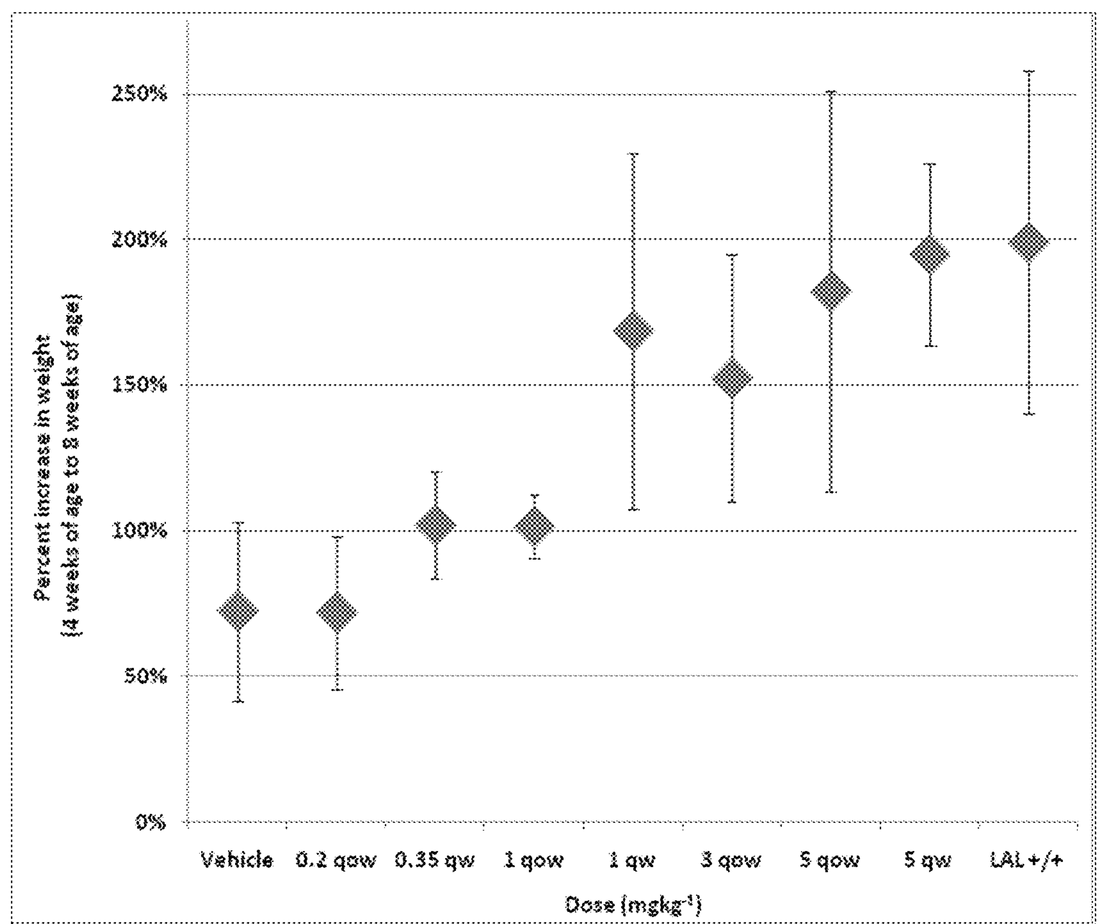
FIG. 26 depicts percent increase in body weight in LAL-deficient rats after 4 weeks administration recombinant human LAL (SBC-102) at the indicated levels and schedules, determined at 8 weeks of age.
Figure 27:
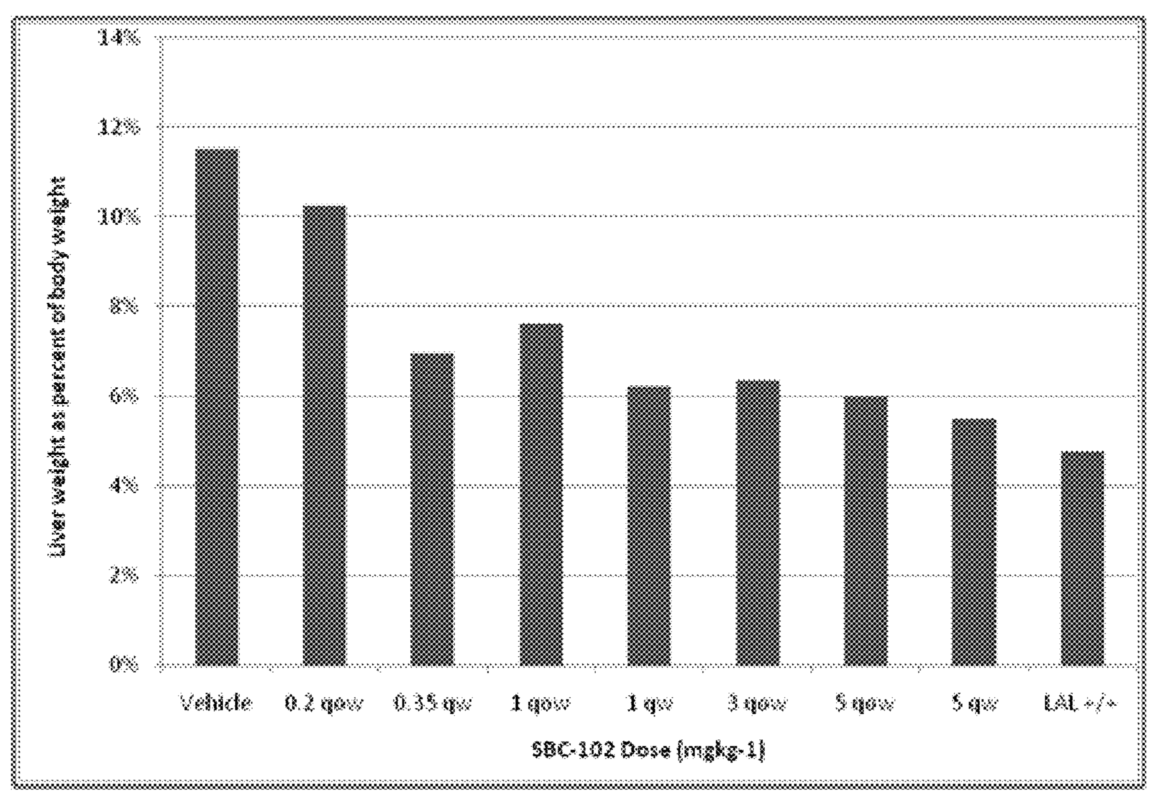
FIG. 27 shows liver weight, as a percent of body weight, in LAL-deficient rats after 4 weeks administration SBC-102 at the indicated levels and schedules, determined at 8 weeks of age.
Figure 28:
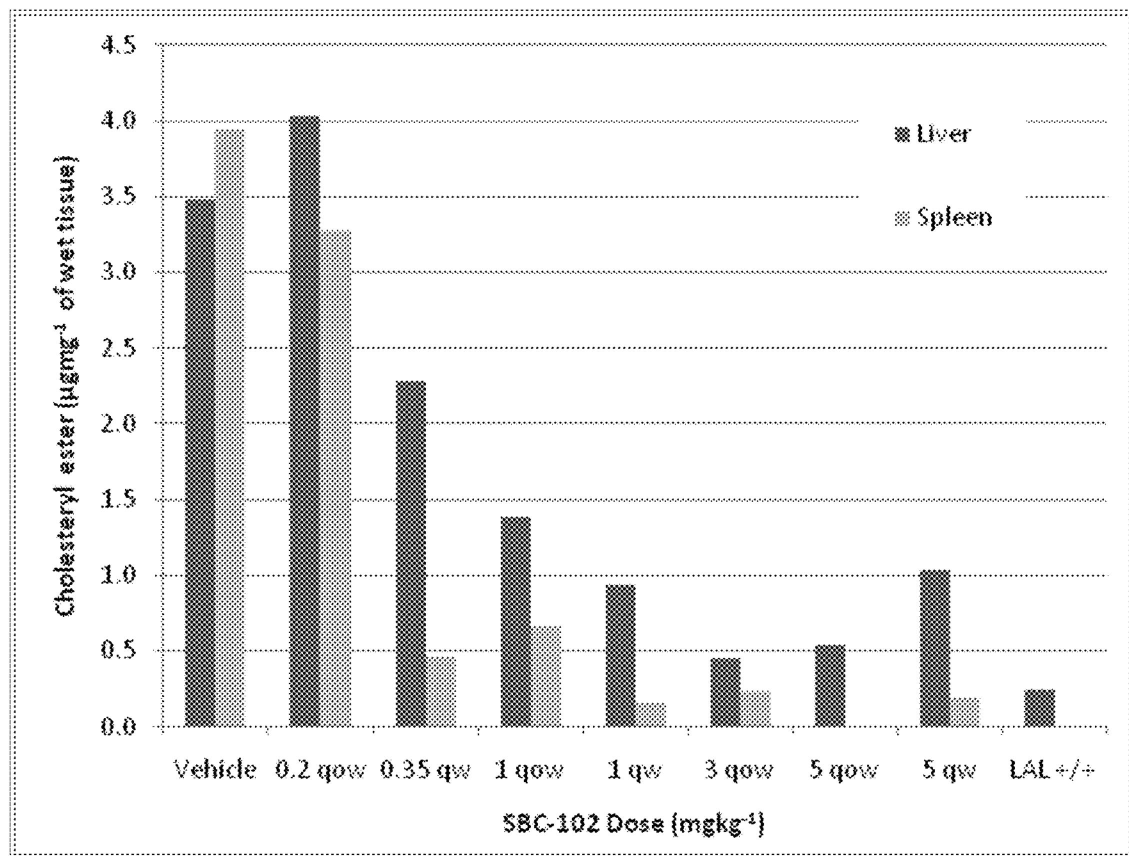
FIG. 28 shows tissue cholesteryl ester levels in LAL-deficient rats after 4 weeks administration SBC-102 at the indicated levels and schedules, determined at 8 weeks of age.

Based on the studies performed above, the pharmacodynamic (PD) effects of a range of doses and dose schedules (qw and qow) of LAL ("SBC-102") were examined in LAL rats. In these studies, SBC-102 was administered by IV injections at dosages of 0.2, 1, 3 and 5 mg/kg, qow, or 0.35, 1 and 5 mg/kg, qw, for 1 month, beginning at 4 weeks of age. Results demonstrate improvements in body weight (BW) gain (FIG. 26), organomegaly (FIG. 27), and tissue substrate levels (FIG. 28). Serum transaminase levels were also reduced as the SBC-102 dose increased, with levels reaching essentially wild-type levels at the higher doses.

Example 17

Administration of Recombinant LAL in a Rat Model

The effects of repeat-dosing with recombinant human lysosomal acid lipase (LAL) on weight, tissue triglycerides and cholesterol, hepatomegaly, splenomegaly, lymphadenopathy, intestinal weight, and other parameters were evaluated in LAL Deficient Donryu rats described in Yoshida and Kuriyama (1990) Laboratory Animal Science, vol. 40, p 486-489 (see also Kuriyama et al. (1990) Journal of Lipid Research, vol. 31, p 1605-1611; Nakagawa et al., (1995)

Journal of Lipid Research, vol. 36, p 2212-2218), the disclosure of which is incorporated in its entirety herein by reference.

At 4 weeks of age, Donryu rats homozygous for the LAL deletion (LAL were assigned into groups to either be dosed with recombinant human LAL produced in a transgenic chicken oviduct system or a saline placebo. Wild-type, age-matched, littermate rats were used as controls. The LAL rats were dosed once a week for four weeks (four doses total) or once every two weeks for four weeks (two doses total) by tail-vein injection as a single dose or in two equal doses given 30 minutes apart. Doses of LAL were 1 mg/kg or 5 mg/kg. Dosing schedule is shown in Table 4. The rats were pretreated with diphenhydramine (5 mg/kg) to counteract potential anaphylactic reactions, a procedure which is based on previous experiences in animal models of enzyme replacement therapy for the treatment of lysosomal storage disease (Shull et al. (1994) Proceedings of the National Academy of Science, vol. 91, p. 1293'7; Bielicki et al. (1999) The Journal of Biological Chemistry, 274, p. 36335; Vogler et al. (1999) Pediatric Research, 45, p. 838), the disclosure of which is incorporated in its entirty herein by referernce.

Figure 29:
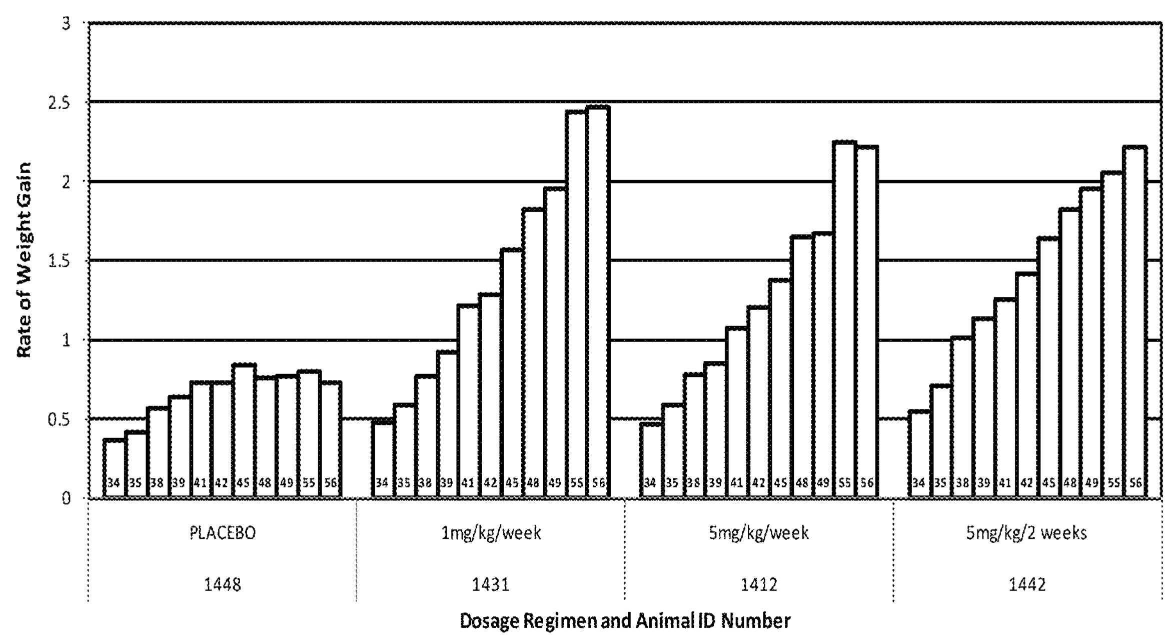
FIG. 29 shows the daily progress in weight gain of rats which were administered either 1 mg/kg of LAL per week or 5 mg/kg of LAL per week or 5 mg/kg of LAL per two weeks.

FIG. 29 shows the daily progress in weight gain of rats which were administered either 1 mg/kg of LAL per week or 5 mg/kg of LAL per week or 5 mg/kg of LAL per two weeks. It can be seen in the figure that there is little or no difference in therapeutic effect between the two dose sizes and frequencies.

TABLE 4

Weighing and Dosing Schedule

| Day from Birth | | Assessments/Injections Performed |
|---|---|---|
| Day 13 | WEIGHED | |
| Day 14 | | |
| Day 20 | | |
| Day 21 | | Pups Weaned |
| Day 24 | | |
| Day 25 | | |
| Day 27 | | |
| Day 28 | | First Injection for administration once every week and once every two weeks |
| Day 31 | | |
| Day 32 | | |
| Day 34 | | |
| Day 35 | | Second Injection for administration once every week |
| Day 38 | | |
| Day 39 | | |
| Day 41 | | |
| Day 42 | | Third Injection for administration once every week; Second administration for once every two weeks |
| Day 45 | | |
| Day 48 | | |
| Day 49 | | Fourth injection for administration once every week |
| Day 55 | | |
| Day 56 | | Necropsy |

Pathologic Examination of $LAL^{-/-}$ Rats Treated with Recombinant LAL

At the termination of the study described in Example 1, study animals were humanely euthanized and necropsied to examine gross pathology, histopathology, and clinical chemistry. The gross necropsy included examination of the external surface of the body, all orifices, and the cranial, thoracic, and abdominal cavities and their contents. Mass of internal organs and tissues were determined for the rats and the organs and tissues were harvested and fixed in 10% neutral-buffered formalin. Following fixation, the tissues were processed and histological slides of hematoxylin and eosin-stained sections were prepared and evaluated.

Figure 30:
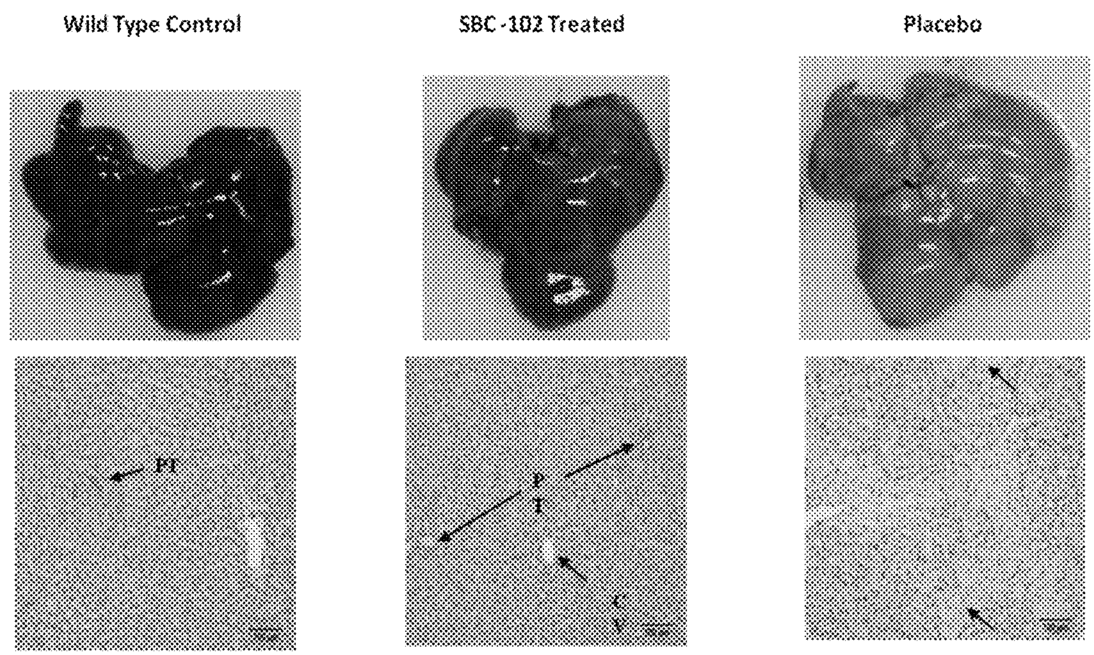
FIG. 30 depicts the gross pathological examination of treated animals showing a substantial normalization in liver size and color as can be seen in the dissection at the top panels and histopathology of liver tissue from LAL of treated rats showing normal liver histology in marked contrast to the substantial accumulation of foamy macrophages in the placebo-treated animals at the bottom panels.

The gross pathological examination of treated animals analyzed showed a substantial normalization in liver size and color as can be seen in the dissection shown in FIG. 30. Organ-to-body weight ratios were determined and demonstrated a reduction in the relative organ size for liver, spleen, mesenteric tissue, duodenum, jejunum and ileum in successfully treated animals which were dissected, as compared to the placebo treated rats (FIG. 23). Histopathology of liver tissue from LAL of treated rats analyzed shows essentially normal liver histology in marked contrast to the substantial accumulation of foamy macrophages in the placebo-treated animals (FIG. 30).

Example 18

Treatment of Wolman Disease (WD) by Administration of Recombinant LAL

At 7 weeks of age a female patient is admitted to the hospital because of difficulty in weight gain and poor progress since birth. At the initial physical examination the patient weighs 3.6 kg (birth weight 3.7 kg) and is thin, with loose skin folds. The abdomen is distended, with firm hepatomegaly of 6 cm and firm splenomegaly of about 4 cm. Enlarged lymph nodes are noted in the groin and muscular activity is weak.

The initial hemoglobin level is 9.2 gm, platelets 506,000, and white blood cells 11,550. Urinalysis is normal, and bone marrow smears reveal vacuolated lymphocytes and numerous foam cells. Serum chemical measurements: total lipids 834 mg/100 ml, phospholipids 176 mg/100 ml, triglycerides 141 mg/100 ml, cholesterol 129 mg/100 ml, bilirubin 0.3 mg/100 ml, alkaline phosphatase 9.0 BU %, SGOT 90 units, SGPT 50 units, cholinesterase 20 units, urea nitrogen 8.3 mg, fasting sugar 45 mg/100 ml. CT scan of the abdomen shows hepatosplenomegaly and bilateral symmetrically enlarged adrenal glands with calcification.

The patient is surgically implanted with a venous vascular access port for dosing. After connecting the port to an ambulatory infusion machine, the patient is pretreated with 1 mg/kg of diphenhydramine 20 minutes prior to LAL infusion in order to counteract potential anaphylactic infusion reactions. The patient is then administered LAL at 1 mg/kg over the course of 5 hours by intravenous infusion. This therapy is repeated one time every 7 days indefinitely.

Within two weeks of administering the first dose of LAL, the patient experiences a significant improvement in weight gain and normalization in size of key abdominal organs as determined by ultrasound. Laboratory results demonstrate that infusion of the LAL restores lysosomal acid lipase activity in the patient and leads to correction of related abnormalities.

Example 19

Treatment of Cholesteryl Ester Storage Disease (CESD) by Administration of Recombinant LAL A 3-year-old boy with a pruritic abdominal rash is examined by his pediatrician. Upon abdominal examination, hepatomegaly is noted by the physician and confirmed by ultrasound. At this point no diagnosis is made and the patient is monitored periodically.

At age 8, he is admitted to the hospital with gastroenteritis. Light microscopy of a liver biopsy shows increased intracytoplasmic glycogen and small lipid droplets in hepatocytes. Electron microscopy shows membrane-bound lipid droplets with small electron dense granules. A working diagnosis of glycogen storage disease type III (DeBrancher disease) is made, but skin fibroblast Debrancher activity is normal.

At age 10, hepatomegaly persists and a second liver biopsy is taken. Light microscopy shows altered lobular architecture of the hepatic parenchyma with distended hepatocytes containing cytoplasmic granules and vacuoles with mild periportal fibrosis. Fibroblast acid lipase activity is found to be 7% of normal, confirming the diagnosis of CESD. Plasma concentrations of total cholesterol (TC), triglycerides (TG), low-density lipoprotein cholesterol (LDL-C) are each above the 95th percentile for age and sex at 7.51, 3.24 and 5.58 mmol/L, respectively, while plasma high-density lipoprotein cholesterol (HDL-C) is below the 5th percentile at 0.47 mmol/L; he has combined hyperlipidemia (hypercholesterolemia, hypertriglyceridemia, hypoalphalipoproteinemia and hyperbetalipoproteinemia).

The patient is surgically implanted with a venous vascular access port for dosing. After connecting the port to an ambulatory infusion machine, the patient is pretreated with 5 mg/kg of diphenhydramine 20 minutes prior to LAL infusion in order to counteract potential anaphylactic infusion reactions. The patient is then administered LAL at 5 mg/kg over the course of 5 hours by intravenous infusion. This therapy is repeated one time every 14 days indefinitely.

Within two weeks of administering the first dose of LAL, the patient experiences a significant improvement in weight gain and normalization in size of key organs as determined by ultrasound. Laboratory results demonstrate that infusion of the LAL restores lysosomal acid lipase activity in the patient and leads to correction of related abnormalities.

Example 20

Description and Composition of the Medicinal Product

The drug substance of LAL described herein ("SBC-102") is a recombinant human lysosomal acid lipase (rhLAL) purified from the egg white produced from transgenic *Gallus*. The excipients used in SBC-102 are similar to those used for other products for lysosomal storage disorders (LSD) currently on the market, and have been selected to maintain stability of the drug product.

SBC-102 is a clear, colorless, sterile liquid provided in a clear, Type I borosilicate glass vial with a non-natural latex (butyl), FluroTec®-coated stopper and aluminum crimp seal. SBC-102 is provided as an aqueous solution comprised of SBC-102 (2 mg/mL), Trisodium Citrate Dihydrate (13.7 mg/mL, USP), Citric Acid Monohydrate (1.57 mg/mL, USP), Human Serum Albumin (10 mg/mL, USP), and Water for Injection (to final volume, USP). The pH of SBC-102 is 5.9±0.2. SBC-102 contains no preservatives and vials are intended for single use only.

TABLE 5

Excipients in SBC-102 (LAL)

| Excipent | CAS number | Grade | Function |
|---|---|---|---|
| Trisodium Citrate Dihydrate | 6132-04-03 | USP | Buffer |
| Citric Acid Monohydrate | 5949-29-1 | USP | Buffer |
| Human Serum Albumin | 70024-90-7 | USP | Stabilizer |

Components of the Drug Product

TABLE 6

Formulation of SBC-102

| Component | Concentration |
|---|---|
| SBC-102 (rhLAL) | 2 mg/mL* |
| Trisodium Citrate Dihydrate | 13.7 mg/mL |
| Citric Acid Monohydrate | 1.57 mg/mL |
| Human Serum Albumin | 10 mg/mL |
| Water for Injection, QS to | 1.0 mL |

Each example in the above specification is provided by way of explanation of the invention, not limitation of the invention. In fact, it will be apparent to those skilled in the art that various modifications, combinations, additions, deletions and variations can be made in the present invention without departing from the scope or spirit of the invention. For instance, features illustrated or described as part of one embodiment can be used in another embodiment to yield a still further embodiment. It is intended that the present invention cover such modifications, combinations, additions, deletions, and variations.

All documents (e.g., U.S. patents, U.S. patent applications, publications) cited in the above specification are incorporated herein by reference. Various modifications and variations of the present invention will be apparent to those skilled in the art without departing from the scope and spirit of the invention.

While this invention has been particularly shown and described with references to example embodiments thereof, it will be understood by those skilled in the art that various changes in form and details may be made therein without departing from the scope of the invention encompassed by the appended claims.

What is claimed is:

1. A nucleic acid vector comprising a nucleic acid sequence encoding human recombinant lysosomal acid lipase comprising the amino acid sequence of SEQ ID NO: 2, 3, 4, or 19, wherein the nucleic acid sequence is operably linked to a promoter and wherein the nucleic acid sequence comprises an adenine (A) at position 93 relative to SEQ ID NO: 5.

2. An isolated host cell transformed with a vector according to claim 1.

3. The vector of claim 1, wherein the vector is configured for expression in a cell of:

(a) an avian;

(b) a mammal;

(c) a bacteria; or (d) a plant.

4. The vector of claim 3, wherein the avian is a chicken, turkey, or quail.

5. The vector of claim 3, wherein the avian cell is an oviduct cell.

6. The vector of claim 5, wherein the oviduct cell is a tubular gland cell.

7. The vector of claim 1, wherein the vector is a retroviral vector or a lentiviral vector.

8. The vector of claim 7, wherein the retroviral vector is a murine leukemia virus (MLV) vector.

9. The vector of claim 1, wherein the promoter comprises at least a portion of a cytomegalovirus (CMV) promoter, a rous-sarcoma virus (RSV) promoter, a β-actin promoter, a murine leukemia virus (MLV) promoter, a mouse mammary tumor virus (MMTV) promoter, an ovalbumin promoter, a lysozyme promoter, a conalbumin promoter, an ovomucoid promoter, an ovomucin promoter, or an ovotransferrin promoter, or wherein the promoter comprises an ovomucoid and ovotransferrin (MDOT) promoter.

10. The vector of claim 9, wherein the vector further comprises:

(a) a replication origin sequence;

(b) an enhancer sequence;

(c) a long terminal repeat (LTR) sequence;

(d) a 5' untranslated region (UTR);

(e) an internal ribosome entry site (IRES) element;

(f) a signal peptide coding sequence operably linked to the human recombinant lysosomal acid lipase;

(g) a 3' UTR;

(h) a polyadenylation sequence; or (i) a selectable marker sequence.

11. A composition comprising the vector of claim 1.

12. A viral particle comprising the vector of claim 1.

13. The nucleic acid vector of claim 1, wherein the nucleic acid sequence of the human lysosomal acid lipase has the sequence of nucleotides 5505-6704 of SEQ ID NO: 6.

* * * * *